United States Patent
Beane-Ebel et al.

(10) Patent No.: US 11,579,140 B2
(45) Date of Patent: Feb. 14, 2023

(54) METHODS RELATED TO BRONCHIAL PREMALIGNANT LESION SEVERITY AND PROGRESSION

(71) Applicants: TRUSTEES OF BOSTON UNIVERSITY, Boston, MA (US); HEALTH RESEARCH, INC., Buffalo, NY (US)

(72) Inventors: Jennifer E. Beane-Ebel, Fort Collins, CO (US); Avrum E. Spira, Newton, MA (US); Marc Lenburg, Brookline, MA (US); Mary E. Reid, Buffalo, NY (US); Sarah Mazzilli, Abington, MA (US)

(73) Assignees: TRUSTEES OF BOSTON UNIVERSITY, Boston, MA (US); HEALTH RESEARCH, INC., Buffalo, NY (US)

( * ) Notice: Subject to any disclaimer, the term of this patent is extended or adjusted under 35 U.S.C. 154(b) by 0 days.

(21) Appl. No.: 16/545,032

(22) Filed: Aug. 20, 2019

(65) Prior Publication Data
US 2020/0057053 A1   Feb. 20, 2020

Related U.S. Application Data

(60) Provisional application No. 62/765,264, filed on Aug. 20, 2018.

(51) Int. Cl.
*C12Q 1/6886* (2018.01)
*G01N 33/574* (2006.01)
*G01N 33/50* (2006.01)
*G16H 50/30* (2018.01)

(52) U.S. Cl.
CPC ....... *G01N 33/5023* (2013.01); *C12Q 1/6886* (2013.01); *G01N 33/5091* (2013.01); *G01N 33/574* (2013.01); *G16H 50/30* (2018.01)

(58) Field of Classification Search
CPC ............... C12Q 1/6883; C12Q 1/6886; C12Q 2600/106; C12Q 2600/112; C12Q 2600/118; C12Q 2600/158
See application file for complete search history.

(56) References Cited

U.S. PATENT DOCUMENTS

| | | |
|---|---|---|
| 2006/0165773 A1 | 7/2006 | Perez-Soler et al. |
| 2010/0055047 A1 | 3/2010 | Zou et al. |
| 2018/0010197 A1 | 1/2018 | Beane-Ebel et al. |
| 2018/0171418 A1 | 6/2018 | Brody et al. |

FOREIGN PATENT DOCUMENTS

WO    2018136919 A2    7/2018

OTHER PUBLICATIONS

Schneider, M. et al. International Journal of Oncology 50:365 (Feb. 2017). (Year: 2017).*

(Continued)

*Primary Examiner* — Diana B Johannsen
(74) *Attorney, Agent, or Firm* — Nixon Peabody LLP; Ronald I. Eisenstein; Nicole D. Kling

(57) ABSTRACT

The technology described herein is directed to methods of treating and diagnosing bronchial premalignant lesions, e.g. by determining the lesion subtype using one or more biomarkers described herein.

15 Claims, 42 Drawing Sheets

(56) References Cited

OTHER PUBLICATIONS

Specht, E. et al. Oncology Research and Treatment 38 (Suppl 5):abstract P461 (Oct. 2015). (Year: 2015).*
Liu, X. et al. International Journal of Oncology 45:1266 (2014). (Year: 2014).*
Lonergan, K. et al. PLoS One 5(2):e9162 (2010). (Year: 2010).*
Alaa, M. et al. Lung Cancer 72:303-308. (Year: 2011).*
Wikman, H. et al. Oncogene 21:5804-5813. (Year: 2002).*
Beane et al. "Detecting the Presence and Progression of Premalignant Lung Lesions via Airway Gene Expression." Clin. Cancer Res. 23(17): 5091-5100 (2017).
Gao et al. "Loss of IFN-gamma Pathway Genes in Tumor Cells as a Mechanism of Resistance to Anti-CTLA-4 Therapy." Cell 167(2): 397-404.e9 (2016).
Gettinger et al. "Impaired HLA Class I Antigen Processing and Presentation as a Mechanism of Acquired Resistance to Immune Checkpoint Inhibitors in Lung Cancer." Cancer Discov 7(12): 1420-1435 (2017).
Kotsakis et al. "Prognostic value of circulating regulatory T cell subsets in untreated non-small cell lung cancer patients." Sci Rep 6: 39247 p. 1-11 (2016).
Pereira et al. "Genomic Profiling of Patient-Derived Xenografts for Lung Cancer Identifies B2M Inactivation Impairing Immunorecognition." Clin. Cancer Res. 23(12): 3203-3213 (2017).
Wang et al. "Expression of CD163, interleukin-10, and interferon-gamma in oral squamous cell carcinoma: mutual relationships and prognostic implications." Eur. J. Oral Sci. 122(3): 202-209 (2014).
Wu et al. "Stromal PD-L1-Positive Regulatory T cells and PD-1-Positive CD8-Positive T cells Define the Response of Different Subsets of Non-Small Cell Lung Cancer to PD-1/PD-L1 Blockade Immunotherapy." J. Thorac Oncol 13(4): 521-532 (2018).
Gustafson et al. "Airway PI3K pathway activation is an early and reversible event in lung cancer development." Science translational medicine 2.26 (2010): 26ra25-26ra25.

* cited by examiner

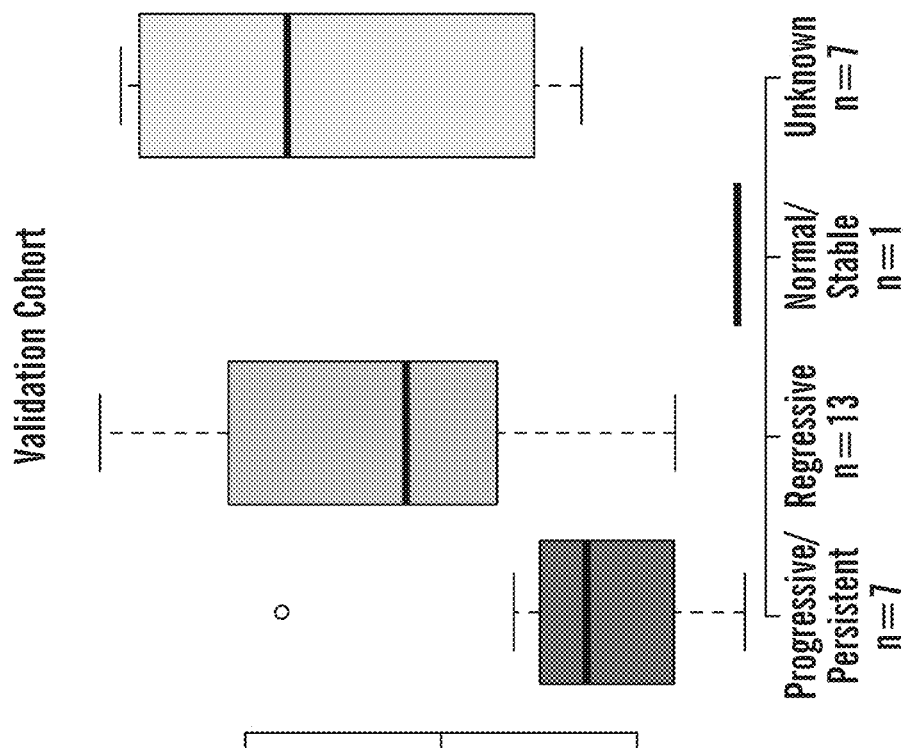
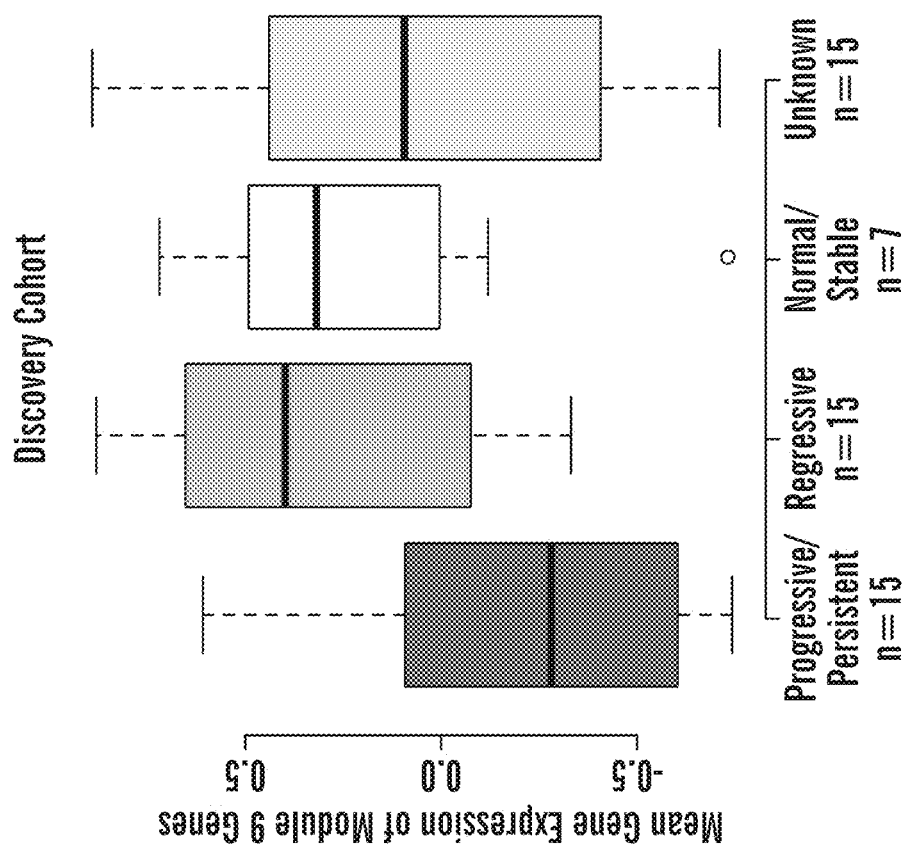
FIG. 4A
FIG. 4B

| Variable | Discovery Cohort | | Validation Cohort | | P-value | |
|---|---|---|---|---|---|---|
| Sample Type | Biopsies | Brushes | Biopsies | Brushes | Biopsies | Brushes |
| Batch/Illumina Flow Cell Assignment | | | | | <2e-16 | <2e-16 |
| 1 | 19/190 (10) | 12/89 (13.5) | 0/105 (0) | 0/48 (0) | | |
| 2 | 18/190 (9.5) | 13/89 (14.6) | 0/105 (0) | 0/48 (0) | | |
| 3 | 22/190 (11.6) | 9/89 (10.1) | 0/105 (0) | 0/48 (0) | | |
| 4 | 19/190 (10) | 10/89 (11.2) | 0/105 (0) | 0/48 (0) | | |
| 5 | 29/190 (15.3) | 2/89 (2.2) | 0/105 (0) | 0/48 (0) | | |
| 6 | 24/190 (12.6) | 8/89 (9.0) | 0/105 (0) | 0/48 (0) | | |
| 7 | 20/190 (10.5) | 11/89 (12.4) | 0/105 (0) | 0/48 (0) | | |
| 8 | 17/190 (8.9) | 14/89 (15.7) | 0/105 (0) | 0/48 (0) | | |
| 9 | 22/190 (11.6) | 10/89 (11.2) | 0/105 (0) | 0/48 (0) | | |
| 10 | 0/190 (0) | 0/89 (0) | 22/105 (10.7) | 9/48 (18.8) | | |
| 11 | 0/190 (0) | 0/89 (0) | 19/105 (9.3) | 10/48 (20.8) | | |
| 12 | 0/190 (0) | 0/89 (0) | 21/105 (10.2) | 10/48 (20.8) | | |
| 13 | 0/190 (0) | 0/89 (0) | 20/105 (9.8) | 12/48 (25) | | |
| 14 | 0/190 (0) | 0/89 (0) | 23/105 (11.2) | 7/48 (14.6) | | |
| Total Reads | 45.5e-6 (7.2e-6) | 45.3e-6 (7.9e-6) | 42.9e-6 (6.3e-6) | 42.6e-6 (4.9e-6) | 1.50E-03 | 0.014 |
| Median Transcript Integrity Number (TIN) | 78.4 (1.9) | 72.6 (3.4) | 76.3 (2.0) | 72.3 (2.8) | 2.08E-10 | 0.59 |
| Percent Uniquely Mapped | 90.1 (2.9) | 89.0 (5.9) | 83.9 (9.6) | 87.6 (4.9) | 2.15E-09 | 0.15 |

*FIG. 5*

| Variable | Discovery Cohort | | Validation Cohort | | P-value | |
|---|---|---|---|---|---|---|
| Sample Type | Biopsies | Brushes | Biopsies | Brushes | Biopsies | Brushes |
| Batch/Illumina Flow Cell Assignment | | | | | <2e-16 | <2e-16 |
| 1 | 19/190 (10) | 12/89 (13.5) | 0/105 (0) | 0/48 (0) | | |
| 2 | 18/190 (9.5) | 13/89 (14.6) | 0/105 (0) | 0/48 (0) | | |
| 3 | 22/190 (11.6) | 9/89 (10.1) | 0/105 (0) | 0/48 (0) | | |
| 4 | 19/190 (10) | 10/89 (11.2) | 0/105 (0) | 0/48 (0) | | |
| 5 | 29/190 (15.3) | 2/89 (2.2) | 0/105 (0) | 0/48 (0) | | |
| 6 | 24/190 (12.6) | 8/89 (9.0) | 0/105 (0) | 0/48 (0) | | |
| 7 | 20/190 (10.5) | 11/89 (12.4) | 0/105 (0) | 0/48 (0) | | |
| 8 | 17/190 (8.9) | 14/89 (15.7) | 0/105 (0) | 0/48 (0) | | |
| 9 | 22/190 (11.6) | 10/89 (11.2) | 0/105 (0) | 0/48 (0) | | |
| 10 | 0/190 (0) | 0/89 (0) | 22/105 (10.7) | 9/48 (18.8) | | |
| 11 | 0/190 (0) | 0/89 (0) | 19/105 (9.3) | 10/48 (20.8) | | |
| 12 | 0/190 (0) | 0/89 (0) | 21/105 (10.2) | 10/48 (20.8) | | |
| 13 | 0/190 (0) | 0/89 (0) | 20/105 (9.8) | 12/48 (25) | | |
| 14 | 0/190 (0) | 0/89 (0) | 23/105 (11.2) | 7/48 (14.6) | | |
| Total Reads | 45.5e+6 (7.2e+6) | 45.3+-6 (7.9e+6) | 42.9e+6 (6.3e+6) | 42.6e+6 (4.9e+6) | 1.50E-03 | 0.014 |
| Median Transcript Integrity Number (TIN) | 78.4 (1.9) | 72.6 (3.4) | 76.3 (2.0) | 72.3 (2.8) | 2.08E-10 | 0.59 |
| Percent Uniquely Mapped | 90.1 (2.9) | 89.0 (5.9) | 83.9 (9.6) | 87.6 (4.9) | 2.15E-09 | 0.15 |

*FIG. 5 (cont.)*

| Cluster Number | Number of Genes | Biological Pathways Associated with Gene Clusters | Key Genes | FDR for Difference between Subtypes |
|---|---|---|---|---|
| 1 | 514 | Extracellular Matrix/Cell Adhesion | Collagens, Lamins, TGFb | 2.7E-36 |
| 2 | 939 | mRNA processing and splicing | RBMs & SRSF | 7.2E-05 |
| 3 | 20 | Transcriptional regulation in response to stimuli - (AP-1) immediate-early response genes | JUN & FOS | 1.9E-01 |
| 4 | 64 | OXPHOS/ETC/TCA | COXs & NDUFs | 3.3E-07 |
| 5 | 209 | Cell Cycle/DNA replication/DNA repair | PCNA, TOP2A, ODC, AURK, RAD, XRCC | 2.0E-31 |
| 6 | 1295 | Cilium organization and assembly | FOXJ1, DYNC | 6.6E-57 |
| 7 | 180 | Ribosomal Proteins/Translation | RPLS & RPSS | 1.9E-13 |
| 8 | 603 | Immune Activation and Inflammatory Response (leukocyte/lymphocyte regulation) | CD8A, CD86, GATA, STAT, IL1B, CD163, CD68 | 3.3E-07 |
| 9 | 112 | Interferon signaling and Antigen Processing and Presentation | SP100, HLAs, STAT1 | 1.3E-02 |

*FIG. 6*

| IF Panel | All Samples | | K5/KI67/Ac-alpha-Tubulin | |
|---|---|---|---|---|
| Variable | Discovery Cohort | Validation Cohort | Discovery Cohort | Validation Cohort |
| Number of Subjects | 20 | 11 | 8 | 3 |
| Number of Samples | 29 | 21 | 9 | 3 |
| Subtype | | | | |
| Normal | 2/29 (7) | 1/21 (5) | | |
| Secretory | 8/29 (28) | 5/21 (24) | 1/9 (11) | 1/3 (33) |
| Inflammatory | 8/29 (28) | 3/21 (14) | 2/9 (22) | 1/3 (33) |
| Proliferative | 11/29 (38) | 12/21 (57) | 5/9 (56) | 1/3 (33) |
| Histology | | | | |
| Normal/Hyperplasia | 9/29 (31) | 2/21 (10) | 3/9 (33) | |
| Squamous Metaplasia | 3/29 (10) | 3/21 (14) | | 2/3 (67) |
| Mild Dysplasia | 2/29 (7) | 4/21 (19) | | |
| Moderate Dysplasia | 8/29 (28) | 9/21 (43) | 3/9 (34) | 1/3 (33) |
| Severe Dysplasia/CIS | 7/29 (24) | 3/21 (14) | 3/9 (33) | |
| Lesion State | | | | |
| Progressive/Persistent | 8/29 (28) | 10/21 (47) | 1/9 (11) | 2/3 (67) |
| Regressive | 6/29 (21) | 6/21 (29) | 4/9 (44) | |
| Unknown or Normal/Stable | 15/29 (51) | 5/21 (24) | 5/9 (55) | 1/3 (33) |
| Smoking Status | | | | |
| Current | 17/29 (59) | 15/21 (71) | 5/9 (56) | 2/3 (67) |
| Former/Never | 12/29 (41) | 6/21 (29) | 4/9 (44) | 1/3 (33) |

*FIG. 7*

| CD68/CD163 | | CD4 | | CD8 | |
|---|---|---|---|---|---|
| Discovery Cohort | Validation Cohort | Discovery Cohort | Validation Cohort | Discovery Cohort | Validation Cohort |
| 19 | 11 | 20 | 11 | 20 | 10 |
| 28 | 19 | 29 | 20 | 28 | 19 |
| 2/28 (7) | 1/19 (5) | 2/29 (7) | 1/20 (5) | 2/28 (7) | 1/19 (5) |
| 8/28 (29) | 4/19 (21) | 8/29 (28) | 5/20 (25) | 8/28 (29) | 5/19 (26) |
| 7/28 (25) | 2/19 (11) | 8/29 (28) | 3/20 (15) | 8/28 (29) | 3/19 (16) |
| 11/28 (39) | 12/19 (63) | 11/29 (39) | 11/20 (55) | 10/28 (35) | 10/19 (53) |
| 9/28 (32) | 1/19 (5) | 9/29 (31) | 2/20 (10) | 9/28 (32) | 2/19 (11) |
| 3/28 (11) | 3/19 (15) | 3/29 (10) | 3/20 (15) | 3/28 (11) | 3/19 (16) |
| 2/28 (7) | 4/19 (21) | 2/29 (7) | 4/20 (20) | 2/28 (7) | 4/19 (21) |
| 7/28 (25) | 8/19 (42) | 8/29 (28) | 8/20 (40) | 7/28 (25) | 7/19 (36) |
| 7/28 (25) | 4/19 (21) | 7/29 (24) | 3/20 (15) | 7/28 (25) | 3/19 (16) |
| 8/28 (29) | 9/19 (48) | 8/29 (28) | 9/20 (45) | 7/28 (25) | 9/19 (48) |
| 5/28 (18) | 5/19 (26) | 6/29 (21) | 6/20 (30) | 6/28 (21) | 5/19 (26) |
| 15/28 (54) | 5/19 (26) | 15/29 (51) | 5/20 (25) | 15/28 (54) | 5/19 (26) |
| 16/28 (57) | 15/19 (79) | 17/29 (59) | 14/20 (70) | 17/28 (61) | 13/19 (68) |
| 14/28 (43) | 4/19 (21) | 12/29 (41) | 6/20 (30) | 11/28 (39) | 6/19 (32) |

FIG. 7 (cont.)

| IF Panel | All Samples | | Samples Used for Scoring Each Panel K5/KI67/Ac-alpha-Tubulin | |
|---|---|---|---|---|
| Variable | Discovery Cohort | Validation Cohort | Discovery Cohort | Validation Cohort |
| Number of Subjects | 17 | 12 | 7 | 2 |
| Number of Samples | 27 | 20 | 8 | 2 |
| Subtype | | | | |
| Normal-like | 2/27 (7) | 1/20 (5) | 1/8 (13) | 0/2 (0) |
| Secretory | 7/27 (26) | 5/20 (25) | 1/8 (13) | 0/2 (0) |
| Inflammatory | 8/27 (30) | 3/20 (15) | 2/8 (25) | 1/2 (50) |
| Proliferative | 10/27 (37) | 11/20 (55) | 4/8 (50) | 1/2 (50) |
| Histology | | | | |
| Normal/Hyperplasia | 9/27 (33) | 2/20 (10) | 3/8 (38) | 0/2 (0) |
| Squamous Metaplasia | 3/27 (11) | 3/20 (15) | 0/8 (0) | 1/2 (50) |
| Mild Dysplasia | 1/27 (4) | 4/20 (20) | 0/8 (0) | 0/2 (0) |
| Moderate Dysplasia | 8/27 (30) | 9/20 (45) | 3/8 (38) | 1/2 (50) |
| Severe Dysplasia/CIS | 6/27 (22) | 2/20 (10) | 2/8 (25) | 0/2 (0) |
| Lesion State | | | | |
| Progressive/Persistent | 7/27 (26) | 10/20 (50) | 1/8 (13) | 1/2 (50) |
| Regressive | 6/27 (22) | 5/20 (25) | 3/8 (38) | 0/2 (0) |
| Unknown or Normal/Stable | 14/27 (52) | 5/20 (25) | 4/8 (50) | 1/2 (50) |
| Smoking Status | | | | |
| Current | 15/27 (56) | 12/20 (60) | 6/8 (75) | 1/2 (50) |
| Former/Never | 12/27 (44) | 8/20 (40) | 2/8 (25) | 1/2 (50) |

FIG. 7 (cont.)

| Samples Used for Scoring Each Panel | | | | | | |
|---|---|---|---|---|---|---|
| CD68/CD163 | | CD4 | | CD8 | | |
| Discovery Cohort | Validation Cohort | Discovery Cohort | Validation Cohort | Discovery Cohort | Validation Cohort | |
| 17 | 12 | 17 | 11 | 17 | 11 | |
| 25 | 18 | 27 | 19 | 26 | 18 | |
| 2/25 (8) | 1/18 (6) | 2/27 (7) | 1/19 (5) | 2/26 (8) | 1/18 (6) | |
| 7/25 (28) | 4/18 (22) | 7/27 (26) | 5/19 (26) | 7/26 (27) | 5/18 (28) | |
| 7/25 (28) | 2/18 (11) | 8/27 (30) | 3/19 (16) | 8/26 (31) | 3/18 (17) | |
| 9/25 (36) | 11/18 (61) | 10/27 (37) | 10/19 (53) | 9/26 (35) | 9/18 (50) | |
| 9/25 (36) | 1/18 (6) | 9/27 (33) | 2/19 (11) | 9/26 (35) | 2/18 (11) | |
| 3/25 (12) | 3/18 (17) | 3/27 (11) | 3/19 (16) | 3/26 (12) | 3/18 (17) | |
| 1/25 (4) | 4/18 (22) | 1/27 (4) | 4/19 (21) | 1/26 (4) | 4/18 (22) | |
| 7/25 (28) | 8/18 (44) | 8/27 (30) | 8/19 (42) | 7/26 (27) | 7/18 (39) | |
| 5/25 (20) | 2/18 (11) | 6/27 (22) | 2/19 (11) | 6/26 (23) | 2/18 (11) | |
| 7/25 (28) | 9/18 (50) | 7/27 (26) | 10/19 (53) | 6/26 (23) | 9/18 (50) | |
| 5/25 (20) | 5/18 (28) | 6/27 (22) | 4/19 (21) | 6/26 (23) | 4/18 (22) | |
| 13/25 (52) | 4/18 (22) | 14/27 (52) | 5/19 (26) | 14/26 (54) | 5/18 (28) | |
| 13/25 (52) | 12/18 (67) | 15/27 (56) | 11/19 (58) | 14/26 (54) | 10/18 (56) | |
| 12/25 (48) | 6/18 (33) | 12/27 (44) | 8/19 (42) | 12/26 (46) | 8/18 (44) | |

FIG. 7 (cont.)

METHODS RELATED TO BRONCHIAL PREMALIGNANT LESION SEVERITY AND PROGRESSION

CROSS-REFERENCE TO RELATED APPLICATIONS

This application claims benefit under 35 U.S.C. § 119(e) of U.S. Provisional Application No. 62/765,264 filed Aug. 20, 2018, the contents of which are incorporated herein by reference in their entirety.

GOVERNMENT SUPPORT

This invention was made with Government Support under Contract No. CA196408 awarded by the National Institutes of Health. The Government has certain rights in the invention.

TECHNICAL FIELD

The technology described herein relates to treatment, diagnosis, and monitoring of treatment for bronchial premalignant lesions.

BACKGROUND

Lung squamous cell cancer develops from non-cancerous lesions in the airway known as bronchial premalignant lesions. The presence of persistent or progressive dysplastic bronchial premalignant lesions is a marker of increased lung cancer risk both at the lesion site (where they are the presumed precursors of squamous cell lung cancer) and elsewhere in the lung. Not all bronchial premalignant lesions progress to invasive cancer, and those that do, progress at variable rates with variable outcomes. At present, there are no tools available in the clinic to identify which lesions will progress to cancer and which will not. Additionally, the current technology for detecting bronchial premalignant lesions is via autofluorescence and white-light bronchoscopy. A bronchoscopy procedure is invasive and is only moderately sensitive and specific at detecting small bronchial premalignant lesions as it requires visualization of the lesions. Finally, to date, the only treatment for bronchial premalignant lesions is to remove the lesions via surgery or bronchoscopy.

SUMMARY

The inventors have now developed: 1) tests for the presence of bronchial premalignant lesions (some of which do not require bronchoscopy and use the surprising finding that normal tissues elsewhere in the airway exhibit biomarkers indicating the presence of bronchial premalignant lesions in the subject), 2) methods for determining if the bronchial premalignant lesions is likely to progress to cancer, 3) new therapies for bronchial premalignant lesions which target the underlying molecular changes which characterize the bronchial premalignant lesions.

Accordingly, provided herein one aspect is a method of treating bronchial premalignant lesions, the method comprising: administering at least one of: (i) both a bronchoscopy-based procedure to survey the central airway and a chest CT scan; (ii) at least every 6 months, one of a bronchoscopy-based procedure to survey the central airway and a chest CT scan; and/or (iii) at least one anti-proliferative drug; to a subject determined to have at least one of: (a) an increased level of expression of at least one module 5 gene as compared to a non-proliferative lesion reference level; and (b) a decreased level of expression of at least one module 6 gene as compared to a non-proliferative lesion reference level.

In one embodiment of this aspect and all other aspects provided herein, the at least one module 5 gene is selected from the group consisting of: RACGAP1 and TPX2; and the at least one module 6 gene is selected from the group consisting of: NEK11 and IFT88.

In another embodiment of this aspect and all other aspects provided herein, the subject is further determined to have an increased level of expression of at least one module 7 or module 4 gene.

In another embodiment of this aspect and all other aspects provided herein, the at least one module 7 or module 4 gene is selected from the group consisting of: COX6A1; COX7A2; RPL26; and RPL23.

In another embodiment of this aspect and all other aspects provided herein, the level of expression of each of the genes of Table 15 is determined. The method of any of claims 1-5, wherein the at least one anti-proliferative drug is selected from the group consisting of: Acetylcholine receptor antagonist; Acetylcholinesterase inhibitors; Adenosine receptor antagonists; Adrenergic receptor antagonists; AKT inhibitors; Angiotensin receptor antagonists; Apoptosis stimulants; Aurora kinase inhibitors; CDK inhibitors; Cyclooxygenase inhibitors; Cytokine production inhibitors; Dehydrogenase inhibitors; DNA protein kinase inhibitors; focal adhesion inhibitors; Dopamine receptor antagonist; EGFR inhibitors; ERK1 and ERK2 phosphorylation inhibitors; Estrogen receptor agonists; EZH2 inhibitors; FLT3 inhibitors; Glucocorticoid receptor agonists; Glutamate receptor antagonists; HDAC inhibitors; Histamine receptor antagonists; Histone lysine methyltransferase inhibitors; HSP inhibitors; IKK inhibitors; Ion channel antagonists; JAK inhibitors; JNK inhibitors; KIT inhibitors; Leucine rich repeat kinase inhibitors; MDM inhibitors; mediator release inhibitors; MEK inhibitors; MTOR inhibitors; Monoamine oxidase inhibitors; NFkB pathway inhibitors; nucleophosmin inhibitors; PARP inhibitors; PPAR receptor agonists; PI3K inhibitors; tyrosine kinase inhibitors; Phosphodiesterase inhibitors; protein kinase inhibitors; RAF inhibitors; RNA polymerase inhibitors; topoisomerase inhibitors; RNA synthesis inhibitors; SIRT inhibitors; sodium channel blockers; VEGFR inhibitors; and Vitamin D receptor agonists.

In another embodiment of this aspect and all other aspects provided herein, the anti-proliferative drug is administered as an inhaled formulation or topical formulation.

In another embodiment of this aspect and all other aspects provided herein, the anti-proliferative drug is administered during a bronchoscopy-based procedure.

In another embodiment of this aspect and all other aspects provided herein, the anti-proliferative drug is administered systemically.

In another embodiment of this aspect and all other aspects provided herein, the anti-proliferative drug is administered during a bronchoscopy-based procedure and systemically.

Another aspect provided herein relates to a method of treating bronchial premalignant lesions, the method comprising: administering at least one of: (i) both a bronchoscopy-based procedure to survey the central airway and a chest CT scan; (ii) at least every 6 months, one of a bronchoscopy-based procedure to survey the central airway and a chest CT scan; and/or (iii) at least one anti-proliferative drug; to a subject determined to have at least one of: (a) an increased level of expression of at least one module 5 gene as compared to a non-proliferative lesion reference level; and (b) a decreased level of expression of at least one module 6 gene as compared to a non-proliferative lesion reference level, wherein the subject is further determined to have a decreased level of expression of at least one module 9 gene as compared to a non-proliferative lesion reference level and/or an increased level of expression of at least one module 10 gene as compared to a non-proliferative lesion reference level.

In one embodiment of this aspect and all other aspects provided herein, the subject determined to have a decreased level of expression of at least one module 9 gene and/or an increased level of expression of at least one module 10 gene is administered at least one of:
  i. both a bronchoscopy-based procedure to survey the central airway wherein the lesions are biopsied to remove abnormal tissue and a chest CT scan;
  ii. at least every 6 months, one of a bronchoscopy-based procedure to survey the central airway wherein the lesions are biopsied to remove abnormal tissue and a chest CT scan; and/or
  iii. at least one immune stimulating drug.

Also provided herein, in another aspect, is a method of treating bronchial premalignant lesions, the method comprising: administering at least one of: (i) both a bronchoscopy-based procedure to survey the central airway wherein the lesions are biopsied to remove abnormal tissue and a chest CT scan; (ii) at least every 6 months, one of a bronchoscopy-based procedure to survey the central airway wherein the lesions are biopsied to remove abnormal tissue and a chest CT scan; and/or (iii) at least one immune stimulating drug; to a subject determined to have a decreased level of expression of at least one module 9 gene as compared to a non-proliferative lesion reference level and/or an increased level of expression of at least one module 10 gene as compared to a non-proliferative lesion reference level.

In one embodiment of this aspect and all other aspects provided herein, the module 9 gene is selected from the group consisting of: EPSTI1; UBE2L6; B2M and TAP1.

In another embodiment of this aspect and all other aspects provided herein, the at least one gene module 9 gene is selected from Table 16.

In another embodiment of this aspect and all other aspects provided herein, the module 10 gene is selected from the group consisting of: CACNB3 and MAPK10.

In another embodiment of this aspect and all other aspects provided herein, the at least one immune stimulating drug is selected from the group consisting of: immune-checkpoint inhibitors (e.g. inhibitors against, PD-1, PD-L1, CTLA4, and LAG3); drugs that stimulate interferon signaling (e.g. anti-viral drugs that improve interferon signaling); DNA synthesis inhibitors; IMDH inhibitors; CDK inhibitors; ribonucleotide reductase inhibitors; dihydrofolate reductase inhibitors; topoisomerase inhibitors; FLT3 inhibitors; IGF-1 inhibitors; MEK inhibitors; aurora kinase inhibitors; PKC inhibitors; RAF inhibitors; PDFGR/KIT inhibitors; VEGFR inhibitors; SRC inhibitors; retinoid receptor agonists; HDAC inhibitors; DNA methyltransferase inhibitors; and EZH2 inhibitors.

Another aspect provided herein relates to a method of treating bronchial premalignant lesions, the method comprising: administering at least one of: (i) both a bronchoscopy-based procedure to survey the central airway and a chest CT scan; (ii) at least every 6 months, one of a bronchoscopy-based procedure to survey the central airway and a chest CT scan; and/or (iii) at least one anti-inflammatory drug; to a subject determined to have at least one of: (a) an increased level of expression of at least one module 2 gene as compared to a non-inflammatory reference level; and (b) a decreased level of expression of at least one module 6 gene as compared to a non-inflammatory reference level.

In one embodiment of this aspect and all other aspects provided herein, the at least one module 2 gene is selected from the group consisting of: MSANTD2, CCNL2, and LUC7L; and the at least one module 6 gene is selected from the group consisting of: NEK11 and IFT88.

In another embodiment of this aspect and all other aspects provided herein, the subject is further determined to have an increased level of expression of at least one module 7 gene, module 1 gene, or module 8 gene and/or decreased level of expression of at least one module 4 gene or one module 5 gene.

In another embodiment of this aspect and all other aspects provided herein, the at least one module 7 gene is selected from the group consisting of: RPL26 and RPL23.

In another embodiment of this aspect and all other aspects provided herein, the at least one module 1 gene is selected from the group consisting of: KIRREL; PHLDB1; and MARVELD1.

In another embodiment of this aspect and all other aspects provided herein, the at least one module 8 gene is selected from the group consisting of: DOC2; CD53; and LAPTM.

In another embodiment of this aspect and all other aspects provided herein, the at least one module 4 gene is selected from the group consisting of: COX6A1 and COX7A2

In another embodiment of this aspect and all other aspects provided herein, the at least one module 5 gene is selected from the group consisting of: RACGAP1 and TPX2

In another embodiment of this aspect and all other aspects provided herein, the level of expression of each of the genes of Table 15 is determined.

In another embodiment of this aspect and all other aspects provided herein, the at least one anti-inflammatory drug is selected from the group consisting of: Acetylcholine receptor antagonists; Acetylcholinesterase inhibitors; Adenosine receptor antagonists; Adrenergic receptor antagonists; Angiotensin receptor antagonists; Anti-IL1B antibodies; Apoptosis stimulants; Aurora kinase inhibitors; CDK inhibitors; Cyclooxygenase inhibitors; Cytokine production inhibitors; Dehydrogenase inhibitors; Dopamine receptor antagonists; EGFR inhibitors; ERK1 and ERK2 phosphorylation inhibitors; Estrogen receptor agonists; FLT3 inhibitors; Glucocorticoid receptor agonists; Glutamate receptor antagonists; HDAC inhibitors; Histamine receptor antagonists; Histone lysine methyltransferase inhibitors; HSP inhibitors; IKK inhibitors; Ion channel antagonists; KIT inhibitors; Leucine rich repeat kinase inhibitors; MEK inhibitors; MDM inhibitors; Phosphodiesterase inhibitors; Monoamine oxidase inhibitors; MTOR inhibitors; NFkB pathway inhibitors; nucleophosmin inhibitors; PARP inhibitors; PI3K inhibitors; PPAR receptor agonists; protein synthesis inhibitors (e.g. chloramphenicol); RAF inhibitors; SIRT inhibitors; Sodium channel blockers; TGF beta receptor inhibitors; Topoisomerase inhibitors; Tyrosine kinase inhibitors; VEGFR inhibitors; and Vitamin D receptor agonists.

In another embodiment of this aspect and all other aspects provided herein, the anti-inflammatory drug is administered during a bronchoscopy-based procedure.

In another embodiment of this aspect and all other aspects provided herein, the anti-inflammatory drug is administered systemically.

In another embodiment of this aspect and all other aspects provided herein, the anti-inflammatory drug is administered during a bronchoscopy-based procedure and systemically.

In another embodiment of this aspect and all other aspects provided herein, the at least one gene is selected from Table 14.

In another embodiment of this aspect and all other aspects provided herein, the level of expression of each of the genes of Table 14 is determined.

In another embodiment of this aspect and all other aspects provided herein, whereby the development of lung cancer lung squamous cell carcinoma is prevented, delayed, or slowed.

In another embodiment of this aspect and all other aspects provided herein, wherein the lung cancer is lung squamous cell carcinoma.

In another embodiment of this aspect and all other aspects provided herein, the level of expression is the level of expression in an endobronchial biopsy, endobronchial brushing sample, large airway biopsy, large airway brushing sample, nasal epithelial cells, sputum, or blood obtained from the subject.

In another embodiment of this aspect and all other aspects provided herein, the level of expression is the level of expression in a bronchial brushing obtained from the right or left mainstem bronchus.

In another embodiment of this aspect and all other aspects provided herein, the biopsy or brushing sample comprises morphologically-normal tissues or cells.

In another embodiment of this aspect and all other aspects provided herein, the biopsy or brushing sample consists of morphologically-normal tissues or cells.

In another embodiment of this aspect and all other aspects provided herein, the level of expression is the level of expression in a sample comprising bronchial premalignant lesion cells.

In another embodiment of this aspect and all other aspects provided herein, the level of expression is the level of expression in a sample comprising morphologically-normal cells.

In another embodiment of this aspect and all other aspects provided herein, the subject is a smoker or former smoker.

BRIEF DESCRIPTION OF THE DRAWINGS

(FIG. 1A) Genes (n=3,936) organized into 9 gene co-expression modules were used to discover four molecular subtypes (Proliferative, Inflammatory, Secretory, and Normal-like) across the 190 DC biopsies using consensus clustering. The heatmap shows semi-supervised hierarchal clustering of z-score normalized gene expression across the 3,936 genes and 190 DC biopsies. The top bar represents the four molecular subtypes: Proliferative (n=52 samples), Inflammatory (n=37 samples), Secretory (n=61 samples), and Normal-like (n=40 samples). Throughout all figures, the four molecule subtypes are represented by four shades of grey, increasing in lightness respective to the order given in the previous sentence. On the left side of the heatmap, the mean of the first principal component calculated across module genes is plotted for each subtype. On the right side of the heatmap, a summary of enriched biological pathways is listed for each module. (FIG. 1B) Bubbleplots showing significant associations (p<0.01 by Fisher's Exact Test) between the molecular subtypes and smoking status, biopsy histological grade, and the predicted LUSC tumor molecular subtypes. The columns represent the 4 molecular subtypes (Proliferative, Inflammatory, Secretory, and Normal-like) and the diameter of the circle is proportional to the number of samples within each subtype that have the row phenotype. (FIG. 1C) Boxplot of expression values of MKI67 in biopsies with normal or hyperplasia histology (n=8, 16, 26, 18 in Proliferative, Inflammatory, Secretory, and Normal-like subtypes, respectively). The MKI67 expression levels of the Proliferative subtype are significantly greater than non-Proliferative subtype samples (FDR=3.4e-10) (FIG. 1D) Boxplot of expression values of MKI67 in biopsies with dysplastic histology (n=33, 11, 19, 9 in Proliferative, Inflammatory, Secretory, and Normal subtypes, respectively). The MKI67 expression levels of the Proliferative subtype are significantly greater than non-Proliferative subtype samples (FDR=3.1e-8). (FIG. 1E) Immunofluorescent staining demonstrating the increased MKI67 and KRT5 staining and reduced TUB1A1 staining in the Proliferative subtype in concordance with the expression of the corresponding marker genes. The representative samples shown for the Proliferative and Inflammatory subtypes have dysplasia histology while the samples shown for the Secretory and Normal-like subtypes have normal histology (Magnification 200×).

(FIG. 2A) The 190 DC biopsies and the 3,936 genes were used to build a 22-gene nearest centroid molecular subtype classifier. Semi-supervised hierarchal clustering of z-score normalized gene expression across the 22 classifier genes and 190 DC biopsies training samples. (FIG. 2B) The 22-gene nearest centroid molecular subtype classifier was used to predict the molecular subtypes of the 105 VC biopsies. Semi-supervised hierarchal clustering of z-score normalized gene expression across 22 genes and 105 VC is plotted. The rows of the heatmap give the gene name and module membership, and the column color bar shows molecular subtype membership. (FIG. 2C) Bubbleplots showing significant associations (p<0.01 by Fisher's Exact Test) between the VC molecular subtypes and smoking status, biopsy histological grade, and the predicted LUSC tumor molecular subtypes. The columns represent the 4 molecular subtypes (Proliferative, Inflammatory, Secretory, and Normal) and the radius of the circle is proportional to the number of samples within each subtype that have the row phenotype. (FIG. 2D) Bubbleplots showing significant associations (p<0.01 by Fisher's Exact Test) between the VC molecular subtypes and smoking status, biopsy histological grade, and the predicted LUSC tumor molecular subtypes. The columns represent the 4 molecular subtypes (Proliferative, Inflammatory, Secretory, and Normal-like) and the radius of the circle is proportional to the number of samples within each subtype that have the row phenotype.

(FIG. 3A) The DC (left) and VC (right) cohorts, showing the number of brushes (y-axis) predicted to be positive for the Proliferative subtype that have at least one biopsy (y-axis) with a classification of the Proliferative subtype at the time the brush was sampled. (FIG. 3B) Boxplots of PC1 for Modules 4, 5, 6, and 7 (y-axis) across the four molecular subtypes for each cohort (x-axis). The asterisk indicates significant differences between the Proliferative subtype versus all other samples (FDR<0.05). (FIG. 3C) Boxplots of PC1 for Modules 4, 5, 6, and 7 (y-axis) across the four molecular subtypes for each cohort (x-axis). The asterisk indicates significant differences between the Proliferative subtype versus all other samples (FDR<0.05).

FIGS. 4A-4H demonstrate that the module enriched for interferon signaling and antigen processing is associated with biopsy progression/persistence and a depletion of innate and adaptive immune cells in the Proliferative subtype. (FIGS. 4A and 4F) Metagene expression of Module 9 genes among DC biopsies within the Proliferative subtype (p=0.002 between the progressive/persistent versus regressive biopsies). Biopsy progression/regression was defined for each biopsy based on the histology of the biopsy and the worst histology recorded for the same lung anatomic location in the future. Histology changes between normal, hyperplasia, and metaplasia were classified as "normal stable", decreases in histological dysplasia grade or changes from dysplastic histology to normal/hyperplasia/metaplasia were classified as "regressive", lack of future histological data was classified as "unknown", and everything else was classified as "progressive/persistent." (FIGS. 4B and 4G) Boxplot of the percentages of CD68 and CD163, CD68, CD163, CD4, and CD8 positively stained cells between progressive/persistent and regressive biopsies (p<0.001 for all comparisons). The x-axis labels indicate the number of regions (R) enumerated across (P) subjects for each stain and outcome group depicted in the boxplot. Biopsies were included in the analysis if their clinical outcome was concordant with the Module 9 score. (FIG. 4B) Metagene expression of Module 9 genes among VC biopsies within the Proliferative subtype (p=0.03 between the progressive/persistent versus regressive biopsies). (FIG. 4C) Top: Z-score normalized gene expression across the 112 genes in Module 9 and the DC biopsies (left) and the VC biopsies (right). Each heatmap is supervised according to the Module 9 GSVA scores. Top bars indicate the histological grade of the biopsies and their progression status. Bottom: xCell results indicating the relative abundance of immune cell types across the DC biopsies (left) and the VC biopsies (right). Immune cell types displayed are significantly associated with lesion progressive/persistence (FDR<0.05 in both the DC and VC after adjusting for differences in epithelial cell content). (FIG. 4D) Representative histology where the dashed line denoted the separate of epithelium and stromal compartment Top panels: A progressive severe dysplasia has reduced presence of immune cells demonstrated by the marked reduction in expression of M2 macrophages (CD68/163 staining, double positive cells indicated by the arrows) and CD8 T cells. (sample corresponds to *P in FIG. 4C.) Bottom panels: A regressive moderate dysplasia has increased presence of immune cells including M2 macrophages (CD68/163 staining double positive cells indicated by the arrows) and CD8 T cells. (samples correspond to *R in FIG. 4C.) (FIGS. 4E and 4H) Boxplots of the percentages of CD68 and CD163, CD68, CD163, CD4, and CD8 positively stained cells between progressive/persistent and regressive biopsies (p<0.001 for all comparisons). The x-axis labels indicate the number of regions (R) enumerated across (P) subjects for each stain and outcome group depicted in the boxplot. Biopsies were included in the analysis if their clinical outcome was concordant with the Module 9 score.

FIG. 5 depicts Batch Information and Alignment Statistics on Samples in both the Discovery and Validation cohorts. Statistical tests between the Discovery and Validation cohorts were performed using Fisher's Exact Test for categorical variables and Student's T-Test for continuous variable. Percentages are reported for categorical variables and mean and standard deviations are reported for continuous variables.

FIG. 6 depicts a summary of Gene Modules. The module number, number of genes in the module, biological pathways and select genes associated with the module, and an FDR value for the difference in GSVA scores for the module between the molecular subtypes are reported.

FIG. 7 depicts a List of Samples used for Immunofluorescence Studies.

(FIGS. 10A-10D) Discovery cohort biopsies. (FIGS. 10E-10H) Validation cohort biopsies. (FIG. 10A) and (FIG. 10E) show boxplots of gene expression levels of LUSC driver genes identified by TCGA across the molecular subtypes. (FIG. 10B) and (FIG. 10F) show boxplots of gene expression levels of cell type marker genes across the molecular subtypes. (FIG. 10C) and (FIG. 10G) show boxplots of GSVA scores calculated using Dvorak et al. gene sets across the molecular subtypes. (FIG. 10D) and (FIG. 10H) show boxplots of ESTIMATE algorithm scores across the molecular subtypes. The ESTIMATE algorithm estimates the stromal (StromalScore), immune (Immune Score), and epithelial (ESTIMATEScore) cell fractions in each sample. High immune and stromal scores indicate a high fraction of stromal and immune cells while low epithelial scores indicate a high fraction of epithelial cells.

DETAILED DESCRIPTION

Figure 1A:
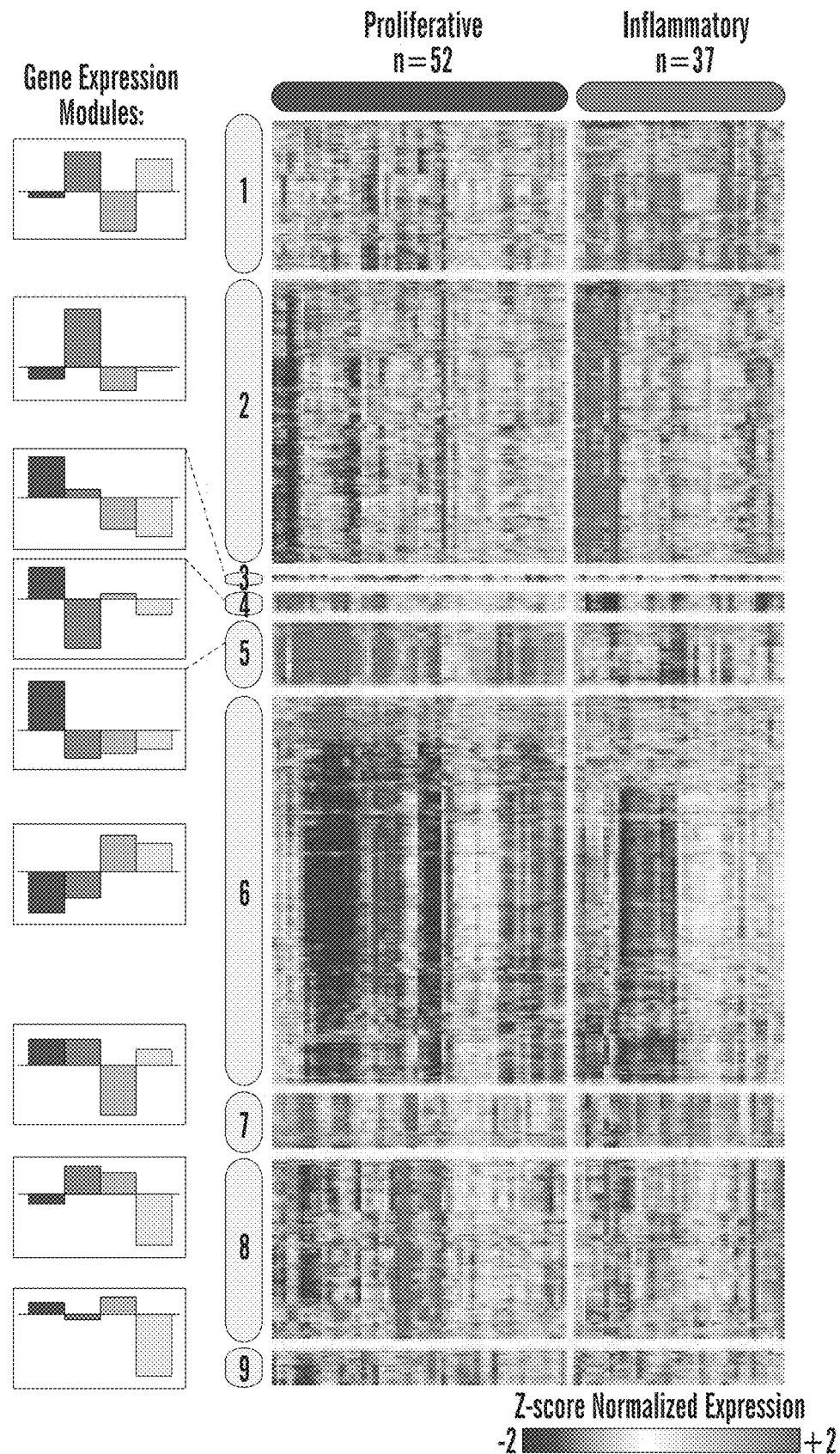
FIGS. 1A-1E demonstrate that endobronchial biopsies divide into four distinct molecular subtypes that correlate with clinical and molecular phenotypes.
Figure 1A:
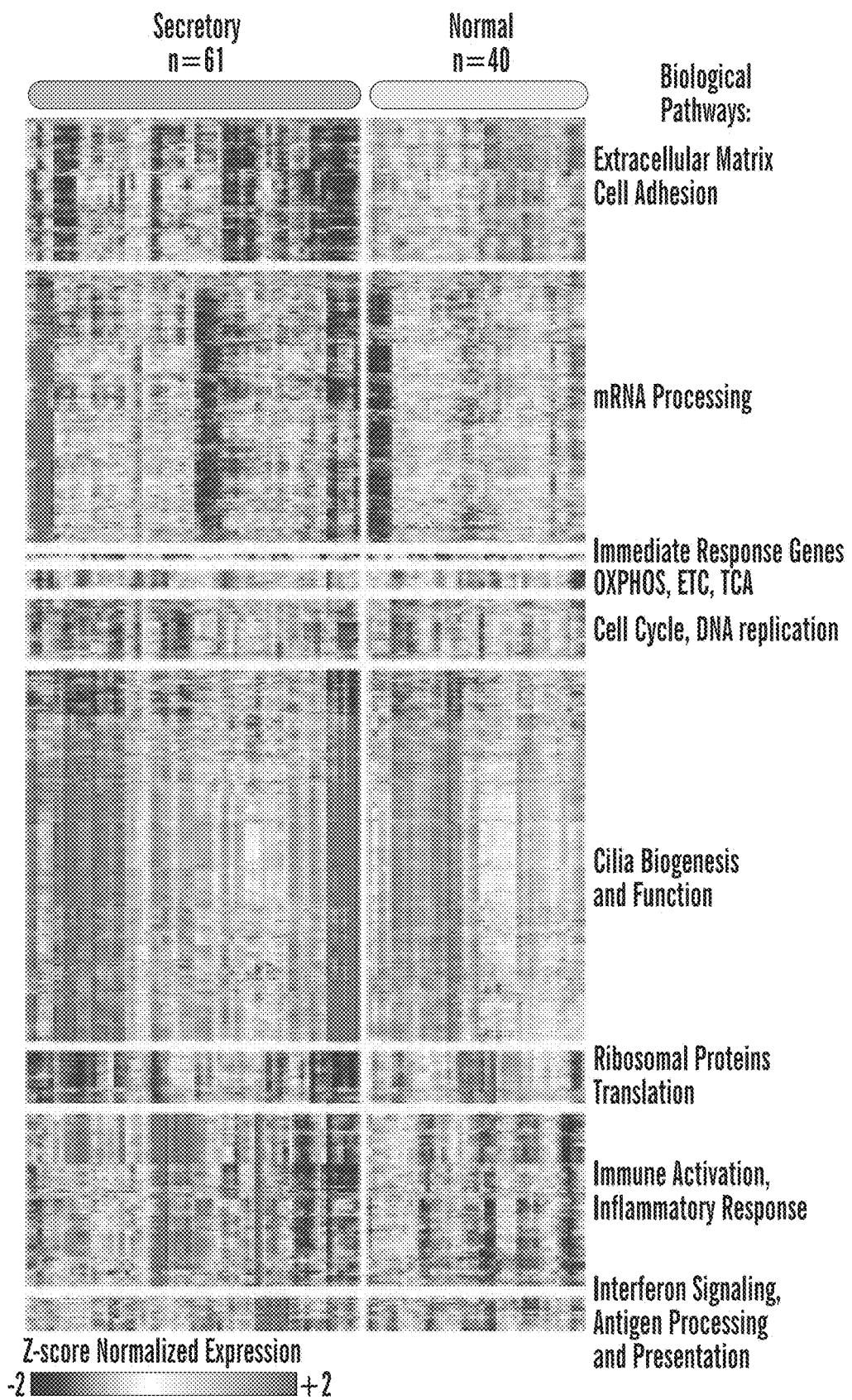

As described herein, the inventors have discovered that premalignant lesions in the airway of a subject can be characterized as being one of five: types: normal-like, secretory, inflammatory, progressive proliferative, and persistent proliferative. Identifying the premalignant lesion as one of these types permits more effective treatment of the subject, as different types of lesions will be responsive to different treatments and require different treatment and monitoring regimes. Accordingly, provided herein are methods of treatment relating to the treatment of bronchial premalignant lesions in a subject. Such methods can comprise assays, tests, and/or identification of the lesion type and administration of therapeutic regimens appropriate for that lesion type.

As used herein, "premalignant lesion" refers to an epithelial lesion or dysplasia which is a precursor or can be a precursor to cancer. The basement membrane is intact with no possibility of metastatic spread, as opposed to cancer. A bronchial premalignant lesion is a premalignant lesion present in the bronchial epithelium of a subject. Bronchial premalignant lesions are typically small and can be difficult to visualize using conventional white light bronchoscopy.

The bronchial premalignant lesions can exhibit one of five phenotypes described herein, namely progressive proliferative, persistent proliferative, secretory, inflammatory, and normal-like. The subtype names reference the key differences in molecular pathway activity which differentiate the subtypes from each other. The different phenotypes of lesion can be distinguished from each other and from normal tissue by use of the gene expression patterns described herein. As explained in detail elsewhere herein, the gene expression patterns identified herein relate to 10 modules of genes, where each module is a group of genes with similar expression patterns across the different bronchial premalignant lesion subtypes. The identity of each of the modules, e.g. the genes that comprise each module, are provided in Table 13 herein. Briefly, proliferative lesions (both progressive and persistent) are distinguished by having increased module 4, 5, and 7 expression and decreased module 6 expression. Progressive proliferative lesions can be distinguished from persistent proliferative lesions in that they have decreased module 9 expression and/or increased module 10 expression. Secretory lesions are distinguished by an increase in module 6 expression and a decrease in module 1 expression and optionally, an increase in module 8 expression and a decrease in modules 2, 5, and 7 expression. Normal-like subtype is distinguished by an increase in module 6 expression and a decrease in module 9 expression and optionally, an increase in module 1 expression and a decrease in module 8 expression.

Standard treatment for subjects at risk of lung cancer, or who have been identified to have bronchial premalignant lesions, is annual screening for lung cancer (e.g. a bronchoscopy and/or chest CT scan). When a subject has a proliferative bronchial premalignant lesion, such treatment is no longer sufficient and the subject should be treated more aggressively. Accordingly, in one aspect of any of the embodiments, provided herein is a method of treating bronchial premalignant lesions, the method comprising administering at least one of: i) both a bronchoscopy-based procedure to survey the central airway and a chest CT scan; ii) at least every 6 months, at least one of a bronchoscopy-based procedure to survey the central airway and a chest CT scan; and/or iii) at least one anti-proliferative drug to a subject determined to have at least one of a) an increased level of expression of at least one module 5 gene as compared to a reference level; and b) a decreased level of expression of at least one module 6 gene as compared to a reference level. In one aspect of any of the embodiments, provided herein is a method of treating bronchial premalignant lesions, the method comprising determining a subject as to have at least one of a) an increased level of expression of at least one module 5 gene as compared to a reference level; and b) a decreased level of expression of at least one module 6 gene as compared to a reference level and administering at least one of: i) both a bronchoscopy-based procedure to survey the central airway and a chest CT scan; ii) at least about every 6 months (e.g., at least every 1, 2, 3, 4, 5, or 6 months), at least one of a bronchoscopy-based procedure to survey the central airway and a chest CT scan; and/or iii) at least one anti-proliferative drug to the subject. In some embodiments of any of the aspects, the reference level is a non-proliferative reference level.

In some embodiments, if the subject is determined not to have at least one of a) an increased level of expression of at least one module 5 gene as compared to a reference level;

and b) a decreased level of expression of at least one module 6 gene as compared to a reference level, the subject is not administered an anti-proliferative drug and is administered a bronchoscopy-based procedure to survey the central airway and/or a chest CT scan no more frequently than every 6 months (e.g., no more frequently than every 6, 7, 8, 9, 10, 11, or 12 months). In some embodiments, if the subject is determined not to have a) an increased level of expression of at least one module 5 gene as compared to a reference level; and b) a decreased level of expression of at least one module 6 gene as compared to a reference level, the subject is not administered an anti-proliferative drug and is administered a bronchoscopy-based procedure to survey the central airway and/or a chest CT scan no more frequently than every 6 months (e.g., no more frequently than every 6, 7, 8, 9, 10, 11, or 12 months).

Module 5 and 6 gene expression, in a bronchial brushing sample, is sufficient to identify a subject having a proliferative subtype lesion. This avoids the need to visualize and/or sample the actual lesion. Accordingly, in one aspect of any of the embodiments, provided herein is a method of treating bronchial premalignant lesions, the method comprising administering at least one of: i) both a bronchoscopy-based procedure to survey the central airway and a chest CT scan; ii) at least every 6 months, at least one of a bronchoscopy-based procedure to survey the central airway and a chest CT scan; and/or iii) at least one anti-proliferative drug to a subject determined to have, in a bronchial brushing sample, a) an increased level of expression of at least one module 5 gene as compared to a reference level; and b) a decreased level of expression of at least one module 6 gene as compared to a reference level. In one aspect of any of the embodiments, provided herein is a method of treating bronchial premalignant lesions, the method comprising determining a subject to have, in a bronchial brushing sample obtained from the subject, a) an increased level of expression of at least one module 5 gene as compared to a reference level; and b) a decreased level of expression of at least one module 6 gene as compared to a reference level and administering at least one of: i) both a bronchoscopy-based procedure to survey the central airway and a chest CT scan; ii) at least every 6 months, at least one of a bronchoscopy-based procedure to survey the central airway and a chest CT scan; and/or iii) at least one anti-proliferative drug to the subject. In some embodiments of any of the aspects, the reference level is a non-proliferative reference level. In some embodiments of any of the aspects, the bronchial brushing is taken from a morphologically-normal location in the right or left mainstem bronchus. In some embodiments of any of the aspects, the bronchial brushing is taken from a visually-normal location in the right or left mainstem bronchus.

Module 5 and 6 genes are provided in Table 13. The at least one module 5 gene and/or module 6 gene can be any one or more of the module 5 and 6 genes listed in Table 13.

In some embodiments of any of the aspects, the level of expression of at least one module 5 gene or at least one module 6 gene is determined. In some embodiments of any of the aspects, the level of expression of two or more module 5 genes or two or more module 6 genes is determined. In some embodiments of any of the aspects, the level of expression of each module 5 gene or each module 6 gene of Table 13 is determined.

In some embodiments of any of the aspects, the level of expression of at least one module 5 gene and at least one module 6 gene is determined. In some embodiments of any of the aspects, the level of expression of two or more module 5 genes and two or more module 6 genes is determined. In some embodiments of any of the aspects, the level of expression of each module 5 gene and each module 6 gene of Table 13 is determined.

In some embodiments of any of the aspects, the at least one module 5 gene comprises or is RACGAP1 or TPX2. In some embodiments of any of the aspects, the at least one module 5 gene comprises or is RACGAP1 and TPX2. In some embodiments of any of the aspects, the at least one module 6 gene comprises or is NEK11 or IFT88. In some embodiments of any of the aspects, the at least one module 6 gene comprises or is NEK11 and IFT88.

The proliferative subtype is further distinguished by increased expression of module 7 and/or 4. Accordingly, in some embodiments of any of the aspects, the subject is further determined to have an increased level of expression of at least one module 7 or module 4 gene as compared to a reference level. In some embodiments of any of the aspects, the subject is further determined to have an increased level of expression of at least one module 7 and at least one module 4 gene as compared to a reference level. In some embodiments of any of the aspects, the reference level is a non-proliferative reference level.

Module 4 and 7 genes are provided in Table 13. The at least one module 4 gene and/or module 7 gene can be any one or more of the module 4 and 7 genes listed in Table 13.

In some embodiments of any of the aspects, the level of expression of at least one module 4 gene or at least one module 7 gene is determined. In some embodiments of any of the aspects, the level of expression of two or more module 4 genes or two or more module 7 genes is determined. In some embodiments of any of the aspects, the level of expression of each module 4 gene or each module 7 gene of Table 13 is determined.

In some embodiments of any of the aspects, the level of expression of at least one module 4 gene and at least one module 7 gene is determined. In some embodiments of any of the aspects, the level of expression of two or more module 4 genes and two or more module 7 genes is determined. In some embodiments of any of the aspects, the level of expression of each module 4 gene and each module 7 gene of Table 13 is determined.

In some embodiments of any of the aspects, the at least one module 4 gene comprises or is COX6A1 or COX7A2. In some embodiments of any of the aspects, the at least one module 4 gene comprises or is COX6A1 and COX7A2. In some embodiments of any of the aspects, the at least one module 7 gene comprises or is RPL26 or RPL23. In some embodiments of any of the aspects, the at least one module 7 gene comprises or is RPL26 and RPL23.

When a subject has a progressive proliferative bronchial premalignant lesion, aggressive treatment, even beyond that provided for proliferative bronchial premalignant lesion, can be indicated. Accordingly, in one aspect of any of the embodiments, provided herein is a method of treating bronchial premalignant lesions, the method comprising administering at least one of: i) both a bronchoscopy-based procedure to survey the central airway and a chest CT scan; ii) at least every 6 months, at least one of a bronchoscopy-based procedure to survey the central airway and a chest CT scan; iii) at least one immune stimulating drug and/or iv) at least one immune stimulating drug and at least one anti-proliferative drug to a subject determined to have a decreased level of expression of at least one module 9 gene as compared to a reference level and/or an increased level of expression of at least one module 10 gene as compared to a reference level. In one aspect of any of the embodiments, provided herein is a method of treating bronchial premalignant lesions, the method comprising a) determining a subject as to have a decreased level of expression of at least one module 9 gene as compared to a reference level and/or an increased level of expression of at least one module 10 gene as compared to a reference level and b) administering at least one of: i) both a bronchoscopy-based procedure to survey the central airway and a chest CT scan; ii) at least every 6 months, at least one of a bronchoscopy-based procedure to survey the central airway and a chest CT scan; iii) at least one immune stimulating drug and/or iv) at least one immune stimulating drug and at least one anti-proliferative drug to the subject. In some embodiments of any of the aspects, the reference level is a non-proliferative reference level. In some embodiments of any of the aspects, the bronchoscopy-based procedure further comprises biopsy of the lesions to remove abnormal tissue.

In some embodiments, if the subject is determined not to have a decreased level of expression of at least one module 9 gene as compared to a reference level and/or not to have an increased level of expression of at least one module 10 gene as compared to a reference level, the subject i) is not administered an immune stimulating drug, ii) is not administered both an immune stimulating drug and an anti-proliferative drug, iii) is administered a bronchoscopy-based procedure and/or a chest CT scan no more frequently than every 6 months (e.g., no more frequently than every 6, 7, 8, 9, 10, 11, or 12 months), and/or iv) is not administered a bronchoscopy-based procedure to biopsy lesions to remove abnormal tissue.

Module 9 genes are provided in Table 13. The at least one module 9 gene can be any one or more of the module 9 genes listed in Table 13. Module 9 genes are provided in Table 16. The at least one module 9 gene can be any one or more of the module 9 genes listed in Table 16.

In some embodiments of any of the aspects, the level of expression of two or more module 9 gene is determined. In some embodiments of any of the aspects, the level of expression of each module 9 gene of Table 13 is determined. In some embodiments of any of the aspects, the level of expression of each module 9 gene of Table 16 is determined.

In some embodiments of any of the aspects, the at least one module 9 gene comprises or is EPSTI1; UBE2L6; B2M and/or TAP1. In some embodiments of any of the aspects, the at least one module 9 gene comprises or is EPSTI1; UBE2L6; B2M; and TAP1. In some embodiments of any of the aspects, the at least one module 9 gene comprises or is a pairwise combination of any of:
EPSTI1 and UBE2L6
EPSTI1 and B2M
EPSTI1 and TAP1
UBE2L6 and B2M
UBE2L6 and TAP1
B2M and TAP1
In some embodiments of any of the aspects, the at least one
  module 9 gene comprises or is a three-way combination
  of any of:
EPSTI1; UBE2L6; and B2M
EPSTI1; UBE2L6; and TAP1
EPSTI1; B2M; and TAP1
TAP1; UBE2L6; and B2M Module 10 genes are provided in Table 13. The at least one module 10 gene can be any one or more of the module 9 genes listed in Table 13. In some embodiments of any of the aspects, the level of expression of both module 10 genes is determined. In some embodiments of any of the aspects, the at least one module 10 gene comprises or is CACNB3 or MAPK10. In some embodiments of any of the aspects, the at least one module 10 gene comprises or is CACNB3 and MAPK10.

When a subject has an inflammatory bronchial premalignant lesion aggressive and/or anti-inflammatory treatment can be beneficial. Accordingly, in one aspect of any of the embodiments, provided herein is a method of treating bronchial premalignant lesions, the method comprising administering at least one of: i) both a bronchoscopy-based procedure to survey the central airway and a chest CT scan; ii) at least every 6 months, at least one of a bronchoscopy-based procedure to survey the central airway and a chest CT scan; and/or iii) at least one anti-inflammatory drug to a subject determined to have at least one of a) an increased level of expression of at least one module 2 gene as compared to a reference level; and b) a decreased level of expression of at least one module 6 gene as compared to a reference level. In one aspect of any of the embodiments, provided herein is a method of treating bronchial premalignant lesions, the method comprising determining a subject as to have at least one of a) an increased level of expression of at least one module 2 gene as compared to a reference level; and b) a decreased level of expression of at least one module 6 gene as compared to a reference level and administering at least one of: i) both a bronchoscopy-based procedure to survey the central airway and a chest CT scan; ii) at least every 6 months, at least one of a bronchoscopy-based procedure to survey the central airway and a chest CT scan; and/or iii) at least one anti-inflammatory drug to the subject. In some embodiments of any of the aspects, the reference level is a non-inflammatory reference level.

In some embodiments, if the subject is determined not to have at least one of a) an increased level of expression of at least one module 2 gene as compared to a reference level; and b) a decreased level of expression of at least one module 6 gene as compared to a reference level, the subject is not administered an anti-inflammatory drug and is administered a bronchoscopy-based procedure to survey the central airway and/or a chest CT scan no more frequently than every 6 months (e.g., no more frequently than every 6, 7, 8, 9, 10, 11, or 12 months). In some embodiments, if the subject is determined not to have a) an increased level of expression of at least one module 2 gene as compared to a reference level; and b) a decreased level of expression of at least one module 6 gene as compared to a reference level, the subject is not administered an anti-inflammatory drug and is administered a bronchoscopy-based procedure to survey the central airway and/or a chest CT scan no more frequently than every 6 months (e.g., no more frequently than every 6, 7, 8, 9, 10, 11, or 12 months).

Module 2 and 6 genes are provided in Table 13. The at least one module 2 gene and/or module 6 gene can be any one or more of the module 5 and 6 genes listed in Table 13.

In some embodiments of any of the aspects, the level of expression of at least one module 2 gene or at least one module 6 gene is determined. In some embodiments of any of the aspects, the level of expression of two or more module 2 genes or two or more module 6 genes is determined. In some embodiments of any of the aspects, the level of expression of each module 2 gene or each module 6 gene of Table 13 is determined.

In some embodiments of any of the aspects, the level of expression of at least one module 2 gene and at least one module 6 gene is determined. In some embodiments of any of the aspects, the level of expression of two or more module 2 genes and two or more module 6 genes is determined. In some embodiments of any of the aspects, the level of expression of each module 2 gene and each module 6 gene of Table 13 is determined.

In some embodiments of any of the aspects, the at least one module 2 gene comprises or is MSANTD2, CCNL2, or LUC7L. In some embodiments of any of the aspects, the at least one module 2 gene comprises or is MSANTD2 and LUC7L. In some embodiments of any of the aspects, the at least one module 2 gene comprises or is MSANTD2 and CCNL2. In some embodiments of any of the aspects, the at least one module 2 gene comprises or is CCNL2 and LUC7L. In some embodiments of any of the aspects, the at least one module 2 gene comprises or is MSANTD2, CCNL2, and LUC7L. In some embodiments of any of the aspects, the at least one module 6 gene comprises or is NEK11 or IFT88. In some embodiments of any of the aspects, the at least one module 6 gene comprises or is NEK11 and IFT88.

The inflammatory subtype is further distinguished by increased expression of module 7, 1 and/or 8 and/or decreased expression of module 4 and/or 5. Accordingly, in some embodiments of any of the aspects, the subject is further determined to have at least one of: i) an increased level of expression of at least one module 7, module 1, and/or or module 8 gene, and ii) a decreased level of expression of at least one module 4 or module 5 gene as compared to a reference level. In some embodiments of any of the aspects, the subject is further determined to have at least one of: i) an increased level of expression of at least one module 7, module 1, and/or or module 8 gene, and ii) a decreased level of expression of at least one module 4 or module 5 gene as compared to a reference level. In some embodiments of any of the aspects, the reference level is a non-inflammatory reference level.

Module 7, 1, 8, 4 and 5 genes are provided in Table 13. The at least one module 7, 1, 8, 4, and/or 5 gene can be any one or more of the module 7, 1, 8, 4, and/or 5 genes listed in Table 13. In some embodiments of any of the aspects, the level of expression of each module 7, 1, 8, 4 and/or 5 gene of Table 13 is determined. In some embodiments of any of the aspects, the level of expression of each module 7, 1, 8, 4 and 5 gene of Table 13 is determined.

In some embodiments of any of the aspects, the at least one module 4 gene comprises or is COX6A1 or COX7A2. In some embodiments of any of the aspects, the at least one module 4 gene comprises or is COX6A1 and COX7A2. In some embodiments of any of the aspects, the at least one module 7 gene comprises or is RPL26 or RPL23. In some embodiments of any of the aspects, the at least one module 7 gene comprises or is RPL26 and RPL23. In some embodiments of any of the aspects, the at least one module 5 gene comprises or is RACGAP1 or TPX2. In some embodiments of any of the aspects, the at least one module 5 gene comprises or is RACGAP1 and TPX2. In some embodiments of any of the aspects, the at least one module 1 gene comprises or is KIRREL; PHLDB1; or MARVELD1. In some embodiments of any of the aspects, the at least one module 1 gene comprises or is PHLDB1 and MARVELD1. In some embodiments of any of the aspects, the at least one module 1 gene comprises or is KIRREL and PHLDB1. In some embodiments of any of the aspects, the at least one module 1 gene comprises or is KIRREL and MARVELD1. In some embodiments of any of the aspects, the at least one module 1 gene comprises or is KIRREL; PHLDB1; and MARVELD1. In some embodiments of any of the aspects, the at least one module 8 gene comprises or is DCO2; CD53; or LAPTM. In some embodiments of any of the aspects, the at least one module 8 gene comprises or is CD53 and LAPTM. In some embodiments of any of the aspects, the at least one module 8 gene comprises or is DCO2 and CD53. In some embodiments of any of the aspects, the at least one module 8 gene comprises or is DCO2 and LAPTM. In some embodiments of any of the aspects, the at least one module 8 gene comprises or is DCO2; CD53; and LAPTM.

In some embodiments of any of the aspects, the level of expression of each of the genes of Table 15 is determined. In some embodiments of any of the aspects, the level of expression of each of the genes of Table 15 in a bronchial brushing sample is determined.

In some embodiments of any of the aspects, the level of expression of each of the genes of Table 14 is determined. In some embodiments of any of the aspects, the level of expression of each of the genes of Table 14 in a bronchial brushing sample is determined.

In some embodiments of any of the aspects, the methods described herein can further comprise determining the level of expression of any of the following genes: SOX2, NFE2L2, PIK3CA (which are squamous cancer marker genes), KRT5, MUC5AC, TUB1A1, SCGB1A1, and FOXK1 (which are epithelial marker genes).

As described herein, levels of gene expression can be modulated (e.g., increased or decreased) in subjects with premalignant lesions of different subtypes.

In some embodiments of any of the aspects, the method comprises administering a treatment described herein to a subject previously determined to have an expression level(s) as described herein. In some embodiments of any of the aspects, described herein is a method of treating bronchial premalignant lesions in a subject in need thereof, the method comprising: a) first determining the level of expression of the at least one gene in a sample obtained from a subject; and b) then administering a treatment as described herein to the subject if the level of expression of modulated relative to a reference in the manner described herein. In one aspect of any of the embodiments, described herein is a method of treating bronchial premalignant lesions in a subject in need thereof, the method comprising: a) determining if the subject has a modulation of a level of expression as described herein and b) instructing or directing that the subject be administered the appropriate treatment described herein for the particular modulation of expression which has been determined.

In some embodiments of any of the aspects, the step of determining if the subject has modulation of an expression level can comprise i) obtaining or having obtained a sample from the subject and ii) performing or having performed an assay on the sample obtained from the subject to determine/measure the level of expression in the subject. In some embodiments of any of the aspects, the step of determining if the subject has a modulation of a level of expression can comprise performing or having performed an assay on a sample obtained from the subject to determine/measure the level of expression in the subject. In some embodiments of any of the aspects, the step of determining if the subject has a modulation of a level of expression can comprise ordering or requesting an assay on a sample obtained from the subject to determine/measure the level of expression in the subject. In some embodiments of any of the aspects, the step of determining if the subject has a modulation of a level of expression can comprise receiving the results of an assay on a sample obtained from the subject to determine/measure the level of expression in the subject. In some embodiments of any of the aspects, the step of determining if the subject has a modulation of a level of expression can comprise receiving a report, results, or other means of identifying the subject as a subject with a modulation of a level of expression.

In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In some embodiments of any of the aspects, measurement of the level of a target and/or detection of the level or presence of a target, e.g. of an expression product (nucleic acid or polypeptide of one of the genes described herein) or a mutation can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but is not limited to, pre-treatment of a biological sample, e.g., from whole blood to blood serum by differential centrifugation. A biological/chemical transformation can involve the action of at least one enzyme and/or a chemical reagent in a reaction. For example, a DNA sample can be digested into fragments by one or more restriction enzymes, or an exogenous molecule can be attached to a fragmented DNA sample with a ligase. In some embodiments of any of the aspects, a DNA sample can undergo enzymatic replication, e.g., by polymerase chain reaction (PCR).

Transformation, measurement, and/or detection of a target molecule, e.g. a mRNA or polypeptide can comprise contacting a sample obtained from a subject with a reagent (e.g. a detection reagent) which is specific for the target, e.g., a target-specific reagent. In some embodiments of any of the aspects, the target-specific reagent is detectably labeled. In some embodiments of any of the aspects, the target-specific reagent is capable of generating a detectable signal. In some embodiments of any of the aspects, the target-specific reagent generates a detectable signal when the target molecule is present.

Methods to measure gene expression products are known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for the various targets described herein are commercially available and can be used for the purposes of the invention to measure protein expression levels. Alternatively, since the amino acid sequences for the targets described herein are known and publically available at the NCBI website, one of skill in the art can raise their own antibodies against these polypeptides of interest for the purpose of the methods described herein.

The amino acid sequences of the polypeptides described herein have been assigned NCBI and ENSBL accession numbers for different species such as human, mouse and rat. The sequences for any of the genes described herein can be readily retrieved from either database by one of ordinary skill in the art. In some embodiments of any of the aspects, the sequence of a gene, transcript, or polypeptide described herein is the sequence available in the NCBI or ENSMBL database as of the filing date of this application.

In some embodiments of any of the aspects, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments of any of the aspects, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiments of any of the aspects, the immunoassay can be a quantitative or a semi-quantitative immunoassay.

An immunoassay is a biochemical test that measures the concentration of a substance in a biological sample, typically a fluid sample such as blood or serum, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., any of the targets as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce significant color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests used for medical diagnostics, either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick tests, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments of any of the aspects, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, an adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. A dot blot immobilizes a protein sample on a defined region of a support, which is then probed with antibody and labelled secondary antibody as in Western blotting. The intensity of the signal from the detectable label in either format corresponds to the amount of enzyme present, and therefore the amount of polypeptide. Levels can be quantified, for example by densitometry.

In some embodiments of any of the aspects, the level of a target can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In certain embodiments, the gene expression products as described herein can be instead determined by determining the level of messenger RNA (mRNA) expression of the genes described herein. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments of any of the aspects, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein have been assigned NCBI and ENSBL accession numbers for different species such as human, mouse and rat. The sequences for any of the genes described herein can be readily retrieved from either database by one of ordinary skill in the art. In some embodiments of any of the aspects, the sequence of a gene, transcript, or polypeptide described herein is the sequence available in the NCBI or ENSMBL database as of the filing date of this application. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments of any of the aspects, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments of any of the aspects, a detectable label can be a radiolabel including, but not limited to $^{3}$H, $^{125}$I, $^{35}$S, $^{14}$C, $^{32}$P, and $^{33}$P. In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromogenic substrate. Such streptavidin peroxidase detection kits are commercially available, e.g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylene diaminetetraacetic acid (EDTA).

In some embodiments of any of the aspects, the level of expression is the level in a sample obtained from a subject. The term "sample" or "test sample" as used herein denotes a sample taken or isolated from a biological organism, e.g., a blood or tissue sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject. In some embodiments of any of the aspects, the sample obtained from a subject can be a biopsy sample. In some embodiments of any of the aspects, the sample obtained from a subject can be a blood or serum sample.

In some embodiments of any of the aspects, the sample is an endobronchial biopsy, bronchial brushing sample, bronchial biopsy, endobronchial brushing sample, large airway biopsy, large airway brushing sample, nasal epithelial cells, sputum, and/or blood obtained from the subject. In some embodiments of any of the aspects, the sample is a bronchial brushing obtained from the right or left mainstem bronchus. The test sample can be obtained by removing a sample from a subject, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining or having obtained a test sample from a subject. In some embodiments of any of the aspects, the subject can be a human subject. In some embodiments of any of the aspects, the subject can be a subject in need of treatment for (e.g. having or diagnosed as having) premalignant lesions or a subject at risk of or at increased risk of developing bronchial premalignant lesions as described elsewhere herein.

In some embodiments of any of the aspects, the biopsy or brushing sample comprises morphologically-normal tissues or cells, e.g., the tissues or cells are not from a lesion and display normal morphology for their in vivo location. In some embodiments of any of the aspects, the biopsy or brushing sample consists essentially of morphologically-normal tissues or cells. In some embodiments of any of the aspects, the biopsy or brushing sample consists of morphologically-normal tissues or cells.

In some embodiments of any of the aspects, the biopsy or brushing sample comprises visually-normal tissues or cells, e.g., the tissues or cells are not from a lesion and to the unaided human eye have a normal appearance for their in vivo location. In some embodiments of any of the aspects, the biopsy or brushing sample consists essentially of visually-normal tissues or cells. In some embodiments of any of the aspects, the biopsy or brushing sample consists of visually-normal tissues or cells.

In some embodiments of any of the aspects, the biopsy or brushing sample comprises bronchial premalignant lesion cells. In some embodiments of any of the aspects, the biopsy or brushing sample consists essentially of bronchial premalignant lesion cells. In some embodiments of any of the aspects, the biopsy or brushing sample consists of bronchial premalignant lesion cells.

A level which is less than a reference level can be a level which is less by at least about 10%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In some embodiments of any of the aspects, the reference can be a level of the target molecule in a population of subjects who do not have or are not diagnosed as having, and/or do not exhibit signs or symptoms of bronchial premalignant lesions. In some embodiments of any of the aspects, the reference can also be a level of expression of the target molecule in a control sample, a pooled sample of control individuals or a numeric value or range of values based on the same. In some embodiments of any of the aspects, the reference can be the level of a target molecule in a sample obtained from the same subject at an earlier point in time, e.g., the methods described herein can be used to determine if a subject's sensitivity or response to a given therapy is changing over time or if the subtype of their lesions is changing.

In some embodiments of any of the aspects, the level of expression products of no more than 200 other genes is/are determined. In some embodiments of any of the aspects, the level of expression products of no more than 100 other genes is/are determined. In some embodiments of any of the aspects, the level of expression products of no more than 20 other genes is/are determined. In some embodiments of any of the aspects, the level of expression products of no more than 10 other genes is/are determined.

In some embodiments of the foregoing aspects, the expression level of a given gene can be normalized relative to the expression level of one or more reference genes or reference proteins.

In some embodiments, the reference level can be the level in a sample of similar cell type, sample type, sample processing, and/or obtained from a subject of similar age, sex and other demographic parameters as the sample/subject for which the level of expression is to be determined. In some embodiments, the test sample and control reference sample are of the same type, that is, obtained from the same biological source, and comprising the same composition, e.g. the same number and type of cells.

In some embodiments of any of the aspects, the reference level can be a non-proliferative reference level, e.g., the level in a tissue or cell not comprising a proliferative lesion or from a subject who does not have a proliferative lesion. For example, the level can be the level in inflammatory, secretory, or normal-like lesion subtypes or an average or pooling thereof.

In some embodiments, the methods described herein relate to treating a subject having or diagnosed as having bronchial premalignant lesions. Subjects having bronchial premalignant lesions can be identified by a physician using current methods of diagnosing bronchial premalignant lesions. Tests that may aid in a diagnosis of, e.g. bronchial premalignant lesions include, but are not limited to, bronchoscopy, autofluorescence bronchoscopy, etc. A family history of bronchial premalignant lesions or exposure to risk factors for bronchial premalignant lesions (e.g. cigarette smoke) can also aid in determining if a subject is likely to have bronchial premalignant lesions or in making a diagnosis of bronchial premalignant lesions.

The compositions and methods described herein can be administered to a subject having or diagnosed as having bronchial premalignant lesions. In some embodiments, the methods described herein comprise administering an effective amount of compositions described herein to a subject in order to alleviate a symptom of a bronchial premalignant lesions. As used herein, "alleviating a symptom of a bronchial premalignant lesions" is ameliorating any condition or symptom associated with the bronchial premalignant lesions. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The methods described herein can prevent, delay, or slow the development of lung cancer, e.g., lung squamous cell carcinoma. In some embodiments of any of the aspects, the subject treated according to the present methods is not a subject with lung cancer. In some embodiments of any of the aspects, the subject treated according to the present methods is a subject who does not have lung cancer. In some embodiments of any of the aspects, the subject treated according to the present methods is a subject who does not have and has not had lung cancer. In some embodiments of any of the aspects, the subject treated according to the present methods is at risk of lung cancer. In some embodiments of any of the aspects, the subject is a subject with a bronchial premalignant lesion.

In some embodiments of any of the aspects, the subject is a smoker. In some embodiments of any of the aspects, the subject is a former smoker. In some embodiments of any of the aspects, the subject is a non-smoker.

The treatments described herein, e.g. an anti-proliferative drug, anti-inflammatory drug, or immune stimulating drug can be administered systemically, by inhalation, and/or topically to any portion of the airways of a subject (including the nose and mouth). In some embodiments of any of the aspects, a treatment described herein, e.g. an anti-proliferative drug, anti-inflammatory drug, or immune stimulating drug can be administered i) systemically and ii) by inhalation or topically to any portion of the airways of a subject (including the nose and mouth) during a bronchoscopy or brushing collection.

An anti-proliferative drug is a drug that inhibits cell growth and/or division, e.g., cytostatic agents, wherein that is the primary activity of the compound in the relevant context. Non-limiting examples of anti-proliferative drugs can include CDK inhibitors (e.g. purvalanol-a, palbociclib, ribociclib, abemaciclib, and olomoucine II); HDAC inhibitors (e.g. THM-I-94, vorinostat, givinostat); PARP inhibitors (e.g. AG-14361, olaparib, rucaparib, niraparib, talazoparib, veliparib, pamiparib, CEP 9722, E7016, iniparib, 3-aminobenazmide); JAK inhibitors (e.g. JAK3-inhibitor-VI, ruxolitinib, tofacitinib, oclacitinib, baricitinib, peficitinib, filgotinib, cerdulatinib, gandotinib, lestaurtinib, momelotinib, pacritinib, PF-04965842, upadacitinib, fedratinib, cucurbitacin, CHZ868); JNK inhibitors (e.g. ZG-10, AS-601245, AM-111); MTOR inhibitors (e.g. AZD-8055, PI-103, rapamycin, temsirolimus, everolimus, ridaforolimus, rapalogs, sirolimus); FLT3 inhibitors (e.g. lestaurtinib, TG-101348, gilteritinib, quizartinib, midostaurin, sorafenib, sunitinib); PI3K inhibitors (e.g. GDC-0941, PI-828, wortmannin, LY294002, hibiscone C, idelalisib, copanlisib, duvelisib, alpelisib, taselisib, perifosine, buparlisib, umbralisib, PX-866, dactolisib, CUDC-907, voxtalisib, ME-401, IPI-549, SF1126, PR6530, INK1117, pictilisib, XL147, palmoid 529, GSK1059615, ZSTK474, PWT33597, IC87114, TG100-115, CAL263, RP6503, PI-103, GNE-477, AEZS-136); AKT inhibitors (e.g. A-443644, pyrviniumpamoate, VQD-002, perifosine, miltefosine, MK-2206, AZD5363, ipataseritib); tyrosine kinase inhibitors (e.g. aminopurvalanol-a, SU-11652, imatinib, gefitinib, erlotinib, sunitinib, adavosertib, lapatinib); protein kinase inhibitors (e.g. HG-5-113-01, adavosertib, afatinib, axitinib, bosuntinib, cetuximab, conbimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, vemurafenib); RNA polymerase inhibitor (e.g. dactinomycin, triptolide); topoisomerase inhibitors (e.g. pidorubicine, doxorubicin, campothecins, indenosioquinolines, indotecan, imdimitecan, amsacrine, etoposide, teniposide, ICRF-193, genistein); HSP inhibitors (e.g. HSP90-inhibitor, 17-N-Allylamino-17-demethoxygeldanamycin (17AAG), gamitrinib); DNA protein kinase inhibitors (e.g., PIK-75); focal adhesion kinase inhibitors (e.g. PF-562271, PF573,228, PF-271, NVP-226, Y15, PND-1186, GSK2256098, VS-6062, VS-6063, VS-4718); RNA synthesis inhibitor (daunorubicin); mediator release inhibitor (e.g. ER-27319); and EZH2 inhibitors (DZNep, EPZ005687, EI1, GSK126, UNC1999, EPZ-6438, tazemetostat). Further non-limiting examples of anti-proliferative drugs include Acetylcholine receptor antagonists (e.g., clozapine, quetiapine, atropine, benztropine, biperiden, chlorpheniramine, citalopram, dycyclomine, dimenthydrinate, diphenhydramine, doxepin, doxylamine, glycopyrrolate, glycopyrronium, hyoscyamine, ipratropium, orphenadrine, oxitropium, oxybutynin, promethazine, propantheline bromide, scopolamine, solifenacin, solifenacin, tolterodine, tiotropium, trihexyphenidyl, tropicamide, tubocurarine, mecamylamine, hexamethonium, doxacurium, dextromethorphan, bupriopion); Acetylcholinesterase inhibitors (e.g. Physostigmine, Neostigmine, Pyridostigmine, Ambenonium, Demecarium, Rivastigmine, Phenanthrene derivatives, Galantamine, Alpha-Pinene—noncompetitive reversible, Piperidines, Donepezil, Tacrine, Edrophonium, Huperzine A, Ladostigil, Ungeremine, Lactucopicrin, and Acotiamide); Adenosine receptor antagonists (e.g., theophylline and theobromine); Adrenergic receptor antagonists (e.g., Phentolamine, phenoxybenzamine, Propranolol, Nebivilol, Atenolol, Oxprenolol, Metoprolol, Timolol, Pindolol, Nadolol, Pindolol, Esmolol, Acebutolol, Sotalol, Talinolol, Betaxolol, Labetalol, and Carvedilol); Angiotensin receptor antagonists (e.g., candesartan, eprosartan, irbesartan, losartan, olmesartan, telmisartan, valsartan); Apoptosis stimulants (e.g., Asiatic acid, glycodeoxycholic acid); Cyclooxygenase inhibitors (e.g., celecoxib, rofecoxib); Cytokine production inhibitors (e.g., sirolimus, basiliximab, daclizumab); Dehydrogenase inhibitors((e.g., mycophenolate-mofetil, mycophenolic acid); Dopamine receptor antagonist (e.g., benperidol, chlorpromazine, clopenthixol, droperidol, haloperidol, fluphenazine, flupenthixol, fluspirilene, penfluridol, perazine, perphenazine, pimozide, spiperone, sulpiride, thioridazine, amisulpride, aseanapine, aripriprazole, clozapine, loxapine, nemonapride, olanzapine, quetiapine, paliperidone, remoxipride, risperidone, tiapride, ziprasidone, domperidone, bromopride, metoclopramide, eticlopride, nafadotride, raclopride); EGFR inhibitors (e.g., gefitinib, erlotinib, iapatinib, osimertinib, cetuximab, neratinib, pnaitumumab, vandetanib, necitumumab, dacomitinib); ERK1 and ERK2 phosphorylation inhibitors (e.g., RAF, RAS, or MEK inhibitors); Estrogen receptor agonists (e.g., ethinylestradiol, diethylstilbestrol, phytoestrogens, tamoxifen, clomifene, raloxifene); Glutamate receptor antagonists (e.g., AP5, barbiturates, dextromethorphan, dextrorphan, dizoclipin, ibogaine, ifenprodil, ketamine, kynurenic acid, memantine, perampanel, phencyclidine); Histamine receptor antagonists (e.g., cimetidine, ranitidine, famotidine, nizatidine, roxatidine, lafutidine); Histone lysine methyltransferase inhibitors (EPZ004777, EPZ5676, BIX01294); IKK inhibitors (e.g., curcumin, embelin, auranofine, butein, IMD 0354, IKK 16, SC514, BAY 11-7082, MRT67307, BMS-345541, amlexanox, MLN120B); Ion channel antagonists (e.g., erastin); Leucine rich repeat kinase inhibitors (e.g., MLi-2, PF-06447475, GSK2578215, LRKK2-IN1, HG 10/102/01, CZC-25146); MDM inhibitors (e.g., tenovin-2, idasanutlin, SP141 MI-773, RO8994, AMG232, nutlin-3); Monoamine oxidase inhibitors (e.g., hydrazine, isocarboxazid, nialamide, phenelzine, hydracarbazine, tnrylcypromine, befemelane, moclobemide, pirlindole, toloxatone, rasagiline, selegiline, safinamide); nucleophosmin inhibitors (e.g., EAPB0503, NSC348884, Rev37-47 CIGB-300, avrainvillamide, deguelin, EPTG, YTR107); PPAR receptor agonists (e.g. clofibrate, gemfibrozil, ciprofibrate, bezafibrate, fenofibrate, thiazolidinediones, BW501516, aleglitazar, muraglitizar, tesaglitzar); Phosphodiesterase inhibitors (e.g., vinpocetine, ENHA, BAY 60-7550, oxindole, PDP, IBMX, aminophylline, praxanthine, pentoxifylline, theobromine, inamrinone, milrinone, enoximone, anagrelide, cilostazol, pimobendan); SIRT inhibitors (e.g., (s)-2-phentyl-6-chloro, 8-bormo-chroman-4-one, 3'-phenethyloxy-2-anilinobenzamide); sodium channel blockers (e.g., procainamide, quinidine, disopyramide, lidocaine, mexiletine, tocainide, phenytoin, encainide, flecainide, moricizine, propafenone); and Vitamin D receptor agonists (e.g., EB 1089, BXL-01-0029, elocalcitol). In some embodiments, anti-proliferative drugs lacking anti-inflammatory activity in any context described herein can include JAK inhibitors, JNK inhibitors, AKT inhibitors, protein kinase inhibitors, RNA polymerase inhibitors, HSP inhibitors, DNA protein kinase inhibitors, focal adhesion inhibitors, RNA synthesis inhibitors, and mediator release inhibitors.

As used herein, the term "anti-inflammatory" refers to a compound capable of reducing or inhibiting inflammation, wherein that is the primary activity of the compound in the relevant context. As used herein, the term "anti-inflammatory drug" or "anti-inflammatory agent" is used to describe any compound (including its analogs, derivatives, prodrugs and pharmaceutically salts) which can be used reduce or inhibit inflammation. Non-limiting examples of anti-inflammatory drugs can include NFkB pathway inhibitors (e.g. 9-methyl-5H-6-thia-4,5-diaza-chrysene-6,6-dioxide, denosumab, disulfiram, olmesartan, dithiocarbamates, anatabine, BAY 11-7082, palmitoylethanolamide, iguartimod); protein synthesis inhibitors (e.g. chloramphenicol); anti-IL1B antibodies (e.g., Canakinumab); glucocorticoid receptor agonists (e.g. dexamethasone, mifepristone,); and TGF beta receptor inhibitors (e.g. LY-364947, GW-755.55, LY-2109761, galunisertib, SB431542, SB-525334). Further non-limiting examples of anti-proliferative drugs include Acetylcholine receptor antagonist; Acetylcholinesterase inhibitors; Adenosine receptor antagonists; Adrenergic receptor antagonists; Angiotensin receptor antagonists; Apoptosis stimulants; Cyclooxygenase inhibitors; Cytokine production inhibitors; Dehydrogenase inhibitors; Dopamine receptor antagonist; EGFR inhibitors; ERK1 and ERK2 phosphorylation inhibitors; Estrogen receptor agonists; Glutamate receptor antagonists; Histamine receptor antagonists; Histone lysine methyltransferase inhibitors; IKK inhibitors; Ion channel antagonists; Leucine rich repeat kinase inhibitors; MDM inhibitors; Monoamine oxidase inhibitors; nucleophosmin inhibitors; PPAR receptor agonists; Phosphodiesterase inhibitors; SIRT inhibitors; sodium channel blockers; and Vitamin D receptor agonists. In some embodiments, anti-inflammatory drugs lacking anti-proliferative activity in any context described herein can include protein synthesis inhibitors and TGF beta receptor inhibitors.

It is noted herein that a single compound may exhibit multiple activities, e.g., depending on the context. Non-examples of agents that can exhibit primarily an anti-inflammatory activity and/or an anti-proliferative activity, depending on the context (e.g., the subject or cell being administered/contacted with the agent) can include Acetylcholine receptor antagonist, Acetylcholinesterase inhibitors, Adenosine receptor antagonists, Adrenergic receptor antagonists, Angiotensin receptor antagonists, Apoptosis stimulants, Aurora kinase inhibitors, CDK inhibitors, Cyclooxygenase inhibitors, Cytokine production inhibitors, Dehydrogenase inhibitors, Dopamine receptor antagonist, EGFR inhibitors, ERK1 and ERK2 phosphorylation inhibitors, Estrogen receptor agonists, FLT3 inhibitors, Glucocorticoid receptor agonists, Glutamate receptor antagonists, HDAC inhibitors, Histamine receptor antagonists, Histone lysine methyltransferase inhibitors, HSP inhibitors, IKK inhibitors, Ion channel antagonists, KIT inhibitors, Leucine rich repeat kinase inhibitors, MEK inhibitors, MDM inhibitors, Phosphodiesterase inhibitors, Monoamine oxidase inhibitors, MTOR inhibitors, NFkB pathway inhibitors, nucleophosmin inhibitors, PARP inhibitors, PI3K inhibitors, PPAR receptor agonist, RAF inhibitors, SIRT inhibitors, Sodium channel blockers, Topoisomerase inhibitors, Tyrosine kinase inhibitors, VEGFR inhibitors, and a Vitamin D receptor agonists.

An immune-stimulating drug is a drug that increases the activity of the immune system, preferably against cancer or dysplasia cells, wherein that is the primary activity of the compound in the relevant context. As used herein, the term "immune-stimulating drug" or "anti-inflammatory agent" is used to describe any compound (including its analogs, derivatives, prodrugs and pharmaceutically salts) which can be used stimulate the immune system. Non-limiting examples of immune stimulating drugs can include immune-checkpoint inhibitors (e.g. inhibitors against, PD-1, PD-L1, CTLA4, and LAG3); drugs that stimulate interferon signaling (e.g. anti-viral drugs that improve interferon signaling such as Pegintron, Pegasys, referon A, uniferon, multiferon, rebif, avonex, cinnovex, betaseron, actimmune, reiferon, pegetron); DNA synthesis inhibitors (e.g., TAS-102, NC-6004, ganciclovir); CDK inhibitors (e.g. purvalanol-a, palbociclib, ribociclib, abemaciclib, and olomoucine II); ribonucleotide reductase inhibitors (e.g., motexafin, hydroxyurea, fludarabine, cladribine, gemcitabine, tezacitabine, triapine, gallium maltolate, gallium nitrate); dihydrofolate reductase inhibitors (e.g., methotrexate, piritrexam, cycloguanil, JPC-2056); topoisomerase inhibitors (e.g. pidorubicine, doxorubicin, campothecins, indenosioquinolines, indotecan, imdimitecan, amsacrine, etoposide, teniposide, ICRF-193, genistein); FLT3 inhibitors (e.g. lestaurtinib, TG-101348, gilteritinib, quizartinib, midostaurin, sorafenib, sunitinib); IGF-1 inhibitors; MEK inhibitors (e.g., trametinib, cobimetinib, binimetinib, selumetinib, PD-325901, TAK-733); aurora kinase inhibitors (e.g., ZM447439, hesperidin, VX-680); PKC inhibitors (e.g., ruboxistaurin, chelerythrine, miyabenol C, myricitrin, gossypol, verbascoside, BIM-1, bryostate 1, tamoxifen); RAF inhibitors (e.g., vemurafenib, GDC-0879, PLX-4720, sorafenib, dabrafenib, LGX818); PDFGR/KIT inhibitors (e.g., imatinib, sunitinib, sorafenib, pazopanib, nilotinib, motesanib, linifenib); VEGFR inhibitors (e.g., axitinib, cabozantinib, lenvatinib, pazopanib, vandetanib); SRC inhibitors (e.g., KX2-391, bosutinib, saracatinib, PP1, PP2, quercetin, dastabinib); retinoid receptor agonists (e.g., alitretinoin, isoretinoin); HDAC inhibitors (e.g. THM-I-94, vorinostat, givinostat); DNA methyltransferase inhibitors (e.g., azacytidine, decitabine, zeublarine); and EZH2 inhibitors (DZNep, EPZ005687, EI1, GSK126, UNC1999, EPZ-6438, tazemetostat).

In some embodiments, immune stimulating drugs lacking anti-proliferative/inflammatory activity in any context described herein can include immune-checkpoint inhibitors (e.g. inhibitors against, PD-1, PD-L1, CTLA4, and LAG3); drugs that stimulate interferon signaling (e.g. anti-viral drugs that improve interferon signaling); DNA synthesis inhibitors; IMDH inhibitors; ribonucleotide reductase inhibitors; dihydrofolate reductase inhibitors; SRC inhibitors; retinoid receptor agonists; HDAC inhibitors; and DNA methyltransferase inhibitors.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of the composition that is sufficient to provide a particular therapeutic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for gene expression as described herein, among others. The dosage can be determined by a physician and adjusted, as necessary, to suit observed effects of the treatment.

In some embodiments, the technology described herein relates to a pharmaceutical composition comprising a drug as described herein, and optionally a pharmaceutically acceptable carrier. In some embodiments, the active ingredients of the pharmaceutical composition comprise the drug as described herein. In some embodiments, the active ingredients of the pharmaceutical composition consist essentially of the drug as described herein. In some embodiments, the active ingredients of the pharmaceutical composition consist of the drug as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent.

In some embodiments, the pharmaceutical composition comprising a drug as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a drug as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of the drug as disclosed herein can also be incorporated into the parenteral dosage forms of the disclosure, including conventional and controlled-release parenteral dosage forms.

Pharmaceutical compositions comprising a drug can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the drug can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the drug described herein is administered as a monotherapy, e.g., another treatment for the bronchial premalignant lesions is not administered to the subject.

In some embodiments of any of the aspects, the methods described herein can further comprise administering a second agent and/or treatment to the subject, e.g. as part of a combinatorial therapy.

In certain embodiments, an effective dose of a composition comprising a drug as described herein can be administered to a patient once. In certain embodiments, an effective dose of a composition comprising a drug can be administered to a patient repeatedly. For systemic administration, subjects can be administered a therapeutic amount of a composition comprising a drug, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a drug described herein can be administered over a period of time, such as over a 5 minute, 10 minute, 15 minute, 20 minute, or 25 minute period.

The dosage ranges for the administration of a drug, according to the methods described herein depend upon, for example, the form of the drug, its potency, and the extent to which symptoms, markers, or indicators of a condition described herein are desired to be reduced, for example the percentage reduction desired for lesion size or the extent to which, for example, lesion subtype changes are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a drug in, e.g. the treatment of a condition described herein, or to induce a response as described herein (e.g. reduction in lesion size) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of a mouse model of bronchial premalignant lesions. When using an experimental animal model, efficacy of treatment is evidenced when a statistically significant change in a marker is observed, e.g. lesion size or gene expression.

As used herein, "a bronchoscopy-based procedure" refers to any endoscopic technique that permits examination of the bronchus and/or lungs. Bronchoscopy-based procedures can include white light bronchoscopy, autofluorescence bronchoscopy, flexible bronchoscopy, rigid bronchoscopy, bronchoalveolar lavage, and the like. Bronchoscopy-based procedures can further include biopsy, brushing, or tissue sampling. If the In addition to methods of treatment, the methods and biomarker signatures described herein can be applied to methods of predicting the risk of lung cancer in a subject and/or determining the efficacy of treatment or need for further treatment. For example, transition from a proliferative or inflammatory subtype to a normal-like or secretory subtype would indicate that a treatment had been effective or that the treatment can be discontinued.

In one aspect of any of the embodiments, described herein is a method of predicting the risk, or the likelihood of progression to lung cancer in a subject, the method comprising: detecting the level of expression of at least one module 5 gene and/or at least one module 6 gene in a sample obtained from the subject, wherein an increased level of expression of at least one module 5 gene as compared to a non-proliferative lesion reference level; and/or a decreased level of expression of at least one module 6 gene as compared to a non-proliferative lesion reference level indicates an increased risk of or likelihood of progressing to lung cancer. In one aspect of any of the embodiments, described herein is a method of predicting the risk, or the likelihood of progression to lung cancer in a subject, the method comprising: detecting the level of expression of at least one module 5 gene and/or at least one module 6 gene in a sample obtained from the subject at a first time point, and detecting the level of expression of at least one module 5 gene and/or at least one module 6 gene in a sample obtained from the subject at a second, subsequent time point, wherein an increased level of expression of at least one module 5 gene over time; and/or a decreased level of expression of at least one module 6 gene over time indicates an increased risk of or likelihood of progressing to lung cancer.

In one aspect of any of the embodiments, described herein is a method of predicting the risk, or the likelihood of progression to lung cancer in a subject, the method comprising: detecting the level of expression of at least one module 9 gene and/or at least one module 10 gene in a sample obtained from the subject, wherein an increased level of expression of at least one module 10 gene as compared to a non-proliferative lesion reference level; and/or a decreased level of expression of at least one module 9 gene as compared to a non-proliferative lesion reference level indicates an increased risk of or likelihood of progressing to lung cancer. In one aspect of any of the embodiments, described herein is a method of predicting the risk, or the likelihood of progression to lung cancer in a subject, the method comprising: detecting the level of expression of at least one module 10 gene and/or at least one module 9 gene in a sample obtained from the subject at a first time point, and detecting the level of expression of at least one module 9 gene and/or at least one module 10 gene in a sample obtained from the subject at a second, subsequent time point, wherein an increased level of expression of at least one module 10 gene over time; and/or a decreased level of expression of at least one module 9 gene over time indicates an increased risk of or likelihood of progressing to lung cancer.

In one aspect of any of the embodiments, described herein is a method of predicting the risk, or the likelihood of progression to lung cancer in a subject, the method comprising: detecting the level of expression of at least one module 2 gene and/or at least one module 6 gene in a sample obtained from the subject, wherein an increased level of expression of at least one module 2 gene as compared to a non-proliferative lesion reference level; and/or a decreased level of expression of at least one module 6 gene as compared to a non-proliferative lesion reference level indicates an increased risk of or likelihood of progressing to lung cancer. In one aspect of any of the embodiments, described herein is a method of predicting the risk, or the likelihood of progression to lung cancer in a subject, the method comprising: detecting the level of expression of at least one module 2 gene and/or at least one module 6 gene in a sample obtained from the subject at a first time point, and detecting the level of expression of at least one module 2 gene and/or at least one module 6 gene in a sample obtained from the subject at a second, subsequent time point, wherein an increased level of expression of at least one module 2 gene over time; and/or a decreased level of expression of at least one module 6 gene over time indicates an increased risk of or likelihood of progressing to lung cancer.

In one aspect of any of the embodiments, described herein is a method of determining treatment efficacy, the method comprising: detecting the level of expression of at least one module 5 gene and/or at least one module 6 gene in a sample obtained from the subject at a first time point, administering a treatment or candidate treatment, and detecting the level of expression of at least one module 5 gene and/or at least one module 6 gene in a sample obtained from the subject at a second, subsequent time point, wherein a decreased level of expression of at least one module 5 gene over time; and/or an increased level of expression of at least one module 6 gene over time indicates the treatment is effective.

In one aspect of any of the embodiments, described herein is a method of treatment efficacy, the method comprising: detecting the level of expression of at least one module 10 gene and/or at least one module 9 gene in a sample obtained from the subject at a first time point, administering a treatment or candidate treatment, and detecting the level of expression of at least one module 9 gene and/or at least one module 10 gene in a sample obtained from the subject at a second, subsequent time point, wherein an decreased level of expression of at least one module 10 gene over time; and/or an increased level of expression of at least one module 9 gene over time indicates the treatment is effective.

In one aspect of any of the embodiments, described herein is a method of determining treatment efficacy, the method comprising: detecting the level of expression of at least one module 2 gene and/or at least one module 6 gene in a sample obtained from the subject at a first time point, administering a treatment or candidate treatment, and detecting the level of expression of at least one module 2 gene and/or at least one module 6 gene in a sample obtained from the subject at a second, subsequent time point, wherein an decreased level of expression of at least one module 2 gene over time; and/or an increased level of expression of at least one module 6 gene over time indicates the treatment is effective.

In one aspect of any of the embodiments, described herein is a method comprising: detecting the level of expression of at least one module 5 gene and/or at least one module 6 gene in a sample obtained from a subject, wherein the level of expression of no more than 1,000 (e.g., no more than 500, 400, 300, 200, or 100) genes is determined. In one aspect of any of the embodiments, described herein is a method comprising: detecting the level of expression of at least one module 9 gene and/or at least one module 10 gene in a sample obtained from a subject, wherein the level of expression of no more than 1,000 (e.g., no more than 500, 400, 300, 200, or 100) genes is determined. In one aspect of any of the embodiments, described herein is a method comprising: detecting the level of expression of at least one module 2 gene and/or at least one module 6 gene in a sample obtained from a subject, wherein the level of expression of no more than 1,000 (e.g., no more than 500, 400, 300, 200, or 100) genes is determined. In some embodiments of any of the aspects, the sample is a bronchial brushing sample. In some embodiments of any of the aspects, the at least one gene is selected from Table 14 or 15.

TABLE 13

| GeneModule | EnsemblID | GeneSymbols |
|---|---|---|
| 1 | ENSG00000001084 | GCLC |
| 1 | ENSG00000006210 | CX3CL1 |
| 1 | ENSG00000008256 | CYTH3 |
| 1 | ENSG00000010319 | SEMA3G |
| 1 | ENSG00000011028 | MRC2 |
| 1 | ENSG00000011201 | KAL1 |
| 1 | ENSG00000011523 | CEP68 |
| 1 | ENSG00000012660 | ELOVL5 |
| 1 | ENSG00000017483 | SLC38A5 |
| 1 | ENSG00000019144 | PHLDB1 |
| 1 | ENSG00000019549 | SNAI2 |
| 1 | ENSG00000020181 | GPR124 |
| 1 | ENSG00000020577 | SAMD4A |
| 1 | ENSG00000024422 | EHD2 |
| 1 | ENSG00000031081 | ARHGAP31 |
| 1 | ENSG00000035862 | TIMP2 |
| 1 | ENSG00000042832 | TG |

TABLE 13-continued

| GeneModule | EnsemblID | GeneSymbols |
|---|---|---|
| 1 | ENSG00000049130 | KITLG |
| 1 | ENSG00000049540 | ELN |
| 1 | ENSG00000050165 | DKK3 |
| 1 | ENSG00000053747 | LAMA3 |
| 1 | ENSG00000054965 | FAM168A |
| 1 | ENSG00000060140 | STYK1 |
| 1 | ENSG00000061918 | GUCY1B3 |
| 1 | ENSG00000063180 | CA11 |
| 1 | ENSG00000064042 | LIMCH1 |
| 1 | ENSG00000064205 | WISP2 |
| 1 | ENSG00000064300 | NGFR |
| 1 | ENSG00000064989 | CALCRL |
| 1 | ENSG00000065054 | SLC9A3R2 |
| 1 | ENSG00000065320 | NTN1 |
| 1 | ENSG00000067445 | TRO |
| 1 | ENSG00000069122 | GPR116 |
| 1 | ENSG00000069188 | SDK2 |
| 1 | ENSG00000069702 | TGFBR3 |
| 1 | ENSG00000071246 | VASH1 |
| 1 | ENSG00000072041 | SLC6A15 |
| 1 | ENSG00000072195 | SPEG |
| 1 | ENSG00000072210 | ALDH3A2 |
| 1 | ENSG00000072840 | EVC |
| 1 | ENSG00000073067 | CYP2W1 |
| 1 | ENSG00000073282 | TP63 |
| 1 | ENSG00000073712 | FERMT2 |
| 1 | ENSG00000074356 | C17orf85 |
| 1 | ENSG00000074590 | NUAK1 |
| 1 | ENSG00000074660 | SCARF1 |
| 1 | ENSG00000076706 | MCAM |
| 1 | ENSG00000077782 | FGFR1 |
| 1 | ENSG00000078018 | MAP2 |
| 1 | ENSG00000079102 | RUNX1T1 |
| 1 | ENSG00000079308 | TNS1 |
| 1 | ENSG00000080573 | COL5A3 |
| 1 | ENSG00000081052 | COL4A4 |
| 1 | ENSG00000081913 | PHLPP1 |
| 1 | ENSG00000082497 | SERTAD4 |
| 1 | ENSG00000082781 | ITGB5 |
| 1 | ENSG00000085998 | POMGNT1 |
| 1 | ENSG00000087116 | ADAMTS2 |
| 1 | ENSG00000087245 | MMP2 |
| 1 | ENSG00000088367 | EPB41L1 |
| 1 | ENSG00000091136 | LAMB1 |
| 1 | ENSG00000091879 | ANGPT2 |
| 1 | ENSG00000092096 | SLC22A17 |
| 1 | ENSG00000092421 | SEMA6A |
| 1 | ENSG00000092969 | TGFB2 |
| 1 | ENSG00000099953 | MMP11 |
| 1 | ENSG00000100154 | TTC28 |
| 1 | ENSG00000101331 | CCM2L |
| 1 | ENSG00000101665 | SMAD7 |
| 1 | ENSG00000101825 | MXRA5 |
| 1 | ENSG00000102302 | FGD1 |
| 1 | ENSG00000102755 | FLT1 |
| 1 | ENSG00000103196 | CRISPLD2 |
| 1 | ENSG00000103241 | FOXF1 |
| 1 | ENSG00000103723 | AP3B2 |
| 1 | ENSG00000103852 | TTC23 |
| 1 | ENSG00000104953 | TLE6 |
| 1 | ENSG00000105088 | OLFM2 |
| 1 | ENSG00000105227 | PRX |
| 1 | ENSG00000105371 | ICAM4 |
| 1 | ENSG00000105376 | ICAM5 |
| 1 | ENSG00000105419 | MEIS3 |
| 1 | ENSG00000105538 | RASIP1 |
| 1 | ENSG00000105738 | SIPA1L3 |
| 1 | ENSG00000105866 | SP4 |
| 1 | ENSG00000105974 | CAV1 |
| 1 | ENSG00000106070 | GRB10 |
| 1 | ENSG00000106123 | EPHB6 |
| 1 | ENSG00000106333 | PCOLCE |
| 1 | ENSG00000106571 | GLI3 |
| 1 | ENSG00000106624 | AEBP1 |
| 1 | ENSG00000108821 | COL1A1 |
| 1 | ENSG00000108852 | MPP2 |
| 1 | ENSG00000108924 | HLF |
| 1 | ENSG00000109099 | PMP22 |

TABLE 13-continued

| GeneModule | EnsemblID | GeneSymbols |
|---|---|---|
| 1 | ENSG00000109107 | ALDOC |
| 1 | ENSG00000109193 | SULT1E1 |
| 1 | ENSG00000109610 | SOD3 |
| 1 | ENSG00000110002 | VWA5A |
| 1 | ENSG00000110200 | ANAPC15 |
| 1 | ENSG00000110799 | VWF |
| 1 | ENSG00000110811 | LEPREL2 |
| 1 | ENSG00000111341 | MGP |
| 1 | ENSG00000111452 | GPR133 |
| 1 | ENSG00000111799 | COL12A1 |
| 1 | ENSG00000112320 | SOBP |
| 1 | ENSG00000112414 | GPR126 |
| 1 | ENSG00000112562 | SMOC2 |
| 1 | ENSG00000112769 | LAMA4 |
| 1 | ENSG00000112782 | CLIC5 |
| 1 | ENSG00000112902 | SEMA5A |
| 1 | ENSG00000112936 | C7 |
| 1 | ENSG00000112964 | GHR |
| 1 | ENSG00000113140 | SPARC |
| 1 | ENSG00000113555 | PCDH12 |
| 1 | ENSG00000114270 | COL7A1 |
| 1 | ENSG00000114698 | PLSCR4 |
| 1 | ENSG00000114923 | SLC4A3 |
| 1 | ENSG00000115252 | PDE1A |
| 1 | ENSG00000115306 | SPTBN1 |
| 1 | ENSG00000115380 | EFEMP1 |
| 1 | ENSG00000115414 | FN1 |
| 1 | ENSG00000116016 | EPAS1 |
| 1 | ENSG00000116678 | LEPR |
| 1 | ENSG00000116774 | OLFML3 |
| 1 | ENSG00000116962 | NID1 |
| 1 | ENSG00000117013 | KCNQ4 |
| 1 | ENSG00000117122 | MFAP2 |
| 1 | ENSG00000117385 | LEPRE1 |
| 1 | ENSG00000117643 | MAN1C1 |
| 1 | ENSG00000118495 | PLAGL1 |
| 1 | ENSG00000119138 | KLF9 |
| 1 | ENSG00000119681 | LTBP2 |
| 1 | ENSG00000119699 | TGFB3 |
| 1 | ENSG00000119771 | KLHL29 |
| 1 | ENSG00000120156 | TEK |
| 1 | ENSG00000120162 | MOB3B |
| 1 | ENSG00000120318 | ARAP3 |
| 1 | ENSG00000120457 | KCNJ5 |
| 1 | ENSG00000121068 | TBX2 |
| 1 | ENSG00000121075 | TBX4 |
| 1 | ENSG00000122035 | RASL11A |
| 1 | ENSG00000122642 | FKBP9 |
| 1 | ENSG00000122707 | RECK |
| 1 | ENSG00000122778 | KIAA1549 |
| 1 | ENSG00000122786 | CALD1 |
| 1 | ENSG00000123094 | RASSF8 |
| 1 | ENSG00000123384 | LRP1 |
| 1 | ENSG00000124006 | OBSL1 |
| 1 | ENSG00000124406 | ATP8A1 |
| 1 | ENSG00000125266 | EFNB2 |
| 1 | ENSG00000125810 | CD93 |
| 1 | ENSG00000125848 | FLRT3 |
| 1 | ENSG00000126803 | HSPA2 |
| 1 | ENSG00000127329 | PTPRB |
| 1 | ENSG00000127585 | FBXL16 |
| 1 | ENSG00000127920 | GNG11 |
| 1 | ENSG00000127946 | HIP1 |
| 1 | ENSG00000128052 | KDR |
| 1 | ENSG00000128567 | PODXL |
| 1 | ENSG00000128641 | MYO1B |
| 1 | ENSG00000128656 | CHN1 |
| 1 | ENSG00000128791 | TWSG1 |
| 1 | ENSG00000128872 | TMOD2 |
| 1 | ENSG00000128917 | DLL4 |
| 1 | ENSG00000129009 | ISLR |
| 1 | ENSG00000129038 | LOXL1 |
| 1 | ENSG00000129467 | ADCY4 |
| 1 | ENSG00000129474 | AJUBA |
| 1 | ENSG00000129946 | SHC2 |
| 1 | ENSG00000129990 | SYT5 |
| 1 | ENSG00000130052 | STARD8 |
| 1 | ENSG00000130300 | PLVAP |
| 1 | ENSG00000130508 | PXDN |
| 1 | ENSG00000130635 | COL5A1 |
| 1 | ENSG00000131016 | AKAP12 |
| 1 | ENSG00000131477 | RAMP2 |
| 1 | ENSG00000131831 | RAI2 |
| 1 | ENSG00000132688 | NES |
| 1 | ENSG00000133026 | MYH10 |
| 1 | ENSG00000133067 | LGR6 |
| 1 | ENSG00000133110 | POSTN |
| 1 | ENSG00000133121 | STARD13 |
| 1 | ENSG00000133313 | CNDP2 |
| 1 | ENSG00000133687 | TMTC1 |
| 1 | ENSG00000134243 | SORT1 |
| 1 | ENSG00000134245 | WNT2B |
| 1 | ENSG00000134318 | ROCK2 |
| 1 | ENSG00000134352 | IL6ST |
| 1 | ENSG00000134569 | LRP4 |
| 1 | ENSG00000134590 | FAM127A |
| 1 | ENSG00000134627 | PIWIL4 |
| 1 | ENSG00000134802 | SLC43A3 |
| 1 | ENSG00000134853 | PDGFRA |
| 1 | ENSG00000134917 | ADAMTS8 |
| 1 | ENSG00000134986 | NREP |
| 1 | ENSG00000135063 | FAM189A2 |
| 1 | ENSG00000135111 | TBX3 |
| 1 | ENSG00000135423 | GLS2 |
| 1 | ENSG00000135424 | ITGA7 |
| 1 | ENSG00000135775 | COG2 |
| 1 | ENSG00000135862 | LAMC1 |
| 1 | ENSG00000135925 | WNT10A |
| 1 | ENSG00000136114 | THSD1 |
| 1 | ENSG00000136158 | SPRY2 |
| 1 | ENSG00000136160 | EDNRB |
| 1 | ENSG00000136205 | TNS3 |
| 1 | ENSG00000136274 | NACAD |
| 1 | ENSG00000136546 | SCN7A |
| 1 | ENSG00000137273 | FOXF2 |
| 1 | ENSG00000137834 | SMAD6 |
| 1 | ENSG00000137872 | SEMA6D |
| 1 | ENSG00000137962 | ARHGAP29 |
| 1 | ENSG00000138356 | AOX1 |
| 1 | ENSG00000138495 | COX17 |
| 1 | ENSG00000138735 | PDE5A |
| 1 | ENSG00000138792 | ENPEP |
| 1 | ENSG00000138795 | LEF1 |
| 1 | ENSG00000139174 | PRICKLE1 |
| 1 | ENSG00000139211 | AMIGO2 |
| 1 | ENSG00000139263 | LRIG3 |
| 1 | ENSG00000140092 | FBLN5 |
| 1 | ENSG00000140682 | TGFB1I1 |
| 1 | ENSG00000140807 | NKD1 |
| 1 | ENSG00000140937 | CDH11 |
| 1 | ENSG00000141338 | ABCA8 |
| 1 | ENSG00000141622 | RNF165 |
| 1 | ENSG00000141720 | PIP4K2B |
| 1 | ENSG00000141756 | FKBP10 |
| 1 | ENSG00000142156 | COL6A1 |
| 1 | ENSG00000142173 | COL6A2 |
| 1 | ENSG00000142798 | HSPG2 |
| 1 | ENSG00000143067 | ZNF697 |
| 1 | ENSG00000143140 | GJA5 |
| 1 | ENSG00000143341 | HMCN1 |
| 1 | ENSG00000143995 | MEIS1 |
| 1 | ENSG00000144057 | ST6GAL2 |
| 1 | ENSG00000144642 | RBMS3 |
| 1 | ENSG00000144724 | PTPRG |
| 1 | ENSG00000144810 | COL8A1 |
| 1 | ENSG00000144857 | BOC |
| 1 | ENSG00000145040 | UCN2 |
| 1 | ENSG00000145147 | SLIT2 |
| 1 | ENSG00000145675 | PIK3R1 |
| 1 | ENSG00000145777 | TSLP |
| 1 | ENSG00000146648 | EGFR |
| 1 | ENSG00000146966 | DENND2A |
| 1 | ENSG00000147027 | TMEM47 |
| 1 | ENSG00000147257 | GPC3 |
| 1 | ENSG00000147408 | CSGALNACT1 |
| 1 | ENSG00000147862 | NFIB |

TABLE 13-continued

| GeneModule | EnsemblID | GeneSymbols |
|---|---|---|
| 1 | ENSG00000148468 | FAM171A1 |
| 1 | ENSG00000148541 | FAM13C |
| 1 | ENSG00000148600 | CDHR1 |
| 1 | ENSG00000149212 | SESN3 |
| 1 | ENSG00000149294 | NCAM1 |
| 1 | ENSG00000149485 | FADS1 |
| 1 | ENSG00000149564 | ESAM |
| 1 | ENSG00000149575 | SCN2B |
| 1 | ENSG00000149582 | TMEM25 |
| 1 | ENSG00000149596 | JPH2 |
| 1 | ENSG00000149639 | SOGA1 |
| 1 | ENSG00000150048 | CLEC1A |
| 1 | ENSG00000150457 | LATS2 |
| 1 | ENSG00000150471 | LPHN3 |
| 1 | ENSG00000150625 | GPM6A |
| 1 | ENSG00000150938 | CRIM1 |
| 1 | ENSG00000151617 | EDNRA |
| 1 | ENSG00000151632 | AKR1C2 |
| 1 | ENSG00000151914 | DST |
| 1 | ENSG00000152104 | PTPN14 |
| 1 | ENSG00000152217 | SETBP1 |
| 1 | ENSG00000152583 | SPARCL1 |
| 1 | ENSG00000152990 | GPR125 |
| 1 | ENSG00000153162 | BMP6 |
| 1 | ENSG00000153208 | MERTK |
| 1 | ENSG00000153253 | SCN3A |
| 1 | ENSG00000153885 | KCTD15 |
| 1 | ENSG00000154065 | ANKRD29 |
| 1 | ENSG00000154122 | ANKH |
| 1 | ENSG00000154133 | ROBO4 |
| 1 | ENSG00000154188 | ANGPT1 |
| 1 | ENSG00000154310 | TNIK |
| 1 | ENSG00000154342 | WNT3A |
| 1 | ENSG00000154358 | OBSCN |
| 1 | ENSG00000154767 | XPC |
| 1 | ENSG00000154783 | FGD5 |
| 1 | ENSG00000155254 | MARVELD1 |
| 1 | ENSG00000155324 | GRAMD3 |
| 1 | ENSG00000156011 | PSD3 |
| 1 | ENSG00000156395 | TSPAN7 |
| 1 | ENSG00000156966 | B3GNT7 |
| 1 | ENSG00000157240 | FZD1 |
| 1 | ENSG00000157404 | KIT |
| 1 | ENSG00000157510 | AFAP1L1 |
| 1 | ENSG00000157554 | ERG |
| 1 | ENSG00000158270 | COLEC12 |
| 1 | ENSG00000158301 | GPRASP2 |
| 1 | ENSG00000158352 | SHROOM4 |
| 1 | ENSG00000158435 | CNOT11 |
| 1 | ENSG00000159164 | SV2A |
| 1 | ENSG00000159640 | ACE |
| 1 | ENSG00000159692 | CTBP1 |
| 1 | ENSG00000160190 | SLC37A1 |
| 1 | ENSG00000160191 | PDE9A |
| 1 | ENSG00000160469 | BRSK1 |
| 1 | ENSG00000160867 | FGFR4 |
| 1 | ENSG00000161940 | BCL6B |
| 1 | ENSG00000162367 | TAL1 |
| 1 | ENSG00000162407 | PPAP2B |
| 1 | ENSG00000162493 | PDPN |
| 1 | ENSG00000162552 | WNT4 |
| 1 | ENSG00000162576 | MXRA8 |
| 1 | ENSG00000162591 | MEGF6 |
| 1 | ENSG00000162599 | NFIA |
| 1 | ENSG00000162618 | ELTD1 |
| 1 | ENSG00000162627 | SNX7 |
| 1 | ENSG00000162729 | IGSF8 |
| 1 | ENSG00000162733 | DDR2 |
| 1 | ENSG00000162817 | C1orf115 |
| 1 | ENSG00000163072 | NOSTRIN |
| 1 | ENSG00000163273 | NPPC |
| 1 | ENSG00000163328 | GPR155 |
| 1 | ENSG00000163359 | COL6A3 |
| 1 | ENSG00000163378 | EOGT |
| 1 | ENSG00000163430 | FSTL1 |
| 1 | ENSG00000163435 | ELF3 |
| 1 | ENSG00000163520 | FBLN2 |
| 1 | ENSG00000163710 | PCOLCE2 |
| 1 | ENSG00000163827 | LRRC2 |
| 1 | ENSG00000164056 | SPRY1 |
| 1 | ENSG00000164116 | GUCY1A3 |
| 1 | ENSG00000164176 | EDIL3 |
| 1 | ENSG00000164488 | DACT2 |
| 1 | ENSG00000164692 | COL1A2 |
| 1 | ENSG00000164741 | DLC1 |
| 1 | ENSG00000165125 | TRPV6 |
| 1 | ENSG00000165659 | DACH1 |
| 1 | ENSG00000165757 | KIAA1462 |
| 1 | ENSG00000165821 | SALL2 |
| 1 | ENSG00000165995 | CACNB2 |
| 1 | ENSG00000166025 | AMOTL1 |
| 1 | ENSG00000166086 | JAM3 |
| 1 | ENSG00000166105 | GLB1L3 |
| 1 | ENSG00000166147 | FBN1 |
| 1 | ENSG00000166257 | SCN3B |
| 1 | ENSG00000166265 | CYYR1 |
| 1 | ENSG00000166292 | TMEM100 |
| 1 | ENSG00000166398 | KIAA0355 |
| 1 | ENSG00000166482 | MFAP4 |
| 1 | ENSG00000166813 | KIF7 |
| 1 | ENSG00000166886 | NAB2 |
| 1 | ENSG00000167123 | CERCAM |
| 1 | ENSG00000168056 | LTBP3 |
| 1 | ENSG00000168060 | NAALADL1 |
| 1 | ENSG00000168077 | SCARA3 |
| 1 | ENSG00000168264 | IRF2BP2 |
| 1 | ENSG00000168490 | PHYHIP |
| 1 | ENSG00000168497 | SDPR |
| 1 | ENSG00000168502 | SOGA2 |
| 1 | ENSG00000168542 | COL3A1 |
| 1 | ENSG00000168621 | GDNF |
| 1 | ENSG00000168818 | STX18 |
| 1 | ENSG00000168890 | TMEM150A |
| 1 | ENSG00000169047 | IRS1 |
| 1 | ENSG00000169291 | SHE |
| 1 | ENSG00000169302 | STK32A |
| 1 | ENSG00000169418 | NPR1 |
| 1 | ENSG00000169435 | RASSF6 |
| 1 | ENSG00000169504 | CLIC4 |
| 1 | ENSG00000169604 | ANTXR1 |
| 1 | ENSG00000169744 | LDB2 |
| 1 | ENSG00000170017 | ALCAM |
| 1 | ENSG00000170364 | SETMAR |
| 1 | ENSG00000170549 | IRX1 |
| 1 | ENSG00000170558 | CDH2 |
| 1 | ENSG00000170915 | PAQR8 |
| 1 | ENSG00000171016 | PYGO1 |
| 1 | ENSG00000171033 | PKIA |
| 1 | ENSG00000171243 | SOSTDC1 |
| 1 | ENSG00000171346 | KRT15 |
| 1 | ENSG00000171444 | MCC |
| 1 | ENSG00000171462 | DLK2 |
| 1 | ENSG00000171791 | BCL2 |
| 1 | ENSG00000171812 | COL8A2 |
| 1 | ENSG00000171867 | PRNP |
| 1 | ENSG00000172348 | RCAN2 |
| 1 | ENSG00000172458 | IL17D |
| 1 | ENSG00000172638 | EFEMP2 |
| 1 | ENSG00000172889 | EGFL7 |
| 1 | ENSG00000173040 | EVC2 |
| 1 | ENSG00000173210 | ABLIM3 |
| 1 | ENSG00000173269 | MMRN2 |
| 1 | ENSG00000173546 | CSPG4 |
| 1 | ENSG00000173706 | HEG1 |
| 1 | ENSG00000173805 | HAP1 |
| 1 | ENSG00000174059 | CD34 |
| 1 | ENSG00000174226 | SNX31 |
| 1 | ENSG00000174348 | PODN |
| 1 | ENSG00000174370 | C11orf45 |
| 1 | ENSG00000174567 | GOLT1A |
| 1 | ENSG00000174640 | SLCO2A1 |
| 1 | ENSG00000175471 | MCTP1 |
| 1 | ENSG00000175920 | DOK7 |
| 1 | ENSG00000176393 | RNPEP |
| 1 | ENSG00000176428 | VPS37D |
| 1 | ENSG00000176435 | CLEC14A |

TABLE 13-continued

| GeneModule | EnsemblID | GeneSymbols |
|---|---|---|
| 1 | ENSG00000176771 | NCKAP5 |
| 1 | ENSG00000176971 | FIBIN |
| 1 | ENSG00000177076 | ACER2 |
| 1 | ENSG00000177303 | CASKIN2 |
| 1 | ENSG00000177469 | PTRF |
| 1 | ENSG00000177707 | PVRL3 |
| 1 | ENSG00000177732 | SOX12 |
| 1 | ENSG00000178031 | ADAMTSL1 |
| 1 | ENSG00000178222 | RNF212 |
| 1 | ENSG00000178947 | LINC00086 |
| 1 | ENSG00000179104 | TMTC2 |
| 1 | ENSG00000179348 | GATA2 |
| 1 | ENSG00000179431 | FJX1 |
| 1 | ENSG00000179776 | CDH5 |
| 1 | ENSG00000180739 | S1PR5 |
| 1 | ENSG00000180875 | GREM2 |
| 1 | ENSG00000181104 | F2R |
| 1 | ENSG00000182175 | RGMA |
| 1 | ENSG00000182272 | B4GALNT4 |
| 1 | ENSG00000182492 | BGN |
| 1 | ENSG00000182534 | MXRA7 |
| 1 | ENSG00000182621 | PLCB1 |
| 1 | ENSG00000182871 | COL18A1 |
| 1 | ENSG00000182985 | CADM1 |
| 1 | ENSG00000183087 | GAS6 |
| 1 | ENSG00000183160 | TMEM119 |
| 1 | ENSG00000183722 | LHFP |
| 1 | ENSG00000183729 | NPBWR1 |
| 1 | ENSG00000183734 | ASCL2 |
| 1 | ENSG00000183853 | KIRREL |
| 1 | ENSG00000183963 | SMTN |
| 1 | ENSG00000184113 | CLDN5 |
| 1 | ENSG00000184564 | SLITRK6 |
| 1 | ENSG00000184916 | JAG2 |
| 1 | ENSG00000184985 | SORCS2 |
| 1 | ENSG00000185070 | FLRT2 |
| 1 | ENSG00000185418 | TARSL2 |
| 1 | ENSG00000185652 | NTF3 |
| 1 | ENSG00000185668 | POU3F1 |
| 1 | ENSG00000185924 | RTN4RL1 |
| 1 | ENSG00000186260 | MKL2 |
| 1 | ENSG00000186318 | BACE1 |
| 1 | ENSG00000186462 | NAP1L2 |
| 1 | ENSG00000186732 | MPPED1 |
| 1 | ENSG00000186994 | KANK3 |
| 1 | ENSG00000186998 | EMID1 |
| 1 | ENSG00000187068 | C3orf70 |
| 1 | ENSG00000187134 | AKR1C1 |
| 1 | ENSG00000187193 | MT1X |
| 1 | ENSG00000187244 | BCAM |
| 1 | ENSG00000187513 | GJA4 |
| 1 | ENSG00000187678 | SPRY4 |
| 1 | ENSG00000187720 | THSD4 |
| 1 | ENSG00000187955 | COL14A1 |
| 1 | ENSG00000188153 | COL4A5 |
| 1 | ENSG00000188677 | PARVB |
| 1 | ENSG00000189376 | C8orf76 |
| 1 | ENSG00000196139 | AKR1C3 |
| 1 | ENSG00000196569 | LAMA2 |
| 1 | ENSG00000197256 | KANK2 |
| 1 | ENSG00000197321 | SVIL |
| 1 | ENSG00000197380 | DACT3 |
| 1 | ENSG00000197461 | PDGFA |
| 1 | ENSG00000197467 | COL13A1 |
| 1 | ENSG00000197496 | SLC2A10 |
| 1 | ENSG00000197565 | COL4A6 |
| 1 | ENSG00000197614 | MFAP5 |
| 1 | ENSG00000197696 | NMB |
| 1 | ENSG00000198300 | PEG3 |
| 1 | ENSG00000198719 | DLL1 |
| 1 | ENSG00000198728 | LDB1 |
| 1 | ENSG00000198835 | GJC2 |
| 1 | ENSG00000198853 | RUSC2 |
| 1 | ENSG00000198873 | GRK5 |
| 1 | ENSG00000198885 | ITPRIPL1 |
| 1 | ENSG00000204175 | GPRIN2 |
| 1 | ENSG00000204262 | COL5A2 |
| 1 | ENSG00000204301 | NOTCH4 |
| 1 | ENSG00000205795 | CYS1 |
| 1 | ENSG00000211450 | C11orf31 |
| 1 | ENSG00000212747 | FAM127C |
| 1 | ENSG00000213689 | TREX1 |
| 1 | ENSG00000213903 | LTB4R |
| 1 | ENSG00000214860 | EVPLL |
| 1 | ENSG00000215218 | UBE2QL1 |
| 1 | ENSG00000221866 | PLXNA4 |
| 1 | ENSG00000221968 | FADS3 |
| 1 | ENSG00000224652 | LINC00885 |
| 1 | ENSG00000225950 | NTF4 |
| 1 | ENSG00000229852 |  |
| 1 | ENSG00000230937 | MIR205HG |
| 1 | ENSG00000231789 |  |
| 1 | ENSG00000239911 | PRKAG2-AS1 |
| 1 | ENSG00000240583 | AQP1 |
| 1 | ENSG00000240771 | ARHGEF25 |
| 1 | ENSG00000241127 | YAE1D1 |
| 1 | ENSG00000241644 | INMT |
| 1 | ENSG00000243244 | STON1 |
| 1 | ENSG00000250685 |  |
| 1 | ENSG00000251322 | SHANK3 |
| 1 | ENSG00000256309 |  |
| 1 | ENSG00000257026 |  |
| 1 | ENSG00000269113 | TRABD2B |
| 1 | ENSG00000269190 | FBXO17 |
| 1 | ENSG00000269905 |  |
| 1 | ENSG00000272327 |  |
| 1 | ENSG00000272734 | ADIRF-AS1 |
| 2 | ENSG00000001631 | KRIT1 |
| 2 | ENSG00000002016 | RAD52 |
| 2 | ENSG00000003756 | RBM5 |
| 2 | ENSG00000004534 | RBM6 |
| 2 | ENSG00000004777 | ARHGAP33 |
| 2 | ENSG00000006025 | OSBPL7 |
| 2 | ENSG00000006194 | ZNF263 |
| 2 | ENSG00000006530 | AGK |
| 2 | ENSG00000007392 | LUC7L |
| 2 | ENSG00000008128 | CDK11A |
| 2 | ENSG00000009724 | MASP2 |
| 2 | ENSG00000011021 | CLCN6 |
| 2 | ENSG00000011243 | AKAP8L |
| 2 | ENSG00000011376 | LARS2 |
| 2 | ENSG00000013441 | CLK1 |
| 2 | ENSG00000013561 | RNF14 |
| 2 | ENSG00000018189 | RUFY3 |
| 2 | ENSG00000028310 | BRD9 |
| 2 | ENSG00000032219 | ARID4A |
| 2 | ENSG00000033030 | ZCCHC8 |
| 2 | ENSG00000038358 | EDC4 |
| 2 | ENSG00000044446 | PHKA2 |
| 2 | ENSG00000047634 | SCML1 |
| 2 | ENSG00000051009 | FAM160A2 |
| 2 | ENSG00000053438 | NNAT |
| 2 | ENSG00000055955 | ITIH4 |
| 2 | ENSG00000056558 | TRAF1 |
| 2 | ENSG00000058673 | ZC3H11A |
| 2 | ENSG00000059588 | TARBP1 |
| 2 | ENSG00000061936 | SFSWAP |
| 2 | ENSG00000061987 | MON2 |
| 2 | ENSG00000064607 | SUGP2 |
| 2 | ENSG00000064687 | ABCA7 |
| 2 | ENSG00000067191 | CACNB1 |
| 2 | ENSG00000068697 | LAPTM4A |
| 2 | ENSG00000068745 | IP6K2 |
| 2 | ENSG00000069493 | CLEC2D |
| 2 | ENSG00000070476 | ZXDC |
| 2 | ENSG00000070610 | GBA2 |
| 2 | ENSG00000070669 | ASNS |
| 2 | ENSG00000073605 | GSDMB |
| 2 | ENSG00000074582 | BCS1L |
| 2 | ENSG00000074696 | PTPLAD1 |
| 2 | ENSG00000075413 | MARK3 |
| 2 | ENSG00000075826 | SEC31B |
| 2 | ENSG00000077458 | FAM76B |
| 2 | ENSG00000078403 | MLLT10 |
| 2 | ENSG00000079134 | THOC1 |
| 2 | ENSG00000081019 | RSBN1 |

TABLE 13-continued

| GeneModule | EnsemblID | GeneSymbols |
|---|---|---|
| 2 | ENSG00000081665 | ZNF506 |
| 2 | ENSG00000081791 | KIAA0141 |
| 2 | ENSG00000082258 | CCNT2 |
| 2 | ENSG00000084463 | WBP11 |
| 2 | ENSG00000085465 | OVGP1 |
| 2 | ENSG00000087087 | SRRT |
| 2 | ENSG00000087157 | PGS1 |
| 2 | ENSG00000088038 | CNOT3 |
| 2 | ENSG00000088448 | ANKRD10 |
| 2 | ENSG00000089280 | FUS |
| 2 | ENSG00000090432 | MUL1 |
| 2 | ENSG00000090905 | TNRC6A |
| 2 | ENSG00000092094 | OSGEP |
| 2 | ENSG00000092529 | CAPN3 |
| 2 | ENSG00000094631 | HDAC6 |
| 2 | ENSG00000094914 | AAAS |
| 2 | ENSG00000095066 | HOOK2 |
| 2 | ENSG00000095564 | BTAF1 |
| 2 | ENSG00000099251 | HSD17B7P2 |
| 2 | ENSG00000099940 | SNAP29 |
| 2 | ENSG00000099949 | LZTR1 |
| 2 | ENSG00000100038 | TOP3B |
| 2 | ENSG00000100068 | LRP5L |
| 2 | ENSG00000100197 | CYP2D6 |
| 2 | ENSG00000100201 | DDX17 |
| 2 | ENSG00000100288 | CHKB |
| 2 | ENSG00000100416 | TRMU |
| 2 | ENSG00000100445 | SDR39U1 |
| 2 | ENSG00000100483 | VCPKMT |
| 2 | ENSG00000100650 | SRSF5 |
| 2 | ENSG00000100726 | TELO2 |
| 2 | ENSG00000100813 | ACIN1 |
| 2 | ENSG00000100836 | PABPN1 |
| 2 | ENSG00000100941 | PNN |
| 2 | ENSG00000101049 | SGK2 |
| 2 | ENSG00000101104 | PABPC1L |
| 2 | ENSG00000101901 | ALG13 |
| 2 | ENSG00000102057 | KCND1 |
| 2 | ENSG00000102125 | TAZ |
| 2 | ENSG00000102287 | GABRE |
| 2 | ENSG00000102878 | HSF4 |
| 2 | ENSG00000102901 | CENPT |
| 2 | ENSG00000102908 | NFAT5 |
| 2 | ENSG00000103091 | WDR59 |
| 2 | ENSG00000103168 | TAF1C |
| 2 | ENSG00000104365 | IKBKB |
| 2 | ENSG00000104852 | SNRNP70 |
| 2 | ENSG00000104957 | CCDC130 |
| 2 | ENSG00000105127 | AKAP8 |
| 2 | ENSG00000105136 | ZNF419 |
| 2 | ENSG00000105612 | DNASE2 |
| 2 | ENSG00000105875 | WDR91 |
| 2 | ENSG00000106133 | NSUN5P2 |
| 2 | ENSG00000106344 | RBM28 |
| 2 | ENSG00000106608 | URGCP |
| 2 | ENSG00000106635 | BCL7B |
| 2 | ENSG00000108100 | CCNY |
| 2 | ENSG00000108296 | CWC25 |
| 2 | ENSG00000108389 | MTMR4 |
| 2 | ENSG00000108465 | CDK5RAP3 |
| 2 | ENSG00000108474 | PIGL |
| 2 | ENSG00000108654 | DDX5 |
| 2 | ENSG00000108773 | KAT2A |
| 2 | ENSG00000108799 | EZH1 |
| 2 | ENSG00000108848 | LUC7L3 |
| 2 | ENSG00000108963 | DPH1 |
| 2 | ENSG00000109046 | WSB1 |
| 2 | ENSG00000109063 | MYH3 |
| 2 | ENSG00000109920 | FNBP4 |
| 2 | ENSG00000110066 | SUV420H1 |
| 2 | ENSG00000110455 | ACCS |
| 2 | ENSG00000110721 | CHKA |
| 2 | ENSG00000110888 | CAPRIN2 |
| 2 | ENSG00000111011 | RSRC2 |
| 2 | ENSG00000111203 | ITFG2 |
| 2 | ENSG00000111231 | GPN3 |
| 2 | ENSG00000111271 | ACAD10 |
| 2 | ENSG00000111364 | DDX55 |
| 2 | ENSG00000111664 | GNB3 |
| 2 | ENSG00000111785 | RIC8B |
| 2 | ENSG00000111788 | |
| 2 | ENSG00000112309 | B3GAT2 |
| 2 | ENSG00000112357 | PEX7 |
| 2 | ENSG00000112983 | BRD8 |
| 2 | ENSG00000113108 | APBB3 |
| 2 | ENSG00000113240 | CLK4 |
| 2 | ENSG00000113649 | TCERG1 |
| 2 | ENSG00000113971 | NPHP3 |
| 2 | ENSG00000114742 | WDR48 |
| 2 | ENSG00000114770 | ABCC5 |
| 2 | ENSG00000114857 | NKTR |
| 2 | ENSG00000114982 | KANSL3 |
| 2 | ENSG00000115234 | SNX17 |
| 2 | ENSG00000115282 | TTC31 |
| 2 | ENSG00000115459 | ELMOD3 |
| 2 | ENSG00000115524 | SF3B1 |
| 2 | ENSG00000115875 | SRSF7 |
| 2 | ENSG00000116001 | TIA1 |
| 2 | ENSG00000116350 | SRSF4 |
| 2 | ENSG00000116497 | S100PBP |
| 2 | ENSG00000116560 | SFPQ |
| 2 | ENSG00000116580 | GON4L |
| 2 | ENSG00000116584 | ARHGEF2 |
| 2 | ENSG00000116754 | SRSF11 |
| 2 | ENSG00000116883 | |
| 2 | ENSG00000117360 | PRPF3 |
| 2 | ENSG00000117569 | PTBP2 |
| 2 | ENSG00000117616 | C1orf63 |
| 2 | ENSG00000117862 | TXNDC12 |
| 2 | ENSG00000118482 | PHF3 |
| 2 | ENSG00000118557 | PMFBP1 |
| 2 | ENSG00000119707 | RBM25 |
| 2 | ENSG00000119906 | FAM178A |
| 2 | ENSG00000120049 | KCNIP2 |
| 2 | ENSG00000120458 | MSANTD2 |
| 2 | ENSG00000120662 | MTRF1 |
| 2 | ENSG00000120798 | NR2C1 |
| 2 | ENSG00000120832 | MTERFD3 |
| 2 | ENSG00000121274 | PAPD5 |
| 2 | ENSG00000121310 | ECHDC2 |
| 2 | ENSG00000121454 | LHX4 |
| 2 | ENSG00000121716 | PILRB |
| 2 | ENSG00000122085 | MTERFD2 |
| 2 | ENSG00000122257 | RBBP6 |
| 2 | ENSG00000122678 | POLM |
| 2 | ENSG00000122965 | RBM19 |
| 2 | ENSG00000124098 | FAM210B |
| 2 | ENSG00000124160 | NCOA5 |
| 2 | ENSG00000124193 | SRSF6 |
| 2 | ENSG00000124222 | STX16 |
| 2 | ENSG00000124593 | PRICKLE4 |
| 2 | ENSG00000124743 | KLHL31 |
| 2 | ENSG00000125447 | GGA3 |
| 2 | ENSG00000125633 | CCDC93 |
| 2 | ENSG00000125814 | NAPB |
| 2 | ENSG00000125818 | PSMF1 |
| 2 | ENSG00000125846 | ZNF133 |
| 2 | ENSG00000126070 | AGO3 |
| 2 | ENSG00000126217 | MCF2L |
| 2 | ENSG00000126453 | BCL2L12 |
| 2 | ENSG00000126456 | IRF3 |
| 2 | ENSG00000126500 | FLRT1 |
| 2 | ENSG00000126746 | ZNF384 |
| 2 | ENSG00000126775 | ATG14 |
| 2 | ENSG00000127366 | TAS2R5 |
| 2 | ENSG00000127586 | CHTF18 |
| 2 | ENSG00000127957 | PMS2P3 |
| 2 | ENSG00000128000 | ZNF780B |
| 2 | ENSG00000128159 | TUBGCP6 |
| 2 | ENSG00000128563 | PRKRIP1 |
| 2 | ENSG00000128699 | ORMDL1 |
| 2 | ENSG00000128915 | NARG2 |
| 2 | ENSG00000129055 | ANAPC13 |
| 2 | ENSG00000129351 | ILF3 |
| 2 | ENSG00000129472 | RAB2B |
| 2 | ENSG00000129484 | PARP2 |

TABLE 13-continued

| GeneModule | EnsemblID | GeneSymbols |
|---|---|---|
| 2 | ENSG00000129933 | MAU2 |
| 2 | ENSG00000130254 | SAFB2 |
| 2 | ENSG00000130653 | PNPLA7 |
| 2 | ENSG00000130684 | ZNF337 |
| 2 | ENSG00000130948 | HSD17B3 |
| 2 | ENSG00000131051 | RBM39 |
| 2 | ENSG00000131127 | ZNF141 |
| 2 | ENSG00000131398 | KCNC3 |
| 2 | ENSG00000131591 | C1orf159 |
| 2 | ENSG00000131797 | CLUHP3 |
| 2 | ENSG00000132424 | PNISR |
| 2 | ENSG00000132485 | ZRANB2 |
| 2 | ENSG00000132680 | KIAA0907 |
| 2 | ENSG00000132780 | NASP |
| 2 | ENSG00000132793 | LPIN3 |
| 2 | ENSG00000132952 | USPL1 |
| 2 | ENSG00000133318 | RTN3 |
| 2 | ENSG00000133466 | C1QTNF6 |
| 2 | ENSG00000133619 | KRBA1 |
| 2 | ENSG00000133624 | ZNF767 |
| 2 | ENSG00000133858 | ZFC3H1 |
| 2 | ENSG00000134186 | PRPF38B |
| 2 | ENSG00000134253 | TRIM45 |
| 2 | ENSG00000134453 | RBM17 |
| 2 | ENSG00000134744 | ZCCHC11 |
| 2 | ENSG00000134884 | ARGLU1 |
| 2 | ENSG00000135164 | DMTF1 |
| 2 | ENSG00000135407 | AVIL |
| 2 | ENSG00000135437 | RDH5 |
| 2 | ENSG00000135473 | PAN2 |
| 2 | ENSG00000135637 | CCDC142 |
| 2 | ENSG00000135740 | SLC9A5 |
| 2 | ENSG00000135976 | ANKRD36 |
| 2 | ENSG00000136271 | DDX56 |
| 2 | ENSG00000136819 | C9orf78 |
| 2 | ENSG00000137185 | ZSCAN9 |
| 2 | ENSG00000137343 | ATAT1 |
| 2 | ENSG00000137504 | CREBZF |
| 2 | ENSG00000137776 | SLTM |
| 2 | ENSG00000137802 | MAPKBP1 |
| 2 | ENSG00000137817 | PARP6 |
| 2 | ENSG00000137822 | TUBGCP4 |
| 2 | ENSG00000138050 | THUMPD2 |
| 2 | ENSG00000138109 | CYP2C9 |
| 2 | ENSG00000138658 | C4orf21 |
| 2 | ENSG00000138834 | MAPK8IP3 |
| 2 | ENSG00000139190 | VAMP1 |
| 2 | ENSG00000139574 | NPFF |
| 2 | ENSG00000139631 | CSAD |
| 2 | ENSG00000139746 | RBM26 |
| 2 | ENSG00000139908 | TSSK4 |
| 2 | ENSG00000140009 | ESR2 |
| 2 | ENSG00000140181 | HERC2P2 |
| 2 | ENSG00000140398 | NEIL1 |
| 2 | ENSG00000140400 | MAN2C1 |
| 2 | ENSG00000140474 | ULK3 |
| 2 | ENSG00000140488 | CELF6 |
| 2 | ENSG00000140983 | RHOT2 |
| 2 | ENSG00000141068 | KSR1 |
| 2 | ENSG00000141258 | SGSM2 |
| 2 | ENSG00000141551 | CSNK1D |
| 2 | ENSG00000141564 | RPTOR |
| 2 | ENSG00000142102 | ATHL1 |
| 2 | ENSG00000142166 | IFNAR1 |
| 2 | ENSG00000142233 | NTN5 |
| 2 | ENSG00000143178 | TBX19 |
| 2 | ENSG00000143183 | TMCO1 |
| 2 | ENSG00000143190 | POU2F1 |
| 2 | ENSG00000143379 | SETDB1 |
| 2 | ENSG00000143434 | SEMA6C |
| 2 | ENSG00000143442 | POGZ |
| 2 | ENSG00000143630 | HCN3 |
| 2 | ENSG00000144026 | ZNF514 |
| 2 | ENSG00000144161 | ZC3H8 |
| 2 | ENSG00000144524 | COPS7B |
| 2 | ENSG00000145020 | AMT |
| 2 | ENSG00000145029 | NICN1 |
| 2 | ENSG00000145908 | ZNF300 |
| 2 | ENSG00000146021 | KLHL3 |
| 2 | ENSG00000146067 | FAM193B |
| 2 | ENSG00000146215 | CRIP3 |
| 2 | ENSG00000146556 | WASH2P |
| 2 | ENSG00000146826 | C7orf43 |
| 2 | ENSG00000146830 | GIGYF1 |
| 2 | ENSG00000146963 | C7orf55-LUC7L2 |
| 2 | ENSG00000147118 | ZNF182 |
| 2 | ENSG00000147121 | KRBOX4 |
| 2 | ENSG00000147162 | OGT |
| 2 | ENSG00000147174 | ACRC |
| 2 | ENSG00000147180 | ZNF711 |
| 2 | ENSG00000147437 | GNRH1 |
| 2 | ENSG00000147576 | ADHFE1 |
| 2 | ENSG00000147789 | ZNF7 |
| 2 | ENSG00000147854 | UHRF2 |
| 2 | ENSG00000148200 | NR6A1 |
| 2 | ENSG00000148399 | DPH7 |
| 2 | ENSG00000149532 | CPSF7 |
| 2 | ENSG00000151006 | PRSS53 |
| 2 | ENSG00000151303 | AGAP11 |
| 2 | ENSG00000151376 | ME3 |
| 2 | ENSG00000151849 | CENPJ |
| 2 | ENSG00000152042 | NBPF11 |
| 2 | ENSG00000152117 | |
| 2 | ENSG00000152433 | ZNF547 |
| 2 | ENSG00000152520 | PAN3 |
| 2 | ENSG00000152527 | PLEKHH2 |
| 2 | ENSG00000152795 | HNRNPDL |
| 2 | ENSG00000152926 | ZNF117 |
| 2 | ENSG00000153291 | SLC25A27 |
| 2 | ENSG00000153666 | GOLGA8I |
| 2 | ENSG00000153914 | SREK1 |
| 2 | ENSG00000154144 | TBRG1 |
| 2 | ENSG00000154263 | ABCA10 |
| 2 | ENSG00000154832 | CXXC1 |
| 2 | ENSG00000155229 | MMS19 |
| 2 | ENSG00000155256 | ZFYVE27 |
| 2 | ENSG00000155657 | TTN |
| 2 | ENSG00000155903 | RASA2 |
| 2 | ENSG00000156639 | ZFAND3 |
| 2 | ENSG00000156642 | NPTN |
| 2 | ENSG00000157306 | |
| 2 | ENSG00000157741 | UBN2 |
| 2 | ENSG00000157764 | BRAF |
| 2 | ENSG00000158286 | RNF207 |
| 2 | ENSG00000158805 | ZNF276 |
| 2 | ENSG00000158815 | FGF17 |
| 2 | ENSG00000159086 | PAXBP1 |
| 2 | ENSG00000159140 | SON |
| 2 | ENSG00000159346 | ADIPOR1 |
| 2 | ENSG00000159461 | AMFR |
| 2 | ENSG00000160072 | ATAD3B |
| 2 | ENSG00000160323 | ADAMTS13 |
| 2 | ENSG00000160781 | PAQR6 |
| 2 | ENSG00000160828 | STAG3L2 |
| 2 | ENSG00000160953 | MUM1 |
| 2 | ENSG00000160961 | ZNF333 |
| 2 | ENSG00000161265 | U2AF1L4 |
| 2 | ENSG00000161547 | SRSF2 |
| 2 | ENSG00000161664 | ASB16 |
| 2 | ENSG00000161912 | ADCY10P1 |
| 2 | ENSG00000162086 | ZNF75A |
| 2 | ENSG00000162231 | NXF1 |
| 2 | ENSG00000162408 | NOL9 |
| 2 | ENSG00000162461 | SLC25A34 |
| 2 | ENSG00000162526 | TSSK3 |
| 2 | ENSG00000162572 | SCNN1D |
| 2 | ENSG00000162601 | MYSM1 |
| 2 | ENSG00000162650 | ATXN7L2 |
| 2 | ENSG00000162735 | PEX19 |
| 2 | ENSG00000162997 | PRORSD1P |
| 2 | ENSG00000163354 | DCST2 |
| 2 | ENSG00000163660 | CCNL1 |
| 2 | ENSG00000163714 | U2SURP |
| 2 | ENSG00000163728 | TTC14 |
| 2 | ENSG00000163867 | ZMYM6 |

TABLE 13-continued

| GeneModule | EnsemblID | GeneSymbols |
|---|---|---|
| 2 | ENSG00000163945 | UVSSA |
| 2 | ENSG00000164048 | ZNF589 |
| 2 | ENSG00000164073 | MFSD8 |
| 2 | ENSG00000164074 | C4orf29 |
| 2 | ENSG00000164241 | C5orf63 |
| 2 | ENSG00000164406 | LEAP2 |
| 2 | ENSG00000164548 | TRA2A |
| 2 | ENSG00000164877 | MICALL2 |
| 2 | ENSG00000164879 | CA3 |
| 2 | ENSG00000165275 | TRMT10B |
| 2 | ENSG00000165494 | PCF11 |
| 2 | ENSG00000165699 | TSC1 |
| 2 | ENSG00000165792 | METTL17 |
| 2 | ENSG00000165819 | METTL3 |
| 2 | ENSG00000166012 | TAF1D |
| 2 | ENSG00000166169 | POLL |
| 2 | ENSG00000166261 | ZNF202 |
| 2 | ENSG00000166321 | NUDT13 |
| 2 | ENSG00000166343 | MSS51 |
| 2 | ENSG00000166405 | RIC3 |
| 2 | ENSG00000166432 | ZMAT1 |
| 2 | ENSG00000166436 | TRIM66 |
| 2 | ENSG00000166667 | SPDYE6 |
| 2 | ENSG00000166762 | CATSPER2 |
| 2 | ENSG00000166801 | FAM111A |
| 2 | ENSG00000166887 | VPS39 |
| 2 | ENSG00000167280 | ENGASE |
| 2 | ENSG00000167302 | ENTHD2 |
| 2 | ENSG00000167371 | PRRT2 |
| 2 | ENSG00000167380 | ZNF226 |
| 2 | ENSG00000167524 | |
| 2 | ENSG00000167549 | CORO6 |
| 2 | ENSG00000167566 | NCKAP5L |
| 2 | ENSG00000167615 | LENG8 |
| 2 | ENSG00000167674 | |
| 2 | ENSG00000167702 | KIFC2 |
| 2 | ENSG00000167766 | ZNF83 |
| 2 | ENSG00000167978 | SRRM2 |
| 2 | ENSG00000168005 | C11orf84 |
| 2 | ENSG00000168010 | ATG16L2 |
| 2 | ENSG00000168066 | SF1 |
| 2 | ENSG00000168096 | ANKS3 |
| 2 | ENSG00000168137 | SETD5 |
| 2 | ENSG00000168310 | IRF2 |
| 2 | ENSG00000168395 | ING5 |
| 2 | ENSG00000168566 | SNRNP48 |
| 2 | ENSG00000168614 | NBPF9 |
| 2 | ENSG00000168876 | ANKRD49 |
| 2 | ENSG00000168887 | C2orf68 |
| 2 | ENSG00000168939 | SPRY3 |
| 2 | ENSG00000168970 | JMJD7-PLA2G4B |
| 2 | ENSG00000169045 | HNRNPH1 |
| 2 | ENSG00000169131 | ZNF354A |
| 2 | ENSG00000169203 | |
| 2 | ENSG00000169246 | NPIPB3 |
| 2 | ENSG00000169592 | INO80E |
| 2 | ENSG00000169660 | HEXDC |
| 2 | ENSG00000169885 | CALML6 |
| 2 | ENSG00000169914 | OTUD3 |
| 2 | ENSG00000170049 | KCNAB3 |
| 2 | ENSG00000170074 | FAM153A |
| 2 | ENSG00000170234 | PWWP2A |
| 2 | ENSG00000170581 | STAT2 |
| 2 | ENSG00000170919 | TPT1-AS1 |
| 2 | ENSG00000170949 | ZNF160 |
| 2 | ENSG00000171163 | ZNF692 |
| 2 | ENSG00000171456 | ASXL1 |
| 2 | ENSG00000171824 | EXOSC10 |
| 2 | ENSG00000172273 | HINFP |
| 2 | ENSG00000172345 | STARD5 |
| 2 | ENSG00000172354 | GNB2 |
| 2 | ENSG00000172650 | AGAP5 |
| 2 | ENSG00000172732 | MUS81 |
| 2 | ENSG00000172803 | SNX32 |
| 2 | ENSG00000172890 | NADSYN1 |
| 2 | ENSG00000173064 | HECTD4 |
| 2 | ENSG00000173209 | AHSA2 |
| 2 | ENSG00000173275 | ZNF449 |
| 2 | ENSG00000173531 | MST1 |
| 2 | ENSG00000173575 | CHD2 |
| 2 | ENSG00000173681 | CXorf23 |
| 2 | ENSG00000173991 | TCAP |
| 2 | ENSG00000174093 | |
| 2 | ENSG00000174194 | AGAP8 |
| 2 | ENSG00000174353 | STAG3L3 |
| 2 | ENSG00000174652 | ZNF266 |
| 2 | ENSG00000175066 | GK5 |
| 2 | ENSG00000175265 | GOLGA8A |
| 2 | ENSG00000175309 | PHYKPL |
| 2 | ENSG00000175322 | ZNF519 |
| 2 | ENSG00000175455 | CCDC14 |
| 2 | ENSG00000175787 | ZNF169 |
| 2 | ENSG00000176444 | CLK2 |
| 2 | ENSG00000176681 | LRRC37A |
| 2 | ENSG00000176946 | THAP4 |
| 2 | ENSG00000177042 | TMEM80 |
| 2 | ENSG00000177202 | SPACA4 |
| 2 | ENSG00000177225 | PDDC1 |
| 2 | ENSG00000177479 | ARIH2 |
| 2 | ENSG00000177485 | ZBTB33 |
| 2 | ENSG00000177595 | PIDD |
| 2 | ENSG00000177853 | ZNF518A |
| 2 | ENSG00000177943 | MAMDC4 |
| 2 | ENSG00000178028 | DMAP1 |
| 2 | ENSG00000178038 | ALS2CL |
| 2 | ENSG00000178188 | SH2B1 |
| 2 | ENSG00000178252 | WDR6 |
| 2 | ENSG00000178338 | ZNF354B |
| 2 | ENSG00000178397 | FAM220A |
| 2 | ENSG00000178567 | EPM2AIP1 |
| 2 | ENSG00000178761 | FAM219B |
| 2 | ENSG00000179304 | FAM156B |
| 2 | ENSG00000179406 | LINC00174 |
| 2 | ENSG00000179979 | CRIPAK |
| 2 | ENSG00000180113 | TDRD6 |
| 2 | ENSG00000180855 | ZNF443 |
| 2 | ENSG00000180902 | D2HGDH |
| 2 | ENSG00000181045 | SLC26A11 |
| 2 | ENSG00000181523 | SGSH |
| 2 | ENSG00000181852 | RNF41 |
| 2 | ENSG00000182230 | FAM153B |
| 2 | ENSG00000182308 | DCAF4L1 |
| 2 | ENSG00000182310 | SPACA6P |
| 2 | ENSG00000182324 | KCNJ14 |
| 2 | ENSG00000182378 | PLCXD1 |
| 2 | ENSG00000182473 | EXOC7 |
| 2 | ENSG00000182484 | WASH6P |
| 2 | ENSG00000182646 | FAM156A |
| 2 | ENSG00000182685 | BRICD5 |
| 2 | ENSG00000182796 | TMEM198B |
| 2 | ENSG00000182841 | RRP7B |
| 2 | ENSG00000182873 | |
| 2 | ENSG00000182944 | EWSR1 |
| 2 | ENSG00000182983 | ZNF662 |
| 2 | ENSG00000182986 | ZNF320 |
| 2 | ENSG00000183281 | PLGLB1 |
| 2 | ENSG00000183291 | |
| 2 | ENSG00000183423 | LRIT3 |
| 2 | ENSG00000183718 | TRIM52 |
| 2 | ENSG00000184343 | SRPK3 |
| 2 | ENSG00000184402 | SS18L1 |
| 2 | ENSG00000184441 | |
| 2 | ENSG00000184465 | WDR27 |
| 2 | ENSG00000184634 | MED12 |
| 2 | ENSG00000184640 | 9-Sep |
| 2 | ENSG00000184677 | ZBTB40 |
| 2 | ENSG00000184787 | UBE2G2 |
| 2 | ENSG00000184863 | RBM33 |
| 2 | ENSG00000184925 | LCN12 |
| 2 | ENSG00000185101 | ANO9 |
| 2 | ENSG00000185122 | HSF1 |
| 2 | ENSG00000185128 | TBC1D3F |
| 2 | ENSG00000185189 | NRBP2 |
| 2 | ENSG00000185219 | ZNF445 |
| 2 | ENSG00000185246 | PRPF39 |

TABLE 13-continued

| GeneModule | EnsemblID | GeneSymbols |
|---|---|---|
| 2 | ENSG00000185324 | CDK10 |
| 2 | ENSG00000185485 | SDHAP1 |
| 2 | ENSG00000185596 | WASH3P |
| 2 | ENSG00000185684 | EP400NL |
| 2 | ENSG00000185829 | ARL17A |
| 2 | ENSG00000185842 | DNAH14 |
| 2 | ENSG00000185864 | NPIPB4 |
| 2 | ENSG00000185946 | RNPC3 |
| 2 | ENSG00000185986 | SDHAP3 |
| 2 | ENSG00000186088 | GSAP |
| 2 | ENSG00000186166 | CCDC84 |
| 2 | ENSG00000186204 | CYP4F12 |
| 2 | ENSG00000186275 | NBPF12 |
| 2 | ENSG00000186283 | TOR3A |
| 2 | ENSG00000186301 | MST1P2 |
| 2 | ENSG00000186376 | ZNF75D |
| 2 | ENSG00000186566 | GPATCH8 |
| 2 | ENSG00000186567 | CEACAM19 |
| 2 | ENSG00000186715 | MST1L |
| 2 | ENSG00000186812 | ZNF397 |
| 2 | ENSG00000186814 | ZSCAN30 |
| 2 | ENSG00000186834 | HEXIM1 |
| 2 | ENSG00000186908 | ZDHHC17 |
| 2 | ENSG00000187066 | TMEM262 |
| 2 | ENSG00000187961 | KLHL17 |
| 2 | ENSG00000188206 | HNRNPU-AS1 |
| 2 | ENSG00000188227 | ZNF793 |
| 2 | ENSG00000188234 | AGAP4 |
| 2 | ENSG00000188428 | BLOC1S5 |
| 2 | ENSG00000188529 | SRSF10 |
| 2 | ENSG00000188554 | NBR1 |
| 2 | ENSG00000188738 | FSIP2 |
| 2 | ENSG00000188811 | NHLRC3 |
| 2 | ENSG00000188827 | SLX4 |
| 2 | ENSG00000189007 | ADAT2 |
| 2 | ENSG00000189136 | UBE2Q2P1 |
| 2 | ENSG00000196074 | SYCP2 |
| 2 | ENSG00000196123 | KIAA0895L |
| 2 | ENSG00000196295 | |
| 2 | ENSG00000196296 | ATP2A1 |
| 2 | ENSG00000196387 | ZNF140 |
| 2 | ENSG00000196409 | ZNF658 |
| 2 | ENSG00000196440 | ARMCX4 |
| 2 | ENSG00000196644 | GPR89C |
| 2 | ENSG00000196648 | GOLGA6L20 |
| 2 | ENSG00000196670 | ZFP62 |
| 2 | ENSG00000196689 | TRPV1 |
| 2 | ENSG00000196696 | PDXDC2P |
| 2 | ENSG00000196757 | ZNF700 |
| 2 | ENSG00000196912 | ANKRD36B |
| 2 | ENSG00000197119 | SLC25A29 |
| 2 | ENSG00000197124 | ZNF682 |
| 2 | ENSG00000197162 | ZNF785 |
| 2 | ENSG00000197182 | |
| 2 | ENSG00000197343 | ZNF655 |
| 2 | ENSG00000197558 | SSPO |
| 2 | ENSG00000197608 | ZNF841 |
| 2 | ENSG00000197681 | TBC1D3 |
| 2 | ENSG00000197774 | EME2 |
| 2 | ENSG00000197857 | ZNF44 |
| 2 | ENSG00000197948 | FCHSD1 |
| 2 | ENSG00000197961 | ZNF121 |
| 2 | ENSG00000197976 | AKAP17A |
| 2 | ENSG00000197989 | SNHG12 |
| 2 | ENSG00000198035 | AGAP9 |
| 2 | ENSG00000198040 | ZNF84 |
| 2 | ENSG00000198064 | |
| 2 | ENSG00000198105 | ZNF248 |
| 2 | ENSG00000198150 | |
| 2 | ENSG00000198198 | SZT2 |
| 2 | ENSG00000198231 | DDX42 |
| 2 | ENSG00000198276 | UCKL1 |
| 2 | ENSG00000198393 | ZNF26 |
| 2 | ENSG00000198556 | ZNF789 |
| 2 | ENSG00000198563 | DDX39B |
| 2 | ENSG00000198590 | C3orf35 |
| 2 | ENSG00000198625 | MDM4 |
| 2 | ENSG00000198799 | LRIG2 |
| 2 | ENSG00000203392 | |
| 2 | ENSG00000203667 | COX20 |
| 2 | ENSG00000203709 | C1orf132 |
| 2 | ENSG00000203761 | MSTO2P |
| 2 | ENSG00000203815 | FAM231D |
| 2 | ENSG00000203880 | PCMTD2 |
| 2 | ENSG00000204149 | AGAP6 |
| 2 | ENSG00000204164 | BMS1P5 |
| 2 | ENSG00000204271 | SPIN3 |
| 2 | ENSG00000204305 | AGER |
| 2 | ENSG00000204311 | DFNB59 |
| 2 | ENSG00000204348 | DXO |
| 2 | ENSG00000204351 | SKIV2L |
| 2 | ENSG00000204410 | MSH5 |
| 2 | ENSG00000204514 | ZNF814 |
| 2 | ENSG00000204576 | PRR3 |
| 2 | ENSG00000204681 | GABBR1 |
| 2 | ENSG00000204946 | ZNF783 |
| 2 | ENSG00000205047 | |
| 2 | ENSG00000205085 | FAM71F2 |
| 2 | ENSG00000205238 | SPDYE2 |
| 2 | ENSG00000205307 | SAP25 |
| 2 | ENSG00000205560 | CPT1B |
| 2 | ENSG00000205583 | STAG3L1 |
| 2 | ENSG00000205885 | C1RL-AS1 |
| 2 | ENSG00000205890 | |
| 2 | ENSG00000205923 | CEMP1 |
| 2 | ENSG00000205959 | |
| 2 | ENSG00000206149 | HERC2P9 |
| 2 | ENSG00000206417 | H1FX-AS1 |
| 2 | ENSG00000206573 | SETD5-AS1 |
| 2 | ENSG00000211454 | AKR7L |
| 2 | ENSG00000212123 | PRR22 |
| 2 | ENSG00000212127 | TAS2R14 |
| 2 | ENSG00000212694 | |
| 2 | ENSG00000213139 | CRYGS |
| 2 | ENSG00000213190 | MLLT11 |
| 2 | ENSG00000213246 | SUPT4H1 |
| 2 | ENSG00000213339 | QTRT1 |
| 2 | ENSG00000213347 | MXD3 |
| 2 | ENSG00000213443 | |
| 2 | ENSG00000213599 | SLX1A-SULT1A3 |
| 2 | ENSG00000213901 | SLC23A3 |
| 2 | ENSG00000213918 | DNASE1 |
| 2 | ENSG00000213983 | AP1G2 |
| 2 | ENSG00000213999 | MEF2B |
| 2 | ENSG00000214021 | TTLL3 |
| 2 | ENSG00000214135 | |
| 2 | ENSG00000214176 | PLEKHM1P |
| 2 | ENSG00000214279 | |
| 2 | ENSG00000214331 | |
| 2 | ENSG00000214455 | RCN1P2 |
| 2 | ENSG00000214756 | METTL12 |
| 2 | ENSG00000214765 | SEPT7P2 |
| 2 | ENSG00000214783 | POLR2J4 |
| 2 | ENSG00000214826 | DDX12P |
| 2 | ENSG00000214827 | MTCP1 |
| 2 | ENSG00000215022 | |
| 2 | ENSG00000215041 | NEURL4 |
| 2 | ENSG00000215126 | CBWD7 |
| 2 | ENSG00000215158 | |
| 2 | ENSG00000215252 | GOLGA8B |
| 2 | ENSG00000215298 | |
| 2 | ENSG00000215375 | MYL5 |
| 2 | ENSG00000215417 | MIR17HG |
| 2 | ENSG00000215424 | MCM3AP-AS1 |
| 2 | ENSG00000215440 | NPEPL1 |
| 2 | ENSG00000215513 | PI4KAP1 |
| 2 | ENSG00000215769 | |
| 2 | ENSG00000215788 | TNFRSF25 |
| 2 | ENSG00000216937 | CCDC7 |
| 2 | ENSG00000218891 | ZNF579 |
| 2 | ENSG00000220201 | ZGLP1 |
| 2 | ENSG00000221944 | TIGD1 |
| 2 | ENSG00000221978 | CCNL2 |
| 2 | ENSG00000223509 | |

TABLE 13-continued

| GeneModule | EnsemblID | GeneSymbols |
|---|---|---|
| 2 | ENSG00000223705 | NSUN5P1 |
| 2 | ENSG00000223745 | |
| 2 | ENSG00000223839 | FAM95B1 |
| 2 | ENSG00000223959 | AFG3L1P |
| 2 | ENSG00000224186 | C5orf66 |
| 2 | ENSG00000224660 | SH3BP5-AS1 |
| 2 | ENSG00000224956 | |
| 2 | ENSG00000224975 | INE1 |
| 2 | ENSG00000225032 | |
| 2 | ENSG00000225138 | |
| 2 | ENSG00000225313 | |
| 2 | ENSG00000225373 | WASH5P |
| 2 | ENSG00000225697 | SLC26A6 |
| 2 | ENSG00000225828 | FAM229A |
| 2 | ENSG00000225855 | RUSC1-AS1 |
| 2 | ENSG00000225892 | |
| 2 | ENSG00000226232 | |
| 2 | ENSG00000226332 | |
| 2 | ENSG00000226696 | LENG8-AS1 |
| 2 | ENSG00000226763 | SRRM5 |
| 2 | ENSG00000227232 | WASH7P |
| 2 | ENSG00000227543 | SPAG5-AS1 |
| 2 | ENSG00000227671 | MIR3916 |
| 2 | ENSG00000227896 | |
| 2 | ENSG00000228274 | |
| 2 | ENSG00000228315 | GUSBP11 |
| 2 | ENSG00000228393 | LINC01004 |
| 2 | ENSG00000228409 | CCT6P1 |
| 2 | ENSG00000228492 | RAB11FIP1P1 |
| 2 | ENSG00000228784 | LINC00954 |
| 2 | ENSG00000229180 | |
| 2 | ENSG00000229186 | ADAM1A |
| 2 | ENSG00000230124 | |
| 2 | ENSG00000230373 | GOLGA6L5P |
| 2 | ENSG00000230454 | |
| 2 | ENSG00000230551 | |
| 2 | ENSG00000230606 | |
| 2 | ENSG00000230715 | |
| 2 | ENSG00000232807 | |
| 2 | ENSG00000233137 | |
| 2 | ENSG00000233175 | |
| 2 | ENSG00000233184 | |
| 2 | ENSG00000234072 | |
| 2 | ENSG00000234290 | |
| 2 | ENSG00000234353 | |
| 2 | ENSG00000234420 | ZNF37BP |
| 2 | ENSG00000234585 | CCT6P3 |
| 2 | ENSG00000234616 | JRK |
| 2 | ENSG00000234631 | |
| 2 | ENSG00000234769 | WASH4P |
| 2 | ENSG00000234771 | |
| 2 | ENSG00000234912 | LINC00338 |
| 2 | ENSG00000235016 | |
| 2 | ENSG00000235194 | PPP1R3E |
| 2 | ENSG00000235381 | |
| 2 | ENSG00000235703 | LINC00894 |
| 2 | ENSG00000235999 | |
| 2 | ENSG00000236017 | ASMTL-AS1 |
| 2 | ENSG00000236088 | COX10-AS1 |
| 2 | ENSG00000236144 | |
| 2 | ENSG00000236255 | |
| 2 | ENSG00000236287 | ZBED5 |
| 2 | ENSG00000236438 | FAM157A |
| 2 | ENSG00000237298 | TTN-AS1 |
| 2 | ENSG00000237441 | RGL2 |
| 2 | ENSG00000237491 | |
| 2 | ENSG00000238083 | LRRC37A2 |
| 2 | ENSG00000239382 | ALKBH6 |
| 2 | ENSG00000239665 | |
| 2 | ENSG00000240038 | AMY2B |
| 2 | ENSG00000240053 | LY6G5B |
| 2 | ENSG00000240288 | GHRLOS |
| 2 | ENSG00000240291 | |
| 2 | ENSG00000240731 | |
| 2 | ENSG00000241014 | |
| 2 | ENSG00000241058 | NSUN6 |
| 2 | ENSG00000241404 | EGFL8 |
| 2 | ENSG00000241489 | |
| 2 | ENSG00000241528 | |
| 2 | ENSG00000241769 | LINC00893 |
| 2 | ENSG00000242028 | HYPK |
| 2 | ENSG00000242125 | SNHG3 |
| 2 | ENSG00000242282 | |
| 2 | ENSG00000242384 | TBC1D3H |
| 2 | ENSG00000242802 | AP5Z1 |
| 2 | ENSG00000242861 | |
| 2 | ENSG00000242866 | STRC |
| 2 | ENSG00000243155 | |
| 2 | ENSG00000243302 | |
| 2 | ENSG00000243452 | NBPF15 |
| 2 | ENSG00000243679 | |
| 2 | ENSG00000243708 | PLA2G4B |
| 2 | ENSG00000243716 | NPIPB5 |
| 2 | ENSG00000244119 | PDCL3P4 |
| 2 | ENSG00000244151 | |
| 2 | ENSG00000244480 | |
| 2 | ENSG00000244560 | |
| 2 | ENSG00000244754 | N4BP2L2 |
| 2 | ENSG00000244879 | GABPB1-AS1 |
| 2 | ENSG00000245149 | RNF139-AS1 |
| 2 | ENSG00000245532 | NEAT1 |
| 2 | ENSG00000245849 | RAD51-AS1 |
| 2 | ENSG00000245970 | |
| 2 | ENSG00000246090 | |
| 2 | ENSG00000246339 | EXTL3-AS1 |
| 2 | ENSG00000246451 | |
| 2 | ENSG00000246922 | UBAP1L |
| 2 | ENSG00000247679 | |
| 2 | ENSG00000248019 | FAM13A-AS1 |
| 2 | ENSG00000248124 | RRN3P1 |
| 2 | ENSG00000249087 | C1orf213 |
| 2 | ENSG00000250067 | YJEFN3 |
| 2 | ENSG00000250506 | CDK3 |
| 2 | ENSG00000251022 | THAP9-AS1 |
| 2 | ENSG00000251136 | |
| 2 | ENSG00000251247 | ZNF345 |
| 2 | ENSG00000251364 | |
| 2 | ENSG00000251369 | ZNF550 |
| 2 | ENSG00000251432 | |
| 2 | ENSG00000251562 | MALAT1 |
| 2 | ENSG00000252690 | SCARNA15 |
| 2 | ENSG00000253106 | |
| 2 | ENSG00000253200 | |
| 2 | ENSG00000253352 | TUG1 |
| 2 | ENSG00000254363 | |
| 2 | ENSG00000254413 | CHKB-CPT1B |
| 2 | ENSG00000254815 | |
| 2 | ENSG00000254995 | STX16-NPEPL1 |
| 2 | ENSG00000255031 | |
| 2 | ENSG00000255182 | |
| 2 | ENSG00000255717 | SNHG1 |
| 2 | ENSG00000256028 | |
| 2 | ENSG00000256223 | ZNF10 |
| 2 | ENSG00000256294 | ZNF225 |
| 2 | ENSG00000256525 | POLG2 |
| 2 | ENSG00000256667 | KLRAP1 |
| 2 | ENSG00000257511 | |
| 2 | ENSG00000257621 | |
| 2 | ENSG00000258297 | |
| 2 | ENSG00000258311 | |
| 2 | ENSG00000258441 | LINC00641 |
| 2 | ENSG00000258461 | |
| 2 | ENSG00000258472 | |
| 2 | ENSG00000258634 | |
| 2 | ENSG00000258727 | |
| 2 | ENSG00000258839 | MC1R |
| 2 | ENSG00000258890 | CEP95 |
| 2 | ENSG00000259820 | |
| 2 | ENSG00000259865 | |
| 2 | ENSG00000259891 | |
| 2 | ENSG00000259972 | |
| 2 | ENSG00000259994 | |
| 2 | ENSG00000260091 | |
| 2 | ENSG00000260236 | |
| 2 | ENSG00000260257 | |

TABLE 13-continued

| GeneModule | EnsemblID | GeneSymbols |
|---|---|---|
| 2 | ENSG00000260296 | |
| 2 | ENSG00000260306 | |
| 2 | ENSG00000260565 | ERVK13-1 |
| 2 | ENSG00000260669 | |
| 2 | ENSG00000260711 | |
| 2 | ENSG00000260729 | |
| 2 | ENSG00000260772 | |
| 2 | ENSG00000260778 | MIR940 |
| 2 | ENSG00000260837 | |
| 2 | ENSG00000260872 | |
| 2 | ENSG00000260917 | |
| 2 | ENSG00000260924 | |
| 2 | ENSG00000260942 | CAPN10-AS1 |
| 2 | ENSG00000261015 | |
| 2 | ENSG00000261052 | SULT1A3 |
| 2 | ENSG00000261067 | |
| 2 | ENSG00000261087 | |
| 2 | ENSG00000261136 | |
| 2 | ENSG00000261139 | |
| 2 | ENSG00000261254 | |
| 2 | ENSG00000261286 | |
| 2 | ENSG00000261324 | |
| 2 | ENSG00000261326 | |
| 2 | ENSG00000261355 | |
| 2 | ENSG00000261408 | TEN1-CDK3 |
| 2 | ENSG00000261460 | |
| 2 | ENSG00000261488 | |
| 2 | ENSG00000261490 | |
| 2 | ENSG00000261505 | |
| 2 | ENSG00000261526 | |
| 2 | ENSG00000261556 | |
| 2 | ENSG00000261584 | |
| 2 | ENSG00000261613 | |
| 2 | ENSG00000261799 | |
| 2 | ENSG00000262580 | |
| 2 | ENSG00000262877 | |
| 2 | ENSG00000263020 | |
| 2 | ENSG00000263126 | |
| 2 | ENSG00000263198 | |
| 2 | ENSG00000263272 | |
| 2 | ENSG00000263276 | |
| 2 | ENSG00000263327 | TAPT1-AS1 |
| 2 | ENSG00000264098 | |
| 2 | ENSG00000264112 | |
| 2 | ENSG00000264538 | |
| 2 | ENSG00000264772 | SNORA67 |
| 2 | ENSG00000265298 | |
| 2 | ENSG00000265629 | |
| 2 | ENSG00000265690 | |
| 2 | ENSG00000266086 | |
| 2 | ENSG00000266714 | MYO15B |
| 2 | ENSG00000267152 | |
| 2 | ENSG00000267244 | |
| 2 | ENSG00000267281 | |
| 2 | ENSG00000267283 | |
| 2 | ENSG00000267680 | ZNF224 |
| 2 | ENSG00000267896 | |
| 2 | ENSG00000267940 | |
| 2 | ENSG00000268030 | |
| 2 | ENSG00000268220 | |
| 2 | ENSG00000268471 | MIR4453 |
| 2 | ENSG00000269131 | |
| 2 | ENSG00000269352 | |
| 2 | ENSG00000269399 | |
| 2 | ENSG00000269706 | |
| 2 | ENSG00000269751 | |
| 2 | ENSG00000269821 | KCNQ1OT1 |
| 2 | ENSG00000269928 | |
| 2 | ENSG00000269929 | |
| 2 | ENSG00000269958 | |
| 2 | ENSG00000270012 | |
| 2 | ENSG00000270015 | |
| 2 | ENSG00000270055 | |
| 2 | ENSG00000270069 | |
| 2 | ENSG00000270189 | |
| 2 | ENSG00000270574 | |
| 2 | ENSG00000271344 | |
| 2 | ENSG00000271430 | |
| 2 | ENSG00000271529 | CICP14 |
| 2 | ENSG00000271533 | |
| 2 | ENSG00000271795 | |
| 2 | ENSG00000271816 | |
| 2 | ENSG00000271857 | |
| 2 | ENSG00000271870 | |
| 2 | ENSG00000271895 | |
| 2 | ENSG00000271975 | |
| 2 | ENSG00000271997 | |
| 2 | ENSG00000272077 | |
| 2 | ENSG00000272141 | |
| 2 | ENSG00000272145 | NFYC-AS1 |
| 2 | ENSG00000272216 | |
| 2 | ENSG00000272316 | |
| 2 | ENSG00000272356 | |
| 2 | ENSG00000272455 | |
| 2 | ENSG00000272505 | |
| 2 | ENSG00000272578 | |
| 2 | ENSG00000272589 | ZSWIM8-AS1 |
| 2 | ENSG00000272631 | |
| 2 | ENSG00000272645 | |
| 2 | ENSG00000272658 | |
| 2 | ENSG00000272668 | |
| 2 | ENSG00000272720 | |
| 2 | ENSG00000272752 | STAG3L5P-PVRIG2P-PILRB |
| 2 | ENSG00000272782 | |
| 2 | ENSG00000272849 | |
| 2 | ENSG00000272916 | |
| 2 | ENSG00000272977 | |
| 2 | ENSG00000273000 | |
| 2 | ENSG00000273131 | |
| 2 | ENSG00000273137 | |
| 2 | ENSG00000273151 | |
| 2 | ENSG00000273271 | |
| 2 | ENSG00000273373 | |
| 2 | ENSG00000273466 | |
| 2 | ENSG00000273478 | |
| 3 | ENSG00000067082 | KLF6 |
| 3 | ENSG00000108551 | RASD1 |
| 3 | ENSG00000120129 | DUSP1 |
| 3 | ENSG00000120738 | EGR1 |
| 3 | ENSG00000123358 | NR4A1 |
| 3 | ENSG00000125740 | FOSB |
| 3 | ENSG00000128016 | ZFP36 |
| 3 | ENSG00000128342 | LIF |
| 3 | ENSG00000137331 | IER3 |
| 3 | ENSG00000139318 | DUSP6 |
| 3 | ENSG00000142178 | SIK1 |
| 3 | ENSG00000148339 | SLC25A25 |
| 3 | ENSG00000153234 | NR4A2 |
| 3 | ENSG00000158050 | DUSP2 |
| 3 | ENSG00000159388 | BTG2 |
| 3 | ENSG00000160888 | IER2 |
| 3 | ENSG00000170345 | FOS |
| 3 | ENSG00000171223 | JUNB |
| 3 | ENSG00000177606 | JUN |
| 3 | ENSG00000198355 | PIM3 |
| 4 | ENSG00000062582 | MRPS24 |
| 4 | ENSG00000065518 | NDUFB4 |
| 4 | ENSG00000090266 | NDUFB2 |
| 4 | ENSG00000099341 | PSMD8 |
| 4 | ENSG00000099795 | NDUFB7 |
| 4 | ENSG00000100216 | TOMM22 |
| 4 | ENSG00000103363 | TCEB2 |
| 4 | ENSG00000106153 | CHCHD2 |
| 4 | ENSG00000110801 | PSMD9 |
| 4 | ENSG00000111639 | MRPL51 |
| 4 | ENSG00000111775 | COX6A1 |
| 4 | ENSG00000112695 | COX7A2 |
| 4 | ENSG00000116459 | ATP5F1 |
| 4 | ENSG00000119013 | NDUFB3 |
| 4 | ENSG00000120509 | PDZD11 |
| 4 | ENSG00000125356 | NDUFA1 |
| 4 | ENSG00000125445 | MRPS7 |
| 4 | ENSG00000125995 | ROMO1 |
| 4 | ENSG00000126267 | COX6B1 |

TABLE 13-continued

| GeneModule | EnsemblID | GeneSymbols |
|---|---|---|
| 4 | ENSG00000126768 | TIMM17B |
| 4 | ENSG00000127540 | UQCR11 |
| 4 | ENSG00000127774 | EMC6 |
| 4 | ENSG00000131174 | COX7B |
| 4 | ENSG00000135441 | BLOC1S1 |
| 4 | ENSG00000135940 | COX5B |
| 4 | ENSG00000136930 | PSMB7 |
| 4 | ENSG00000140990 | NDUFB10 |
| 4 | ENSG00000141552 | ANAPC11 |
| 4 | ENSG00000141759 | TXNL4A |
| 4 | ENSG00000143977 | SNRPG |
| 4 | ENSG00000145494 | NDUFS6 |
| 4 | ENSG00000150779 | TIMM8B |
| 4 | ENSG00000151366 | NDUFC2 |
| 4 | ENSG00000155368 | DBI |
| 4 | ENSG00000156411 | C14orf2 |
| 4 | ENSG00000163634 | THOC7 |
| 4 | ENSG00000164405 | UQCRQ |
| 4 | ENSG00000164919 | COX6C |
| 4 | ENSG00000165264 | NDUFB6 |
| 4 | ENSG00000165283 | STOML2 |
| 4 | ENSG00000166136 | NDUFB8 |
| 4 | ENSG00000169020 | ATP5I |
| 4 | ENSG00000169021 | UQCRFS1 |
| 4 | ENSG00000171421 | MRPL36 |
| 4 | ENSG00000172428 | MYEOV2 |
| 4 | ENSG00000172586 | CHCHD1 |
| 4 | ENSG00000173436 | MINOS1 |
| 4 | ENSG00000173915 | USMG5 |
| 4 | ENSG00000176340 | COX8A |
| 4 | ENSG00000177700 | POLR2L |
| 4 | ENSG00000178307 | TMEM11 |
| 4 | ENSG00000178741 | COX5A |
| 4 | ENSG00000183617 | MRPL54 |
| 4 | ENSG00000184076 | UQCR10 |
| 4 | ENSG00000184752 | NDUFA12 |
| 4 | ENSG00000185721 | DRG1 |
| 4 | ENSG00000186010 | NDUFA13 |
| 4 | ENSG00000188612 | SUMO2 |
| 4 | ENSG00000189043 | NDUFA4 |
| 4 | ENSG00000198522 | GPN1 |
| 4 | ENSG00000204922 | C11orf83 |
| 4 | ENSG00000213619 | NDUFS3 |
| 4 | ENSG00000241468 | ATP5J2 |
| 4 | ENSG00000262814 | MRPL12 |
| 5 | ENSG00000000460 | C1orf112 |
| 5 | ENSG00000004142 | POLDIP2 |
| 5 | ENSG00000006634 | DBF4 |
| 5 | ENSG00000007968 | E2F2 |
| 5 | ENSG00000010292 | NCAPD2 |
| 5 | ENSG00000011426 | ANLN |
| 5 | ENSG00000024526 | DEPDC1 |
| 5 | ENSG00000034063 | UHRF1 |
| 5 | ENSG00000040275 | SPDL1 |
| 5 | ENSG00000048140 | TSPAN17 |
| 5 | ENSG00000049541 | RFC2 |
| 5 | ENSG00000051180 | RAD51 |
| 5 | ENSG00000055044 | NOP58 |
| 5 | ENSG00000066279 | ASPM |
| 5 | ENSG00000068489 | PRR11 |
| 5 | ENSG00000072571 | HMMR |
| 5 | ENSG00000075218 | GTSE1 |
| 5 | ENSG00000075702 | WDR62 |
| 5 | ENSG00000077152 | UBE2T |
| 5 | ENSG00000080986 | NDC80 |
| 5 | ENSG00000085840 | ORC1 |
| 5 | ENSG00000085999 | RAD54L |
| 5 | ENSG00000087111 | PIGS |
| 5 | ENSG00000087586 | AURKA |
| 5 | ENSG00000088325 | TPX2 |
| 5 | ENSG00000089685 | BIRC5 |
| 5 | ENSG00000090889 | KIF4A |
| 5 | ENSG00000091651 | ORC6 |
| 5 | ENSG00000093009 | CDC45 |
| 5 | ENSG00000094804 | CDC6 |
| 5 | ENSG00000097046 | CDC7 |
| 5 | ENSG00000100297 | MCM5 |
| 5 | ENSG00000100526 | CDKN3 |
| 5 | ENSG00000100600 | LGMN |
| 5 | ENSG00000101003 | GINS1 |
| 5 | ENSG00000101057 | MYBL2 |
| 5 | ENSG00000101412 | E2F1 |
| 5 | ENSG00000101945 | SUV39H1 |
| 5 | ENSG00000102384 | CENPI |
| 5 | ENSG00000104064 | GABPB1 |
| 5 | ENSG00000104738 | MCM4 |
| 5 | ENSG00000104889 | RNASEH2A |
| 5 | ENSG00000105011 | ASF1B |
| 5 | ENSG00000105135 | ILVBL |
| 5 | ENSG00000106462 | EZH2 |
| 5 | ENSG00000108106 | UBE2S |
| 5 | ENSG00000109805 | NCAPG |
| 5 | ENSG00000111206 | FOXM1 |
| 5 | ENSG00000111247 | RAD51AP1 |
| 5 | ENSG00000111445 | RFC5 |
| 5 | ENSG00000111602 | TIMELESS |
| 5 | ENSG00000112118 | MCM3 |
| 5 | ENSG00000112578 | BYSL |
| 5 | ENSG00000112742 | TTK |
| 5 | ENSG00000112984 | KIF20A |
| 5 | ENSG00000113368 | LMNB1 |
| 5 | ENSG00000113810 | SMC4 |
| 5 | ENSG00000116212 | LRRC42 |
| 5 | ENSG00000116478 | HDAC1 |
| 5 | ENSG00000116830 | TTF2 |
| 5 | ENSG00000117399 | CDC20 |
| 5 | ENSG00000117632 | STMN1 |
| 5 | ENSG00000117724 | CENPF |
| 5 | ENSG00000118193 | KIF14 |
| 5 | ENSG00000119969 | HELLS |
| 5 | ENSG00000120254 | MTHFD1L |
| 5 | ENSG00000120539 | MASTL |
| 5 | ENSG00000120647 | CCDC77 |
| 5 | ENSG00000120802 | TMPO |
| 5 | ENSG00000121152 | NCAPH |
| 5 | ENSG00000121621 | KIF18A |
| 5 | ENSG00000122483 | CCDC18 |
| 5 | ENSG00000122566 | HNRNPA2B1 |
| 5 | ENSG00000122952 | ZWINT |
| 5 | ENSG00000123219 | CENPK |
| 5 | ENSG00000123416 | TUBA1B |
| 5 | ENSG00000123485 | HJURP |
| 5 | ENSG00000123975 | CKS2 |
| 5 | ENSG00000124207 | CSE1L |
| 5 | ENSG00000124766 | SOX4 |
| 5 | ENSG00000125319 | C17orf53 |
| 5 | ENSG00000125944 | HNRNPR |
| 5 | ENSG00000126787 | DLGAP5 |
| 5 | ENSG00000127564 | PKMYT1 |
| 5 | ENSG00000128274 | A4GALT |
| 5 | ENSG00000128944 | KNSTRN |
| 5 | ENSG00000129195 | FAM64A |
| 5 | ENSG00000130202 | PVRL2 |
| 5 | ENSG00000131153 | GINS2 |
| 5 | ENSG00000131269 | ABCB7 |
| 5 | ENSG00000131747 | TOP2A |
| 5 | ENSG00000132313 | MRPL35 |
| 5 | ENSG00000132646 | PCNA |
| 5 | ENSG00000134057 | CCNB1 |
| 5 | ENSG00000134690 | CDCA8 |
| 5 | ENSG00000135451 | TROAP |
| 5 | ENSG00000135476 | ESPL1 |
| 5 | ENSG00000135763 | URB2 |
| 5 | ENSG00000135823 | STX6 |
| 5 | ENSG00000136108 | CKAP2 |
| 5 | ENSG00000136122 | BORA |
| 5 | ENSG00000136492 | BRIP1 |
| 5 | ENSG00000136943 | CTSV |
| 5 | ENSG00000137449 | CPEB2 |
| 5 | ENSG00000137804 | NUSAP1 |
| 5 | ENSG00000137807 | KIF23 |
| 5 | ENSG00000137812 | CASC5 |
| 5 | ENSG00000138092 | CENPO |
| 5 | ENSG00000138160 | KIF11 |
| 5 | ENSG00000138180 | CEP55 |
| 5 | ENSG00000138442 | WDR12 |

TABLE 13-continued

| GeneModule | EnsemblID | GeneSymbols |
|---|---|---|
| 5 | ENSG00000138778 | CENPE |
| 5 | ENSG00000139618 | BRCA2 |
| 5 | ENSG00000139726 | DENR |
| 5 | ENSG00000139734 | DIAPH3 |
| 5 | ENSG00000140525 | FANCI |
| 5 | ENSG00000142731 | PLK4 |
| 5 | ENSG00000142945 | KIF2C |
| 5 | ENSG00000143228 | NUF2 |
| 5 | ENSG00000143476 | DTL |
| 5 | ENSG00000143493 | INTS7 |
| 5 | ENSG00000143621 | ILF2 |
| 5 | ENSG00000143942 | CHAC2 |
| 5 | ENSG00000144554 | FANCD2 |
| 5 | ENSG00000145386 | CCNA2 |
| 5 | ENSG00000145604 | SKP2 |
| 5 | ENSG00000145907 | G3BP1 |
| 5 | ENSG00000146410 | MTFR2 |
| 5 | ENSG00000146670 | CDCA5 |
| 5 | ENSG00000146918 | NCAPG2 |
| 5 | ENSG00000147140 | NONO |
| 5 | ENSG00000147274 | RBMX |
| 5 | ENSG00000147536 | GINS4 |
| 5 | ENSG00000148773 | MKI67 |
| 5 | ENSG00000149554 | CHEK1 |
| 5 | ENSG00000151287 | TEX30 |
| 5 | ENSG00000153044 | CENPH |
| 5 | ENSG00000154839 | SKA1 |
| 5 | ENSG00000154920 | EME1 |
| 5 | ENSG00000156970 | BUB1B |
| 5 | ENSG00000157456 | CCNB2 |
| 5 | ENSG00000159259 | CHAF1B |
| 5 | ENSG00000161800 | RACGAP1 |
| 5 | ENSG00000161888 | SPC24 |
| 5 | ENSG00000162062 | C16orf59 |
| 5 | ENSG00000162063 | CCNF |
| 5 | ENSG00000163507 | KIAA1524 |
| 5 | ENSG00000163808 | KIF15 |
| 5 | ENSG00000163923 | RPL39L |
| 5 | ENSG00000163950 | SLBP |
| 5 | ENSG00000164045 | CDC25A |
| 5 | ENSG00000164109 | MAD2L1 |
| 5 | ENSG00000164611 | PTTG1 |
| 5 | ENSG00000165304 | MELK |
| 5 | ENSG00000165480 | SKA3 |
| 5 | ENSG00000166451 | CENPN |
| 5 | ENSG00000166803 | KIAA0101 |
| 5 | ENSG00000166851 | PLK1 |
| 5 | ENSG00000167513 | CDT1 |
| 5 | ENSG00000167900 | TK1 |
| 5 | ENSG00000168078 | PBK |
| 5 | ENSG00000168393 | DTYMK |
| 5 | ENSG00000168411 | RFWD3 |
| 5 | ENSG00000168496 | FEN1 |
| 5 | ENSG00000168883 | USP39 |
| 5 | ENSG00000169607 | CKAP2L |
| 5 | ENSG00000169679 | BUB1 |
| 5 | ENSG00000170312 | CDK1 |
| 5 | ENSG00000171241 | SHCBP1 |
| 5 | ENSG00000171320 | ESCO2 |
| 5 | ENSG00000171848 | RRM2 |
| 5 | ENSG00000173207 | CKS1B |
| 5 | ENSG00000174442 | ZWILCH |
| 5 | ENSG00000175063 | UBE2C |
| 5 | ENSG00000175216 | CKAP5 |
| 5 | ENSG00000175305 | CCNE2 |
| 5 | ENSG00000176890 | TYMS |
| 5 | ENSG00000177191 | B3GNT8 |
| 5 | ENSG00000178999 | AURKB |
| 5 | ENSG00000179051 | RCC2 |
| 5 | ENSG00000179115 | FARSA |
| 5 | ENSG00000179632 | MAF1 |
| 5 | ENSG00000182481 | KPNA2 |
| 5 | ENSG00000182628 | SKA2 |
| 5 | ENSG00000183763 | TRAIP |
| 5 | ENSG00000183814 | LIN9 |
| 5 | ENSG00000183856 | IQGAP3 |
| 5 | ENSG00000184661 | CDCA2 |
| 5 | ENSG00000185480 | PARPBP |
| 5 | ENSG00000186185 | KIF18B |
| 5 | ENSG00000186871 | ERCC6L |
| 5 | ENSG00000187514 | PTMA |
| 5 | ENSG00000187741 | FANCA |
| 5 | ENSG00000188486 | H2AFX |
| 5 | ENSG00000188610 | FAM72B |
| 5 | ENSG00000189057 | FAM111B |
| 5 | ENSG00000196419 | XRCC6 |
| 5 | ENSG00000196550 | FAM72A |
| 5 | ENSG00000196584 | XRCC2 |
| 5 | ENSG00000198331 | HYLS1 |
| 5 | ENSG00000198826 | ARHGAP11A |
| 5 | ENSG00000198901 | PRC1 |
| 5 | ENSG00000203760 | CENPW |
| 5 | ENSG00000204392 | LSM2 |
| 5 | ENSG00000213186 | TRIM59 |
| 5 | ENSG00000215784 | FAM72D |
| 5 | ENSG00000228716 | DHFR |
| 5 | ENSG00000237649 | KIFC1 |
| 5 | ENSG00000247077 | PGAM5 |
| 6 | ENSG00000001460 | STPG1 |
| 6 | ENSG00000003096 | KLHL13 |
| 6 | ENSG00000003989 | SLC7A2 |
| 6 | ENSG00000004838 | ZMYND10 |
| 6 | ENSG00000004848 | ARX |
| 6 | ENSG00000005100 | DHX33 |
| 6 | ENSG00000005448 | WDR54 |
| 6 | ENSG00000006740 | ARHGAP44 |
| 6 | ENSG00000006837 | CDKL3 |
| 6 | ENSG00000007062 | PROM1 |
| 6 | ENSG00000007174 | DNAH9 |
| 6 | ENSG00000007237 | GAS7 |
| 6 | ENSG00000007384 | RHBDF1 |
| 6 | ENSG00000007866 | TEAD3 |
| 6 | ENSG00000008083 | JARID2 |
| 6 | ENSG00000010361 | FUZ |
| 6 | ENSG00000010626 | LRRC23 |
| 6 | ENSG00000011143 | MKS1 |
| 6 | ENSG00000011295 | TTC19 |
| 6 | ENSG00000011485 | PPP5C |
| 6 | ENSG00000016402 | IL20RA |
| 6 | ENSG00000016864 | GLT8D1 |
| 6 | ENSG00000021300 | PLEKHB1 |
| 6 | ENSG00000021645 | NRXN3 |
| 6 | ENSG00000024862 | CCDC28A |
| 6 | ENSG00000025156 | HSF2 |
| 6 | ENSG00000025772 | TOMM34 |
| 6 | ENSG00000026508 | CD44 |
| 6 | ENSG00000032742 | IFT88 |
| 6 | ENSG00000034239 | EFCAB1 |
| 6 | ENSG00000036672 | USP2 |
| 6 | ENSG00000037474 | NSUN2 |
| 6 | ENSG00000039139 | DNAH5 |
| 6 | ENSG00000042317 | SPATA7 |
| 6 | ENSG00000043514 | TRIT1 |
| 6 | ENSG00000048342 | CC2D2A |
| 6 | ENSG00000048471 | SNX29 |
| 6 | ENSG00000048991 | R3HDM1 |
| 6 | ENSG00000049319 | SRD5A2 |
| 6 | ENSG00000049759 | NEDD4L |
| 6 | ENSG00000049769 | PPP1R3F |
| 6 | ENSG00000050327 | ARHGEF5 |
| 6 | ENSG00000051341 | POLQ |
| 6 | ENSG00000054219 | LY75 |
| 6 | ENSG00000054282 | SDCCAG8 |
| 6 | ENSG00000054392 | HHAT |
| 6 | ENSG00000054983 | GALC |
| 6 | ENSG00000056998 | GYG2 |
| 6 | ENSG00000057019 | DCBLD2 |
| 6 | ENSG00000058085 | LAMC2 |
| 6 | ENSG00000064199 | SPA17 |
| 6 | ENSG00000064692 | SNCAIP |
| 6 | ENSG00000064999 | ANKS1A |
| 6 | ENSG00000065357 | DGKA |
| 6 | ENSG00000065491 | TBC1D22B |
| 6 | ENSG00000065970 | FOXJ2 |
| 6 | ENSG00000066084 | DIP2B |
| 6 | ENSG00000066185 | ZMYND12 |

TABLE 13-continued

| GeneModule | EnsemblID | GeneSymbols |
|---|---|---|
| 6 | ENSG00000066248 | NGEF |
| 6 | ENSG00000066629 | EML1 |
| 6 | ENSG00000067208 | EVI5 |
| 6 | ENSG00000067369 | TP53BP1 |
| 6 | ENSG00000068650 | ATP11A |
| 6 | ENSG00000068885 | IFT80 |
| 6 | ENSG00000068971 | PPP2R5B |
| 6 | ENSG00000070444 | MNT |
| 6 | ENSG00000070718 | AP3M2 |
| 6 | ENSG00000070731 | ST6GALNAC2 |
| 6 | ENSG00000070761 | C16orf80 |
| 6 | ENSG00000071539 | TRIP13 |
| 6 | ENSG00000072133 | RPS6KA6 |
| 6 | ENSG00000072422 | RHOBTB1 |
| 6 | ENSG00000073050 | XRCC1 |
| 6 | ENSG00000073464 | CLCN4 |
| 6 | ENSG00000074621 | SLC24A1 |
| 6 | ENSG00000074964 | ARHGEF10L |
| 6 | ENSG00000075142 | SRI |
| 6 | ENSG00000075240 | GRAMD4 |
| 6 | ENSG00000075568 | TMEM131 |
| 6 | ENSG00000075945 | KIFAP3 |
| 6 | ENSG00000077327 | SPAG6 |
| 6 | ENSG00000077514 | POLD3 |
| 6 | ENSG00000077800 | FKBP6 |
| 6 | ENSG00000078246 | TULP3 |
| 6 | ENSG00000078487 | ZCWPW1 |
| 6 | ENSG00000078900 | TP73 |
| 6 | ENSG00000079156 | OSBPL6 |
| 6 | ENSG00000079335 | CDC14A |
| 6 | ENSG00000080298 | RFX3 |
| 6 | ENSG00000080572 | PIH1D3 |
| 6 | ENSG00000080824 | HSP90AA1 |
| 6 | ENSG00000081870 | HSPB11 |
| 6 | ENSG00000083290 | ULK2 |
| 6 | ENSG00000084764 | MAPRE3 |
| 6 | ENSG00000085063 | CD59 |
| 6 | ENSG00000085433 | WDR47 |
| 6 | ENSG00000086102 | NFX1 |
| 6 | ENSG00000086200 | IPO11 |
| 6 | ENSG00000087053 | MTMR2 |
| 6 | ENSG00000087152 | ATXN7L3 |
| 6 | ENSG00000087365 | SF3B2 |
| 6 | ENSG00000087510 | TFAP2C |
| 6 | ENSG00000087903 | RFX2 |
| 6 | ENSG00000088053 | GP6 |
| 6 | ENSG00000088320 | REM1 |
| 6 | ENSG00000088727 | KIF9 |
| 6 | ENSG00000088833 | NSFL1C |
| 6 | ENSG00000088970 | PLK1S1 |
| 6 | ENSG00000088986 | DYNLL1 |
| 6 | ENSG00000089060 | SLC8B1 |
| 6 | ENSG00000089091 | DZANK1 |
| 6 | ENSG00000089101 | C20orf26 |
| 6 | ENSG00000089123 | TASP1 |
| 6 | ENSG00000090273 | NUDC |
| 6 | ENSG00000090661 | CERS4 |
| 6 | ENSG00000090971 | NAT14 |
| 6 | ENSG00000091181 | IL5RA |
| 6 | ENSG00000092850 | TEKT2 |
| 6 | ENSG00000095261 | PSMD5 |
| 6 | ENSG00000095319 | NUP188 |
| 6 | ENSG00000096433 | ITPR3 |
| 6 | ENSG00000096872 | IFT74 |
| 6 | ENSG00000100012 | SEC14L3 |
| 6 | ENSG00000100124 | ANKRD54 |
| 6 | ENSG00000100162 | CENPM |
| 6 | ENSG00000100211 | CBY1 |
| 6 | ENSG00000100218 | RTDR1 |
| 6 | ENSG00000100228 | RAB36 |
| 6 | ENSG00000100271 | TTLL1 |
| 6 | ENSG00000100294 | MCAT |
| 6 | ENSG00000100345 | MYH9 |
| 6 | ENSG00000100418 | DESI1 |
| 6 | ENSG00000100422 | CERK |
| 6 | ENSG00000100441 | KHNYN |
| 6 | ENSG00000100462 | PRMT5 |
| 6 | ENSG00000100490 | CDKL1 |
| 6 | ENSG00000100583 | SAMD15 |
| 6 | ENSG00000100591 | AHSA1 |
| 6 | ENSG00000100625 | SIX4 |
| 6 | ENSG00000100784 | RPS6KA5 |
| 6 | ENSG00000101052 | IFT52 |
| 6 | ENSG00000101222 | SPEF1 |
| 6 | ENSG00000101448 | EPPIN |
| 6 | ENSG00000101928 | MOSPD1 |
| 6 | ENSG00000102048 | ASB9 |
| 6 | ENSG00000102230 | PCYT1B |
| 6 | ENSG00000102349 | KLF8 |
| 6 | ENSG00000102466 | FGF14 |
| 6 | ENSG00000102543 | CDADC1 |
| 6 | ENSG00000102738 | MRPS31 |
| 6 | ENSG00000102743 | SLC25A15 |
| 6 | ENSG00000102781 | KATNAL1 |
| 6 | ENSG00000102886 | GDPD3 |
| 6 | ENSG00000102996 | MMP15 |
| 6 | ENSG00000103021 | CCDC113 |
| 6 | ENSG00000103042 | SLC38A7 |
| 6 | ENSG00000103160 | HSDL1 |
| 6 | ENSG00000103174 | NAGPA |
| 6 | ENSG00000103194 | USP10 |
| 6 | ENSG00000103260 | METRN |
| 6 | ENSG00000103351 | CLUAP1 |
| 6 | ENSG00000103494 | RPGRIP1L |
| 6 | ENSG00000103540 | CCP110 |
| 6 | ENSG00000103599 | IQCH |
| 6 | ENSG00000103647 | CORO2B |
| 6 | ENSG00000103740 | ACSBG1 |
| 6 | ENSG00000103994 | ZNF106 |
| 6 | ENSG00000103995 | CEP152 |
| 6 | ENSG00000104237 | RP1 |
| 6 | ENSG00000104361 | NIPAL2 |
| 6 | ENSG00000104427 | ZC2HC1A |
| 6 | ENSG00000104472 | CHRAC1 |
| 6 | ENSG00000104490 | NCALD |
| 6 | ENSG00000104549 | SQLE |
| 6 | ENSG00000104723 | TUSC3 |
| 6 | ENSG00000105258 | POLR2I |
| 6 | ENSG00000105278 | ZFR2 |
| 6 | ENSG00000105519 | CAPS |
| 6 | ENSG00000105948 | TTC26 |
| 6 | ENSG00000105982 | RNF32 |
| 6 | ENSG00000106012 | IQCE |
| 6 | ENSG00000106049 | HIBADH |
| 6 | ENSG00000106052 | TAX1BP1 |
| 6 | ENSG00000106125 | FAM188B |
| 6 | ENSG00000106399 | RPA3 |
| 6 | ENSG00000106459 | NRF1 |
| 6 | ENSG00000106477 | CEP41 |
| 6 | ENSG00000106701 | FSD1L |
| 6 | ENSG00000106992 | AK1 |
| 6 | ENSG00000107185 | RGP1 |
| 6 | ENSG00000107186 | MPDZ |
| 6 | ENSG00000107249 | GLIS3 |
| 6 | ENSG00000107521 | HPS1 |
| 6 | ENSG00000107816 | LZTS2 |
| 6 | ENSG00000107957 | SH3PXD2A |
| 6 | ENSG00000108187 | PBLD |
| 6 | ENSG00000108395 | TRIM37 |
| 6 | ENSG00000108406 | DHX40 |
| 6 | ENSG00000108479 | GALK1 |
| 6 | ENSG00000108641 | B9D1 |
| 6 | ENSG00000108733 | PEX12 |
| 6 | ENSG00000108753 | HNF1B |
| 6 | ENSG00000108819 | PPP1R9B |
| 6 | ENSG00000108946 | PRKAR1A |
| 6 | ENSG00000108947 | EFNB3 |
| 6 | ENSG00000109083 | IFT20 |
| 6 | ENSG00000109171 | SLAIN2 |
| 6 | ENSG00000109501 | WFS1 |
| 6 | ENSG00000109680 | TBC1D19 |
| 6 | ENSG00000109685 | WHSC1 |
| 6 | ENSG00000109762 | SNX25 |
| 6 | ENSG00000109771 | LRP2BP |
| 6 | ENSG00000109944 | C11orf63 |
| 6 | ENSG00000110025 | SNX15 |

TABLE 13-continued

| GeneModule | EnsemblID | GeneSymbols |
|---|---|---|
| 6 | ENSG00000110318 | KIAA1377 |
| 6 | ENSG00000110841 | PPFIBP1 |
| 6 | ENSG00000111145 | ELK3 |
| 6 | ENSG00000111218 | PRMT8 |
| 6 | ENSG00000111254 | AKAP3 |
| 6 | ENSG00000111262 | KCNA1 |
| 6 | ENSG00000111321 | LTBR |
| 6 | ENSG00000111325 | OGFOD2 |
| 6 | ENSG00000111450 | STX2 |
| 6 | ENSG00000111554 | MDM1 |
| 6 | ENSG00000111647 | UHRF1BP1L |
| 6 | ENSG00000111674 | ENO2 |
| 6 | ENSG00000111728 | ST8SIA1 |
| 6 | ENSG00000111834 | RSPH4A |
| 6 | ENSG00000111837 | MAK |
| 6 | ENSG00000111877 | MCM9 |
| 6 | ENSG00000111879 | FAM184A |
| 6 | ENSG00000111907 | TPD52L1 |
| 6 | ENSG00000111961 | SASH1 |
| 6 | ENSG00000112183 | RBM24 |
| 6 | ENSG00000112186 | CAP2 |
| 6 | ENSG00000112530 | PACRG |
| 6 | ENSG00000112539 | C6orf118 |
| 6 | ENSG00000112559 | MDFI |
| 6 | ENSG00000112584 | FAM120B |
| 6 | ENSG00000112667 | DNPH1 |
| 6 | ENSG00000112796 | ENPP5 |
| 6 | ENSG00000112981 | NME5 |
| 6 | ENSG00000113141 | IK |
| 6 | ENSG00000113318 | MSH3 |
| 6 | ENSG00000113456 | RAD1 |
| 6 | ENSG00000113583 | C5orf15 |
| 6 | ENSG00000113645 | WWC1 |
| 6 | ENSG00000113946 | CLDN16 |
| 6 | ENSG00000113966 | ARL6 |
| 6 | ENSG00000114446 | IFT57 |
| 6 | ENSG00000114455 | HHLA2 |
| 6 | ENSG00000114473 | IQCG |
| 6 | ENSG00000114656 | KIAA1257 |
| 6 | ENSG00000114670 | NEK11 |
| 6 | ENSG00000114805 | PLCH1 |
| 6 | ENSG00000114904 | NEK4 |
| 6 | ENSG00000115107 | STEAP3 |
| 6 | ENSG00000115145 | STAM2 |
| 6 | ENSG00000115216 | NRBP1 |
| 6 | ENSG00000115423 | DNAH6 |
| 6 | ENSG00000115425 | PECR |
| 6 | ENSG00000115486 | GGCX |
| 6 | ENSG00000115685 | PPP1R7 |
| 6 | ENSG00000115750 | TAF1B |
| 6 | ENSG00000115947 | ORC4 |
| 6 | ENSG00000115970 | THADA |
| 6 | ENSG00000115998 | C2orf42 |
| 6 | ENSG00000116032 | GRIN3B |
| 6 | ENSG00000116127 | ALMS1 |
| 6 | ENSG00000116128 | BCL9 |
| 6 | ENSG00000116525 | TRIM62 |
| 6 | ENSG00000116675 | DNAJC6 |
| 6 | ENSG00000116793 | PHTF1 |
| 6 | ENSG00000116885 | OSCP1 |
| 6 | ENSG00000116957 | TBCE |
| 6 | ENSG00000117016 | RIMS3 |
| 6 | ENSG00000117477 | CCDC181 |
| 6 | ENSG00000117602 | RCAN3 |
| 6 | ENSG00000118096 | IFT46 |
| 6 | ENSG00000118307 | CASC1 |
| 6 | ENSG00000118407 | FILIP1 |
| 6 | ENSG00000118418 | HMGN3 |
| 6 | ENSG00000118420 | UBE3D |
| 6 | ENSG00000118690 | ARMC2 |
| 6 | ENSG00000118965 | WDR35 |
| 6 | ENSG00000118997 | DNAH7 |
| 6 | ENSG00000119147 | C2orf40 |
| 6 | ENSG00000119328 | FAM206A |
| 6 | ENSG00000119333 | WDR34 |
| 6 | ENSG00000119397 | CNTRL |
| 6 | ENSG00000119401 | TRIM32 |
| 6 | ENSG00000119402 | FBXW2 |
| 6 | ENSG00000119636 | CCDC176 |
| 6 | ENSG00000119640 | ACYP1 |
| 6 | ENSG00000119650 | IFT43 |
| 6 | ENSG00000119661 | DNAL1 |
| 6 | ENSG00000119685 | TTLL5 |
| 6 | ENSG00000119689 | DLST |
| 6 | ENSG00000119698 | PPP4R4 |
| 6 | ENSG00000119703 | ZC2HC1C |
| 6 | ENSG00000119782 | FKBP1B |
| 6 | ENSG00000120051 | CCDC147 |
| 6 | ENSG00000120055 | C10orf95 |
| 6 | ENSG00000120256 | LRP11 |
| 6 | ENSG00000120262 | CCDC170 |
| 6 | ENSG00000120279 | MYCT1 |
| 6 | ENSG00000120306 | CYSTM1 |
| 6 | ENSG00000120658 | ENOX1 |
| 6 | ENSG00000120685 | PROSER1 |
| 6 | ENSG00000120694 | HSPH1 |
| 6 | ENSG00000121057 | AKAP1 |
| 6 | ENSG00000121413 | ZSCAN18 |
| 6 | ENSG00000121486 | TRMT1L |
| 6 | ENSG00000121671 | CRY2 |
| 6 | ENSG00000122376 | FAM35A |
| 6 | ENSG00000122507 | BBS9 |
| 6 | ENSG00000122970 | IFT81 |
| 6 | ENSG00000123607 | TTC21B |
| 6 | ENSG00000123810 | B9D2 |
| 6 | ENSG00000123977 | DAW1 |
| 6 | ENSG00000124074 | ENKD1 |
| 6 | ENSG00000124237 | C20orf85 |
| 6 | ENSG00000124678 | TCP11 |
| 6 | ENSG00000124749 | COL21A1 |
| 6 | ENSG00000125124 | BBS2 |
| 6 | ENSG00000125384 | PTGER2 |
| 6 | ENSG00000125409 | TEKT3 |
| 6 | ENSG00000125482 | TTF1 |
| 6 | ENSG00000125531 | C20orf195 |
| 6 | ENSG00000125733 | TRIP10 |
| 6 | ENSG00000125779 | PANK2 |
| 6 | ENSG00000125871 | MGME1 |
| 6 | ENSG00000125968 | ID1 |
| 6 | ENSG00000125991 | ERGIC3 |
| 6 | ENSG00000126107 | HECTD3 |
| 6 | ENSG00000126391 | FRMD8 |
| 6 | ENSG00000126432 | PRDX5 |
| 6 | ENSG00000126773 | PCNXL4 |
| 6 | ENSG00000126777 | KTN1 |
| 6 | ENSG00000126778 | SIX1 |
| 6 | ENSG00000126870 | WDR60 |
| 6 | ENSG00000127399 | LRRC61 |
| 6 | ENSG00000127824 | TUBA4A |
| 6 | ENSG00000127863 | TNFRSF19 |
| 6 | ENSG00000127914 | AKAP9 |
| 6 | ENSG00000127952 | STYXL1 |
| 6 | ENSG00000128346 | C22orf23 |
| 6 | ENSG00000128408 | RIBC2 |
| 6 | ENSG00000128536 | CDHR3 |
| 6 | ENSG00000128581 | RABL5 |
| 6 | ENSG00000128607 | KLHDC10 |
| 6 | ENSG00000128881 | TTBK2 |
| 6 | ENSG00000128891 | C15orf57 |
| 6 | ENSG00000129007 | CALML4 |
| 6 | ENSG00000129028 | THAP10 |
| 6 | ENSG00000129151 | BBOX1 |
| 6 | ENSG00000129295 | LRRC6 |
| 6 | ENSG00000129521 | EGLN3 |
| 6 | ENSG00000129654 | FOXJ1 |
| 6 | ENSG00000129951 | |
| 6 | ENSG00000130177 | CDC16 |
| 6 | ENSG00000130363 | RSPH3 |
| 6 | ENSG00000130413 | STK33 |
| 6 | ENSG00000130433 | CACNG6 |
| 6 | ENSG00000130511 | SSBP4 |
| 6 | ENSG00000130560 | UBAC1 |
| 6 | ENSG00000130640 | TUBGCP2 |
| 6 | ENSG00000130762 | ARHGEF16 |
| 6 | ENSG00000130770 | ATPIF1 |
| 6 | ENSG00000130962 | PRRG1 |

TABLE 13-continued

| GeneModule | EnsemblID | GeneSymbols |
|---|---|---|
| 6 | ENSG00000131437 | KIF3A |
| 6 | ENSG00000131470 | PSMC3IP |
| 6 | ENSG00000131697 | NPHP4 |
| 6 | ENSG00000131711 | MAP1B |
| 6 | ENSG00000131828 | PDHA1 |
| 6 | ENSG00000131848 | ZSCAN5A |
| 6 | ENSG00000131941 | RHPN2 |
| 6 | ENSG00000131969 | ABHD12B |
| 6 | ENSG00000132003 | ZSWIM4 |
| 6 | ENSG00000132004 | FBXW9 |
| 6 | ENSG00000132010 | ZNF20 |
| 6 | ENSG00000132122 | SPATA6 |
| 6 | ENSG00000132139 | GAS2L2 |
| 6 | ENSG00000132259 | CNGA4 |
| 6 | ENSG00000132321 | IQCA1 |
| 6 | ENSG00000132549 | VPS13B |
| 6 | ENSG00000132554 | RGS22 |
| 6 | ENSG00000132640 | BTBD3 |
| 6 | ENSG00000132664 | POLR3F |
| 6 | ENSG00000132768 | DPH2 |
| 6 | ENSG00000133056 | PIK3C2B |
| 6 | ENSG00000133065 | SLC41A1 |
| 6 | ENSG00000133104 | SPG20 |
| 6 | ENSG00000133115 | STOML3 |
| 6 | ENSG00000133131 | MORC4 |
| 6 | ENSG00000133216 | EPHB2 |
| 6 | ENSG00000133256 | PDE6B |
| 6 | ENSG00000133488 | SEC14L4 |
| 6 | ENSG00000133627 | ACTR3B |
| 6 | ENSG00000133640 | LRRIQ1 |
| 6 | ENSG00000133678 | TMEM254 |
| 6 | ENSG00000133739 | LRRCC1 |
| 6 | ENSG00000133958 | UNC79 |
| 6 | ENSG00000134138 | MEIS2 |
| 6 | ENSG00000134247 | PTGFRN |
| 6 | ENSG00000135070 | ISCA1 |
| 6 | ENSG00000135205 | CCDC146 |
| 6 | ENSG00000135245 | HILPDA |
| 6 | ENSG00000135315 | KIAA1009 |
| 6 | ENSG00000135338 | LCA5 |
| 6 | ENSG00000135406 | PRPH |
| 6 | ENSG00000135519 | KCNH3 |
| 6 | ENSG00000135535 | CD164 |
| 6 | ENSG00000135537 | LACE1 |
| 6 | ENSG00000135549 | PKIB |
| 6 | ENSG00000135597 | REPS1 |
| 6 | ENSG00000135931 | ARMC9 |
| 6 | ENSG00000135951 | TSGA10 |
| 6 | ENSG00000135966 | TGFBRAP1 |
| 6 | ENSG00000136044 | APPL2 |
| 6 | ENSG00000136319 | TTC5 |
| 6 | ENSG00000136448 | NMT1 |
| 6 | ENSG00000136449 | MYCBPAP |
| 6 | ENSG00000136451 | VEZF1 |
| 6 | ENSG00000136715 | SAP130 |
| 6 | ENSG00000136811 | ODF2 |
| 6 | ENSG00000136918 | WDR38 |
| 6 | ENSG00000137266 | SLC22A23 |
| 6 | ENSG00000137274 | BPHL |
| 6 | ENSG00000137414 | FAM8A1 |
| 6 | ENSG00000137434 | C6orf52 |
| 6 | ENSG00000137473 | TTC29 |
| 6 | ENSG00000137494 | ANKRD42 |
| 6 | ENSG00000137601 | NEK1 |
| 6 | ENSG00000137691 | C11orf70 |
| 6 | ENSG00000137707 | BTG4 |
| 6 | ENSG00000137819 | PAQR5 |
| 6 | ENSG00000137821 | LRRC49 |
| 6 | ENSG00000137960 | GIPC2 |
| 6 | ENSG00000138002 | IFT172 |
| 6 | ENSG00000138036 | DYNC2LI1 |
| 6 | ENSG00000138041 | SMEK2 |
| 6 | ENSG00000138175 | ARL3 |
| 6 | ENSG00000138400 | MDH1B |
| 6 | ENSG00000138433 | CIR1 |
| 6 | ENSG00000138443 | ABI2 |
| 6 | ENSG00000138587 | MNS1 |
| 6 | ENSG00000138622 | HCN4 |
| 6 | ENSG00000138640 | FAM13A |
| 6 | ENSG00000138670 | RASGEF1B |
| 6 | ENSG00000138769 | CDKL2 |
| 6 | ENSG00000138771 | SHROOM3 |
| 6 | ENSG00000138823 | MTTP |
| 6 | ENSG00000139537 | CCDC65 |
| 6 | ENSG00000139624 | CERS5 |
| 6 | ENSG00000139714 | MORN3 |
| 6 | ENSG00000139971 | C14orf37 |
| 6 | ENSG00000139974 | SLC38A6 |
| 6 | ENSG00000140025 | EFCAB11 |
| 6 | ENSG00000140043 | PTGR2 |
| 6 | ENSG00000140057 | AK7 |
| 6 | ENSG00000140284 | SLC27A2 |
| 6 | ENSG00000140403 | DNAJA4 |
| 6 | ENSG00000140463 | BBS4 |
| 6 | ENSG00000140481 | CCDC33 |
| 6 | ENSG00000140527 | WDR93 |
| 6 | ENSG00000140564 | FURIN |
| 6 | ENSG00000140600 | SH3GL3 |
| 6 | ENSG00000140632 | GLYR1 |
| 6 | ENSG00000140876 | NUDT7 |
| 6 | ENSG00000141012 | GALNS |
| 6 | ENSG00000141013 | GAS8 |
| 6 | ENSG00000141098 | GFOD2 |
| 6 | ENSG00000141294 | LRRC46 |
| 6 | ENSG00000141376 | BCAS3 |
| 6 | ENSG00000141499 | WRAP53 |
| 6 | ENSG00000141510 | TP53 |
| 6 | ENSG00000141580 | WDR45B |
| 6 | ENSG00000141665 | FBXO15 |
| 6 | ENSG00000142621 | FHAD1 |
| 6 | ENSG00000142655 | PEX14 |
| 6 | ENSG00000142677 | IL22RA1 |
| 6 | ENSG00000143093 | STRIP1 |
| 6 | ENSG00000143156 | NME7 |
| 6 | ENSG00000143179 | UCK2 |
| 6 | ENSG00000143222 | UFC1 |
| 6 | ENSG00000143258 | USP21 |
| 6 | ENSG00000143479 | DYRK3 |
| 6 | ENSG00000143499 | SMYD2 |
| 6 | ENSG00000143537 | ADAM15 |
| 6 | ENSG00000143595 | AQP10 |
| 6 | ENSG00000143633 | C1orf131 |
| 6 | ENSG00000143653 | SCCPDH |
| 6 | ENSG00000143786 | CNIH3 |
| 6 | ENSG00000143933 | CALM2 |
| 6 | ENSG00000143951 | WDPCP |
| 6 | ENSG00000144061 | NPHP1 |
| 6 | ENSG00000144233 | AMMECR1L |
| 6 | ENSG00000144451 | SPAG16 |
| 6 | ENSG00000144504 | ANKMY1 |
| 6 | ENSG00000145075 | CCDC39 |
| 6 | ENSG00000145331 | TRMT10A |
| 6 | ENSG00000145414 | NAF1 |
| 6 | ENSG00000145491 | ROPN1L |
| 6 | ENSG00000145945 | FAM50B |
| 6 | ENSG00000145982 | FARS2 |
| 6 | ENSG00000146038 | DCDC2 |
| 6 | ENSG00000146083 | RNF44 |
| 6 | ENSG00000146221 | TCTE1 |
| 6 | ENSG00000146233 | CYP39A1 |
| 6 | ENSG00000146242 | TPBG |
| 6 | ENSG00000146243 | IRAK1BP1 |
| 6 | ENSG00000146376 | ARHGAP18 |
| 6 | ENSG00000146722 | |
| 6 | ENSG00000146729 | GBAS |
| 6 | ENSG00000146733 | PSPH |
| 6 | ENSG00000146856 | AGBL3 |
| 6 | ENSG00000147003 | TMEM27 |
| 6 | ENSG00000147117 | ZNF157 |
| 6 | ENSG00000147202 | DIAPH2 |
| 6 | ENSG00000147224 | PRPS1 |
| 6 | ENSG00000147231 | CXorf57 |
| 6 | ENSG00000147316 | MCPH1 |
| 6 | ENSG00000147400 | CETN2 |
| 6 | ENSG00000147457 | CHMP7 |
| 6 | ENSG00000147894 | C9orf72 |

TABLE 13-continued

| GeneModule | EnsemblID | GeneSymbols |
|---|---|---|
| 6 | ENSG00000148057 | IDNK |
| 6 | ENSG00000148219 | ASTN2 |
| 6 | ENSG00000148225 | WDR31 |
| 6 | ENSG00000148660 | CAMK2G |
| 6 | ENSG00000148814 | LRRC27 |
| 6 | ENSG00000148842 | CNNM2 |
| 6 | ENSG00000149050 | ZNF214 |
| 6 | ENSG00000149179 | C11orf49 |
| 6 | ENSG00000149201 | CCDC81 |
| 6 | ENSG00000149292 | TTC12 |
| 6 | ENSG00000149300 | C11orf52 |
| 6 | ENSG00000149328 | GLB1L2 |
| 6 | ENSG00000149480 | MTA2 |
| 6 | ENSG00000149573 | MPZL2 |
| 6 | ENSG00000149782 | PLCB3 |
| 6 | ENSG00000150281 | CTF1 |
| 6 | ENSG00000150433 | TMEM218 |
| 6 | ENSG00000150456 | N6AMT2 |
| 6 | ENSG00000150628 | SPATA4 |
| 6 | ENSG00000150667 | FSIP1 |
| 6 | ENSG00000150764 | DIXDC1 |
| 6 | ENSG00000150773 | PIH1D2 |
| 6 | ENSG00000150873 | C2orf50 |
| 6 | ENSG00000151023 | ENKUR |
| 6 | ENSG00000151065 | DCP1B |
| 6 | ENSG00000151320 | AKAP6 |
| 6 | ENSG00000151338 | MIPOL1 |
| 6 | ENSG00000151413 | NUBPL |
| 6 | ENSG00000151445 | VIPAS39 |
| 6 | ENSG00000151575 | TEX9 |
| 6 | ENSG00000151689 | INPP1 |
| 6 | ENSG00000151773 | CCDC122 |
| 6 | ENSG00000151779 | NBAS |
| 6 | ENSG00000152076 | CCDC74B |
| 6 | ENSG00000152464 | RPP38 |
| 6 | ENSG00000152503 | TRIM36 |
| 6 | ENSG00000152582 | SPEF2 |
| 6 | ENSG00000152611 | CAPSL |
| 6 | ENSG00000152763 | WDR78 |
| 6 | ENSG00000152936 | IFLTD1 |
| 6 | ENSG00000153132 | CLGN |
| 6 | ENSG00000153140 | CETN3 |
| 6 | ENSG00000153237 | CCDC148 |
| 6 | ENSG00000153347 | FAM81B |
| 6 | ENSG00000153531 | ADPRHL1 |
| 6 | ENSG00000153558 | FBXL2 |
| 6 | ENSG00000153560 | UBP1 |
| 6 | ENSG00000153714 | LURAP1L |
| 6 | ENSG00000153774 | CFDP1 |
| 6 | ENSG00000153789 | FAM92B |
| 6 | ENSG00000153832 | FBXO36 |
| 6 | ENSG00000153896 | ZNF599 |
| 6 | ENSG00000153904 | DDAH1 |
| 6 | ENSG00000153930 | ANKFN1 |
| 6 | ENSG00000154124 | FAM105B |
| 6 | ENSG00000154153 | FAM134B |
| 6 | ENSG00000154240 | CEP112 |
| 6 | ENSG00000154380 | ENAH |
| 6 | ENSG00000154479 | CCDC173 |
| 6 | ENSG00000154556 | SORBS2 |
| 6 | ENSG00000154760 | SLFN13 |
| 6 | ENSG00000154917 | RAB6B |
| 6 | ENSG00000154930 | ACSS1 |
| 6 | ENSG00000155026 | RSPH10B |
| 6 | ENSG00000155085 | AK9 |
| 6 | ENSG00000155096 | AZIN1 |
| 6 | ENSG00000155189 | AGPAT5 |
| 6 | ENSG00000155530 | LRGUK |
| 6 | ENSG00000155666 | KDM8 |
| 6 | ENSG00000155749 | ALS2CR12 |
| 6 | ENSG00000155761 | SPAG17 |
| 6 | ENSG00000155816 | FMN2 |
| 6 | ENSG00000155974 | GRIP1 |
| 6 | ENSG00000156030 | ELMSAN1 |
| 6 | ENSG00000156049 | GNA14 |
| 6 | ENSG00000156050 | FAM161B |
| 6 | ENSG00000156171 | DRAM2 |
| 6 | ENSG00000156172 | C8orf37 |
| 6 | ENSG00000156206 | C15orf26 |
| 6 | ENSG00000156232 | WHAMM |
| 6 | ENSG00000156299 | TIAM1 |
| 6 | ENSG00000156313 | RPGR |
| 6 | ENSG00000156463 | SH3RF2 |
| 6 | ENSG00000156958 | GALK2 |
| 6 | ENSG00000157227 | MMP14 |
| 6 | ENSG00000157330 | C1orf158 |
| 6 | ENSG00000157423 | HYDIN |
| 6 | ENSG00000157429 | ZNF19 |
| 6 | ENSG00000157470 | FAM81A |
| 6 | ENSG00000157538 | DSCR3 |
| 6 | ENSG00000157578 | LCA5L |
| 6 | ENSG00000157653 | C9orf43 |
| 6 | ENSG00000157796 | WDR19 |
| 6 | ENSG00000157856 | DRC1 |
| 6 | ENSG00000157869 | RAB28 |
| 6 | ENSG00000158023 | WDR66 |
| 6 | ENSG00000158113 | LRRC43 |
| 6 | ENSG00000158122 | AAED1 |
| 6 | ENSG00000158234 | FAIM |
| 6 | ENSG00000158296 | SLC13A3 |
| 6 | ENSG00000158423 | RIBC1 |
| 6 | ENSG00000158428 | C2orf62 |
| 6 | ENSG00000158445 | KCNB1 |
| 6 | ENSG00000158486 | DNAH3 |
| 6 | ENSG00000158669 | AGPAT6 |
| 6 | ENSG00000158850 | B4GALT3 |
| 6 | ENSG00000159079 | C21orf59 |
| 6 | ENSG00000159239 | C2orf81 |
| 6 | ENSG00000159685 | CHCHD6 |
| 6 | ENSG00000159713 | TPPP3 |
| 6 | ENSG00000159714 | ZDHHC1 |
| 6 | ENSG00000160051 | IQCC |
| 6 | ENSG00000160145 | KALRN |
| 6 | ENSG00000160183 | TMPRSS3 |
| 6 | ENSG00000160188 | RSPH1 |
| 6 | ENSG00000160345 | C9orf116 |
| 6 | ENSG00000160613 | PCSK7 |
| 6 | ENSG00000160753 | RUSC1 |
| 6 | ENSG00000160803 | UBQLN4 |
| 6 | ENSG00000160949 | TONSL |
| 6 | ENSG00000160991 | ORAI2 |
| 6 | ENSG00000161036 | LRWD1 |
| 6 | ENSG00000161040 | FBXL13 |
| 6 | ENSG00000161326 | DUSP14 |
| 6 | ENSG00000161328 | LRRC56 |
| 6 | ENSG00000161513 | FDXR |
| 6 | ENSG00000161905 | ALOX15 |
| 6 | ENSG00000162040 | HS3ST6 |
| 6 | ENSG00000162105 | SHANK2 |
| 6 | ENSG00000162148 | PPP1R32 |
| 6 | ENSG00000162302 | RPS6KA4 |
| 6 | ENSG00000162543 | UBXN10 |
| 6 | ENSG00000162598 | C1orf87 |
| 6 | ENSG00000162600 | OMA1 |
| 6 | ENSG00000162616 | DNAJB4 |
| 6 | ENSG00000162620 | LRRIQ3 |
| 6 | ENSG00000162643 | WDR63 |
| 6 | ENSG00000162755 | KLHDC9 |
| 6 | ENSG00000162769 | FLVCR1 |
| 6 | ENSG00000162814 | SPATA17 |
| 6 | ENSG00000162999 | DUSP19 |
| 6 | ENSG00000163001 | CCDC104 |
| 6 | ENSG00000163006 | CCDC138 |
| 6 | ENSG00000163040 | CCDC74A |
| 6 | ENSG00000163060 | TEKT4 |
| 6 | ENSG00000163071 | SPATA18 |
| 6 | ENSG00000163075 | |
| 6 | ENSG00000163083 | INHBB |
| 6 | ENSG00000163093 | BBS5 |
| 6 | ENSG00000163125 | RPRD2 |
| 6 | ENSG00000163138 | PACRGL |
| 6 | ENSG00000163214 | DHX57 |
| 6 | ENSG00000163251 | FZD5 |
| 6 | ENSG00000163263 | C1orf189 |
| 6 | ENSG00000163322 | FAM175A |
| 6 | ENSG00000163349 | HIPK1 |

TABLE 13-continued

| GeneModule | EnsemblID | GeneSymbols |
|---|---|---|
| 6 | ENSG00000163491 | NEK10 |
| 6 | ENSG00000163512 | AZI2 |
| 6 | ENSG00000163521 | GLB1L |
| 6 | ENSG00000163576 | EFHB |
| 6 | ENSG00000163596 | ICA1L |
| 6 | ENSG00000163617 | KIAA1407 |
| 6 | ENSG00000163624 | CDS1 |
| 6 | ENSG00000163655 | GMPS |
| 6 | ENSG00000163686 | ABHD6 |
| 6 | ENSG00000163818 | LZTFL1 |
| 6 | ENSG00000163875 | MEAF6 |
| 6 | ENSG00000163879 | DNALI1 |
| 6 | ENSG00000164002 | EXO5 |
| 6 | ENSG00000164099 | PRSS12 |
| 6 | ENSG00000164114 | MAP9 |
| 6 | ENSG00000164118 | CEP44 |
| 6 | ENSG00000164185 | ZNF474 |
| 6 | ENSG00000164306 | PRIMPOL |
| 6 | ENSG00000164402 | 8-Sep |
| 6 | ENSG00000164404 | GDF9 |
| 6 | ENSG00000164411 | GJB7 |
| 6 | ENSG00000164440 | TXLNB |
| 6 | ENSG00000164465 | DCBLD1 |
| 6 | ENSG00000164542 | KIAA0895 |
| 6 | ENSG00000164627 | KIF6 |
| 6 | ENSG00000164674 | SYTL3 |
| 6 | ENSG00000164675 | IQUB |
| 6 | ENSG00000164746 | C7orf57 |
| 6 | ENSG00000164758 | MED30 |
| 6 | ENSG00000164818 | HEATR2 |
| 6 | ENSG00000164938 | TP53INP1 |
| 6 | ENSG00000164953 | TMEM67 |
| 6 | ENSG00000164970 | FAM219A |
| 6 | ENSG00000164972 | C9orf24 |
| 6 | ENSG00000165029 | ABCA1 |
| 6 | ENSG00000165084 | C8orf34 |
| 6 | ENSG00000165097 | KDM1B |
| 6 | ENSG00000165118 | C9orf64 |
| 6 | ENSG00000165124 | SVEP1 |
| 6 | ENSG00000165164 | CXorf22 |
| 6 | ENSG00000165185 | KIAA1958 |
| 6 | ENSG00000165209 | STRBP |
| 6 | ENSG00000165219 | GAPVD1 |
| 6 | ENSG00000165309 | ARMC3 |
| 6 | ENSG00000165383 | LRRC18 |
| 6 | ENSG00000165506 | DNAAF2 |
| 6 | ENSG00000165533 | TTC8 |
| 6 | ENSG00000165695 | AK8 |
| 6 | ENSG00000165698 | C9orf9 |
| 6 | ENSG00000165724 | ZMYND19 |
| 6 | ENSG00000165730 | STOX1 |
| 6 | ENSG00000165807 | PPP1R36 |
| 6 | ENSG00000166165 | CKB |
| 6 | ENSG00000166171 | DPCD |
| 6 | ENSG00000166173 | LARP6 |
| 6 | ENSG00000166246 | C16orf71 |
| 6 | ENSG00000166262 | FAM227B |
| 6 | ENSG00000166263 | STXBP4 |
| 6 | ENSG00000166275 | C10orf32 |
| 6 | ENSG00000166311 | SMPD1 |
| 6 | ENSG00000166313 | APBB1 |
| 6 | ENSG00000166323 | C11orf65 |
| 6 | ENSG00000166352 | C11orf74 |
| 6 | ENSG00000166402 | TUB |
| 6 | ENSG00000166435 | XRRA1 |
| 6 | ENSG00000166455 | C16orf46 |
| 6 | ENSG00000166526 | ZNF3 |
| 6 | ENSG00000166578 | IQCD |
| 6 | ENSG00000166592 | RRAD |
| 6 | ENSG00000166596 | WDR16 |
| 6 | ENSG00000166946 | CCNDBP1 |
| 6 | ENSG00000166959 | MS4A8 |
| 6 | ENSG00000166963 | MAP1A |
| 6 | ENSG00000167065 | DUSP18 |
| 6 | ENSG00000167094 | TTC16 |
| 6 | ENSG00000167113 | COQ4 |
| 6 | ENSG00000167131 | CCDC103 |
| 6 | ENSG00000167136 | ENDOG |
| 6 | ENSG00000167186 | COQ7 |
| 6 | ENSG00000167216 | KATNAL2 |
| 6 | ENSG00000167523 | SPATA33 |
| 6 | ENSG00000167550 | RHEBL1 |
| 6 | ENSG00000167552 | TUBA1A |
| 6 | ENSG00000167646 | DNAAF3 |
| 6 | ENSG00000167733 | HSD11B1L |
| 6 | ENSG00000167740 | CYB5D2 |
| 6 | ENSG00000167858 | TEKT1 |
| 6 | ENSG00000167904 | TMEM68 |
| 6 | ENSG00000167962 | ZNF598 |
| 6 | ENSG00000168014 | C2CD3 |
| 6 | ENSG00000168038 | ULK4 |
| 6 | ENSG00000168314 | MOBP |
| 6 | ENSG00000168350 | DEGS2 |
| 6 | ENSG00000168487 | BMP1 |
| 6 | ENSG00000168575 | SLC20A2 |
| 6 | ENSG00000168589 | DYNLRB2 |
| 6 | ENSG00000168658 | VWA3B |
| 6 | ENSG00000168675 | LDLRAD4 |
| 6 | ENSG00000168734 | PKIG |
| 6 | ENSG00000168754 | FAM178B |
| 6 | ENSG00000168772 | CXXC4 |
| 6 | ENSG00000168778 | TCTN2 |
| 6 | ENSG00000168884 | TNIP2 |
| 6 | ENSG00000168938 | PPIC |
| 6 | ENSG00000169064 | ZBBX |
| 6 | ENSG00000169126 | ARMC4 |
| 6 | ENSG00000169189 | NSMCE1 |
| 6 | ENSG00000169213 | RAB3B |
| 6 | ENSG00000169379 | ARL13B |
| 6 | ENSG00000169550 | MUC15 |
| 6 | ENSG00000169902 | TPST1 |
| 6 | ENSG00000169905 | TOR1AIP2 |
| 6 | ENSG00000170231 | FABP6 |
| 6 | ENSG00000170264 | FAM161A |
| 6 | ENSG00000170270 | C14orf142 |
| 6 | ENSG00000170469 | SPATA24 |
| 6 | ENSG00000170482 | SLC23A1 |
| 6 | ENSG00000170509 | HSD17B13 |
| 6 | ENSG00000170871 | KIAA0232 |
| 6 | ENSG00000170959 | DCDC1 |
| 6 | ENSG00000171132 | PRKCE |
| 6 | ENSG00000171160 | MORN4 |
| 6 | ENSG00000171174 | RBKS |
| 6 | ENSG00000171428 | NAT1 |
| 6 | ENSG00000171517 | LPAR3 |
| 6 | ENSG00000171533 | MAP6 |
| 6 | ENSG00000171574 | ZNF584 |
| 6 | ENSG00000171595 | DNAI2 |
| 6 | ENSG00000171757 | LRRC34 |
| 6 | ENSG00000171793 | CTPS1 |
| 6 | ENSG00000171798 | KNDC1 |
| 6 | ENSG00000171885 | AQP4 |
| 6 | ENSG00000171962 | LRRC48 |
| 6 | ENSG00000172164 | SNTB1 |
| 6 | ENSG00000172301 | COPRS |
| 6 | ENSG00000172361 | CCDC11 |
| 6 | ENSG00000172426 | RSPH9 |
| 6 | ENSG00000172578 | KLHL6 |
| 6 | ENSG00000172671 | ZFAND4 |
| 6 | ENSG00000172955 | ADH6 |
| 6 | ENSG00000173013 | CCDC96 |
| 6 | ENSG00000173208 | ABCD2 |
| 6 | ENSG00000173226 | IQCB1 |
| 6 | ENSG00000173627 | APOBEC4 |
| 6 | ENSG00000173838 | 10-Mar |
| 6 | ENSG00000173947 | PIFO |
| 6 | ENSG00000174007 | CEP19 |
| 6 | ENSG00000174132 | FAM174A |
| 6 | ENSG00000174156 | GSTA3 |
| 6 | ENSG00000174343 | CHRNA9 |
| 6 | ENSG00000174456 | C12orf76 |
| 6 | ENSG00000174483 | BBS1 |
| 6 | ENSG00000174586 | ZNF497 |
| 6 | ENSG00000174628 | IQCK |
| 6 | ENSG00000174705 | SH3PXD2B |
| 6 | ENSG00000174776 | WDR49 |

TABLE 13-continued

| GeneModule | EnsemblID | GeneSymbols |
|---|---|---|
| 6 | ENSG00000174796 | THAP6 |
| 6 | ENSG00000174808 | BTC |
| 6 | ENSG00000174898 | CATSPERD |
| 6 | ENSG00000175279 | APITD1 |
| 6 | ENSG00000175376 | EIF1AD |
| 6 | ENSG00000175664 | TEX26 |
| 6 | ENSG00000175697 | GPR156 |
| 6 | ENSG00000175792 | RUVBL1 |
| 6 | ENSG00000175970 | UNC119B |
| 6 | ENSG00000176040 | TMPRSS7 |
| 6 | ENSG00000176171 | BNIP3 |
| 6 | ENSG00000176209 | SMIM19 |
| 6 | ENSG00000176381 | PRR18 |
| 6 | ENSG00000176401 | EID2B |
| 6 | ENSG00000176485 | PLA2G16 |
| 6 | ENSG00000176563 | CNTD1 |
| 6 | ENSG00000176601 | MAP3K19 |
| 6 | ENSG00000176714 | CCDC121 |
| 6 | ENSG00000176986 | SEC24C |
| 6 | ENSG00000177103 | DSCAML1 |
| 6 | ENSG00000177112 | MRVI1-AS1 |
| 6 | ENSG00000177398 | UMODL1 |
| 6 | ENSG00000177459 | C8orf47 |
| 6 | ENSG00000177508 | IRX3 |
| 6 | ENSG00000177640 | CASC2 |
| 6 | ENSG00000177674 | AGTRAP |
| 6 | ENSG00000177994 | C2orf73 |
| 6 | ENSG00000178053 | MLF1 |
| 6 | ENSG00000178075 | GRAMD1C |
| 6 | ENSG00000178125 | PPP1R42 |
| 6 | ENSG00000178149 | DALRD3 |
| 6 | ENSG00000178425 | NT5DC1 |
| 6 | ENSG00000178460 | MCMDC2 |
| 6 | ENSG00000178467 | P4HTM |
| 6 | ENSG00000178568 | ERBB4 |
| 6 | ENSG00000178665 | ZNF713 |
| 6 | ENSG00000178732 | GP5 |
| 6 | ENSG00000178796 | RIIAD1 |
| 6 | ENSG00000178965 | C1orf173 |
| 6 | ENSG00000179029 | TMEM107 |
| 6 | ENSG00000179071 | CCDC89 |
| 6 | ENSG00000179133 | C10orf67 |
| 6 | ENSG00000179195 | ZNF664 |
| 6 | ENSG00000179240 | |
| 6 | ENSG00000179598 | PLD6 |
| 6 | ENSG00000179813 | FAM216B |
| 6 | ENSG00000179902 | C1orf194 |
| 6 | ENSG00000180098 | TRNAU1AP |
| 6 | ENSG00000180263 | FGD6 |
| 6 | ENSG00000180346 | TIGD2 |
| 6 | ENSG00000180481 | GLIPR1L2 |
| 6 | ENSG00000180509 | KCNE1 |
| 6 | ENSG00000180769 | WDFY3-AS2 |
| 6 | ENSG00000180787 | ZFP3 |
| 6 | ENSG00000180914 | OXTR |
| 6 | ENSG00000181004 | BBS12 |
| 6 | ENSG00000181322 | NME9 |
| 6 | ENSG00000181481 | RNF135 |
| 6 | ENSG00000181619 | GPR135 |
| 6 | ENSG00000182093 | WRB |
| 6 | ENSG00000182224 | CYB5D1 |
| 6 | ENSG00000182329 | |
| 6 | ENSG00000182504 | CEP97 |
| 6 | ENSG00000182518 | FAM104B |
| 6 | ENSG00000182768 | NGRN |
| 6 | ENSG00000182957 | SPATA13 |
| 6 | ENSG00000183117 | CSMD1 |
| 6 | ENSG00000183161 | FANCF |
| 6 | ENSG00000183207 | RUVBL2 |
| 6 | ENSG00000183273 | CCDC60 |
| 6 | ENSG00000183323 | CCDC125 |
| 6 | ENSG00000183346 | C10orf107 |
| 6 | ENSG00000183576 | TNFAIP8L3 |
| 6 | ENSG00000183628 | DGCR6 |
| 6 | ENSG00000183644 | C11orf88 |
| 6 | ENSG00000183690 | EFHC2 |
| 6 | ENSG00000183784 | C9orf66 |
| 6 | ENSG00000183826 | BTBD9 |
| 6 | ENSG00000183831 | ANKRD45 |
| 6 | ENSG00000183914 | DNAH2 |
| 6 | ENSG00000183941 | HIST2H4A |
| 6 | ENSG00000184154 | LRTOMT |
| 6 | ENSG00000184349 | EFNA5 |
| 6 | ENSG00000184385 | C21orf128 |
| 6 | ENSG00000184500 | PROS1 |
| 6 | ENSG00000184613 | NELL2 |
| 6 | ENSG00000184702 | 5-Sep |
| 6 | ENSG00000184731 | FAM110C |
| 6 | ENSG00000184886 | PIGW |
| 6 | ENSG00000184898 | RBM43 |
| 6 | ENSG00000184939 | ZFP90 |
| 6 | ENSG00000184986 | TMEM121 |
| 6 | ENSG00000185055 | EFCAB10 |
| 6 | ENSG00000185158 | LRRC37B |
| 6 | ENSG00000185220 | PGBD2 |
| 6 | ENSG00000185222 | WBP5 |
| 6 | ENSG00000185250 | PPIL6 |
| 6 | ENSG00000185261 | KIAA0825 |
| 6 | ENSG00000185267 | CDNF |
| 6 | ENSG00000185305 | ARL15 |
| 6 | ENSG00000185361 | TNFAIP8L1 |
| 6 | ENSG00000185379 | RAD51D |
| 6 | ENSG00000185420 | SMYD3 |
| 6 | ENSG00000185608 | MRPL40 |
| 6 | ENSG00000185681 | MORN5 |
| 6 | ENSG00000185875 | THNSL1 |
| 6 | ENSG00000185989 | RASA3 |
| 6 | ENSG00000186094 | AGBL4 |
| 6 | ENSG00000186104 | CYP2R1 |
| 6 | ENSG00000186132 | C2orf76 |
| 6 | ENSG00000186198 | SLC51B |
| 6 | ENSG00000186231 | KLHL32 |
| 6 | ENSG00000186314 | PRELID2 |
| 6 | ENSG00000186329 | TMEM212 |
| 6 | ENSG00000186352 | ANKRD37 |
| 6 | ENSG00000186471 | AKAP14 |
| 6 | ENSG00000186496 | ZNF396 |
| 6 | ENSG00000186523 | FAM86B1 |
| 6 | ENSG00000186625 | KATNA1 |
| 6 | ENSG00000186638 | KIF24 |
| 6 | ENSG00000186687 | LYRM7 |
| 6 | ENSG00000186889 | TMEM17 |
| 6 | ENSG00000186952 | TMEM232 |
| 6 | ENSG00000186973 | FAM183A |
| 6 | ENSG00000186976 | EFCAB6 |
| 6 | ENSG00000187079 | TEAD1 |
| 6 | ENSG00000187122 | SLIT1 |
| 6 | ENSG00000187189 | TSPYL4 |
| 6 | ENSG00000187240 | DYNC2H1 |
| 6 | ENSG00000187260 | WDR86 |
| 6 | ENSG00000187535 | IFT140 |
| 6 | ENSG00000187624 | C17orf97 |
| 6 | ENSG00000187642 | C1orf170 |
| 6 | ENSG00000187695 | |
| 6 | ENSG00000187726 | DNAJB13 |
| 6 | ENSG00000187733 | AMY1C |
| 6 | ENSG00000188010 | MORN2 |
| 6 | ENSG00000188039 | NWD1 |
| 6 | ENSG00000188229 | TUBB4B |
| 6 | ENSG00000188316 | ENO4 |
| 6 | ENSG00000188352 | FOCAD |
| 6 | ENSG00000188396 | TCTEX1D4 |
| 6 | ENSG00000188452 | CERKL |
| 6 | ENSG00000188523 | C9orf171 |
| 6 | ENSG00000188596 | C12orf55 |
| 6 | ENSG00000188659 | FAM154B |
| 6 | ENSG00000188817 | SNTN |
| 6 | ENSG00000188921 | PTPLAD2 |
| 6 | ENSG00000188931 | C1orf192 |
| 6 | ENSG00000189157 | FAM47E |
| 6 | ENSG00000196090 | PTPRT |
| 6 | ENSG00000196169 | KIF19 |
| 6 | ENSG00000196230 | TUBB |
| 6 | ENSG00000196236 | XPNPEP3 |
| 6 | ENSG00000196277 | GRM7 |
| 6 | ENSG00000196437 | ZNF569 |

TABLE 13-continued

| GeneModule | EnsemblID | GeneSymbols |
|---|---|---|
| 6 | ENSG00000196476 | C20orf96 |
| 6 | ENSG00000196482 | ESRRG |
| 6 | ENSG00000196535 | MYO18A |
| 6 | ENSG00000196659 | TTC30B |
| 6 | ENSG00000196693 | ZNF33B |
| 6 | ENSG00000196704 | AMZ2 |
| 6 | ENSG00000196814 | MVB12B |
| 6 | ENSG00000196872 | KIAA1211L |
| 6 | ENSG00000196890 | HIST3H2BB |
| 6 | ENSG00000197057 | DTHD1 |
| 6 | ENSG00000197122 | SRC |
| 6 | ENSG00000197168 | NEK5 |
| 6 | ENSG00000197208 | SLC22A4 |
| 6 | ENSG00000197580 | BCO2 |
| 6 | ENSG00000197584 | KCNMB2 |
| 6 | ENSG00000197603 | C5orf42 |
| 6 | ENSG00000197653 | DNAH10 |
| 6 | ENSG00000197748 | WDR96 |
| 6 | ENSG00000197826 | C4orf22 |
| 6 | ENSG00000197889 | MEIG1 |
| 6 | ENSG00000197980 | LEKR1 |
| 6 | ENSG00000198003 | CCDC151 |
| 6 | ENSG00000198088 | NUP62CL |
| 6 | ENSG00000198125 | MB |
| 6 | ENSG00000198157 | HMGN5 |
| 6 | ENSG00000198182 | ZNF607 |
| 6 | ENSG00000198551 | ZNF627 |
| 6 | ENSG00000198553 | KCNRG |
| 6 | ENSG00000198624 | CCDC69 |
| 6 | ENSG00000198668 | CALM1 |
| 6 | ENSG00000198718 | FAM179B |
| 6 | ENSG00000198729 | PPP1R14C |
| 6 | ENSG00000198815 | FOXJ3 |
| 6 | ENSG00000198825 | INPP5F |
| 6 | ENSG00000198860 | TSEN15 |
| 6 | ENSG00000198894 | CIPC |
| 6 | ENSG00000198919 | DZIP3 |
| 6 | ENSG00000198945 | L3MBTL3 |
| 6 | ENSG00000198947 | DMD |
| 6 | ENSG00000198960 | ARMCX6 |
| 6 | ENSG00000203301 | |
| 6 | ENSG00000203372 | |
| 6 | ENSG00000203485 | INF2 |
| 6 | ENSG00000203499 | FAM83H-AS1 |
| 6 | ENSG00000203666 | EFCAB2 |
| 6 | ENSG00000203705 | TATDN3 |
| 6 | ENSG00000203734 | ECT2L |
| 6 | ENSG00000203778 | FAM229B |
| 6 | ENSG00000203797 | DDO |
| 6 | ENSG00000203865 | ATP1A1OS |
| 6 | ENSG00000203965 | EFCAB7 |
| 6 | ENSG00000203985 | LDLRAD1 |
| 6 | ENSG00000204052 | LRRC73 |
| 6 | ENSG00000204070 | SYS1 |
| 6 | ENSG00000204104 | TRAF3IP1 |
| 6 | ENSG00000204356 | NELFE |
| 6 | ENSG00000204390 | HSPA1L |
| 6 | ENSG00000204428 | LY6G5C |
| 6 | ENSG00000204438 | GPANK1 |
| 6 | ENSG00000204566 | C10orf115 |
| 6 | ENSG00000204599 | TRIM39 |
| 6 | ENSG00000204666 | |
| 6 | ENSG00000204682 | CASC10 |
| 6 | ENSG00000204711 | C9orf135 |
| 6 | ENSG00000204815 | TTC25 |
| 6 | ENSG00000204852 | TCTN1 |
| 6 | ENSG00000204860 | FAM201A |
| 6 | ENSG00000204950 | LRRC10B |
| 6 | ENSG00000205084 | TMEM231 |
| 6 | ENSG00000205129 | C4orf47 |
| 6 | ENSG00000205231 | TTLL10-AS1 |
| 6 | ENSG00000205240 | OR7E36P |
| 6 | ENSG00000205593 | DENND6B |
| 6 | ENSG00000205730 | ITPRIPL2 |
| 6 | ENSG00000205758 | CRYZL1 |
| 6 | ENSG00000205808 | PPAPDC2 |
| 6 | ENSG00000205930 | C21orf49 |
| 6 | ENSG00000206053 | HN1L |
| 6 | ENSG00000206199 | ANKUB1 |
| 6 | ENSG00000206567 | |
| 6 | ENSG00000213085 | CCDC19 |
| 6 | ENSG00000213123 | TCTEX1D2 |
| 6 | ENSG00000213297 | ZNF625-ZNF20 |
| 6 | ENSG00000213533 | TMEM110 |
| 6 | ENSG00000213753 | CENPBD1P1 |
| 6 | ENSG00000213904 | LIPE-AS1 |
| 6 | ENSG00000213937 | CLDN9 |
| 6 | ENSG00000214114 | MYCBP |
| 6 | ENSG00000214174 | AMZ2P1 |
| 6 | ENSG00000214413 | BBIP1 |
| 6 | ENSG00000214447 | FAM187A |
| 6 | ENSG00000214575 | CPEB1 |
| 6 | ENSG00000214706 | IFRD2 |
| 6 | ENSG00000215187 | FAM166B |
| 6 | ENSG00000215217 | C5orf49 |
| 6 | ENSG00000215475 | SIAH3 |
| 6 | ENSG00000215845 | TSTD1 |
| 6 | ENSG00000219626 | FAM228B |
| 6 | ENSG00000221821 | C6orf226 |
| 6 | ENSG00000221838 | AP4M1 |
| 6 | ENSG00000221995 | TIAF1 |
| 6 | ENSG00000222046 | DCDC2B |
| 6 | ENSG00000223343 | |
| 6 | ENSG00000223547 | ZNF844 |
| 6 | ENSG00000223658 | |
| 6 | ENSG00000224038 | |
| 6 | ENSG00000224049 | |
| 6 | ENSG00000224165 | DNAJC27-AS1 |
| 6 | ENSG00000224281 | SLC25A5-AS1 |
| 6 | ENSG00000224479 | |
| 6 | ENSG00000224699 | LAMTOR5-AS1 |
| 6 | ENSG00000225302 | |
| 6 | ENSG00000225361 | PPP1R26-AS1 |
| 6 | ENSG00000225377 | |
| 6 | ENSG00000225431 | |
| 6 | ENSG00000225766 | |
| 6 | ENSG00000226026 | |
| 6 | ENSG00000226137 | BAIAP2-AS1 |
| 6 | ENSG00000226471 | |
| 6 | ENSG00000226644 | |
| 6 | ENSG00000226711 | FAM66C |
| 6 | ENSG00000226754 | |
| 6 | ENSG00000227084 | |
| 6 | ENSG00000227308 | |
| 6 | ENSG00000227630 | LINC01132 |
| 6 | ENSG00000227695 | DNMBP-AS1 |
| 6 | ENSG00000227877 | LINC00948 |
| 6 | ENSG00000228084 | |
| 6 | ENSG00000228242 | |
| 6 | ENSG00000228723 | SRGAP3-AS2 |
| 6 | ENSG00000228858 | |
| 6 | ENSG00000228889 | UBAC2-AS1 |
| 6 | ENSG00000229124 | VIM-AS1 |
| 6 | ENSG00000229980 | TOB1-AS1 |
| 6 | ENSG00000230062 | ANKRD66 |
| 6 | ENSG00000230873 | STMND1 |
| 6 | ENSG00000230943 | |
| 6 | ENSG00000231023 | LINC00326 |
| 6 | ENSG00000231028 | LINC00271 |
| 6 | ENSG00000231043 | |
| 6 | ENSG00000231621 | |
| 6 | ENSG00000231738 | TSPAN19 |
| 6 | ENSG00000231980 | |
| 6 | ENSG00000232415 | |
| 6 | ENSG00000232453 | |
| 6 | ENSG00000232859 | LYRM9 |
| 6 | ENSG00000232862 | |
| 6 | ENSG00000233170 | |
| 6 | ENSG00000233382 | NKAPP1 |
| 6 | ENSG00000233730 | |
| 6 | ENSG00000233936 | |
| 6 | ENSG00000234465 | PINLYP |
| 6 | ENSG00000234478 | |

TABLE 13-continued

| GeneModule | EnsemblID | GeneSymbols |
|---|---|---|
| 6 | ENSG00000234684 | SDCBP2-AS1 |
| 6 | ENSG00000234911 | TEX21P |
| 6 | ENSG00000235106 | LINC00094 |
| 6 | ENSG00000235142 | |
| 6 | ENSG00000235162 | C12orf75 |
| 6 | ENSG00000235453 | TOPORS-AS1 |
| 6 | ENSG00000235527 | |
| 6 | ENSG00000236914 | |
| 6 | ENSG00000237188 | |
| 6 | ENSG00000239467 | |
| 6 | ENSG00000240137 | |
| 6 | ENSG00000240204 | SMKR1 |
| 6 | ENSG00000240875 | LINC00886 |
| 6 | ENSG00000241935 | HOGA1 |
| 6 | ENSG00000241990 | |
| 6 | ENSG00000242808 | SOX2-OT |
| 6 | ENSG00000242852 | ZNF709 |
| 6 | ENSG00000243069 | ARHGEF26-AS1 |
| 6 | ENSG00000243627 | |
| 6 | ENSG00000243660 | ZNF487 |
| 6 | ENSG00000243667 | WDR92 |
| 6 | ENSG00000243701 | LINC00883 |
| 6 | ENSG00000243710 | WDR65 |
| 6 | ENSG00000243836 | WDR86-AS1 |
| 6 | ENSG00000243910 | TUBA4B |
| 6 | ENSG00000244968 | LIFR-AS1 |
| 6 | ENSG00000245025 | |
| 6 | ENSG00000245248 | USP2-AS1 |
| 6 | ENSG00000245317 | |
| 6 | ENSG00000245573 | BDNF-AS |
| 6 | ENSG00000245694 | CRNDE |
| 6 | ENSG00000245750 | |
| 6 | ENSG00000246016 | |
| 6 | ENSG00000246250 | |
| 6 | ENSG00000246308 | |
| 6 | ENSG00000246705 | H2AFJ |
| 6 | ENSG00000247081 | |
| 6 | ENSG00000247271 | ZBED5-AS1 |
| 6 | ENSG00000247311 | |
| 6 | ENSG00000247363 | |
| 6 | ENSG00000247746 | USP51 |
| 6 | ENSG00000247796 | |
| 6 | ENSG00000247853 | |
| 6 | ENSG00000248008 | DYNLL1-AS1 |
| 6 | ENSG00000248508 | SRP14-AS1 |
| 6 | ENSG00000248712 | CCDC153 |
| 6 | ENSG00000248801 | |
| 6 | ENSG00000248905 | FMN1 |
| 6 | ENSG00000248932 | |
| 6 | ENSG00000249042 | |
| 6 | ENSG00000249241 | |
| 6 | ENSG00000249348 | UGDH-AS1 |
| 6 | ENSG00000249481 | SPATS1 |
| 6 | ENSG00000249610 | |
| 6 | ENSG00000249621 | |
| 6 | ENSG00000250056 | LINC01018 |
| 6 | ENSG00000250462 | LRRC37BP1 |
| 6 | ENSG00000250510 | GPR162 |
| 6 | ENSG00000250790 | |
| 6 | ENSG00000251307 | |
| 6 | ENSG00000251503 | APITD1-CORT |
| 6 | ENSG00000251602 | |
| 6 | ENSG00000251669 | FAM86EP |
| 6 | ENSG00000253302 | STAU2-AS1 |
| 6 | ENSG00000253320 | |
| 6 | ENSG00000253379 | |
| 6 | ENSG00000253719 | ATXN7L3B |
| 6 | ENSG00000253948 | |
| 6 | ENSG00000254024 | |
| 6 | ENSG00000254389 | RHPN1-AS1 |
| 6 | ENSG00000254473 | |
| 6 | ENSG00000254608 | |
| 6 | ENSG00000254837 | |
| 6 | ENSG00000255036 | |
| 6 | ENSG00000255277 | ABCC6P2 |
| 6 | ENSG00000256061 | DYX1C1 |
| 6 | ENSG00000256073 | C21orf119 |
| 6 | ENSG00000257057 | LINC01171 |
| 6 | ENSG00000257084 | |
| 6 | ENSG00000257108 | NHLRC4 |
| 6 | ENSG00000257542 | OR7E47P |
| 6 | ENSG00000257698 | |
| 6 | ENSG00000258334 | |
| 6 | ENSG00000258539 | |
| 6 | ENSG00000258701 | LINC00638 |
| 6 | ENSG00000258940 | |
| 6 | ENSG00000259087 | |
| 6 | ENSG00000259225 | |
| 6 | ENSG00000259251 | |
| 6 | ENSG00000259264 | |
| 6 | ENSG00000259319 | |
| 6 | ENSG00000259426 | |
| 6 | ENSG00000259577 | |
| 6 | ENSG00000259802 | |
| 6 | ENSG00000259901 | |
| 6 | ENSG00000260018 | |
| 6 | ENSG00000260057 | |
| 6 | ENSG00000260136 | |
| 6 | ENSG00000260328 | |
| 6 | ENSG00000260372 | AQP4-AS1 |
| 6 | ENSG00000260517 | |
| 6 | ENSG00000260526 | |
| 6 | ENSG00000260604 | |
| 6 | ENSG00000260643 | |
| 6 | ENSG00000260908 | |
| 6 | ENSG00000260951 | |
| 6 | ENSG00000261188 | |
| 6 | ENSG00000261572 | |
| 6 | ENSG00000261652 | C15orf65 |
| 6 | ENSG00000261759 | |
| 6 | ENSG00000261777 | |
| 6 | ENSG00000263011 | |
| 6 | ENSG00000263812 | LINC00908 |
| 6 | ENSG00000265666 | |
| 6 | ENSG00000265688 | MAFG-AS1 |
| 6 | ENSG00000265752 | |
| 6 | ENSG00000266947 | |
| 6 | ENSG00000267100 | ILF3-AS1 |
| 6 | ENSG00000267106 | C19orf82 |
| 6 | ENSG00000267128 | RNF157-AS1 |
| 6 | ENSG00000267348 | |
| 6 | ENSG00000267390 | |
| 6 | ENSG00000267439 | |
| 6 | ENSG00000267848 | |
| 6 | ENSG00000268061 | NAPA-AS1 |
| 6 | ENSG00000268175 | |
| 6 | ENSG00000268565 | |
| 6 | ENSG00000269916 | |
| 6 | ENSG00000270021 | |
| 6 | ENSG00000270362 | HMGN3-AS1 |
| 6 | ENSG00000270504 | |
| 6 | ENSG00000270820 | |
| 6 | ENSG00000271133 | |
| 6 | ENSG00000271853 | |
| 6 | ENSG00000272079 | |
| 6 | ENSG00000272086 | |
| 6 | ENSG00000272106 | |
| 6 | ENSG00000272143 | FGF14-AS2 |
| 6 | ENSG00000272168 | CASC15 |
| 6 | ENSG00000272288 | |
| 6 | ENSG00000272323 | |
| 6 | ENSG00000272442 | |
| 6 | ENSG00000272502 | |
| 6 | ENSG00000272514 | |
| 6 | ENSG00000272831 | |
| 6 | ENSG00000272902 | |
| 6 | ENSG00000273061 | |
| 6 | ENSG00000273071 | |
| 7 | ENSG00000008988 | RPS20 |
| 7 | ENSG00000063046 | EIF4B |
| 7 | ENSG00000063177 | RPL18 |
| 7 | ENSG00000071082 | RPL31 |
| 7 | ENSG00000083845 | RPS5 |
| 7 | ENSG00000084090 | STARD7 |
| 7 | ENSG00000089009 | RPL6 |

TABLE 13-continued

| GeneModule | EnsemblID | GeneSymbols |
|---|---|---|
| 7 | ENSG00000089157 | RPLP0 |
| 7 | ENSG00000089289 | IGBP1 |
| 7 | ENSG00000100129 | EIF3L |
| 7 | ENSG00000100316 | RPL3 |
| 7 | ENSG00000100353 | EIF3D |
| 7 | ENSG00000100814 | CCNB1IP1 |
| 7 | ENSG00000104408 | EIF3E |
| 7 | ENSG00000104529 | EEF1D |
| 7 | ENSG00000105193 | RPS16 |
| 7 | ENSG00000105202 | FBL |
| 7 | ENSG00000105372 | RPS19 |
| 7 | ENSG00000105373 | GLTSCR2 |
| 7 | ENSG00000105640 | RPL18A |
| 7 | ENSG00000107625 | DDX50 |
| 7 | ENSG00000108107 | RPL28 |
| 7 | ENSG00000108298 | RPL19 |
| 7 | ENSG00000108604 | SMARCD2 |
| 7 | ENSG00000109475 | RPL34 |
| 7 | ENSG00000110700 | RPS13 |
| 7 | ENSG00000111678 | C12orf57 |
| 7 | ENSG00000112306 | RPS12 |
| 7 | ENSG00000114391 | RPL24 |
| 7 | ENSG00000114942 | EEF1B2 |
| 7 | ENSG00000115268 | RPS15 |
| 7 | ENSG00000116251 | RPL22 |
| 7 | ENSG00000117543 | DPH5 |
| 7 | ENSG00000118181 | RPS25 |
| 7 | ENSG00000118816 | CCNI |
| 7 | ENSG00000122026 | RPL21 |
| 7 | ENSG00000122406 | RPL5 |
| 7 | ENSG00000124614 | RPS10 |
| 7 | ENSG00000125691 | RPL23 |
| 7 | ENSG00000125743 | SNRPD2 |
| 7 | ENSG00000126088 | UROD |
| 7 | ENSG00000129158 | SERGEF |
| 7 | ENSG00000130159 | ECSIT |
| 7 | ENSG00000130255 | RPL36 |
| 7 | ENSG00000130312 | MRPL34 |
| 7 | ENSG00000131143 | COX4I1 |
| 7 | ENSG00000131469 | RPL27 |
| 7 | ENSG00000133112 | TPT1 |
| 7 | ENSG00000134419 | RPS15A |
| 7 | ENSG00000135390 | ATP5G2 |
| 7 | ENSG00000136104 | RNASEH2B |
| 7 | ENSG00000136710 | CCDC115 |
| 7 | ENSG00000136942 | RPL35 |
| 7 | ENSG00000137054 | POLR1E |
| 7 | ENSG00000137154 | RPS6 |
| 7 | ENSG00000137818 | RPLP1 |
| 7 | ENSG00000137970 | RPL7P9 |
| 7 | ENSG00000138326 | RPS24 |
| 7 | ENSG00000139239 | RPL14P1 |
| 7 | ENSG00000140905 | GCSH |
| 7 | ENSG00000140988 | RPS2 |
| 7 | ENSG00000142534 | RPS11 |
| 7 | ENSG00000142541 | RPL13A |
| 7 | ENSG00000142676 | RPL11 |
| 7 | ENSG00000142937 | RPS8 |
| 7 | ENSG00000143947 | RPS27A |
| 7 | ENSG00000144713 | RPL32 |
| 7 | ENSG00000144741 | SLC25A26 |
| 7 | ENSG00000145425 | RPS3A |
| 7 | ENSG00000145592 | RPL37 |
| 7 | ENSG00000145741 | BTF3 |
| 7 | ENSG00000147403 | RPL10 |
| 7 | ENSG00000147604 | RPL7 |
| 7 | ENSG00000147654 | EBAG9 |
| 7 | ENSG00000147677 | EIF3H |
| 7 | ENSG00000148303 | RPL7A |
| 7 | ENSG00000149273 | RPS3 |
| 7 | ENSG00000149806 | FAU |
| 7 | ENSG00000151353 | TMEM18 |
| 7 | ENSG00000156482 | RPL30 |
| 7 | ENSG00000156508 | EEF1A1 |
| 7 | ENSG00000156853 | ZNF689 |
| 7 | ENSG00000161016 | RPL8 |
| 7 | ENSG00000161970 | RPL26 |
| 7 | ENSG00000162244 | RPL29 |
| 7 | ENSG00000163344 | PMVK |
| 7 | ENSG00000163682 | RPL9 |
| 7 | ENSG00000164587 | RPS14 |
| 7 | ENSG00000166441 | RPL27A |
| 7 | ENSG00000166902 | MRPL16 |
| 7 | ENSG00000167526 | RPL13 |
| 7 | ENSG00000168028 | RPSA |
| 7 | ENSG00000169100 | SLC25A6 |
| 7 | ENSG00000169714 | CNBP |
| 7 | ENSG00000170889 | RPS9 |
| 7 | ENSG00000171858 | RPS21 |
| 7 | ENSG00000171863 | RPS7 |
| 7 | ENSG00000172809 | RPL38 |
| 7 | ENSG00000173726 | TOMM20 |
| 7 | ENSG00000174444 | RPL4 |
| 7 | ENSG00000174547 | MRPL11 |
| 7 | ENSG00000174748 | RPL15 |
| 7 | ENSG00000175061 | FAM211A-AS1 |
| 7 | ENSG00000175390 | EIF3F |
| 7 | ENSG00000177410 | ZFAS1 |
| 7 | ENSG00000177600 | RPLP2 |
| 7 | ENSG00000177954 | RPS27 |
| 7 | ENSG00000178464 | |
| 7 | ENSG00000182774 | RPS17L |
| 7 | ENSG00000182899 | RPL35A |
| 7 | ENSG00000183405 | RPS7P1 |
| 7 | ENSG00000184779 | RPS17 |
| 7 | ENSG00000185641 | |
| 7 | ENSG00000186468 | RPS23 |
| 7 | ENSG00000188243 | COMMD6 |
| 7 | ENSG00000188846 | RPL14 |
| 7 | ENSG00000189343 | RPS2P46 |
| 7 | ENSG00000196205 | EEF1A1P5 |
| 7 | ENSG00000196531 | NACA |
| 7 | ENSG00000196683 | TOMM7 |
| 7 | ENSG00000197756 | RPL37A |
| 7 | ENSG00000197958 | RPL12 |
| 7 | ENSG00000198034 | RPS4X |
| 7 | ENSG00000198242 | RPL23A |
| 7 | ENSG00000198546 | ZNF511 |
| 7 | ENSG00000198755 | RPL10A |
| 7 | ENSG00000198918 | RPL39 |
| 7 | ENSG00000204196 | |
| 7 | ENSG00000204387 | C6orf48 |
| 7 | ENSG00000204628 | GNB2L1 |
| 7 | ENSG00000205246 | RPSAP58 |
| 7 | ENSG00000212802 | RPL15P3 |
| 7 | ENSG00000213178 | |
| 7 | ENSG00000213442 | RPL18AP3 |
| 7 | ENSG00000213553 | RPLP0P6 |
| 7 | ENSG00000213741 | RPS29 |
| 7 | ENSG00000213860 | RPL21P75 |
| 7 | ENSG00000214046 | SMIM7 |
| 7 | ENSG00000214113 | LYRM4 |
| 7 | ENSG00000214389 | RPS3AP26 |
| 7 | ENSG00000214485 | RPL7P1 |
| 7 | ENSG00000214784 | |
| 7 | ENSG00000215021 | PHB2 |
| 7 | ENSG00000218426 | |
| 7 | ENSG00000220749 | RPL21P28 |
| 7 | ENSG00000220842 | |
| 7 | ENSG00000221983 | UBA52 |
| 7 | ENSG00000226084 | |
| 7 | ENSG00000226221 | |
| 7 | ENSG00000227063 | RPL41P1 |
| 7 | ENSG00000227081 | |
| 7 | ENSG00000229117 | RPL41 |
| 7 | ENSG00000229638 | RPL4P4 |
| 7 | ENSG00000230629 | RPS23P8 |
| 7 | ENSG00000231500 | RPS18 |
| 7 | ENSG00000232472 | EEF1B2P3 |
| 7 | ENSG00000232573 | RPL3P4 |
| 7 | ENSG00000233476 | EEF1A1P6 |
| 7 | ENSG00000233762 | |
| 7 | ENSG00000233913 | |
| 7 | ENSG00000233927 | RPS28 |
| 7 | ENSG00000234741 | GAS5 |

TABLE 13-continued

| GeneModule | EnsemblID | GeneSymbols |
|---|---|---|
| 7 | ENSG00000234797 | RPS3AP6 |
| 7 | ENSG00000234851 |  |
| 7 | ENSG00000235065 | RPL24P2 |
| 7 | ENSG00000235552 | RPL6P27 |
| 7 | ENSG00000236552 | RPL13AP5 |
| 7 | ENSG00000240087 |  |
| 7 | ENSG00000240342 | RPS2P5 |
| 7 | ENSG00000241343 | RPL36A |
| 7 | ENSG00000242071 | RPL7AP6 |
| 7 | ENSG00000242299 |  |
| 7 | ENSG00000243199 |  |
| 7 | ENSG00000244313 |  |
| 7 | ENSG00000244398 |  |
| 7 | ENSG00000244716 |  |
| 7 | ENSG00000245910 | SNHG6 |
| 7 | ENSG00000254772 | EEF1G |
| 7 | ENSG00000265681 | RPL17 |
| 7 | ENSG00000269893 | SNHG8 |
| 8 | ENSG00000000938 | FGR |
| 8 | ENSG00000005844 | ITGAL |
| 8 | ENSG00000006074 | CCL18 |
| 8 | ENSG00000006075 | CCL3 |
| 8 | ENSG00000008516 | MMP25 |
| 8 | ENSG00000009790 | TRAF3IP3 |
| 8 | ENSG00000010295 | IFFO1 |
| 8 | ENSG00000010671 | BTK |
| 8 | ENSG00000010810 | FYN |
| 8 | ENSG00000011600 | TYROBP |
| 8 | ENSG00000012779 | ALOX5 |
| 8 | ENSG00000013725 | CD6 |
| 8 | ENSG00000015285 | WAS |
| 8 | ENSG00000018280 | SLC11A1 |
| 8 | ENSG00000019169 | MARCO |
| 8 | ENSG00000023902 | PLEKHO1 |
| 8 | ENSG00000026297 | RNASET2 |
| 8 | ENSG00000027869 | SH2D2A |
| 8 | ENSG00000028137 | TNFRSF1B |
| 8 | ENSG00000033327 | GAB2 |
| 8 | ENSG00000038945 | MSR1 |
| 8 | ENSG00000043462 | LCP2 |
| 8 | ENSG00000048740 | CELF2 |
| 8 | ENSG00000054967 | RELT |
| 8 | ENSG00000057657 | PRDM1 |
| 8 | ENSG00000059377 | TBXAS1 |
| 8 | ENSG00000059728 | MXD1 |
| 8 | ENSG00000059804 | SLC2A3 |
| 8 | ENSG00000062282 | DGAT2 |
| 8 | ENSG00000064201 | TSPAN32 |
| 8 | ENSG00000065413 | ANKRD44 |
| 8 | ENSG00000065675 | PRKCQ |
| 8 | ENSG00000066294 | CD84 |
| 8 | ENSG00000066336 | SPI1 |
| 8 | ENSG00000068831 | RASGRP2 |
| 8 | ENSG00000069424 | KCNAB2 |
| 8 | ENSG00000072401 | UBE2D1 |
| 8 | ENSG00000072694 | FCGR2B |
| 8 | ENSG00000072786 | STK10 |
| 8 | ENSG00000072818 | ACAP1 |
| 8 | ENSG00000073921 | PICALM |
| 8 | ENSG00000074706 | IPCEF1 |
| 8 | ENSG00000074966 | TXK |
| 8 | ENSG00000075624 | ACTB |
| 8 | ENSG00000075884 | ARHGAP15 |
| 8 | ENSG00000076641 | PAG1 |
| 8 | ENSG00000076662 | ICAM3 |
| 8 | ENSG00000076928 | ARHGEF1 |
| 8 | ENSG00000077420 | APBB1IP |
| 8 | ENSG00000077984 | CST7 |
| 8 | ENSG00000078589 | P2RY10 |
| 8 | ENSG00000079263 | SP140 |
| 8 | ENSG00000081059 | TCF7 |
| 8 | ENSG00000081087 | OSTM1 |
| 8 | ENSG00000081237 | PTPRC |
| 8 | ENSG00000081320 | STK17B |
| 8 | ENSG00000082074 | FYB |
| 8 | ENSG00000085265 | FCN1 |
| 8 | ENSG00000085514 | PILRA |
| 8 | ENSG00000086300 | SNX10 |
| 8 | ENSG00000086730 | LAT2 |
| 8 | ENSG00000087266 | SH3BP2 |
| 8 | ENSG00000088827 | SIGLEC1 |
| 8 | ENSG00000089327 | FXYD5 |
| 8 | ENSG00000089639 | GMIP |
| 8 | ENSG00000089820 | ARHGAP4 |
| 8 | ENSG00000090339 | ICAM1 |
| 8 | ENSG00000090674 | MCOLN1 |
| 8 | ENSG00000091106 | NLRC4 |
| 8 | ENSG00000092929 | UNC13D |
| 8 | ENSG00000095303 | PTGS1 |
| 8 | ENSG00000095370 | SH2D3C |
| 8 | ENSG00000096996 | IL12RB1 |
| 8 | ENSG00000099308 | MAST3 |
| 8 | ENSG00000099985 | OSM |
| 8 | ENSG00000100055 | CYTH4 |
| 8 | ENSG00000100060 | MFNG |
| 8 | ENSG00000100351 | GRAP2 |
| 8 | ENSG00000100365 | NCF4 |
| 8 | ENSG00000100368 | CSF2RB |
| 8 | ENSG00000100385 | IL2RB |
| 8 | ENSG00000100599 | RIN3 |
| 8 | ENSG00000100985 | MMP9 |
| 8 | ENSG00000101109 | STK4 |
| 8 | ENSG00000101265 | RASSF2 |
| 8 | ENSG00000101307 | SIRPB1 |
| 8 | ENSG00000101336 | HCK |
| 8 | ENSG00000101916 | TLR8 |
| 8 | ENSG00000102032 | RENBP |
| 8 | ENSG00000102218 | RP2 |
| 8 | ENSG00000102445 | KIAA0226L |
| 8 | ENSG00000102524 | TNFSF13B |
| 8 | ENSG00000102575 | ACP5 |
| 8 | ENSG00000102879 | CORO1A |
| 8 | ENSG00000103005 | USB1 |
| 8 | ENSG00000103187 | COTL1 |
| 8 | ENSG00000103313 | MEFV |
| 8 | ENSG00000103522 | IL21R |
| 8 | ENSG00000103569 | AQP9 |
| 8 | ENSG00000104814 | MAP4K1 |
| 8 | ENSG00000104894 | CD37 |
| 8 | ENSG00000104972 | LILRB1 |
| 8 | ENSG00000104998 | IL27RA |
| 8 | ENSG00000105122 | RASAL3 |
| 8 | ENSG00000105329 | TGFB1 |
| 8 | ENSG00000105339 | DENND3 |
| 8 | ENSG00000105483 | CARD8 |
| 8 | ENSG00000105639 | JAK3 |
| 8 | ENSG00000105835 | NAMPT |
| 8 | ENSG00000105851 | PIK3CG |
| 8 | ENSG00000105967 | TFEC |
| 8 | ENSG00000106066 | CPVL |
| 8 | ENSG00000106348 | IMPDH1 |
| 8 | ENSG00000107099 | DOCK8 |
| 8 | ENSG00000107485 | GATA3 |
| 8 | ENSG00000107551 | RASSF4 |
| 8 | ENSG00000108405 | P2RX1 |
| 8 | ENSG00000108932 | SLC16A6 |
| 8 | ENSG00000108960 | MMD |
| 8 | ENSG00000109743 | BST1 |
| 8 | ENSG00000110031 | LPXN |
| 8 | ENSG00000110047 | EHD1 |
| 8 | ENSG00000110077 | MS4A6A |
| 8 | ENSG00000110079 | MS4A4A |
| 8 | ENSG00000110324 | IL10RA |
| 8 | ENSG00000110395 | CBL |
| 8 | ENSG00000110446 | SLC15A3 |
| 8 | ENSG00000110448 | CD5 |
| 8 | ENSG00000110848 | CD69 |
| 8 | ENSG00000110876 | SELPLG |
| 8 | ENSG00000110934 | BIN2 |
| 8 | ENSG00000111252 | SH2B3 |
| 8 | ENSG00000111348 | ARHGDIB |
| 8 | ENSG00000111679 | PTPN6 |
| 8 | ENSG00000111729 | CLEC4A |
| 8 | ENSG00000112096 | SOD2 |
| 8 | ENSG00000112137 | PHACTR1 |
| 8 | ENSG00000112149 | CD83 |

TABLE 13-continued

| GeneModule | EnsemblID | GeneSymbols |
|---|---|---|
| 8 | ENSG00000112195 | TREML2 |
| 8 | ENSG00000112303 | VNN2 |
| 8 | ENSG00000112531 | QKI |
| 8 | ENSG00000112799 | LY86 |
| 8 | ENSG00000113263 | ITK |
| 8 | ENSG00000113273 | ARSB |
| 8 | ENSG00000114013 | CD86 |
| 8 | ENSG00000114450 | GNB4 |
| 8 | ENSG00000114626 | ABTB1 |
| 8 | ENSG00000114737 | CISH |
| 8 | ENSG00000115085 | ZAP70 |
| 8 | ENSG00000115165 | CYTIP |
| 8 | ENSG00000115232 | ITGA4 |
| 8 | ENSG00000115271 | GCA |
| 8 | ENSG00000115318 | LOXL3 |
| 8 | ENSG00000115325 | DOK1 |
| 8 | ENSG00000115355 | CCDC88A |
| 8 | ENSG00000115604 | IL18R1 |
| 8 | ENSG00000115607 | IL18RAP |
| 8 | ENSG00000115756 | HPCAL1 |
| 8 | ENSG00000115828 | QPCT |
| 8 | ENSG00000115935 | WIPF1 |
| 8 | ENSG00000115956 | PLEK |
| 8 | ENSG00000116017 | ARID3A |
| 8 | ENSG00000116337 | AMPD2 |
| 8 | ENSG00000116701 | NCF2 |
| 8 | ENSG00000116741 | RGS2 |
| 8 | ENSG00000116824 | CD2 |
| 8 | ENSG00000116852 | KIF21B |
| 8 | ENSG00000117009 | KMO |
| 8 | ENSG00000117090 | SLAMF1 |
| 8 | ENSG00000117091 | CD48 |
| 8 | ENSG00000117115 | PADI2 |
| 8 | ENSG00000117281 | CD160 |
| 8 | ENSG00000118263 | KLF7 |
| 8 | ENSG00000118508 | RAB32 |
| 8 | ENSG00000119321 | FKBP15 |
| 8 | ENSG00000119535 | CSF3R |
| 8 | ENSG00000119686 | FLVCR2 |
| 8 | ENSG00000120063 | GNA13 |
| 8 | ENSG00000120709 | FAM53C |
| 8 | ENSG00000120899 | PTK2B |
| 8 | ENSG00000121060 | TRIM25 |
| 8 | ENSG00000121210 | KIAA0922 |
| 8 | ENSG00000121281 | ADCY7 |
| 8 | ENSG00000121797 | CCRL2 |
| 8 | ENSG00000121807 | CCR2 |
| 8 | ENSG00000121966 | CXCR4 |
| 8 | ENSG00000122122 | SASH3 |
| 8 | ENSG00000122188 | LAX1 |
| 8 | ENSG00000122224 | LY9 |
| 8 | ENSG00000122862 | SRGN |
| 8 | ENSG00000122986 | HVCN1 |
| 8 | ENSG00000123329 | ARHGAP9 |
| 8 | ENSG00000123338 | NCKAP1L |
| 8 | ENSG00000123689 | G0S2 |
| 8 | ENSG00000124126 | PREX1 |
| 8 | ENSG00000124203 | ZNF831 |
| 8 | ENSG00000124334 | IL9R |
| 8 | ENSG00000124357 | NAGK |
| 8 | ENSG00000124491 | F13A1 |
| 8 | ENSG00000124731 | TREM1 |
| 8 | ENSG00000125354 | 6-Sep |
| 8 | ENSG00000125538 | IL1B |
| 8 | ENSG00000125637 | PSD4 |
| 8 | ENSG00000125735 | TNFSF14 |
| 8 | ENSG00000125910 | S1PR4 |
| 8 | ENSG00000126246 | IGFLR1 |
| 8 | ENSG00000126262 | FFAR2 |
| 8 | ENSG00000126264 | HCST |
| 8 | ENSG00000126353 | CCR7 |
| 8 | ENSG00000126561 | STAT5A |
| 8 | ENSG00000126860 | EVI2A |
| 8 | ENSG00000126882 | FAM78A |
| 8 | ENSG00000127084 | FGD3 |
| 8 | ENSG00000127152 | BCL11B |
| 8 | ENSG00000127507 | EMR2 |
| 8 | ENSG00000127951 | FGL2 |
| 8 | ENSG00000128271 | ADORA2A |
| 8 | ENSG00000128340 | RAC2 |
| 8 | ENSG00000128383 | APOBEC3A |
| 8 | ENSG00000128815 | WDFY4 |
| 8 | ENSG00000129071 | MBD4 |
| 8 | ENSG00000129226 | CD68 |
| 8 | ENSG00000129277 | CCL4 |
| 8 | ENSG00000129657 | SEC14L1 |
| 8 | ENSG00000129675 | ARHGEF6 |
| 8 | ENSG00000130203 | APOE |
| 8 | ENSG00000130208 | APOC1 |
| 8 | ENSG00000130429 | ARPC1B |
| 8 | ENSG00000130475 | FCHO1 |
| 8 | ENSG00000130592 | LSP1 |
| 8 | ENSG00000130755 | GMFG |
| 8 | ENSG00000130775 | THEMIS2 |
| 8 | ENSG00000130830 | MPP1 |
| 8 | ENSG00000131042 | LILRB2 |
| 8 | ENSG00000131378 | RFTN1 |
| 8 | ENSG00000131401 | NAPSB |
| 8 | ENSG00000131669 | NINJ1 |
| 8 | ENSG00000131724 | IL13RA1 |
| 8 | ENSG00000132182 | NUP210 |
| 8 | ENSG00000132205 | EMILIN2 |
| 8 | ENSG00000132334 | PTPRE |
| 8 | ENSG00000132510 | KDM6B |
| 8 | ENSG00000132514 | CLEC10A |
| 8 | ENSG00000132965 | ALOX5AP |
| 8 | ENSG00000133048 | CHI3L1 |
| 8 | ENSG00000133246 | PRAM1 |
| 8 | ENSG00000133574 | GIMAP4 |
| 8 | ENSG00000133961 | NUMB |
| 8 | ENSG00000134242 | PTPN22 |
| 8 | ENSG00000134516 | DOCK2 |
| 8 | ENSG00000134668 | SPOCD1 |
| 8 | ENSG00000134686 | PHC2 |
| 8 | ENSG00000134698 | AGO4 |
| 8 | ENSG00000134830 | C5AR2 |
| 8 | ENSG00000134954 | ETS1 |
| 8 | ENSG00000135074 | ADAM19 |
| 8 | ENSG00000135077 | HAVCR2 |
| 8 | ENSG00000135218 | CD36 |
| 8 | ENSG00000135426 | TESPA1 |
| 8 | ENSG00000135439 | AGAP2 |
| 8 | ENSG00000135604 | STX11 |
| 8 | ENSG00000135636 | DYSF |
| 8 | ENSG00000135838 | NPL |
| 8 | ENSG00000135905 | DOCK10 |
| 8 | ENSG00000136040 | PLXNC1 |
| 8 | ENSG00000136111 | TBC1D4 |
| 8 | ENSG00000136167 | LCP1 |
| 8 | ENSG00000136250 | AOAH |
| 8 | ENSG00000136286 | MYO1G |
| 8 | ENSG00000136404 | TM6SF1 |
| 8 | ENSG00000136490 | LIMD2 |
| 8 | ENSG00000136560 | TANK |
| 8 | ENSG00000136867 | SLC31A2 |
| 8 | ENSG00000136869 | TLR4 |
| 8 | ENSG00000137076 | TLN1 |
| 8 | ENSG00000137078 | SIT1 |
| 8 | ENSG00000137265 | IRF4 |
| 8 | ENSG00000137462 | TLR2 |
| 8 | ENSG00000137491 | SLCO2B1 |
| 8 | ENSG00000137575 | SDCBP |
| 8 | ENSG00000137752 | CASP1 |
| 8 | ENSG00000137841 | PLCB2 |
| 8 | ENSG00000138378 | STAT4 |
| 8 | ENSG00000138621 | PPCDC |
| 8 | ENSG00000138964 | PARVG |
| 8 | ENSG00000139193 | CD27 |
| 8 | ENSG00000139278 | GLIPR1 |
| 8 | ENSG00000139370 | SLC15A4 |
| 8 | ENSG00000139436 | GIT2 |
| 8 | ENSG00000140030 | GPR65 |
| 8 | ENSG00000140368 | PSTPIP1 |
| 8 | ENSG00000140379 | BCL2A1 |
| 8 | ENSG00000140678 | ITGAX |
| 8 | ENSG00000140749 | IGSF6 |

TABLE 13-continued

| GeneModule | EnsemblID | GeneSymbols |
|---|---|---|
| 8 | ENSG00000140931 | CMTM3 |
| 8 | ENSG00000140968 | IRF8 |
| 8 | ENSG00000141293 | SKAP1 |
| 8 | ENSG00000141298 | SSH2 |
| 8 | ENSG00000141480 | ARRB2 |
| 8 | ENSG00000141506 | PIK3R5 |
| 8 | ENSG00000141576 | RNF157 |
| 8 | ENSG00000142185 | TRPM2 |
| 8 | ENSG00000142227 | EMP3 |
| 8 | ENSG00000142347 | MYO1F |
| 8 | ENSG00000142512 | SIGLEC10 |
| 8 | ENSG00000143110 | C1orf162 |
| 8 | ENSG00000143119 | CD53 |
| 8 | ENSG00000143226 | FCGR2A |
| 8 | ENSG00000143382 | ADAMTSL4 |
| 8 | ENSG00000143546 | S100A8 |
| 8 | ENSG00000143851 | PTPN7 |
| 8 | ENSG00000144218 | AFF3 |
| 8 | ENSG00000144815 | NXPE3 |
| 8 | ENSG00000145416 | 1-Mar |
| 8 | ENSG00000145569 | FAM105A |
| 8 | ENSG00000145649 | GZMA |
| 8 | ENSG00000145819 | ARHGAP26 |
| 8 | ENSG00000146070 | PLA2G7 |
| 8 | ENSG00000146094 | DOK3 |
| 8 | ENSG00000146112 | PPP1R18 |
| 8 | ENSG00000146192 | FGD2 |
| 8 | ENSG00000146278 | PNRC1 |
| 8 | ENSG00000146285 | SCML4 |
| 8 | ENSG00000146592 | CREB5 |
| 8 | ENSG00000146859 | TMEM140 |
| 8 | ENSG00000147010 | SH3KBP1 |
| 8 | ENSG00000147065 | MSN |
| 8 | ENSG00000147168 | IL2RG |
| 8 | ENSG00000147251 | DOCK11 |
| 8 | ENSG00000147416 | ATP6V1B2 |
| 8 | ENSG00000147443 | DOK2 |
| 8 | ENSG00000147454 | SLC25A37 |
| 8 | ENSG00000147459 | DOCK5 |
| 8 | ENSG00000147872 | PLIN2 |
| 8 | ENSG00000148572 | NRBF2 |
| 8 | ENSG00000148908 | RGS10 |
| 8 | ENSG00000149091 | DGKZ |
| 8 | ENSG00000149177 | PTPRJ |
| 8 | ENSG00000149781 | FERMT3 |
| 8 | ENSG00000150337 | FCGR1A |
| 8 | ENSG00000150681 | RGS18 |
| 8 | ENSG00000150867 | PIP4K2A |
| 8 | ENSG00000151490 | PTPRO |
| 8 | ENSG00000151651 | ADAM8 |
| 8 | ENSG00000151702 | FLI1 |
| 8 | ENSG00000151726 | ACSL1 |
| 8 | ENSG00000151948 | GLT1D1 |
| 8 | ENSG00000152213 | ARL11 |
| 8 | ENSG00000152270 | PDE3B |
| 8 | ENSG00000152495 | CAMK4 |
| 8 | ENSG00000153071 | DAB2 |
| 8 | ENSG00000153179 | RASSF3 |
| 8 | ENSG00000153283 | CD96 |
| 8 | ENSG00000153317 | ASAP1 |
| 8 | ENSG00000153395 | LPCAT1 |
| 8 | ENSG00000153563 | CD8A |
| 8 | ENSG00000154016 | GRAP |
| 8 | ENSG00000154451 | GBP5 |
| 8 | ENSG00000154589 | LY96 |
| 8 | ENSG00000155307 | SAMSN1 |
| 8 | ENSG00000155465 | SLC7A7 |
| 8 | ENSG00000155629 | PIK3AP1 |
| 8 | ENSG00000155659 | VSIG4 |
| 8 | ENSG00000155849 | ELMO1 |
| 8 | ENSG00000155926 | SLA |
| 8 | ENSG00000156273 | BACH1 |
| 8 | ENSG00000157350 | ST3GAL2 |
| 8 | ENSG00000157551 | KCNJ15 |
| 8 | ENSG00000158517 | NCF1 |
| 8 | ENSG00000158714 | SLAMF8 |
| 8 | ENSG00000158869 | FCER1G |
| 8 | ENSG00000159189 | C1QC |
| 8 | ENSG00000159322 | ADPGK |
| 8 | ENSG00000159618 | GPR114 |
| 8 | ENSG00000159753 | RLTPR |
| 8 | ENSG00000160185 | UBASH3A |
| 8 | ENSG00000160219 | GAB3 |
| 8 | ENSG00000160255 | ITGB2 |
| 8 | ENSG00000160326 | SLC2A6 |
| 8 | ENSG00000160593 | AMICA1 |
| 8 | ENSG00000160654 | CD3G |
| 8 | ENSG00000160883 | HK3 |
| 8 | ENSG00000160999 | SH2B2 |
| 8 | ENSG00000161570 | CCL5 |
| 8 | ENSG00000161791 | FMNL3 |
| 8 | ENSG00000161929 | SCIMP |
| 8 | ENSG00000162511 | LAPTM5 |
| 8 | ENSG00000162676 | GFI1 |
| 8 | ENSG00000162711 | NLRP3 |
| 8 | ENSG00000162739 | SLAMF6 |
| 8 | ENSG00000163154 | TNFAIP8L2 |
| 8 | ENSG00000163162 | RNF149 |
| 8 | ENSG00000163219 | ARHGAP25 |
| 8 | ENSG00000163220 | S100A9 |
| 8 | ENSG00000163376 | KBTBD8 |
| 8 | ENSG00000163421 | PROK2 |
| 8 | ENSG00000163464 | CXCR1 |
| 8 | ENSG00000163519 | TRAT1 |
| 8 | ENSG00000163563 | MNDA |
| 8 | ENSG00000163564 | PYHIN1 |
| 8 | ENSG00000163600 | ICOS |
| 8 | ENSG00000163823 | CCR1 |
| 8 | ENSG00000164691 | TAGAP |
| 8 | ENSG00000165030 | NFIL3 |
| 8 | ENSG00000165168 | CYBB |
| 8 | ENSG00000165178 | NCF1C |
| 8 | ENSG00000166128 | RAB8B |
| 8 | ENSG00000166340 | TPP1 |
| 8 | ENSG00000166501 | PRKCB |
| 8 | ENSG00000166523 | CLEC4E |
| 8 | ENSG00000166716 | ZNF592 |
| 8 | ENSG00000166927 | MS4A7 |
| 8 | ENSG00000167208 | SNX20 |
| 8 | ENSG00000167261 | DPEP2 |
| 8 | ENSG00000167286 | CD3D |
| 8 | ENSG00000167483 | FAM129C |
| 8 | ENSG00000167613 | LAIR1 |
| 8 | ENSG00000167680 | SEMA6B |
| 8 | ENSG00000167851 | CD300A |
| 8 | ENSG00000168067 | MAP4K2 |
| 8 | ENSG00000168071 | CCDC88B |
| 8 | ENSG00000168404 | MLKL |
| 8 | ENSG00000168421 | RHOH |
| 8 | ENSG00000168685 | IL7R |
| 8 | ENSG00000168918 | INPP5D |
| 8 | ENSG00000169180 | XPO6 |
| 8 | ENSG00000169220 | RGS14 |
| 8 | ENSG00000169228 | RAB24 |
| 8 | ENSG00000169403 | PTAFR |
| 8 | ENSG00000169413 | RNASE6 |
| 8 | ENSG00000169442 | CD52 |
| 8 | ENSG00000169508 | GPR183 |
| 8 | ENSG00000169554 | ZEB2 |
| 8 | ENSG00000169826 | CSGALNACT2 |
| 8 | ENSG00000169896 | ITGAM |
| 8 | ENSG00000170323 | FABP4 |
| 8 | ENSG00000170458 | CD14 |
| 8 | ENSG00000170525 | PFKFB3 |
| 8 | ENSG00000170542 | SERPINB9 |
| 8 | ENSG00000170909 | OSCAR |
| 8 | ENSG00000170956 | CEACAM3 |
| 8 | ENSG00000171049 | FPR2 |
| 8 | ENSG00000171051 | FPR1 |
| 8 | ENSG00000171488 | LRRC8C |
| 8 | ENSG00000171608 | PIK3CD |
| 8 | ENSG00000171659 | GPR34 |
| 8 | ENSG00000171700 | RGS19 |
| 8 | ENSG00000171777 | RASGRP4 |
| 8 | ENSG00000171860 | C3AR1 |
| 8 | ENSG00000172081 | MOB3A |

TABLE 13-continued

| GeneModule | EnsemblID | GeneSymbols |
|---|---|---|
| 8 | ENSG00000172116 | CD8B |
| 8 | ENSG00000172216 | CEBPB |
| 8 | ENSG00000172243 | CLEC7A |
| 8 | ENSG00000172322 | CLEC12A |
| 8 | ENSG00000172349 | IL16 |
| 8 | ENSG00000172543 | CTSW |
| 8 | ENSG00000172575 | RASGRP1 |
| 8 | ENSG00000172673 | THEMIS |
| 8 | ENSG00000173020 | ADRBK1 |
| 8 | ENSG00000173110 | HSPA6 |
| 8 | ENSG00000173200 | PARP15 |
| 8 | ENSG00000173281 | PPP1R3B |
| 8 | ENSG00000173369 | C1QB |
| 8 | ENSG00000173372 | C1QA |
| 8 | ENSG00000173391 | OLR1 |
| 8 | ENSG00000173535 | TNFRSF10C |
| 8 | ENSG00000173559 | NABP1 |
| 8 | ENSG00000173638 | SLC19A1 |
| 8 | ENSG00000173757 | STAT5B |
| 8 | ENSG00000173762 | CD7 |
| 8 | ENSG00000173868 | PHOSPHO1 |
| 8 | ENSG00000174004 | NRROS |
| 8 | ENSG00000174125 | TLR1 |
| 8 | ENSG00000174579 | MSL2 |
| 8 | ENSG00000174600 | CMKLR1 |
| 8 | ENSG00000174718 | KIAA1551 |
| 8 | ENSG00000175463 | TBC1D10C |
| 8 | ENSG00000175489 | LRRC25 |
| 8 | ENSG00000175857 | GAPT |
| 8 | ENSG00000176390 | CRLF3 |
| 8 | ENSG00000177105 | RHOG |
| 8 | ENSG00000177575 | CD163 |
| 8 | ENSG00000177663 | IL17RA |
| 8 | ENSG00000177885 | GRB2 |
| 8 | ENSG00000178562 | CD28 |
| 8 | ENSG00000178607 | ERN1 |
| 8 | ENSG00000179361 | ARID3B |
| 8 | ENSG00000180096 | 1-Sep |
| 8 | ENSG00000180353 | HCLS1 |
| 8 | ENSG00000180448 | HMHA1 |
| 8 | ENSG00000180871 | CXCR2 |
| 8 | ENSG00000180953 | ST20 |
| 8 | ENSG00000181381 | DDX60L |
| 8 | ENSG00000181409 | AATK |
| 8 | ENSG00000181631 | P2RY13 |
| 8 | ENSG00000182022 | CHST15 |
| 8 | ENSG00000182287 | AP1S2 |
| 8 | ENSG00000182487 | NCF1B |
| 8 | ENSG00000182511 | FES |
| 8 | ENSG00000182578 | CSF1R |
| 8 | ENSG00000182866 | LCK |
| 8 | ENSG00000182885 | GPR97 |
| 8 | ENSG00000183019 | C19orf59 |
| 8 | ENSG00000183023 | SLC8A1 |
| 8 | ENSG00000183484 | GPR132 |
| 8 | ENSG00000183688 | FAM101B |
| 8 | ENSG00000183748 | |
| 8 | ENSG00000183918 | SH2D1A |
| 8 | ENSG00000184014 | DENND5A |
| 8 | ENSG00000184060 | ADAP2 |
| 8 | ENSG00000184371 | CSF1 |
| 8 | ENSG00000184588 | PDE4B |
| 8 | ENSG00000184602 | SNN |
| 8 | ENSG00000184730 | APOBR |
| 8 | ENSG00000184922 | FMNL1 |
| 8 | ENSG00000185201 | IFITM2 |
| 8 | ENSG00000185215 | TNFAIP2 |
| 8 | ENSG00000185339 | TCN2 |
| 8 | ENSG00000185477 | GPRIN3 |
| 8 | ENSG00000185811 | IKZF1 |
| 8 | ENSG00000185862 | EVI2B |
| 8 | ENSG00000185947 | ZNF267 |
| 8 | ENSG00000186074 | CD300LF |
| 8 | ENSG00000186469 | GNG2 |
| 8 | ENSG00000186517 | ARHGAP30 |
| 8 | ENSG00000186635 | ARAP1 |
| 8 | ENSG00000186818 | LILRB4 |
| 8 | ENSG00000187116 | LILRA5 |
| 8 | ENSG00000187239 | FNBP1 |
| 8 | ENSG00000187474 | FPR3 |
| 8 | ENSG00000187688 | TRPV2 |
| 8 | ENSG00000187764 | SEMA4D |
| 8 | ENSG00000187796 | CARD9 |
| 8 | ENSG00000187994 | RINL |
| 8 | ENSG00000188404 | SELL |
| 8 | ENSG00000188820 | FAM26F |
| 8 | ENSG00000188895 | MSL1 |
| 8 | ENSG00000188906 | LRRK2 |
| 8 | ENSG00000189067 | LITAF |
| 8 | ENSG00000196511 | TPK1 |
| 8 | ENSG00000196549 | MME |
| 8 | ENSG00000196663 | TECPR2 |
| 8 | ENSG00000196843 | ARID5A |
| 8 | ENSG00000196954 | CASP4 |
| 8 | ENSG00000197081 | IGF2R |
| 8 | ENSG00000197249 | SERPINA1 |
| 8 | ENSG00000197471 | SPN |
| 8 | ENSG00000197629 | MPEG1 |
| 8 | ENSG00000197860 | SGTB |
| 8 | ENSG00000197872 | FAM49A |
| 8 | ENSG00000198053 | SIRPA |
| 8 | ENSG00000198223 | CSF2RA |
| 8 | ENSG00000198286 | CARD11 |
| 8 | ENSG00000198771 | RCSD1 |
| 8 | ENSG00000198821 | CD247 |
| 8 | ENSG00000198837 | DENND4B |
| 8 | ENSG00000198846 | TOX |
| 8 | ENSG00000198851 | CD3E |
| 8 | ENSG00000198879 | SFMBT2 |
| 8 | ENSG00000203747 | FCGR3A |
| 8 | ENSG00000204136 | GGTA1P |
| 8 | ENSG00000204160 | ZDHHC18 |
| 8 | ENSG00000204267 | TAP2 |
| 8 | ENSG00000204397 | CARD16 |
| 8 | ENSG00000204472 | AIF1 |
| 8 | ENSG00000204482 | LST1 |
| 8 | ENSG00000204516 | MICB |
| 8 | ENSG00000204577 | LILRB3 |
| 8 | ENSG00000204947 | ZNF425 |
| 8 | ENSG00000205269 | TMEM170B |
| 8 | ENSG00000205744 | DENND1C |
| 8 | ENSG00000211689 | TRGC1 |
| 8 | ENSG00000213203 | GIMAP1 |
| 8 | ENSG00000213402 | PTPRCAP |
| 8 | ENSG00000213445 | SIPA1 |
| 8 | ENSG00000213654 | GPSM3 |
| 8 | ENSG00000213658 | LAT |
| 8 | ENSG00000213809 | KLRK1 |
| 8 | ENSG00000215114 | UBXN2B |
| 8 | ENSG00000216490 | IFI30 |
| 8 | ENSG00000217128 | FNIP1 |
| 8 | ENSG00000217555 | CKLF |
| 8 | ENSG00000224397 | |
| 8 | ENSG00000227191 | TRGC2 |
| 8 | ENSG00000227507 | LTB |
| 8 | ENSG00000229164 | TRAC |
| 8 | ENSG00000229644 | NAMPTL |
| 8 | ENSG00000235568 | NFAM1 |
| 8 | ENSG00000239998 | LILRA2 |
| 8 | ENSG00000241839 | PLEKHO2 |
| 8 | ENSG00000241878 | PISD |
| 8 | ENSG00000242539 | |
| 8 | ENSG00000244482 | LILRA6 |
| 8 | ENSG00000247774 | PCED1B-AS1 |
| 8 | ENSG00000250264 | |
| 8 | ENSG00000255398 | HCAR3 |
| 8 | ENSG00000256007 | ARAP1-AS1 |
| 8 | ENSG00000258227 | CLEC5A |
| 8 | ENSG00000265206 | MIR142 |
| 8 | ENSG00000267121 | |
| 8 | ENSG00000268001 | |
| 8 | ENSG00000269215 | |
| 8 | ENSG00000269728 | |
| 9 | ENSG00000002549 | LAP3 |
| 9 | ENSG00000013374 | NUB1 |
| 9 | ENSG00000019582 | CD74 |

TABLE 13-continued

| GeneModule | EnsemblID | GeneSymbols |
|---|---|---|
| 9 | ENSG00000026950 | BTN3A1 |
| 9 | ENSG00000055332 | EIF2AK2 |
| 9 | ENSG00000059378 | PARP12 |
| 9 | ENSG00000067066 | SP100 |
| 9 | ENSG00000068079 | IFI35 |
| 9 | ENSG00000089692 | LAG3 |
| 9 | ENSG00000092010 | PSME1 |
| 9 | ENSG00000100336 | APOL4 |
| 9 | ENSG00000100342 | APOL1 |
| 9 | ENSG00000100911 | PSME2 |
| 9 | ENSG00000106785 | TRIM14 |
| 9 | ENSG00000107201 | DDX58 |
| 9 | ENSG00000111331 | OAS3 |
| 9 | ENSG00000111335 | OAS2 |
| 9 | ENSG00000111801 | BTN3A3 |
| 9 | ENSG00000112763 | BTN2A1 |
| 9 | ENSG00000114127 | XRN1 |
| 9 | ENSG00000115267 | IFIH1 |
| 9 | ENSG00000115415 | STAT1 |
| 9 | ENSG00000117228 | GBP1 |
| 9 | ENSG00000119917 | IFIT3 |
| 9 | ENSG00000121858 | TNFSF10 |
| 9 | ENSG00000123240 | OPTN |
| 9 | ENSG00000123609 | NMI |
| 9 | ENSG00000124201 | ZNFX1 |
| 9 | ENSG00000124226 | RNF114 |
| 9 | ENSG00000124508 | BTN2A2 |
| 9 | ENSG00000125347 | IRF1 |
| 9 | ENSG00000126709 | IFI6 |
| 9 | ENSG00000128284 | APOL3 |
| 9 | ENSG00000128335 | APOL2 |
| 9 | ENSG00000130303 | BST2 |
| 9 | ENSG00000130487 | KLHDC7B |
| 9 | ENSG00000130589 | HELZ2 |
| 9 | ENSG00000131203 | IDO1 |
| 9 | ENSG00000132109 | TRIM21 |
| 9 | ENSG00000132274 | TRIM22 |
| 9 | ENSG00000133106 | EPSTI1 |
| 9 | ENSG00000134326 | CMPK2 |
| 9 | ENSG00000135148 | TRAFD1 |
| 9 | ENSG00000136816 | TOR1B |
| 9 | ENSG00000137628 | DDX60 |
| 9 | ENSG00000137959 | IFI44L |
| 9 | ENSG00000137965 | IFI44 |
| 9 | ENSG00000138496 | PARP9 |
| 9 | ENSG00000138642 | HERC6 |
| 9 | ENSG00000138755 | CXCL9 |
| 9 | ENSG00000140105 | WARS |
| 9 | ENSG00000140464 | PML |
| 9 | ENSG00000140853 | NLRC5 |
| 9 | ENSG00000152778 | IFIT5 |
| 9 | ENSG00000156587 | UBE2L6 |
| 9 | ENSG00000157601 | MX1 |
| 9 | ENSG00000158773 | USF1 |
| 9 | ENSG00000160710 | ADAR |
| 9 | ENSG00000160932 | LY6E |
| 9 | ENSG00000162654 | GBP4 |
| 9 | ENSG00000163840 | DTX3L |
| 9 | ENSG00000164136 | IL15 |
| 9 | ENSG00000165949 | IFI27 |
| 9 | ENSG00000166278 | C2 |
| 9 | ENSG00000166710 | B2M |
| 9 | ENSG00000168062 | BATF2 |
| 9 | ENSG00000168394 | TAP1 |
| 9 | ENSG00000168961 | LGALS9 |
| 9 | ENSG00000169245 | CXCL10 |
| 9 | ENSG00000173193 | PARP14 |
| 9 | ENSG00000173821 | RNF213 |
| 9 | ENSG00000177409 | SAMD9L |
| 9 | ENSG00000179344 | HLA-DQB1 |
| 9 | ENSG00000179583 | CIITA |
| 9 | ENSG00000185338 | SOCS1 |
| 9 | ENSG00000185404 | SP140L |
| 9 | ENSG00000185880 | TRIM69 |
| 9 | ENSG00000186470 | BTN3A2 |
| 9 | ENSG00000187608 | ISG15 |
| 9 | ENSG00000188282 | RUFY4 |
| 9 | ENSG00000188313 | PLSCR1 |
| 9 | ENSG00000196126 | HLA-DRB1 |
| 9 | ENSG00000196735 | HLA-DQA1 |
| 9 | ENSG00000197142 | ACSL5 |
| 9 | ENSG00000197536 | C5orf56 |
| 9 | ENSG00000204252 | HLA-DOA |
| 9 | ENSG00000204257 | HLA-DMA |
| 9 | ENSG00000204261 | TAPSAR1 |
| 9 | ENSG00000204264 | PSMB8 |
| 9 | ENSG00000204287 | HLA-DRA |
| 9 | ENSG00000204525 | HLA-C |
| 9 | ENSG00000204592 | HLA-E |
| 9 | ENSG00000204642 | HLA-F |
| 9 | ENSG00000205220 | PSMB10 |
| 9 | ENSG00000205436 | EXOC3L4 |
| 9 | ENSG00000206337 | HCP5 |
| 9 | ENSG00000206503 | HLA-A |
| 9 | ENSG00000213886 | UBD |
| 9 | ENSG00000213928 | IRF9 |
| 9 | ENSG00000221963 | APOL6 |
| 9 | ENSG00000223865 | HLA-DPB1 |
| 9 | ENSG00000225131 | PSME2P2 |
| 9 | ENSG00000225492 | GBP1P1 |
| 9 | ENSG00000231389 | HLA-DPA1 |
| 9 | ENSG00000231925 | TAPBP |
| 9 | ENSG00000232629 | HLA-DQB2 |
| 9 | ENSG00000234745 | HLA-B |
| 9 | ENSG00000237988 | OR2I1P |
| 9 | ENSG00000240065 | PSMB9 |
| 9 | ENSG00000242574 | HLA-DMB |
| 9 | ENSG00000263013 | |
| 9 | ENSG00000269640 | |
| 10 | ENSG00000167535 | CACNB3 |
| 10 | ENSG00000109339 | MAPK10 |

TABLE 14

22 genes that were selected from the 3,936 to predict the molecular subtypes in the Validation Cohort (endobronchial biopsies)

| Gene Module | Gene Name | EnsemblID |
|---|---|---|
| 1 | PHLDB1 | ENSG00000019144 |
| 1 | MARVELD1 | ENSG00000155254 |
| 1 | KIRREL1 | ENSG00000183853 |
| 2 | CCNL2 | ENSG00000221978 |
| 2 | MSANTD2 | ENSG00000120458 |
| 2 | LUC7L | ENSG00000007392 |
| 3 | BTG2 | ENSG00000159388 |
| 3 | ZFP36 | ENSG00000128016 |
| 4 | COX6A1 | ENSG00000111775 |
| 4 | COX7A2 | ENSG00000112695 |
| 5 | RACGAP1 | ENSG00000161800 |
| 5 | TPX2 | ENSG00000088325 |
| 6 | NEK11 | ENSG00000114670 |
| 6 | IFT88 | ENSG00000032742 |
| 7 | RPL26 | ENSG00000161970 |
| 7 | RPL23 | ENSG00000125691 |
| 8 | DOCK2 | ENSG00000134516 |
| 8 | CD53 | ENSG00000143119 |
| 8 | LAPTM5 | ENSG00000162511 |
| 9 | UBE2L6 | ENSG00000156587 |
| 9 | EPSTI1 | ENSG00000133106 |
| 9 | TAP1 | ENSG00000168394 |

TABLE 15

8 genes that were selected out of the 22 genes (Table 14) to predict the Proliferative subtype or not in the bronchial brushes

| Gene Module | Gene Name | EnsemblID |
|---|---|---|
| 4 | COX6A1 | ENSG00000111775 |
| 4 | COX7A2 | ENSG00000112695 |
| 5 | RACGAP1 | ENSG00000161800 |
| 5 | TPX2 | ENSG00000088325 |
| 6 | NEK11 | ENSG00000114670 |
| 6 | IFT88 | ENSG00000032742 |
| 7 | RPL26 | ENSG00000161970 |
| 7 | RPL23 | ENSG00000125691 |

TABLE 16

112 genes used to predict progression/persistence versus regression in endobronchial biopsies classified to be in the Proliferative subtype. Genes in Module 9 associated with progression/regression. These genes are contained within Table 13.

| EnsemblID | GeneSymbols |
|---|---|
| ENSG00000002549 | LAP3 |
| ENSG00000013374 | NUB1 |
| ENSG00000019582 | CD74 |
| ENSG00000026950 | BTN3A1 |
| ENSG00000055332 | EIF2AK2 |
| ENSG00000059378 | PARP12 |
| ENSG00000067066 | SP100 |
| ENSG00000068079 | IFI35 |
| ENSG00000089692 | LAG3 |
| ENSG00000092010 | PSME1 |
| ENSG00000100336 | APOL4 |
| ENSG00000100342 | APOL1 |
| ENSG00000100911 | PSME2 |
| ENSG00000106785 | TRIM14 |
| ENSG00000107201 | DDX58 |
| ENSG00000111331 | OAS3 |
| ENSG00000111335 | OAS2 |
| ENSG00000111801 | BTN3A3 |
| ENSG00000112763 | BTN2A1 |
| ENSG00000114127 | XRN1 |
| ENSG00000115267 | IFIH1 |
| ENSG00000115415 | STAT1 |
| ENSG00000117228 | GBP1 |
| ENSG00000119917 | IFIT3 |
| ENSG00000121858 | TNFSF10 |
| ENSG00000123240 | OPTN |
| ENSG00000123609 | NMI |
| ENSG00000124201 | ZNFX1 |
| ENSG00000124226 | RNF114 |
| ENSG00000124508 | BTN2A2 |
| ENSG00000125347 | IRF1 |
| ENSG00000126709 | IFI6 |
| ENSG00000128284 | APOL3 |
| ENSG00000128335 | APOL2 |
| ENSG00000130303 | BST2 |
| ENSG00000130487 | KLHDC7B |
| ENSG00000130589 | HELZ2 |
| ENSG00000131203 | IDO1 |
| ENSG00000132109 | TRIM21 |
| ENSG00000132274 | TRIM22 |
| ENSG00000133106 | EPSTI1 |
| ENSG00000134326 | CMPK2 |
| ENSG00000135148 | TRAFD1 |
| ENSG00000136816 | TOR1B |
| ENSG00000137628 | DDX60 |
| ENSG00000137959 | IFI44L |
| ENSG00000137965 | IFI44 |
| ENSG00000138496 | PARP9 |
| ENSG00000138642 | HERC6 |
| ENSG00000138755 | CXCL9 |
| ENSG00000140105 | WARS |
| ENSG00000140464 | PML |
| ENSG00000140853 | NLRC5 |
| ENSG00000152778 | IFIT5 |
| ENSG00000156587 | UBE2L6 |
| ENSG00000157601 | MX1 |
| ENSG00000158773 | USF1 |
| ENSG00000160710 | ADAR |
| ENSG00000160932 | LY6E |
| ENSG00000162654 | GBP4 |
| ENSG00000163840 | DTX3L |
| ENSG00000164136 | IL15 |
| ENSG00000165949 | IFI27 |
| ENSG00000166278 | C2 |
| ENSG00000166710 | B2M |
| ENSG00000168062 | BATF2 |
| ENSG00000168394 | TAP1 |
| ENSG00000168961 | LGALS9 |
| ENSG00000169245 | CXCL10 |
| ENSG00000173193 | PARP14 |
| ENSG00000173821 | RNF213 |
| ENSG00000177409 | SAMD9L |
| ENSG00000179344 | HLA-DQB1 |
| ENSG00000179583 | CIITA |
| ENSG00000185338 | SOCS1 |
| ENSG00000185404 | SP140L |
| ENSG00000185880 | TRIM69 |
| ENSG00000186470 | BTN3A2 |
| ENSG00000187608 | ISG15 |
| ENSG00000188282 | RUFY4 |
| ENSG00000188313 | PLSCR1 |
| ENSG00000196126 | HLA-DRB1 |
| ENSG00000196735 | HLA-DQA1 |
| ENSG00000197142 | ACSL5 |
| ENSG00000197536 | C5orf56 |
| ENSG00000204252 | HLA-DOA |
| ENSG00000204257 | HLA-DMA |
| ENSG00000204261 | TAPSAR1 |
| ENSG00000204264 | PSMB8 |
| ENSG00000204287 | HLA-DRA |
| ENSG00000204525 | HLA-C |
| ENSG00000204592 | HLA-E |
| ENSG00000204642 | HLA-F |
| ENSG00000205220 | PSMB10 |
| ENSG00000205436 | EXOC3L4 |
| ENSG00000206337 | HCP5 |
| ENSG00000206503 | HLA-A |
| ENSG00000213886 | UBD |
| ENSG00000213928 | IRF9 |
| ENSG00000221963 | APOL6 |
| ENSG00000223865 | HLA-DPB1 |
| ENSG00000225131 | PSME2P2 |
| ENSG00000225492 | GBP1P1 |
| ENSG00000231389 | HLA-DPA1 |
| ENSG00000231925 | TAPBP |
| ENSG00000232629 | HLA-DQB2 |
| ENSG00000234745 | HLA-B |
| ENSG00000237988 | OR2I1P |
| ENSG00000240065 | PSMB9 |
| ENSG00000242574 | HLA-DMB |
| ENSG00000263013 | RP11-876N24.5 |
| ENSG00000269640 | |

The methods described herein relate to the determination of the expression level of at least one gene. In some embodiments of any of the aspects, the at least one gene can be one or more genes selected from Tables 13, 14, 15, and/or 16. In some embodiments of any of the aspects, the gene lists of Tables 13, 14 and 16 are relevant to endobronchial biopsy samples that range in histology from normal to premalignant. In some embodiments of any of the aspects, where the sample is an endobronchial biopsy sample, the one or more genes are selected from Table 13, 14 and/or 16. In some embodiments of any of the aspects, Table 15 is relevant for normal bronchial brushings. In some embodiments of any of the aspects, where the sample is bronchial brushing sample (e.g, of normal tissue), the one or more genes are selected from Table 15.

In some embodiments of any of the aspects, the one or more genes selected from Table 13 or 16 are not B2M, HLA-DRA, HLA-DRB1, or HLA-DPA 1. In some embodiments of any of the aspects, if the one or more genes selected from Table 13 or 16 include B2M, HLA-DRA, HLA-DRB1, and/or HLA-DPA1, at least one additional gene from Table 13 or 16 is selected.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm.; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of bronchial premalignant lesions. A subject can be male or female.

A subject can be one who has been previously diagnosed with or identified as suffering from or having a condition in need of treatment (e.g. bronchial premalignant lesions) or one or more complications related to such a condition, and optionally, have already undergone treatment for bronchial premalignant lesions or the one or more complications related to bronchial premalignant lesions. Alternatively, a subject can also be one who has not been previously diagnosed as having bronchial premalignant lesions or one or more complications related to bronchial premalignant lesions. For example, a subject can be one who exhibits one or more risk factors for bronchial premalignant lesions or one or more complications related to bronchial premalignant lesions or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Marker" in the context of the present invention refers to an expression product, e.g., nucleic acid or polypeptide which is differentially present in a sample taken from subjects having bronchial premalignant lesions of a particular subtype, as compared to a comparable sample taken from control subjects (e.g., a healthy subject). The term "biomarker" is used interchangeably with the term "marker."

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. bronchial premalignant lesion. The term "treating" includes reducing or alleviating at least one adverse effect or symptom of a condition, disease or disorder associated with a bronchial premalignant lesion. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

As used herein, the term "inhibitor" refers to an agent which can decrease the expression and/or activity of the target molecule or activity or process, e.g. by at least 10% or more, e.g. by 10% or more, 50% or more, 70% or more, 80% or more, 90% or more, 95% or more, or 98% or more.

As used herein, the terms "drug", "compound" or "agent" are used interchangeably and refer to molecules and/or compositions. The compounds/agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof. In some embodiments, "drug" as used herein refers to an agent approved for medical use, e.g., by the FDA.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating bronchial premalignant lesions, the method comprising:
   administering at least one of:
      i. both a bronchoscopy-based procedure to survey the central airway and a chest CT scan;
      ii. at least every 6 months, one of a bronchoscopy-based procedure to survey the central airway and a chest CT scan; and/or
      iii. at least one anti-proliferative drug;
   to a subject determined to have at least one of:
   an increased level of expression of at least one module 5 gene as compared to a non-proliferative lesion reference level; and
   a decreased level of expression of at least one module 6 gene as compared to a non-proliferative lesion reference level.
2. The method of paragraph 1, wherein the at least one module 5 gene is selected from the group consisting of:
   RACGAP1 and TPX2; and
   the at least one module 6 gene is selected from the group consisting of:
   NEK11 and IFT88.
3. The method of any of paragraphs 1-2, wherein the subject is further determined to have an increased level of expression of at least one module 7 or module 4 gene.
4. The method of paragraph 3, wherein the at least one module 7 or module 4 gene is selected from the group consisting of:
   COX6A1; COX7A2; RPL26; and RPL23.
5. The method of any of paragraphs 1-4, wherein the level of expression of each of the genes of Table 15 is determined.
6. The method of any of paragraphs 1-5, wherein the at least one anti-proliferative drug is selected from the group consisting of:
   Acetylcholine receptor antagonist; Acetylcholinesterase inhibitors; Adenosine receptor antagonists; Adrenergic receptor antagonists; AKT inhibitors; Angiotensin receptor antagonists; Apoptosis stimulants; Aurora kinase inhibitors; CDK inhibitors; Cyclooxygenase inhibitors; Cytokine production inhibitors; Dehydrogenase inhibitors; DNA protein kinase inhibitors; focal adhesion inhibitors; Dopamine receptor antagonist; EGFR inhibitors; ERK1 and ERK2 phosphorylation inhibitors; Estrogen receptor agonists; EZH2 inhibitors; FLT3 inhibitors; Glucocorticoid receptor agonists; Glutamate receptor antagonists; HDAC inhibitors; Histamine receptor antagonists; Histone lysine methyltransferase inhibitors; HSP inhibitors; IKK inhibitors; Ion channel antagonists; JAK inhibitors; JNK inhibitors; KIT inhibitors; Leucine rich repeat kinase inhibitors; MDM inhibitors; mediator release inhibitors; MEK inhibitors; MTOR inhibitors; Monoamine oxidase inhibitors; NFkB pathway inhibitors; nucleophosmin inhibitors; PARP inhibitors; PPAR receptor agonists; PI3K inhibitors; tyrosine kinase inhibitors; Phosphodiesterase inhibitors; protein kinase inhibitors; RAF inhibitors; RNA polymerase inhibitors; topoisomerase inhibitors; RNA synthesis inhibitors; SIRT inhibitors; sodium channel blockers; VEGFR inhibitors; and Vitamin D receptor agonists.

7. The method of any of paragraphs 1-6, wherein the anti-proliferative drug is administered as an inhaled formulation or topical formulation.

8. The method of any of paragraphs 1-7, wherein the anti-proliferative drug is administered during a bronchoscopy-based procedure.

9. The method of any of paragraphs 1-8, wherein the anti-proliferative drug is administered systemically.

10. The method of any of paragraphs 1-9, wherein the anti-proliferative drug is administered during a bronchoscopy-based procedure and systemically.

11. The method of any of paragraphs 1-10, wherein the subject is further determined to have a decreased level of expression of at least one module 9 gene as compared to a non-proliferative lesion reference level and/or an increased level of expression of at least one module 10 gene as compared to a non-proliferative lesion reference level.

12. The method of paragraph 11, wherein the subject determined to have a decreased level of expression of at least one module 9 gene and/or an increased level of expression of at least one module 10 gene is administered at least one of:
 i. both a bronchoscopy-based procedure to survey the central airway wherein the lesions are biopsied to remove abnormal tissue and a chest CT scan;
 ii. at least every 6 months, one of a bronchoscopy-based procedure to survey the central airway wherein the lesions are biopsied to remove abnormal tissue and a chest CT scan; and/or
 iii. at least one immune stimulating drug.

13. A method of treating bronchial premalignant lesions, the method comprising:
 administering at least one of:
  i. both a bronchoscopy-based procedure to survey the central airway wherein the lesions are biopsied to remove abnormal tissue and a chest CT scan;
  ii. at least every 6 months, one of a bronchoscopy-based procedure to survey the central airway wherein the lesions are biopsied to remove abnormal tissue and a chest CT scan; and/or
  iii. at least one immune stimulating drug;
 to a subject determined to have a decreased level of expression of at least one module 9 gene as compared to a non-proliferative lesion reference level and/or an increased level of expression of at least one module 10 gene as compared to a non-proliferative lesion reference level.

14. The method of any of paragraphs 11-13, wherein the module 9 gene is selected from the group consisting of: EPSTI1; UBE2L6; B2M and TAP1.

15. The method of any of paragraphs 11-14, wherein the at least one gene module 9 gene is selected from Table 16.

16. The method of any of paragraphs 11-15, wherein the module 10 gene is selected from the group consisting of:
 CACNB3 and MAPK10.

17. The method of any of paragraphs 11-16, wherein the at least one immune stimulating drug is selected from the group consisting of:
 immune-checkpoint inhibitors (e.g. inhibitors against, PD-1, PD-L1, CTLA4, and LAG3); drugs that stimulate interferon signaling (e.g. anti-viral drugs that improve interferon signaling); DNA synthesis inhibitors; IMDH inhibitors; CDK inhibitors; ribonucleotide reductase inhibitors; dihydrofolate reductase inhibitors; topoisomerase inhibitors; FLT3 inhibitors; IGF-1 inhibitors; MEK inhibitors; aurora kinase inhibitors; PKC inhibitors; RAF inhibitors; PDFGR/KIT inhibitors; VEGFR inhibitors; SRC inhibitors; retinoid receptor agonists; HDAC inhibitors; DNA methyltransferase inhibitors; and EZH2 inhibitors.

18. A method of treating bronchial premalignant lesions, the method comprising:
 administering at least one of:
  i. both a bronchoscopy-based procedure to survey the central airway and a chest CT scan;
  ii. at least every 6 months, one of a bronchoscopy-based procedure to survey the central airway and a chest CT scan; and/or
  iii. at least one anti-inflammatory drug;
 to a subject determined to have at least one of:
 an increased level of expression of at least one module 2 gene as compared to a non-inflammatory reference level; and
 a decreased level of expression of at least one module 6 gene as compared to a non-inflammatory reference level.

19. The method of paragraph 17, wherein the at least one module 2 gene is selected from the group consisting of: MSANTD2, CCNL2, and LUC7L; and
 the at least one module 6 gene is selected from the group consisting of:
 NEK11 and IFT88.

20. The method of any of paragraphs 17-18, wherein the subject is further determined to have an increased level of expression of at least one module 7 gene, module 1 gene, or module 8 gene and/or decreased level of expression of at least one module 4 gene or one module 5 gene.

21. The method of paragraph 19, wherein the at least one module 7 gene is selected from the group consisting of: RPL26 and RPL23.

22. The method of paragraph 19, wherein the at least one module 1 gene is selected from the group consisting of: KIRREL; PHLDB1; and MARVELD1.

23. The method of paragraph 19, wherein the at least one module 8 gene is selected from the group consisting of: DOC2; CD53; and LAPTM.

24. The method of paragraph 19, wherein the at least one module 4 gene is selected from the group consisting of: COX6A1 and COX7A2

25. The method of paragraph 19, wherein the at least one module 5 gene is selected from the group consisting of: RACGAP1 and TPX2

26. The method of any of paragraphs 17-24, wherein the level of expression of each of the genes of Table 15 is determined.

27. The method of any of paragraphs 17-25, wherein the at least one anti-inflammatory drug is selected from the group consisting of:
Acetylcholine receptor antagonists; Acetylcholinesterase inhibitors; Adenosine receptor antagonists; Adrenergic receptor antagonists; Angiotensin receptor antagonists; Anti-IL1B antibodies; Apoptosis stimulants; Aurora kinase inhibitors; CDK inhibitors; Cyclooxygenase inhibitors; Cytokine production inhibitors; Dehydrogenase inhibitors; Dopamine receptor antagonists; EGFR inhibitors; ERK1 and ERK2 phosphorylation inhibitors; Estrogen receptor agonists; FLT3 inhibitors; Glucocorticoid receptor agonists; Glutamate receptor antagonists; HDAC inhibitors; Histamine receptor antagonists; Histone lysine methyltransferase inhibitors; HSP inhibitors; IKK inhibitors; Ion channel antagonists; KIT inhibitors; Leucine rich repeat kinase inhibitors; MEK inhibitors; MDM inhibitors; Phosphodiesterase inhibitors; Monoamine oxidase inhibitors; MTOR inhibitors; NFkB pathway inhibitors; nucleophosmin inhibitors; PARP inhibitors; PI3K inhibitors; PPAR receptor agonists; protein synthesis inhibitors (e.g. chloramphenicol); RAF inhibitors; SIRT inhibitors; Sodium channel blockers; TGF beta receptor inhibitors; Topoisomerase inhibitors; Tyrosine kinase inhibitors; VEGFR inhibitors; and Vitamin D receptor agonists.

28. The method of any of paragraphs 17-26, wherein the anti-inflammatory drug is administered during a bronchoscopy-based procedure.

29. The method of any of paragraphs 17-27, wherein the anti-inflammatory drug is administered systemically.

30. The method of any of paragraphs 17-28, wherein the anti-inflammatory drug is administered during a bronchoscopy-based procedure and systemically.

31. The method of any of paragraphs 1-29, wherein the at least one gene is selected from Table 14.

32. The method of any of paragraphs 1-30, wherein the level of expression of each of the genes of Table 14 is determined.

33. The method of any of paragraphs 1-31, whereby the development of lung cancer lung squamous cell carcinoma is prevented, delayed, or slowed.

34. The method of any of paragraphs 1-32, wherein the lung cancer is lung squamous cell carcinoma.

35. The method of any of paragraphs 1-33, wherein the level of expression is the level of expression in an endobronchial biopsy, endobronchial brushing sample, large airway biopsy, large airway brushing sample, nasal epithelial cells, sputum, or blood obtained from the subject.

36. The method of any of paragraphs 1-34, wherein the level of expression is the level of expression in a bronchial brushing obtained from the right or left mainstem bronchus.

37. The method of any of paragraphs 34-35, wherein the biopsy or brushing sample comprises morphologically-normal tissues or cells.

38. The method of any of paragraphs 34-35, wherein the biopsy or brushing sample consists of morphologically-normal tissues or cells.

39. The method of any of paragraphs 1-34, wherein the level of expression is the level of expression in a sample comprising bronchial premalignant lesion cells.

40. The method of any of paragraphs 1-35, wherein the level of expression is the level of expression in a sample comprising morphologically-normal cells.

41. The method of any of the paragraphs 1-36, wherein the subject is a smoker or former smoker.

EXAMPLES

Example 1

Molecular Subtyping Reveals Immune Alterations Associated with Progression of Bronchial Premalignant Lesions Described herein is the molecular characterization of bronchial premalignant lesions and the airway field of injury identified epithelial and immune alterations associated with progressive/persistent bronchial dysplasia that can be leveraged to develop lung cancer risk biomarkers and interception strategies.

Bronchial premalignant lesions (PMLs) are precursors of lung squamous cell carcinoma, but have variable outcome, and tools are lacking to identify and treat PMLs at highest risk for progression to invasive cancer. Profiling endobronchial biopsies of PMLs obtained from high-risk smokers by RNA-Seq identified four PML subtypes with differences in epithelial and immune processes. One molecular subtype (Proliferative) is enriched with dysplastic lesions and exhibits up-regulation of metabolic and cell cycle pathways and down-regulation of ciliary processes. RNA-Seq profiles from normal-appearing uninvolved large airway brushings could identify subjects with Proliferative lesions with high specificity. Expression of interferon signaling and antigen processing/presentation pathways are decreased in progressive/persistent Proliferative lesions and immunofluorescence indicates a depletion of innate and adaptive immune cells in these lesions. Molecular biomarkers measured in PMLs or the uninvolved airway can enhance histopathological grading and indicates that immunoprevention strategies may be effective in intercepting the progression of PMLs to lung cancer.

Introduction

Lung cancer (LC) is the leading cause of cancer death taking about 160,000 U.S. lives each year, more than colorectal, pancreatic, breast, and prostate cancers combined. In order to decrease mortality, innovative strategies are needed to intercept cancer development by diagnosing the disease at its earliest and potentially most curable stage. Recent advances based on results from the National Lung Screening Trial (1) are dramatically altering the landscape of early LC detection as computed tomography (CT) screening of high-risk individuals significantly reduces mortality. Despite this progress, biomarkers are needed to select individuals for LC screening as eligibility criteria account for less than 27% of individuals diagnosed with LC in the US (2) and to distinguish between benign or cancerous indeterminate pulmonary nodules as screening has very high false positive rate (>90%). There is also urgent and unmet need to develop personalized therapies earlier in the disease process to "intercept" LC prior to its development in this high-risk population.

Development of LC risk biomarkers and LC interception strategies requires a detailed understanding of the earliest molecular alterations involved in lung carcinogenesis that occur in the respiratory epithelium (3, 4). Exposure to cigarette smoke creates a field of injury throughout the entire respiratory tract by inducing a variety of genomic alterations that can lead to an "at-risk" airway where premalignant lesions (PMLs) and LCs develop. Lung squamous cell carcinoma (LUSC) arises in the epithelial layer of the bronchial airways and is often preceded by the development of PMLs through a stepwise histological progression from normal epithelium to hyperplasia, squamous metaplasia, dysplasia (mild, moderate and severe), carcinoma in situ (CIS), and finally to invasive and then metastatic LUSC (5). In fact, the presence of high-grade persistent or progressive dysplasia (moderate or severe) is a marker of increased LC risk both at the lesion site (where they are the presumed precursors of squamous cell lung cancer) and elsewhere in the lung, although many dysplastic lesions do have varied outcomes (6). Currently, however, effective tools to identify PMLs are lacking at highest risk of progression to invasive carcinoma (7). The development of markers of disease progression would identify patients at high-risk, suggest novel lung cancer chemoprevention agents, and provide molecular biomarkers for monitoring outcome in lung cancer prevention trials.

It is hypothesized herein that molecular characterization of bronchial biopsies containing a mixture of epithelial and immune cells would allow us to identify transcriptomic alterations associated with high-grade histology and premalignant lesion progression. In this study, mRNA sequencing was used to profile endobronchial biopsies and brushings obtained through serial bronchoscopies from high-risk smokers undergoing lung cancer screening by auto-fluorescence bronchoscopy and chest CT. Using the bronchial biopsies, four molecular subtypes associated with clinical phenotypes and biological processes were identified. One subtype (Proliferative subtype) is enriched with biopsies having dysplastic histology, high basal cell and low ciliated cell signals, and expression of proliferation-associated pathways. Genes involved in interferon signaling and T cell mediated immunity were down-regulated among progressive/persistent lesions within the Proliferative subtype compared with regressive lesions and these pathways correlated with decreases in both innate and adaptive immune cell types. Molecular classification of biopsies into a high-grade/ progressive disease group can be used to stratify patients into prevention trials and to monitor efficacy of the treatment. The results also indicate that personalized lung cancer chemoprevention targeting specific cancer-related pathways or the immune system can have potential therapeutic benefits.

Results

Subject Population

In this study, mRNA sequencing was used to profile endobronchial biopsies and brushings obtained through serial bronchoscopy of high-risk smokers undergoing lung cancer screening by auto-fluorescence bronchoscopy and chest CT at the Roswell Park Comprehensive Cancer Center (Roswell) in Buffalo, N.Y. The Discovery Cohort samples were obtained from the Roswell subjects between 2010 and 2012 (DC; n=29 patients, n=191 biopsies, n=91 brushes), and the Validation Cohort samples were obtained between 2012 and 2015 (VC; n=20 patients, n=111 biopsies, and 49 brushes). The subjects are predominantly older smokers, many of which have a history of lung cancer, chronic obstructive pulmonary disease (COPD), and occupational exposures that confer a high-risk of developing lung cancer. Clinical characteristics reported at baseline such as sex, age, smoking status (ever or never) reported at baseline visit, pack-years, prior history of lung cancer, COPD status, and occupational exposures were not significantly different between the two cohorts (Table 1). After sample filtering based on several quality metrics, the DC had 190 biopsies and 89 brushes while the VC had 105 biopsies and 48 brushes. Ninety-four percent of subjects had at least one lung anatomic location sampled 2 or more times via endobronchial biopsy. The DC and VC contained 37.9% and 35.2% biopsies with a histological grade of dysplasia or higher and 23.1% and 19.0% had progressive/persistent dysplasia, respectively (Table 2). A previously described smoking-associated signature (8) was used to predict the smoking status of each sample, as smoking status was only available at baseline, and found that the DC had a higher percentage of biopsies predicted to be current smokers (62.6%) compared with the VC (36.2%). There is no significant difference in smoking status among the bronchial brushings between the two cohorts since only 1 brush is collected per time point. The predicted smoking status was consistent across all procedures for 63% and 70% of the DC and VC subjects, respectively. In terms of RNA sequencing quality, the DC had significantly greater total reads, percent uniquely mapping reads, and median transcript integrity number scores among the biopsies than the VC, but these differences between cohorts were not reflected in the brushes (FIG. 5).

LUSC PMLs within the Discovery Cohort Divide into Distinct Molecular Subtypes

In order to identify gene expression differences associated with LUSC PML histological severity using the endobronchial biopsies, a discovery-based approach was used to identify de novo molecular subtypes based on distinct patterns of gene co-expression (gene modules). The approach was chosen given that there is histological heterogeneity within biopsies and that pathological analyses were conducted using biopsies adjacent to biopsies profiled via mRNA-Seq. First, it was sought to select a set of gene modules that are present across different LUSC datasets. Using weighted gene co-expression network analysis (9) (WGCNA), gene modules were derived in the DC biopsies (n=190 samples, n=16653 genes, n=15 gene modules), the DC brushes (n=89 samples, n=16058 genes, n=47 gene modules), TCGA squamous cell carcinoma (LUSC) tumors (10) (n=471 samples, n=17887 genes, n=55 gene modules), and tracheobronchial samples from mice treated with n-nitrosotris-(2-choroethyl)urea (NTCU) (n=25 samples, n=14897 genes, n=40 gene modules). DC biopsy gene modules that were highly correlated (absolute Pearson correlation coefficient r>0.85) to at least one other non-DC biopsy module within each of the 4 datasets were selected. Genes in the selected modules were filtered by requiring that each gene was also present in at least one of the correlated non-DC biopsy modules, resulting in a set of 9 gene modules that consisted of 3,936 genes in total (FIG. 6). These gene modules identified 4 molecular subtypes within the DC biopsies via consensus clustering: Proliferative (dark blue, n=52 samples, 27.4%), Inflammatory (dark green, n=37 samples, 19.5%), Secretory (light blue, n=61 samples, 32.1%), and Normal-like (light green, n=40 samples, 21.1%) (FIG. 1A, Table 3).

In order to characterize each molecular subtype, the first focus was on identifying biological pathways over-represented in the genes comprising each gene module, as the pattern of gene module expression defines each PML subtype. Each gene module was found to be associated with distinct epithelial and immune biological processes (FIG. 1A, FIG. 6, and Table 5). The Proliferative subtype is specifically characterized by increased expression of genes involved in energy metabolism and cell cycle pathways (Modules 4 and 5). The Secretory and Normal-like subtypes both have increased expression of genes in cilium-associated pathways (Module 6), however, the Normal-like subtype specifically has decreased expression of genes involved in inflammation, regulation of lymphocytes and leukocytes, and antigen processing and presentation pathways (Modules 8 and 9). The Secretory subtype exhibits decreased expression of genes involved in protein translation (Module 7), while RNA processing genes (Module 2) are expressed more highly in the Inflammatory subtype.

Figure 1B:
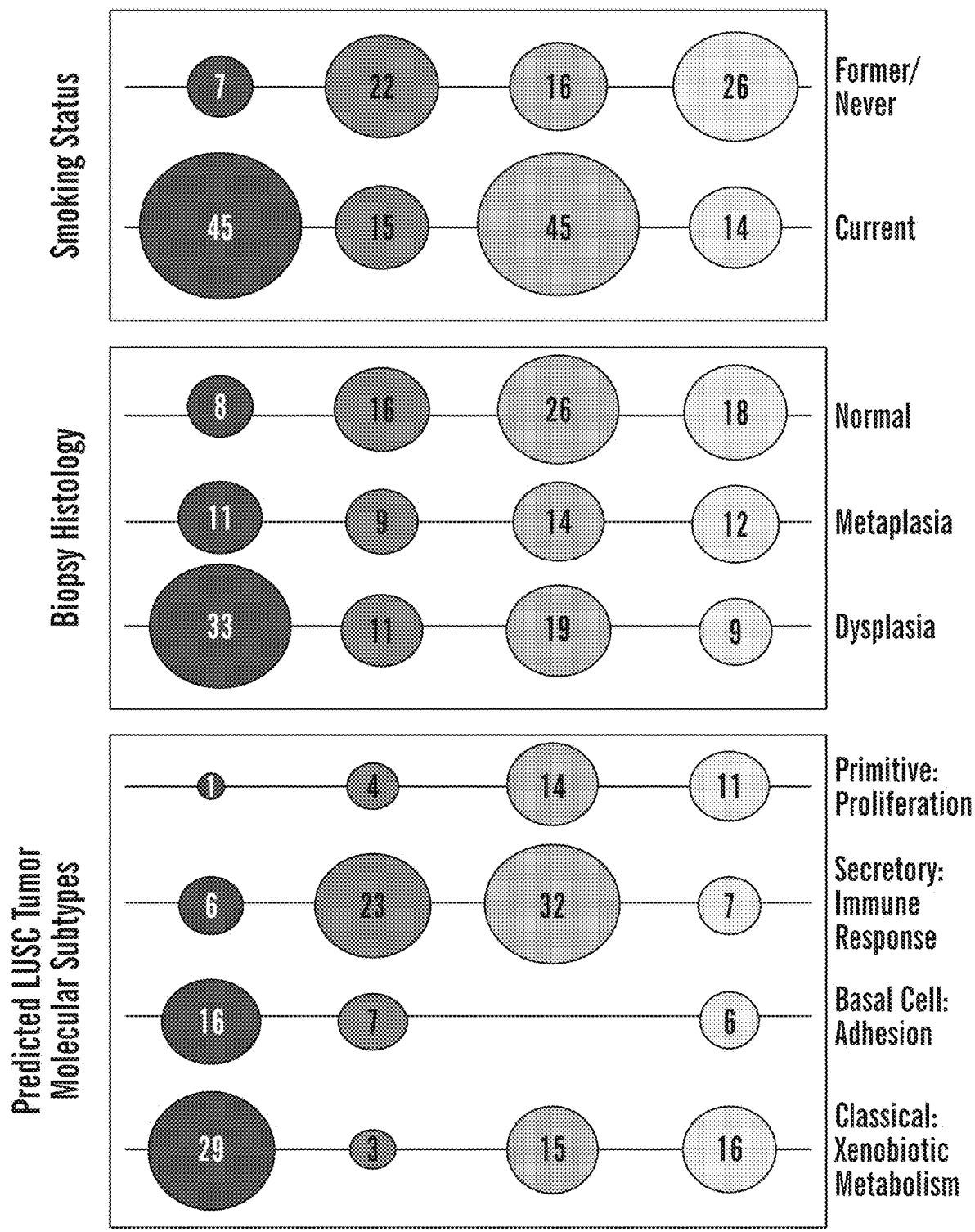
Figure 1B:
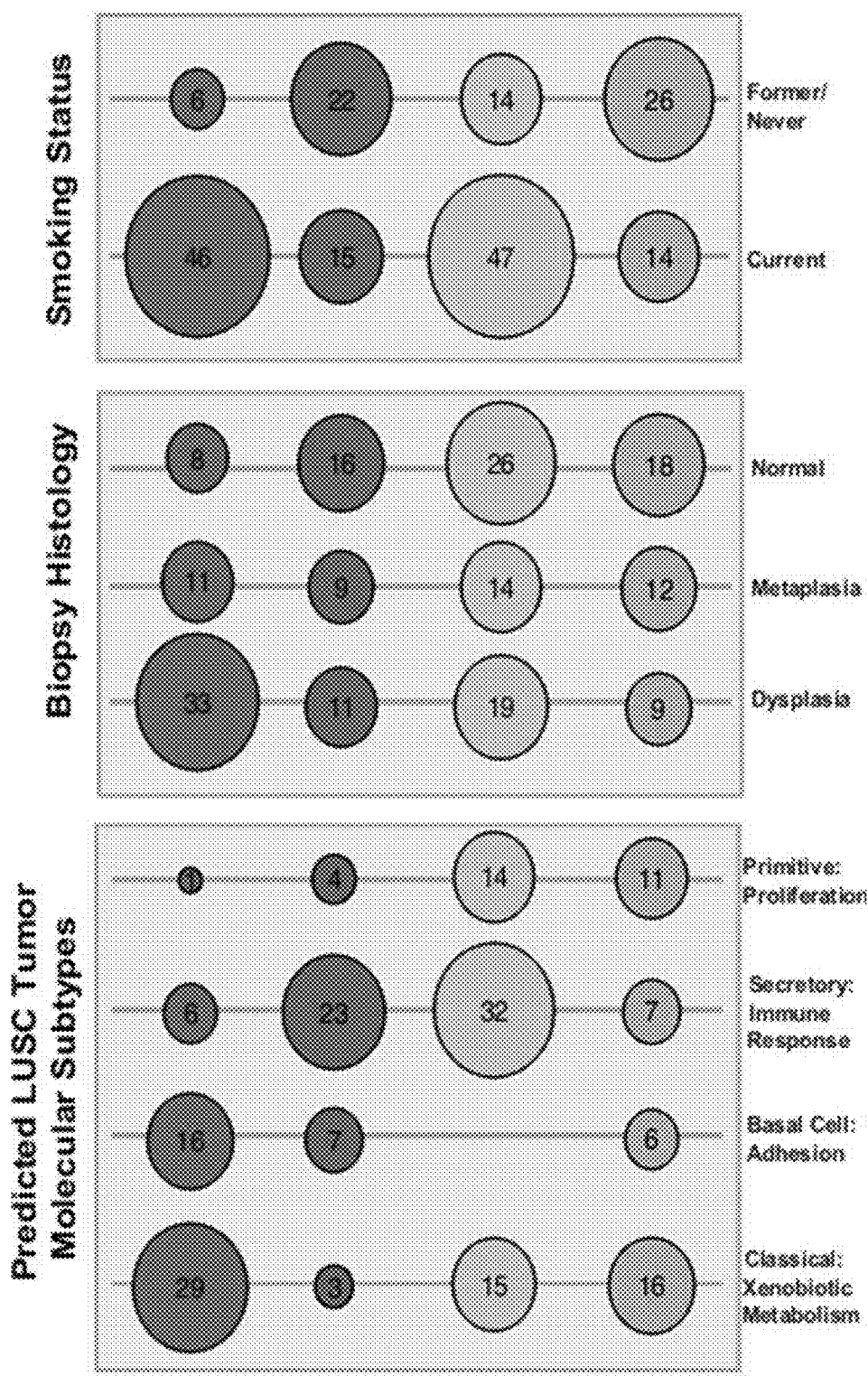
Figure 1D:
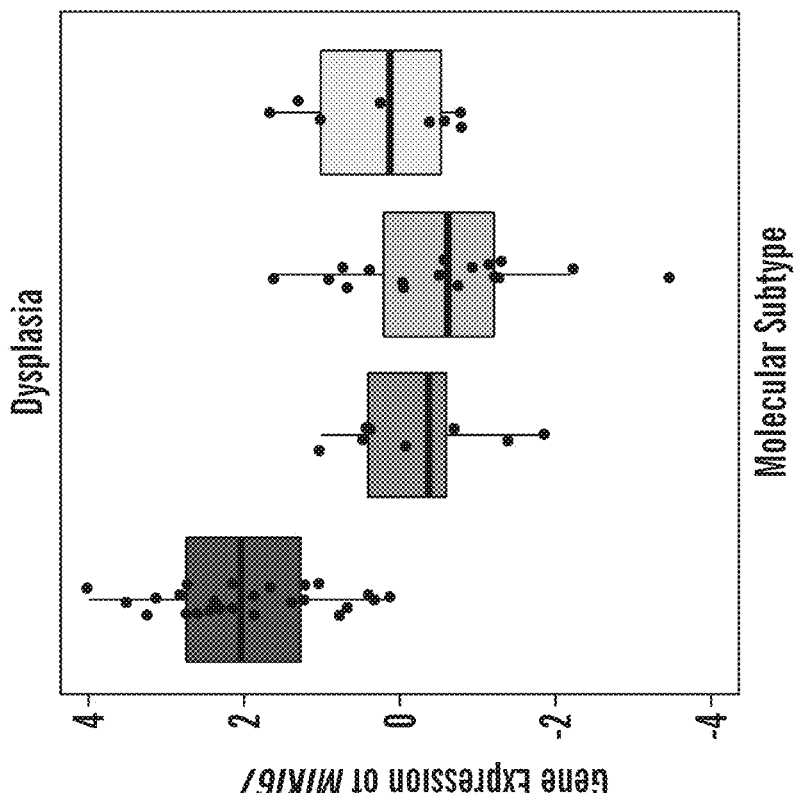
Figure 1C:
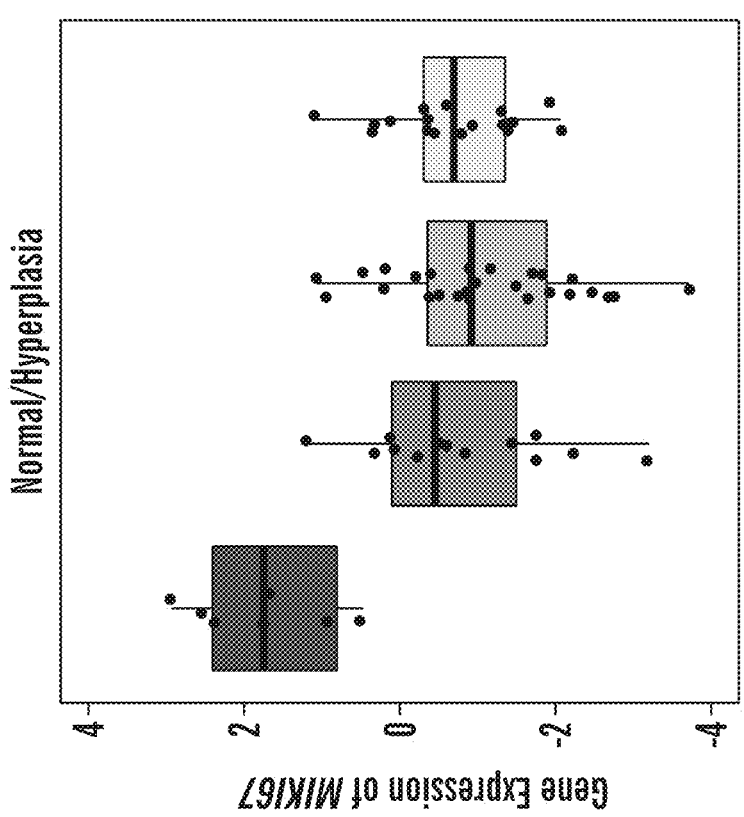
Figure 8:
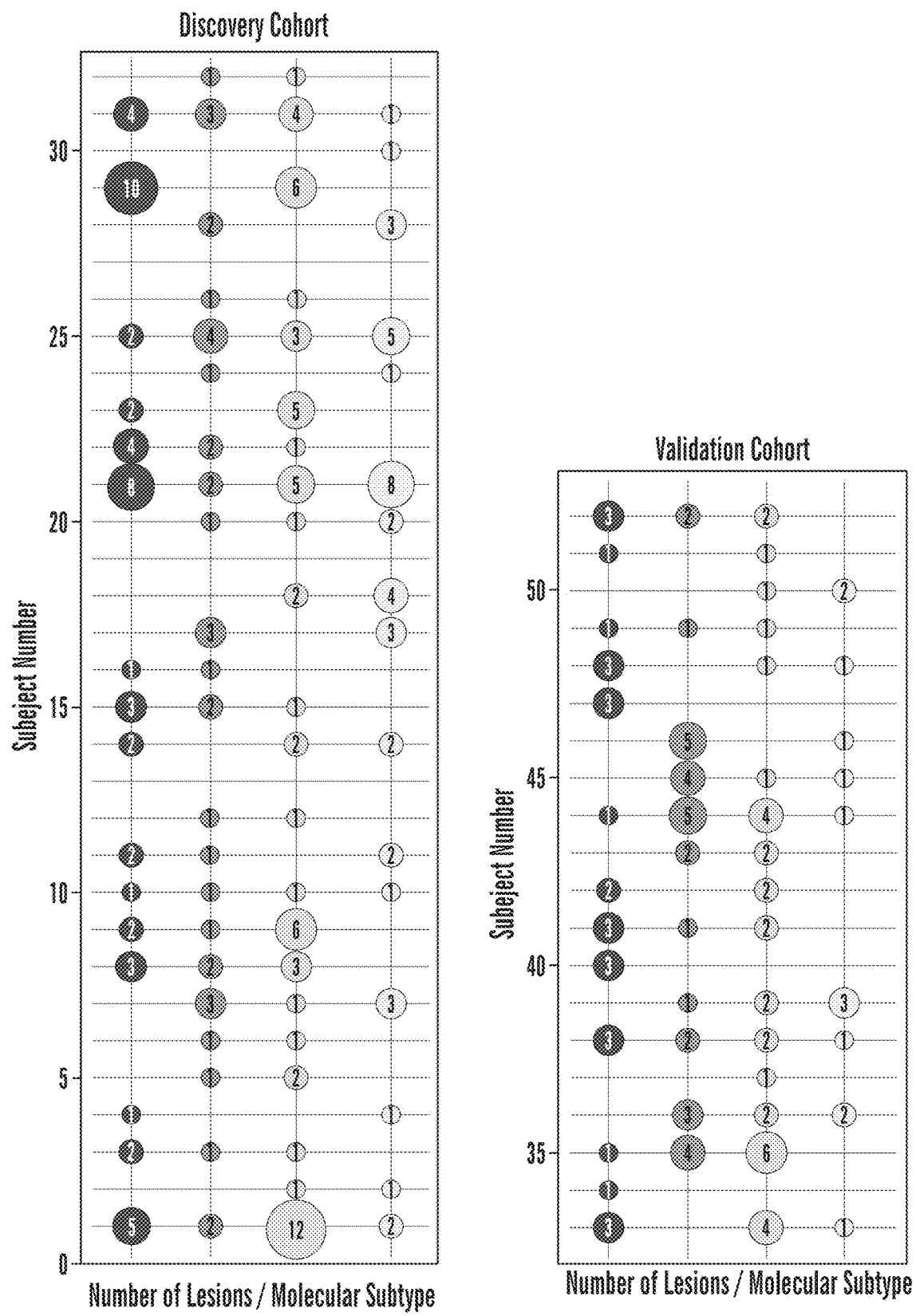
FIG. 8 depicts the distribution of Molecular Subtypes by Subject. The columns represent the 4 molecular subtypes (Proliferative, Inflammatory, Secretory, and Normal-like) and the radius of the circle is proportional to the number of samples within each subtype.
Figure 9:
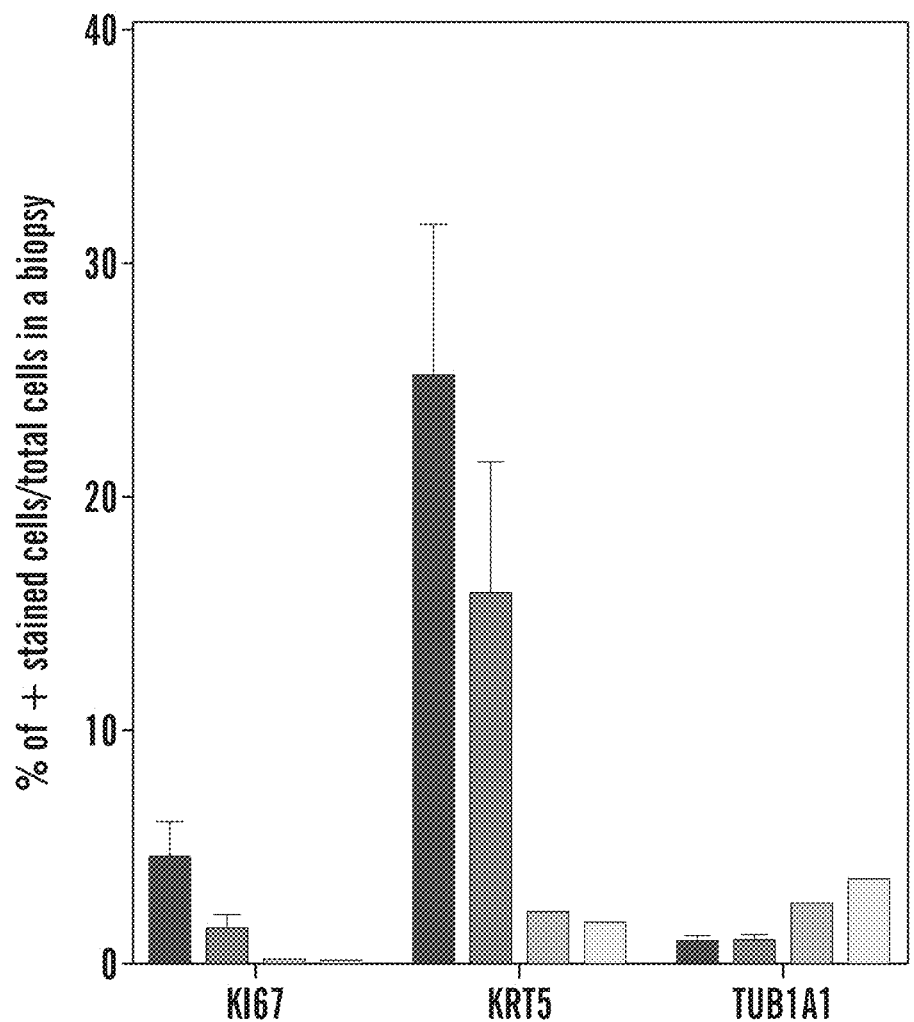
FIG. 9 depicts a graph of Immunofluorescent Staining Quantitation of Proliferation, Basal Cell, and Ciliated Cell Markers across the Molecular Subtypes. Boxplot of immunofluorescent staining quantitation of KI67 (proliferation), KRT5 (basal cell) and TUB1A1 (ciliated cell) across representative samples from each molecular subtype (Proliferative n=4, Inflammatory n=3, Secretory n=1, Normal-like n=1). KI67 and KRT5 staining are significantly higher in samples in the Proliferative subtype (p=0.02 and p=0.01, respectively, for sample differences between the Proliferative subtype and other subtypes). TUB1A1 was lower in samples in the Proliferative and Inflammatory subtypes but did not reach statistical significance (p=0.07 for sample differences between Proliferative and Inflammatory subtypes versus Inflammatory and Secretory subtypes).
Figure 10A:
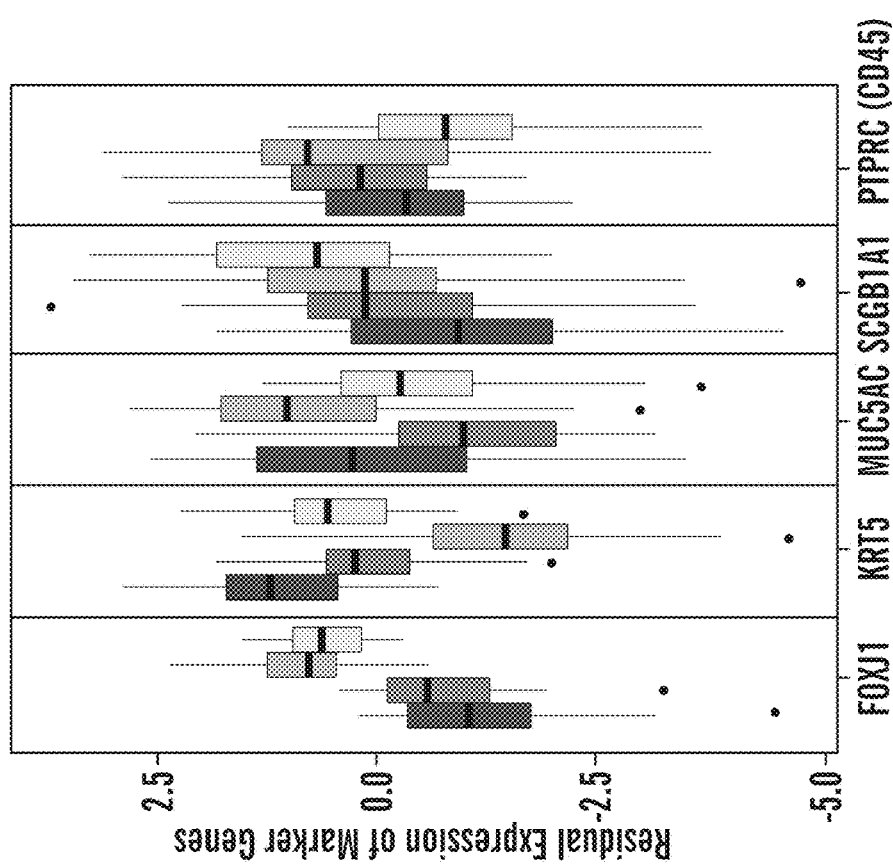
FIGS. 10A-10H depict boxplots of Select Genes and Cell Type Deconvolution Results across the Discovery and Validation Cohorts by Molecular Subtype.

The molecular subtypes were further characterized by their associations with clinical phenotypes and established LUSC tumor molecular subtypes (11, 12). Sample smoking status, the subject from whom the sample was derived, and sample histology demonstrated significant associations with subtype (p<0.01, FIG. 1B, Table 6, FIG. 8). The Proliferative and Secretory subtypes are enriched for current smokers and this association drives the subject enrichment as 79% of subjects maintain their smoking status throughout the study. Additionally, the Proliferative subtype is enriched for biopsies with dysplasia histology (FIG. 1B). The Proliferative subtype has high expression of genes involved in cell cycle processes including the proliferation marker MKI67, which is significantly up-regulated among samples in this subtype compared with samples in other subtypes (FDR=1.0e-30, linear model, based on differential expression analysis between samples in the Proliferative versus the non-Proliferative subtypes across all genes). The gene remained significantly up-regulated in the Proliferative subtype within samples with normal/hyperplasia histology (FDR=3.4e-10, linear model) and samples with dysplasia histology (FDR=3.1e-8, linear model), and these observations are supported by an increase in protein expression in representative samples (p=0.02) (FIG. 1C-1E and FIG. 9). The Proliferative subtype samples also had high concordance with the LUSC-Classical subtype (FIG. 1B). In the TCGA LUSC tumors, the LUSC-Classical subtype was associated with alterations and overexpression of KEAP1 and NFE2L2 as well as amplification of 3q26 with overexpression of SOX2, TP63 and PIK3CA (11). Similarly, our Proliferative PMLs have increased expression of KEAP1, NFE2L2, TP63, and PIK3CA (FDR=1.4e-6, 4.5e-12, 1.4e-9, and 0.03, respectively, linear model) (FIG. 10A). Furthermore, the LUSC-Classical subtype was found to be associated with increased expression of genes involved in energy metabolism, and our Proliferative subtype is in part defined by high expression of Module 4, which is enriched for genes associated with oxidative phosphorylation and the electron transport chain. In contrast, the Inflammatory and Secretory PML subtypes demonstrate enrichment for the LUSC-Secretory subtype. The LUSC-Secretory subtype was associated with processes related to the immune response, and the Inflammatory and Secretory PMLs have the highest expression of Module 8 that is enriched for genes in these same pathways.

Figure 1E:
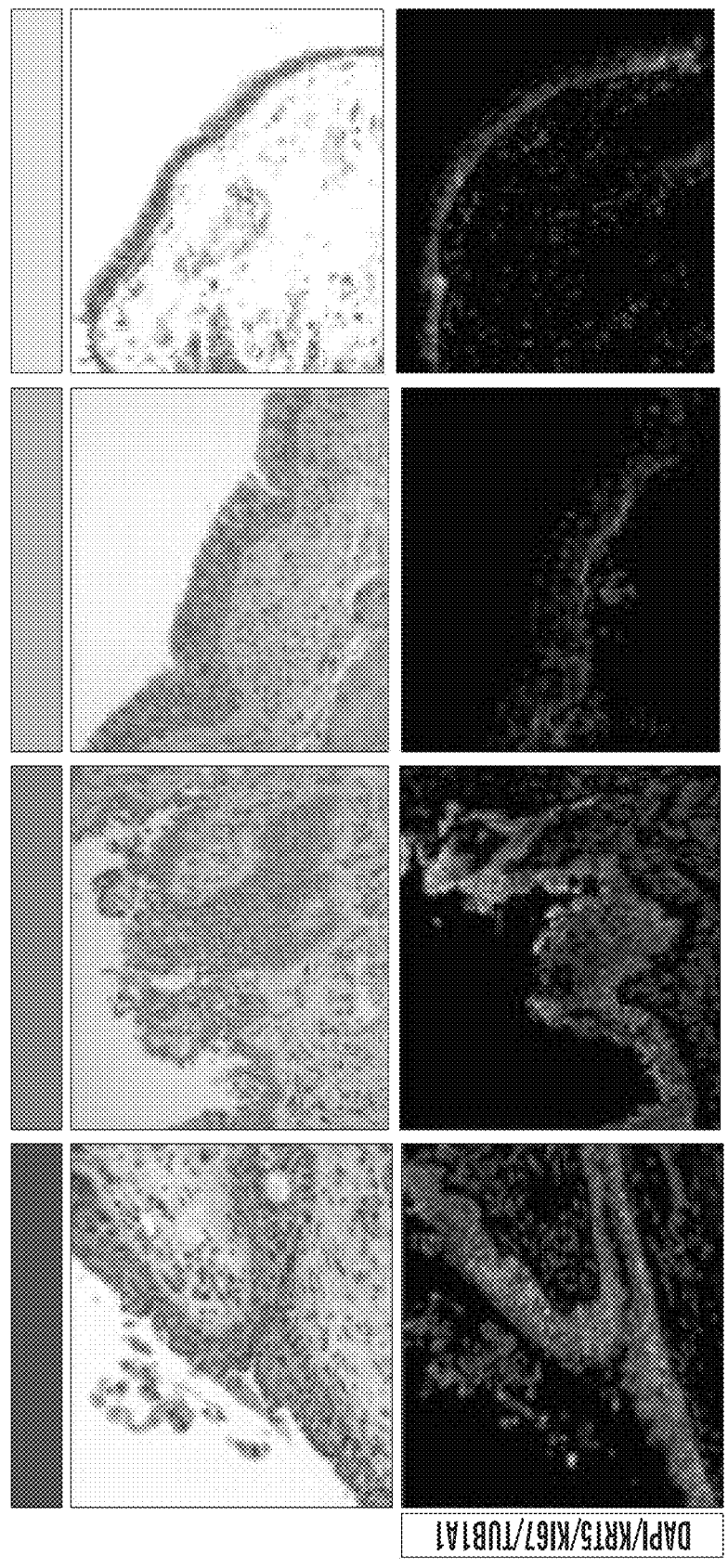
Figure 10B:
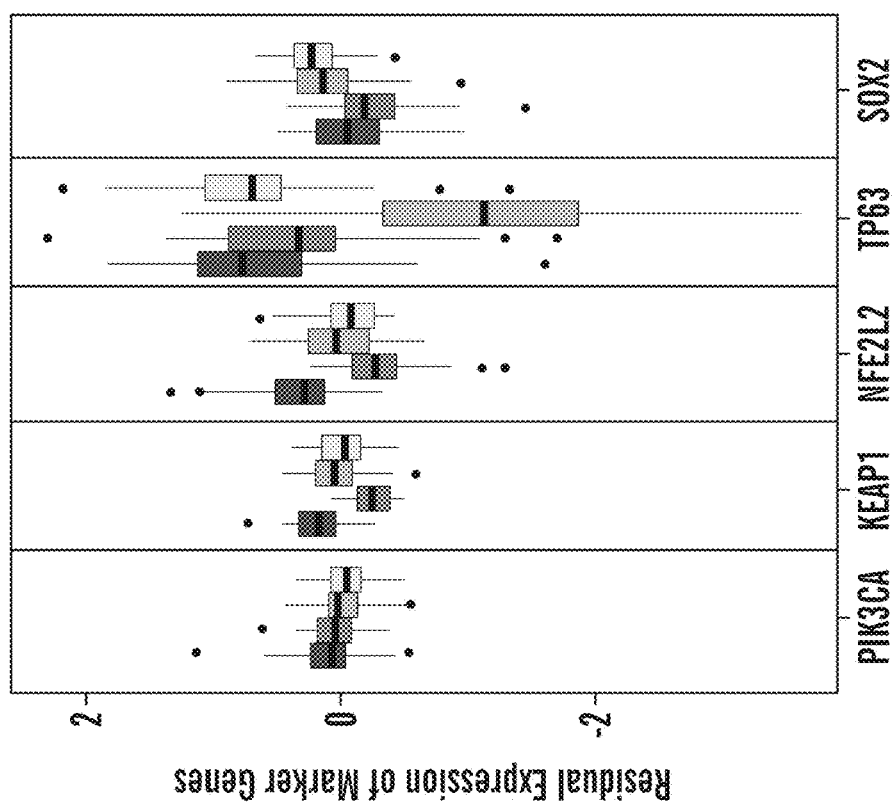
Figure 10D:
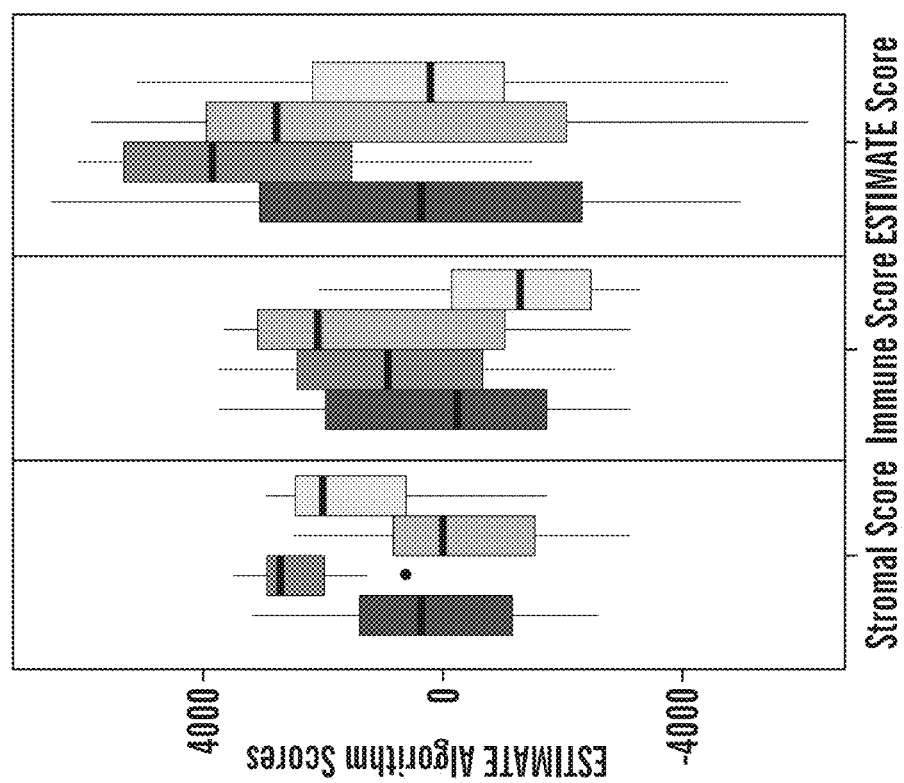
Figure 10C:
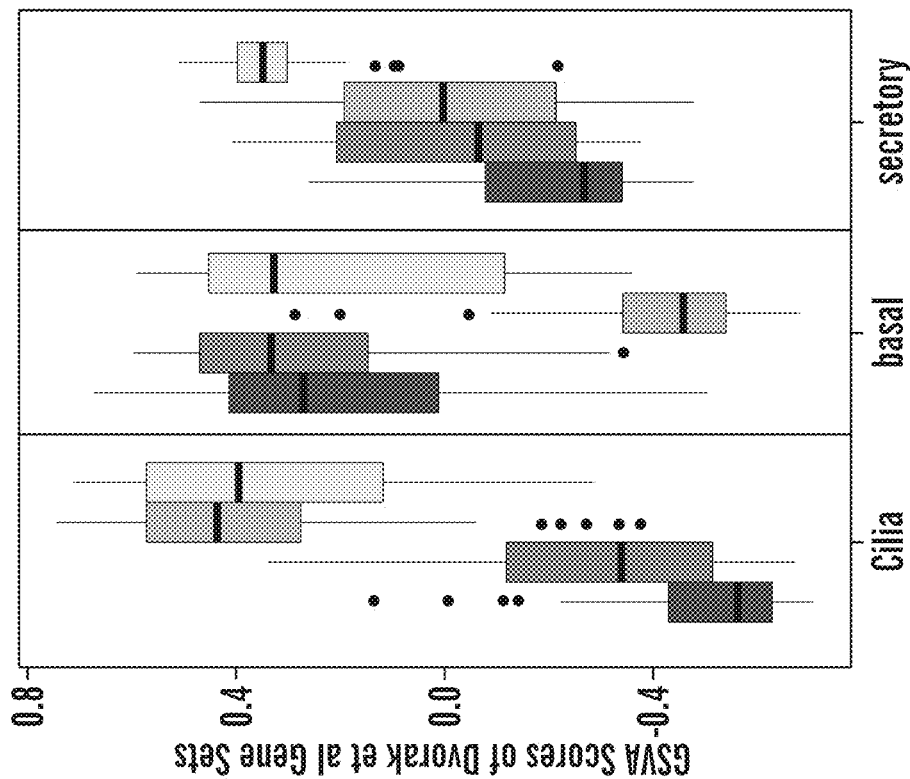
Figure 10E:
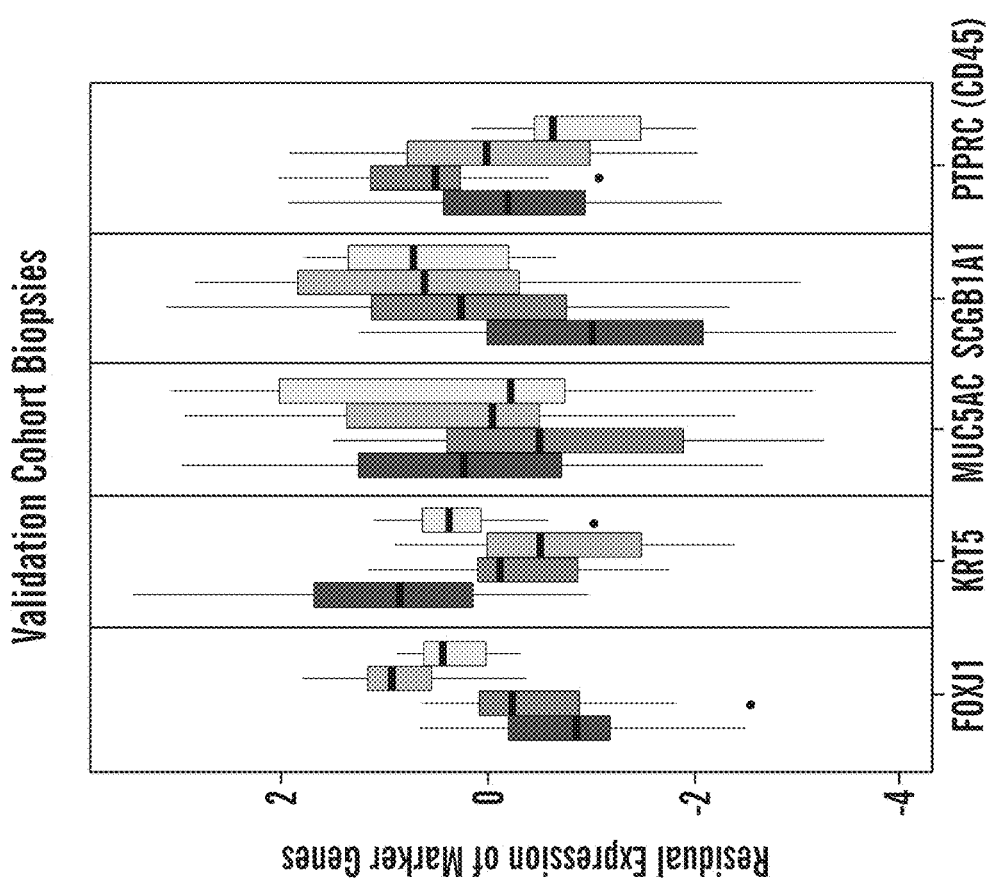

Finally, the extent to which the PML molecular subtypes were driven by differences in epithelial and immune cell type composition by assessing expression of a number of canonical cell type markers was examined. The Inflammatory and Secretory subtypes have higher levels of expression of the white blood cell marker PTPRC (CD45) consistent with enrichment of the LUSC-Secretory subtype (FIG. 10B, FDR=0.12 and 0.01, respectively, linear model). Consistent with the behavior and pathways enriched in Module 6, the ciliated cell marker TUB1A1 expression is decreased in the Inflammatory and Proliferative subtypes (FDR=1.1e-4 and 3.5e-19, respectively, linear model), and this is also shown by a decrease in acetylated a-tubulin staining in representative histological samples (FIG. 1E, FIG. 9). The Proliferative subtype has the highest expression (FDR=2.4e-15,1 linear model) of basal cell marker (KRT5) indicating enrichment of lesions with high-grade histology that tightly correlates with protein expression in representative histology samples (p=0.01) (FIG. 1E, FIG. 9, FIG. 10B, Table 7). Additionally, gene expression of MUC5AC, a marker of goblet epithelial cells, is increased in subtypes enriched for current smokers (Proliferative and Secretory) but is the most significantly increased in the Secretory subtype (FDR=3.4e-5, linear model). In contrast, gene expression of SCGB1A1, a marker of club cells, is the lowest in the Proliferative subtype (FDR=6.1e-5, linear model). The Normal-like subtype is supported by expression of all epithelial cell types and has the lowest expression of CD45 (FDR=7.6e-4, linear model). The expression levels of these marker genes agree with cell type deconvolution methods to examine epithelial and immune cell content (FIG. 10C-10D). The summation of these characterizations highlights epithelial and immune cell associated pathways that are modulated by smoking and PML histology and identifies the Proliferative subtype as a subset of high-grade PMLs that express proliferative and cell cycle-related pathways.

Figure 2A:
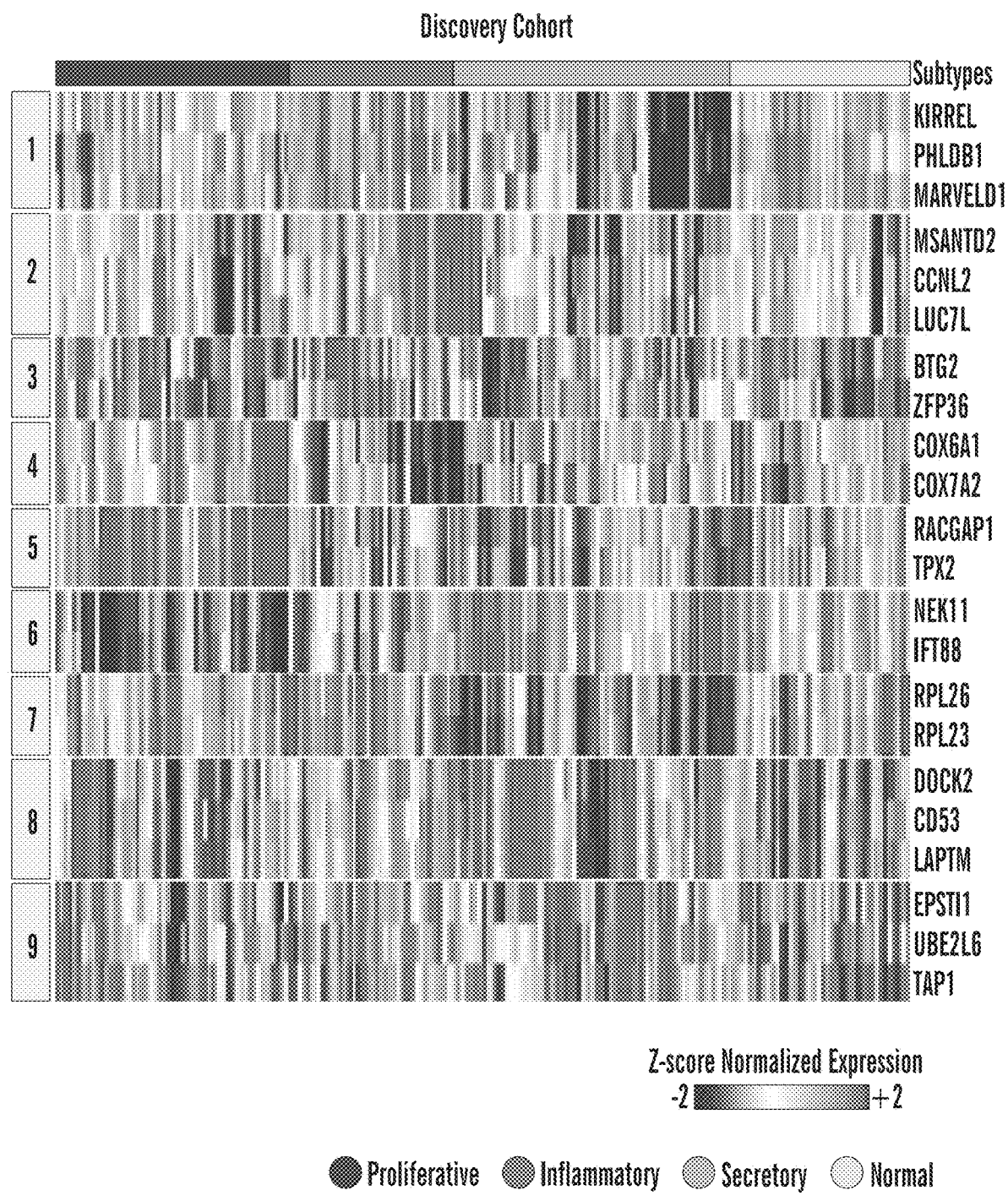
FIGS. 2A-2D demonstrate that phenotypic associations with the molecular subtypes are confirmed in an independent sample set.
Figure 2B:
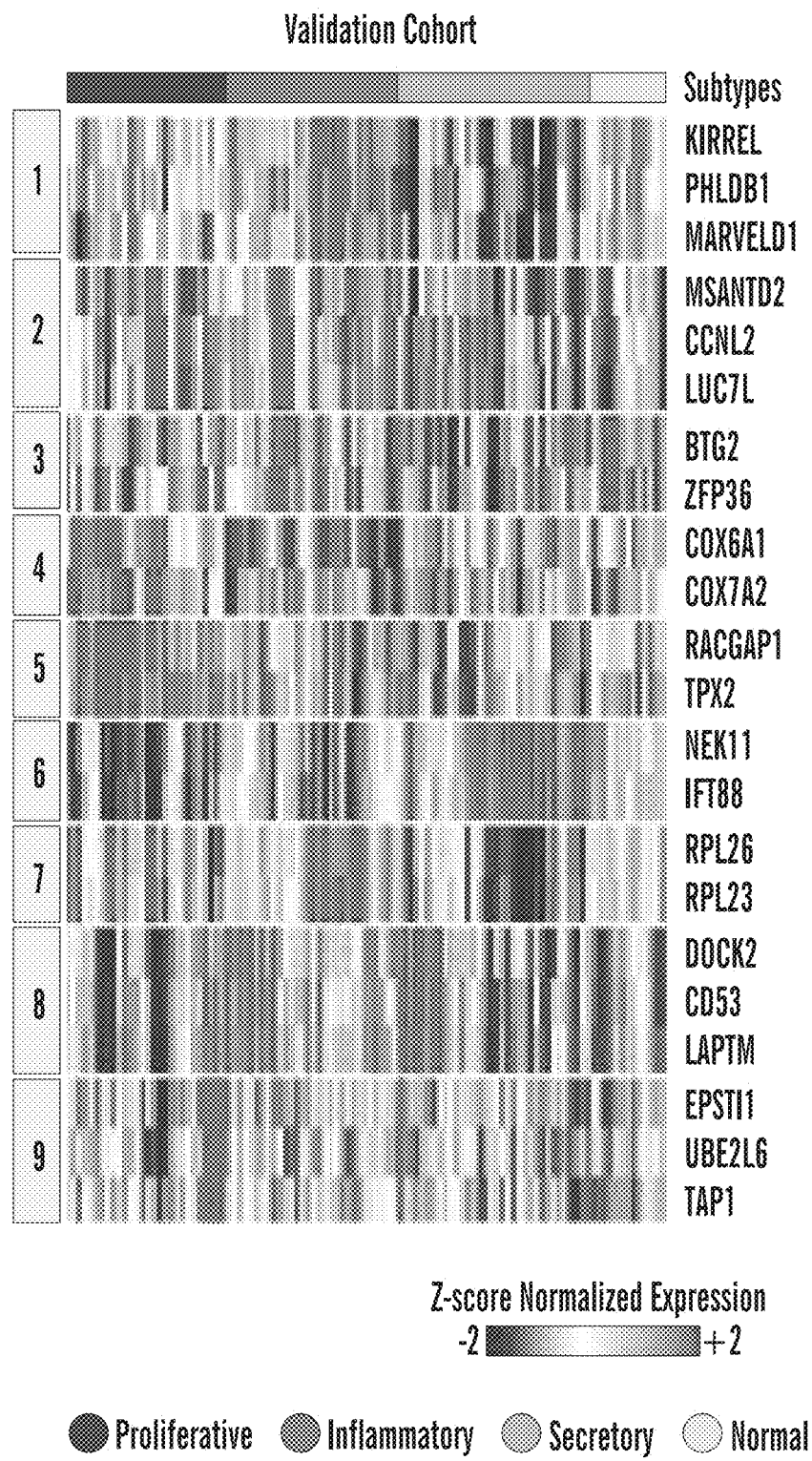
Figure 11:
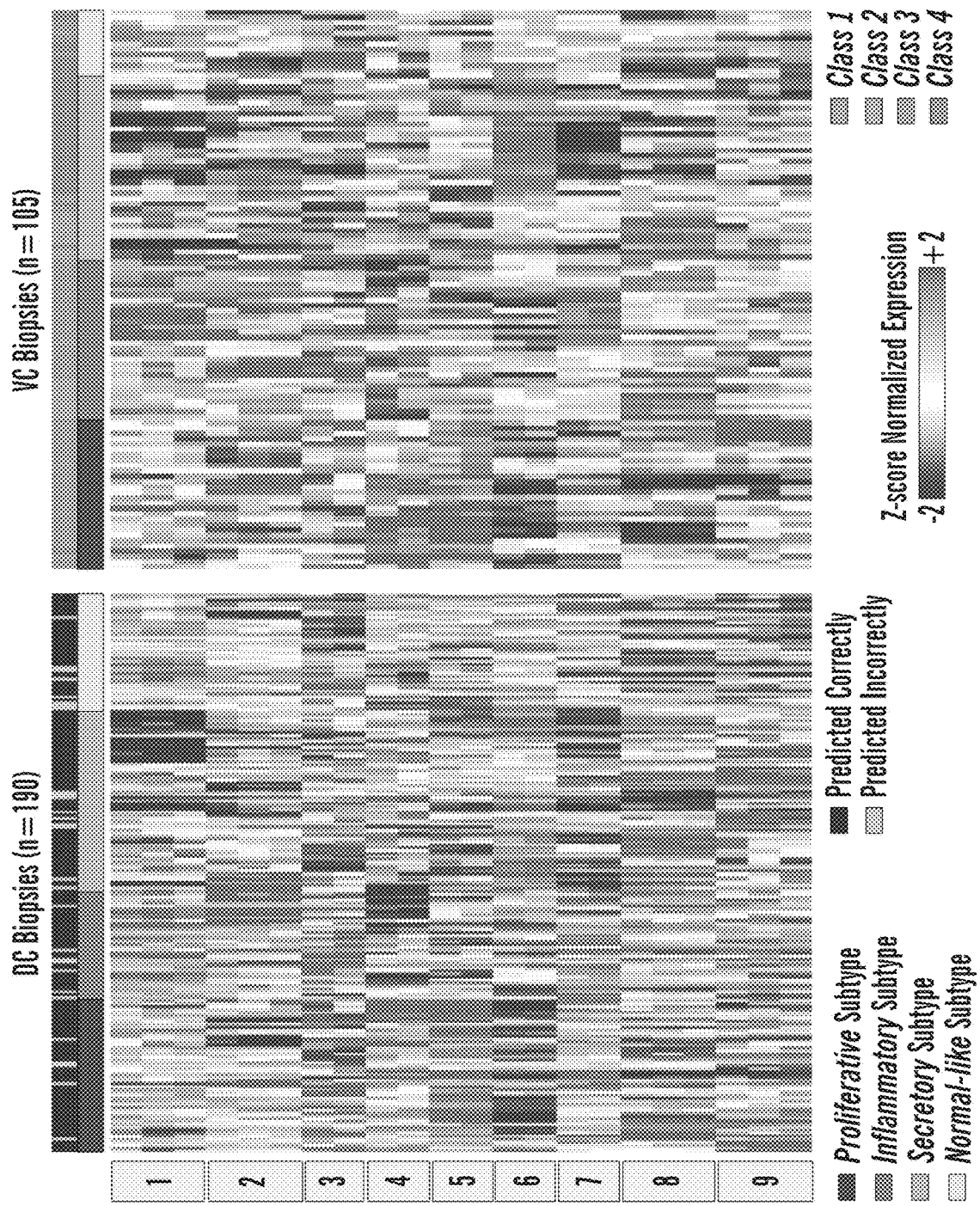
FIG. 11 depicts a heatmap of the 22-gene Molecular Subtype Classifier in the Discovery and Validation Cohort Biopsies. Semi-supervised hierarchal clustering of z-score normalized residual gene expression across the 22 classifier genes and 190 DC biopsies training samples (left) and the 105 VC biopsies (right). The rows of the heatmap show the gene module membership. The first column color bar shows molecular subtype membership in the DC and the 22-gene predict subtype membership in the VC. The second column color bar depicts correct and incorrect predictions in the DC using the 22-gene classifier and molecular subtypes derived by performing consensus clustering across the VC.
Figure 12:
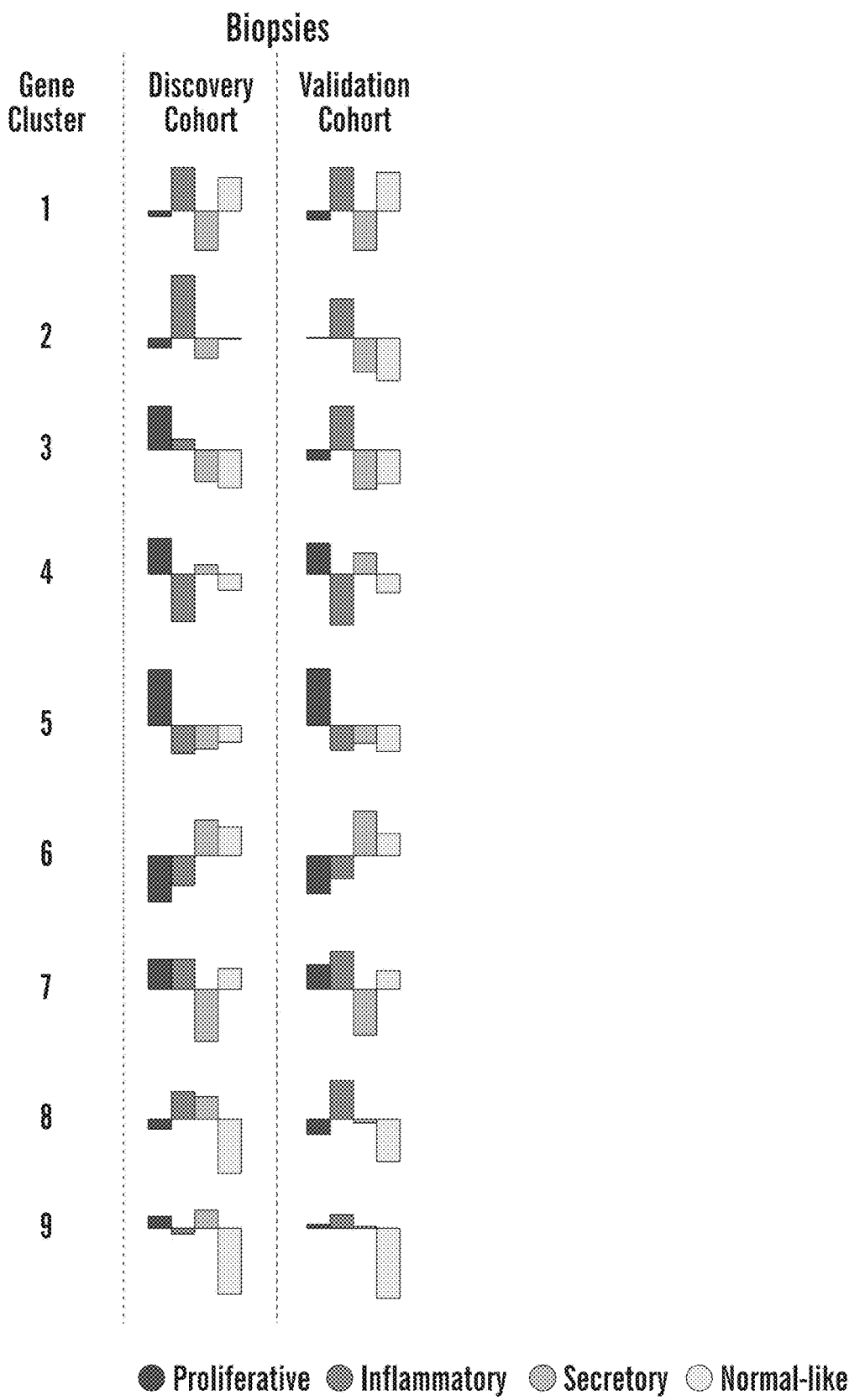
FIG. 12 depicts graphs of gene module behavior across the Molecular Subtypes in the Discovery and Validation Cohort Biopsies. The mean of the first principal component calculated across module genes is plotted for each molecular subtype.

Phenotypic Associations with the Molecular Subtypes are Confirmed in the Validation Cohort Next, it was desired to determine if the heterogeneity captured in the DC biopsy-derived molecular subtypes was reproducible in the VC. A 22-gene nearest centroid molecular subtype predictor was developed by selecting genes representative of each of the 9 gene modules. The predictor has 84.7% accuracy across DC biopsies (training set, FIG. 2A and FIG. 11) with the following misclassification rates per subtype 5/52 (9.6%) in Proliferative, 7/37 (18.9%) in Inflammatory, 9/61 (14.8%) in Secretory, and 8/40 (20%) in Normal-like. The 22-gene classifier was used to predict the molecular subtype of the 105 VC biopsies (FIG. 2B). The VC subtype predictions were evaluated by examining the concordance of metagene scores for each of the 9 modules (using the full set of genes for each module) between the predicted VC subtypes compared with the DC subtypes. The average behavior of Principal Component 1 (PC1) across the subtypes was highly similar (FIG. 12) with few exceptions (namely, Module 3 that had the fewest genes). Additionally, the VC subtype predictions from the 22-gene classifier were compared to subtypes derived in the VC biopsies using the same methodology used to derive the DC subtypes and found significant concordance (p=1.0e-7, with the Proliferative subtype having the greatest concordance between predictions, FIG. 11).

Figure 2C:
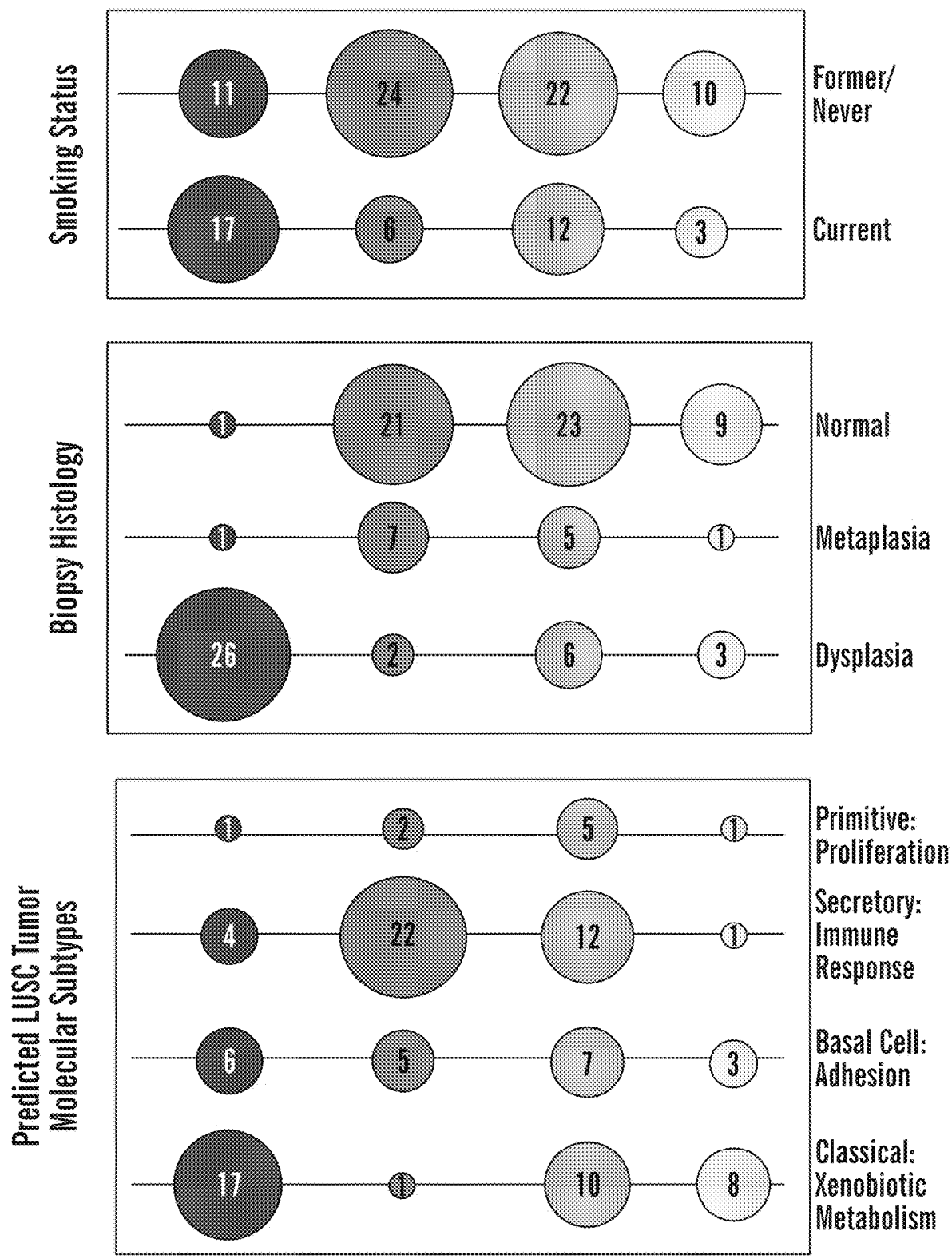
Figure 2D:
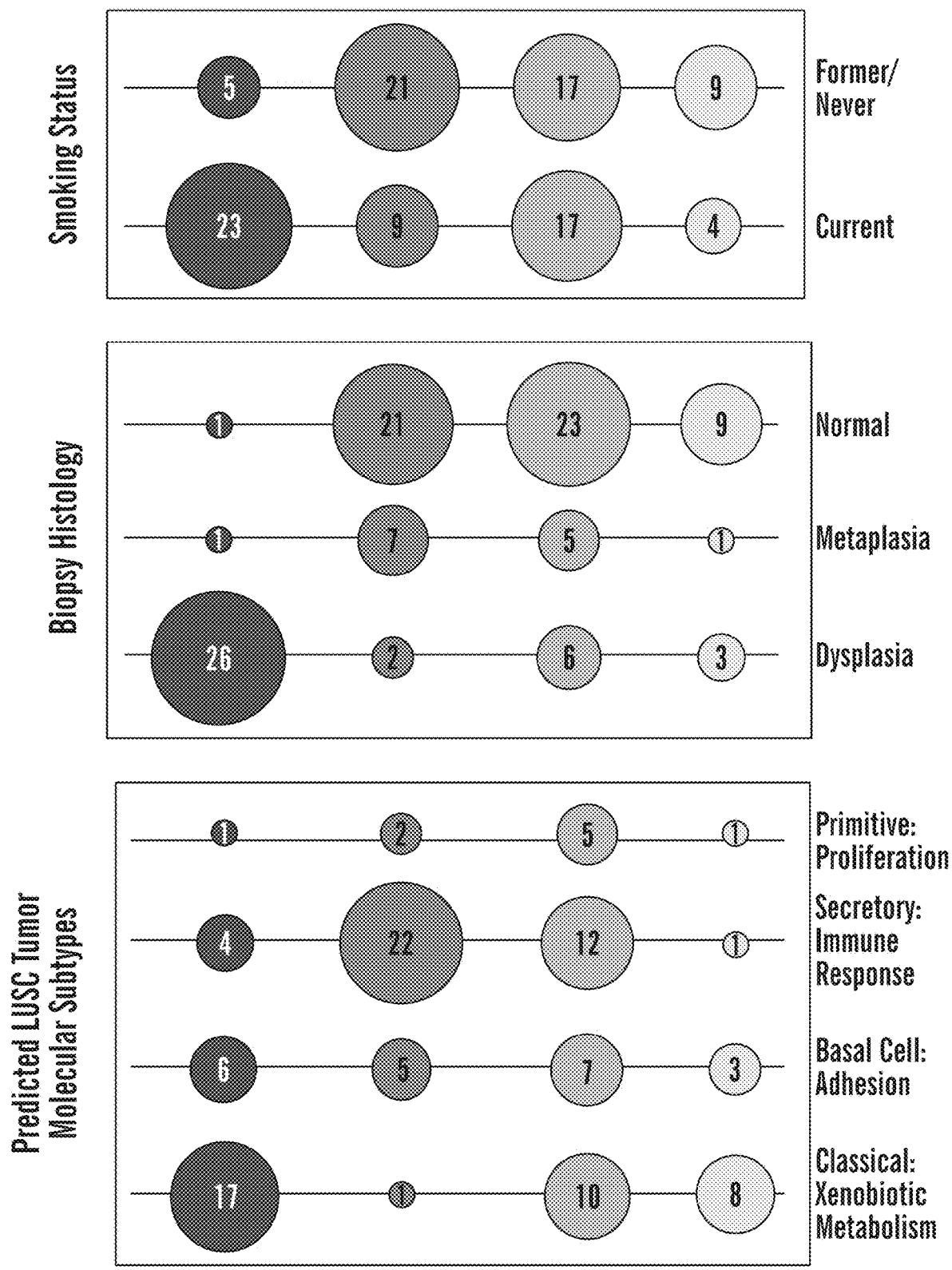
Figure 10F:
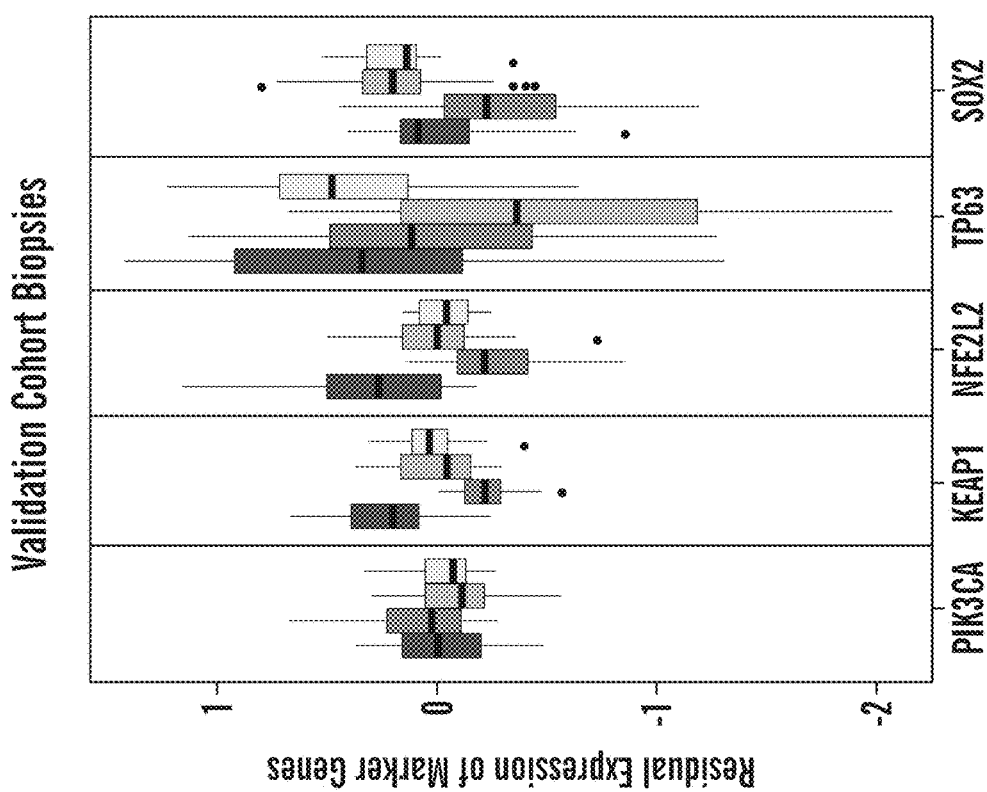
Figure 10G:
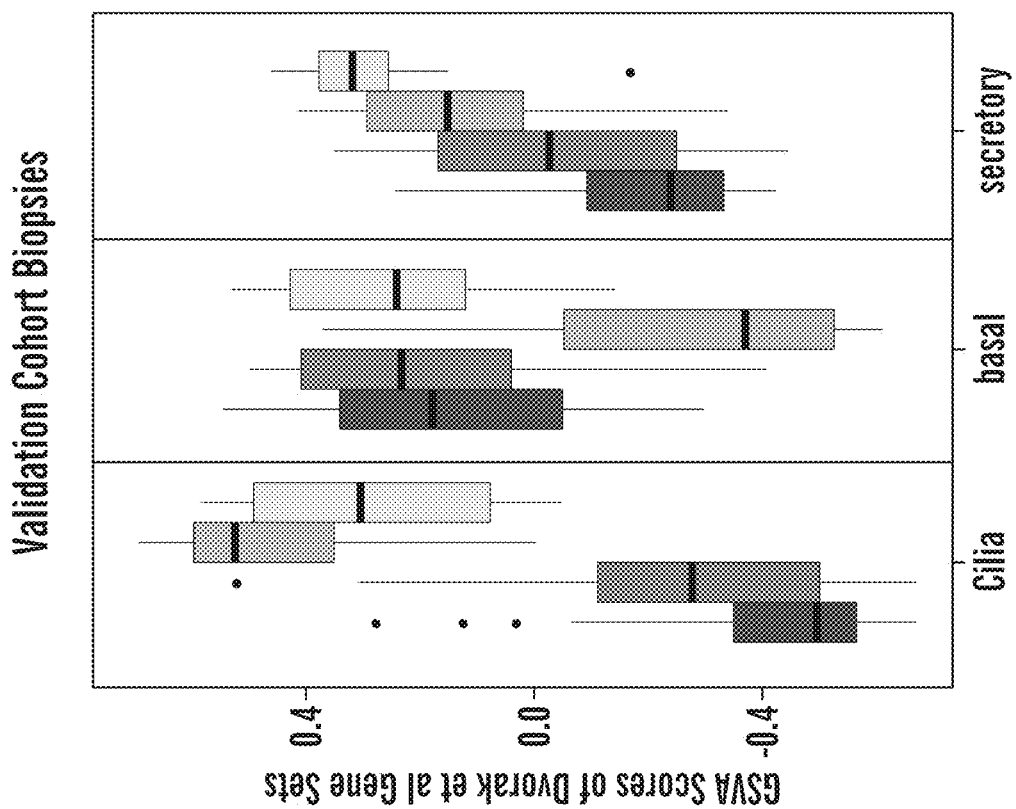
Figure 10H:
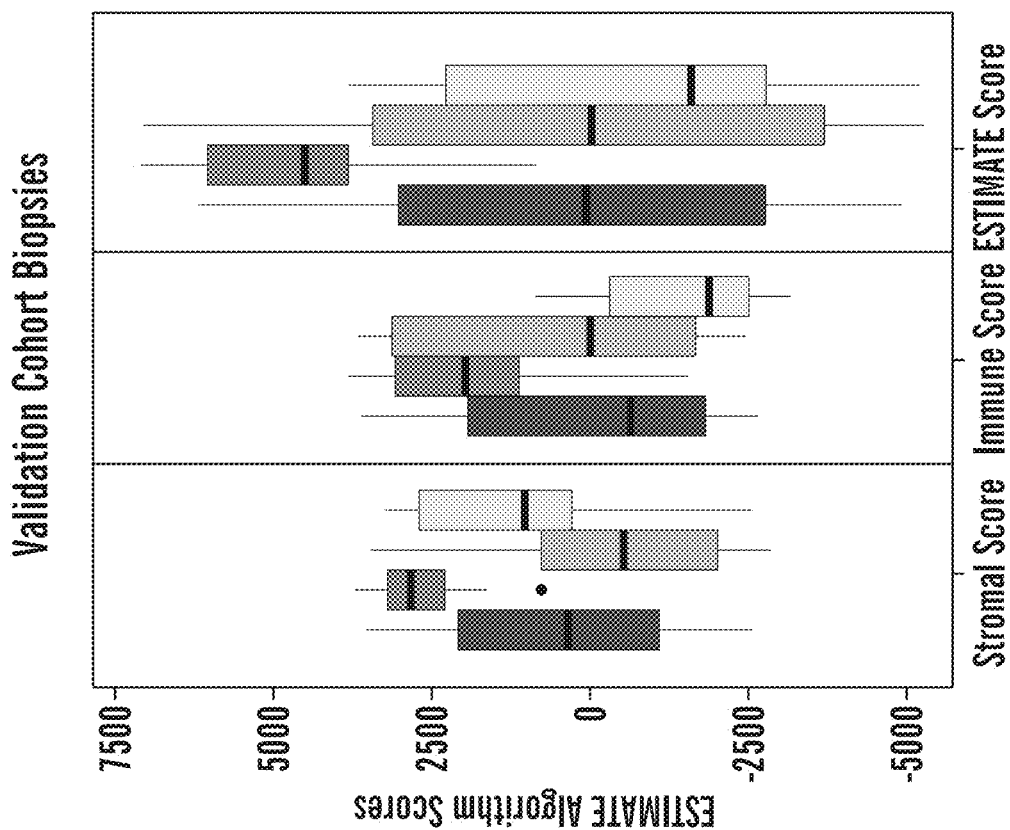

The statistical associations between the VC subtypes (via the 22-gene classifier) and clinical and molecular phenotypes across the VC biopsies are analogous to those observed across the DC biopsies (FIG. 2C, Table 6, FIG. 8 and FIG. 10A-10H). Briefly, the Proliferative subtype is enriched for current smokers, biopsies with dysplasia histology, and the LUSC-Classical tumor subtype (FIG. 2C, Table 6). Epithelial and white blood cell marker gene expression across the VC biopsies reveals higher levels of the white blood cell marker PTPRC (CD45 expression) in the Inflammatory subtype (FDR=0.002) consistent with enrichment of the LUSC-Secretory subtype (FIG. 10F).

The Inflammatory and Proliferative subtypes have reduced ciliated cell marker expression (FOXJ1) consistent with Module 6 (FOXJ1 FDR=0.0005 and FDR=2.62e-6 and Module 6 FDR=5.73e-6 and FDR=4.34e-10, respectively). The Proliferative subtype has the highest expression of basal cell marker KRT5 (FDR=1.67e-7), proliferation marker MKI67 (FDR=3.03e-10), and cell cycle associated Module 5 (FDR=1.23e-18) indicating enrichment of lesions expressing characteristics associated with high-grade histology. Gene expression of SCGB1A1, a marker of club cells, is the lowest in the Proliferative subtype (FDR=1.8e-4). Gene expression of MUC5AC, a marker of goblet epithelial cells, was increased in current smokers and most significantly in the Secretory subtype in the DC biopsies; however, in the VC biopsies this trend is not preserved as current smokers are not enriched in the Secretory subtype. The expression levels of these marker genes agree with other deconvolution methods to examine epithelial and immune cell content (FIG. 10E-10H).

Normal Appearing Airway Field Brushes Reflect Biopsy Molecular Subtype

Figure 3A:
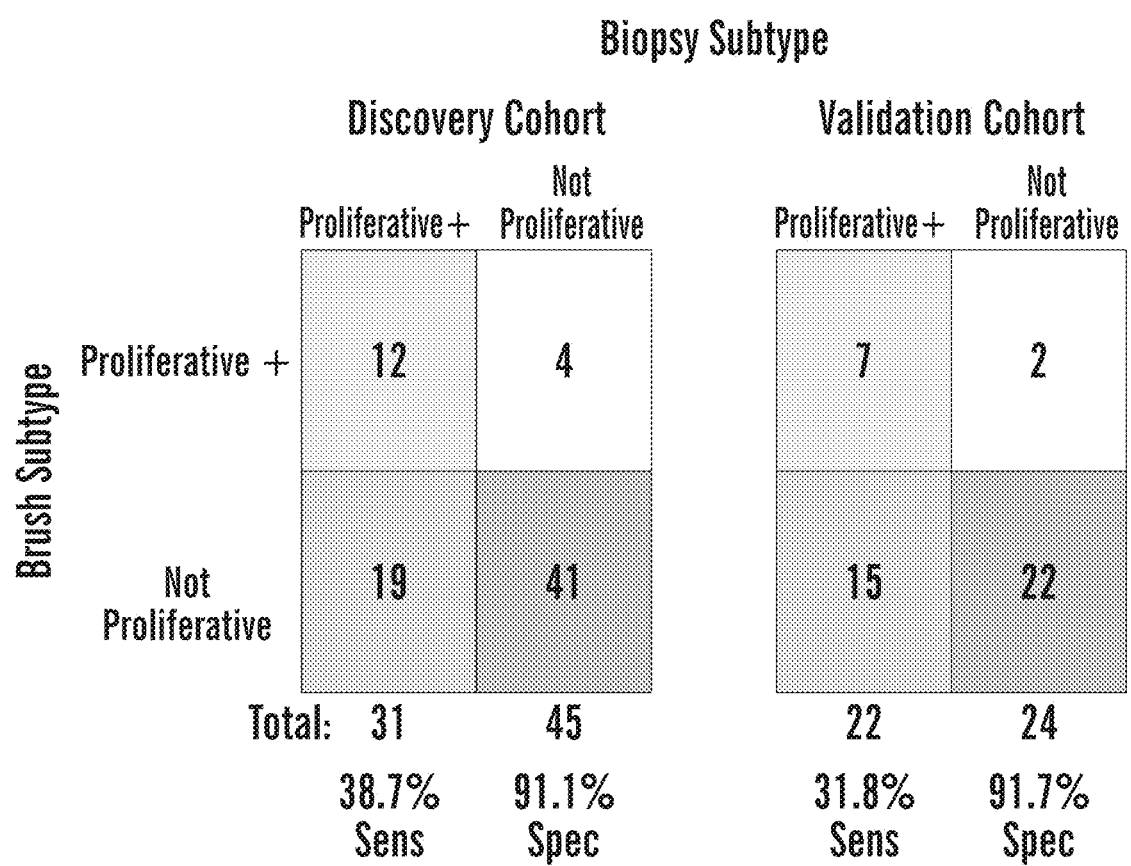
FIGS. 3A-3C demonstrate the performance of the molecular subtype classifier in the large airway brushes from normal appearing epithelium sampled at the same time as the endobronchial biopsies.
Figure 3B:
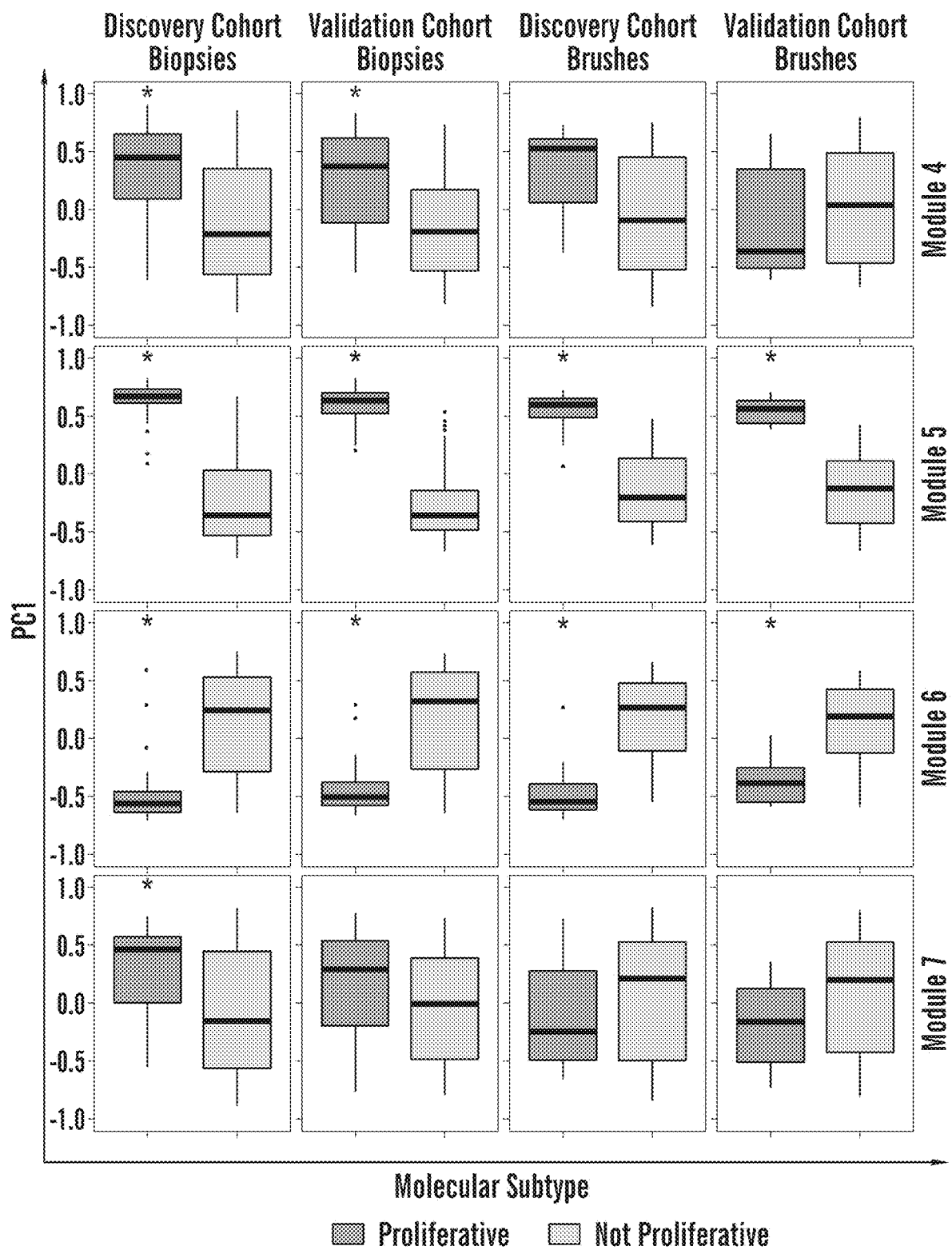
Figure 3C:
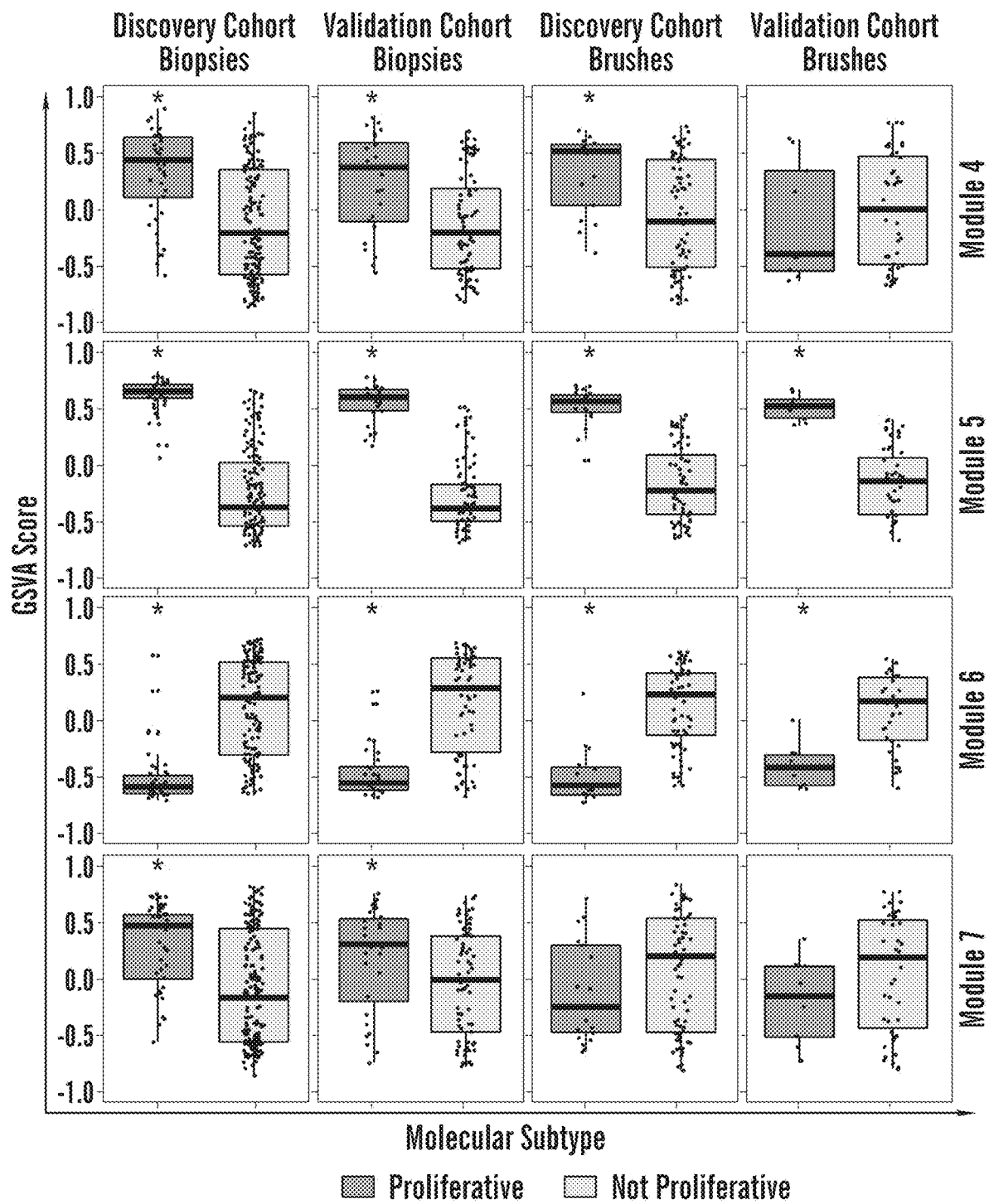

Previously, it was shown that bronchial brushes from normal appearing areas of the mainstem bronchus could predict the presence of PMLs (13); however, that study lacked biopsies and brushes from the same subjects. Above, in both the DC and the VC biopsies, the Proliferative subtype, represents a distinct subtype of PMLs enriched for dysplastic histology expressing metabolic and proliferative pathways. Biopsies classified as the Proliferative subtype may represent a group of PMLs that need close monitoring and intervention. As a result, it was sought to explore whether or not it was possible to predict the presence of Proliferative subtype biopsies using the brushes. The Proliferative subtype is defined by the behavior of Modules 4, 5, 6, and 7 (Table 3), and therefore, the subset of 8 genes (from the 22-gene predictor) that correspond to these Modules was used to predict the presence of the Proliferative subtype across the DC and VC biopsies and brushes. A prediction of the Proliferative subtype in a brush is specific (91% and 92% in the DC and VC biopsies, respectively), but not sensitive (39% and 32% DC and VC biopsies, respectively) at indicating the presence of at least one Proliferative PML detected at the same time point (FIG. 3A). In order to understand the classifier's performance in predicting the Proliferative subtype in brushes, Gene Set Variation Analysis (GSVA)(14) scores were examined for Modules 4, 5, 6, and 7 that define the Proliferative subtype in the DC and VC brushes (FIG. 3B). In the DC and VC brushes, the GSVA scores were significantly different (FDR<0.05) in the Proliferative subtype versus all other samples only for Modules 5 and 6, and thus these most likely contribute the most heavily to Proliferative subtype classification in the brushes. Module 5 contains genes associated with cell cycle and proliferation while Module 6 contains genes associated with cilium assembly and organization. Down-regulation of Modules 5 and 6 in the brushes specifically predicts the presence of a Proliferative subtype PML; however, the absence of these signals in the airway field of injury does not preclude the development of a Proliferative subtype PML.

Immune-associated genes separate proliferative subtype progressive/persistent and regressive PMLs. Previous studies of bronchial PMLs suggest that high-grade lesions (which occur more frequently in current smokers) are more likely to progress to invasive carcinoma (6). Therefore, it was sought to identify molecular alterations associated with subsequent PML progression/persistence (n=15) versus regression (n=15) among the Proliferative subtype DC biopsies, as these may be clinically relevant to identifying appropriate interception strategies. Using GSVA scores calculated across all the DC biopsies for each of the 9 modules, it was calculated which scores were statistically different between progressive/persistent versus regressive disease in the samples belonging to the Proliferative subtype (FIG. 7). It was found that the DC biopsy GSVA Module scores for Module 9 were significantly higher among regressive Proliferative PMLs (p=0.002, linear model FIG. 4A) compared with progressive/persistent Proliferative PMLs. The association between low Module 9 score and progression/persistence is replicated in the VC biopsies (n=7 progressive/persistent and n=13 regressive biopsies; p=0.03,linear model FIG. 4B). The ability of the Module 9 GSVA scores to discriminate between regressive versus progressing/persistent biopsies as measured by the area under the receiver operating characteristic (ROC) was 0.809 and 0.802 in the DC and VC biopsies, respectively.

Figure 4C:
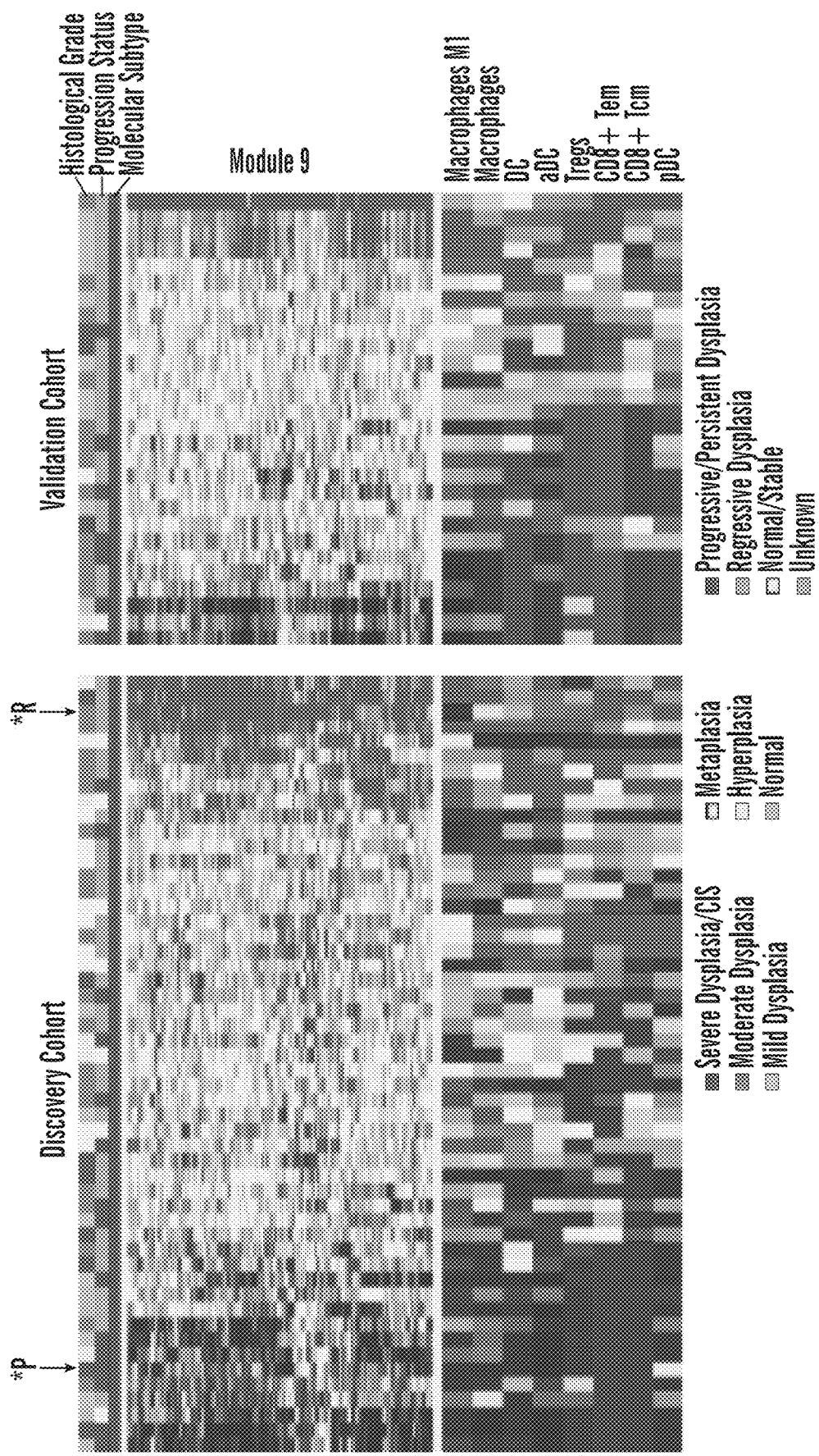
Figure 13:
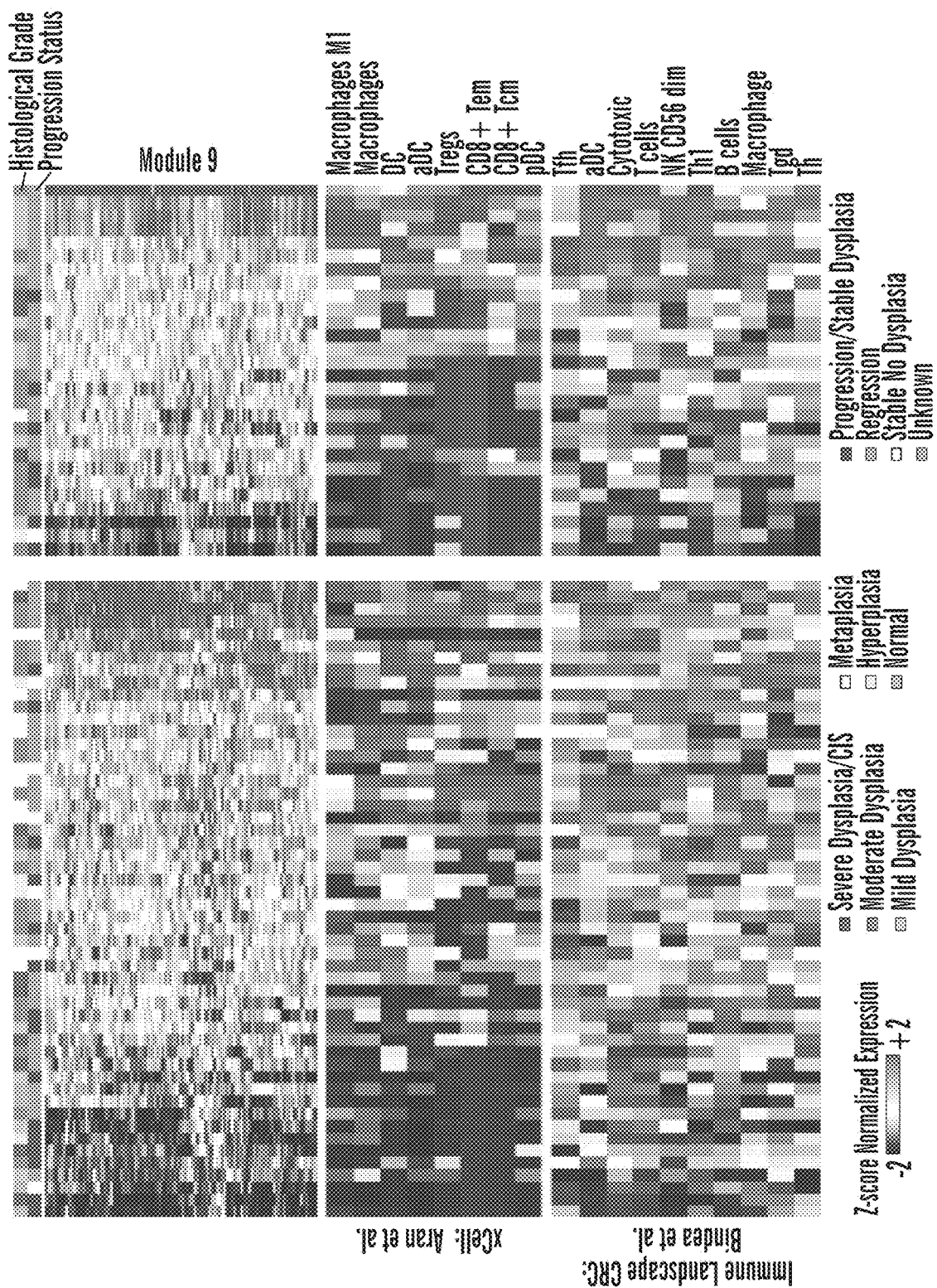
FIG. 13 depicts the concordance between Module 9 and two Cell Type Deconvolution Analyses. Top: Hierarchal clustering of z-score normalized gene expression across the 112 genes in module 9 and the DC biopsies (left) and the VC biopsies (right). Each heatmap is supervised according to the module 9 GSVA scores. Top bars indicate the histological grade of the biopsies and their progression status. xCell results (Middle) and GSVA scores for gene sets described by Bindea et al. (Bottom) indicating the relative abundance of immune cell types across the DC biopsies (left) and the VC biopsies (right). Immune cell types displayed are significantly associated with lesion progression/persistence (FDR<0.05 in both the DC and VC).
Figure 13:
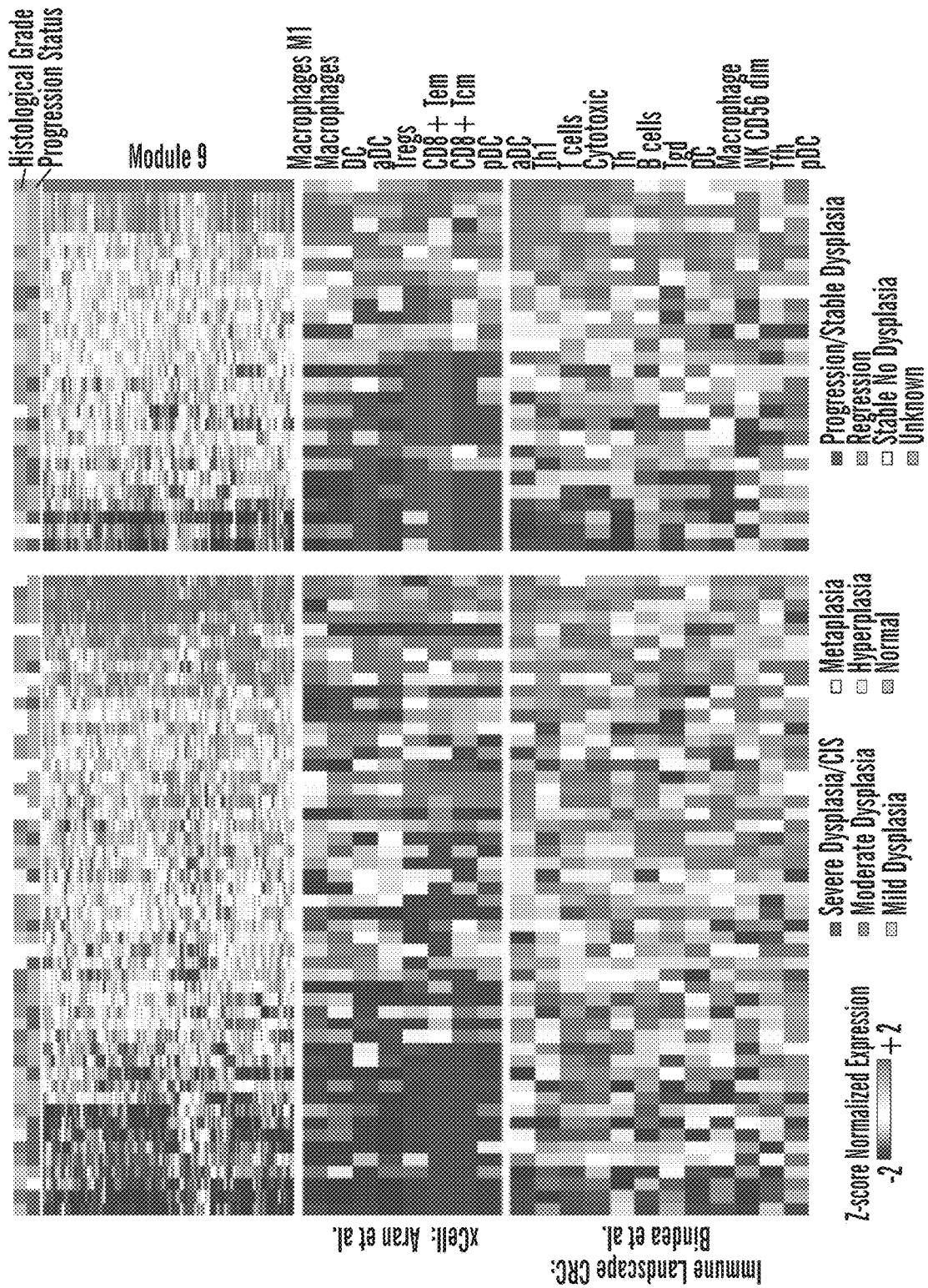

The genes in Module 9 include a number of genes that encode for proteins involved in interferon signaling as well as antigen processing and presentation (SP100, CHTA, CXCL10, SOCS1, GBP1, GBP4, B2M, TAP1, TAPBP, TRIM 14, TRIM21, TRIM22, STAT1, PML, OAS2, OAS3, MX1, ADAR, ISG15, IFI35, IFIT3, IFI27, PSMB8, PSMB9, BST2, IRF1, IRF9, CD74, PSME1, PSME2, HLA-DQA1/DPA1/DPB1/DRA/DQB2/DRB1/DQB1/DMA/DMB/DOA, HLA-A/B/C/E/F) and include the inhibitory receptor LAG3. As a result, it was wanted to evaluate whether or not the presence or absence of innate or adaptive immune cells were associated with Module 9 expression within the Proliferative subtype. In an effort to deconvolute the potential presence of immune cell types, GSVA scores were generated using previously described immune cell signatures (15) and scores for 64 different cell types using the xCell algorithm(16), separately for both the DC and VC biopsies. Significant (FDR<0.05) associations were identified between the cell type scores and Module 9 that were in common between the DC and VC biopsies (FIG. 13) and 8 cell types identified (via xCell) including dendritic cells, activated dendritic cells, plasmacytoid dendritic cells, macrophages, M1 macrophages as well as CD8+ effector memory T cells, CD8+ central memory T cells, and T regulatory cells (FIG. 4C). Taken together, the progressive/persistent biopsies in the Proliferative subtype have down-regulated expression of Module 9 compared with regressive biopsies that correlates with reduced signals from both innate and adaptive immune cell populations.

Figure 4D:
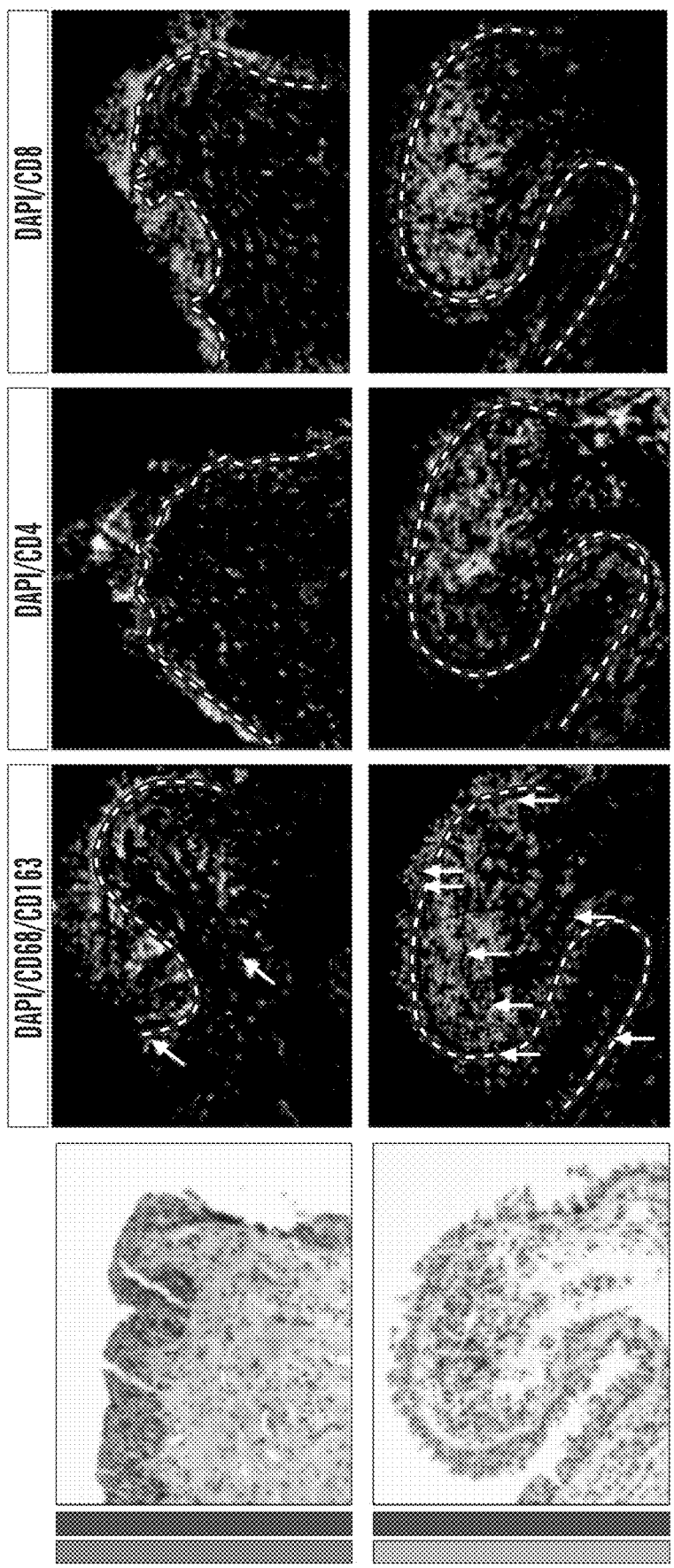
Figure 4E:
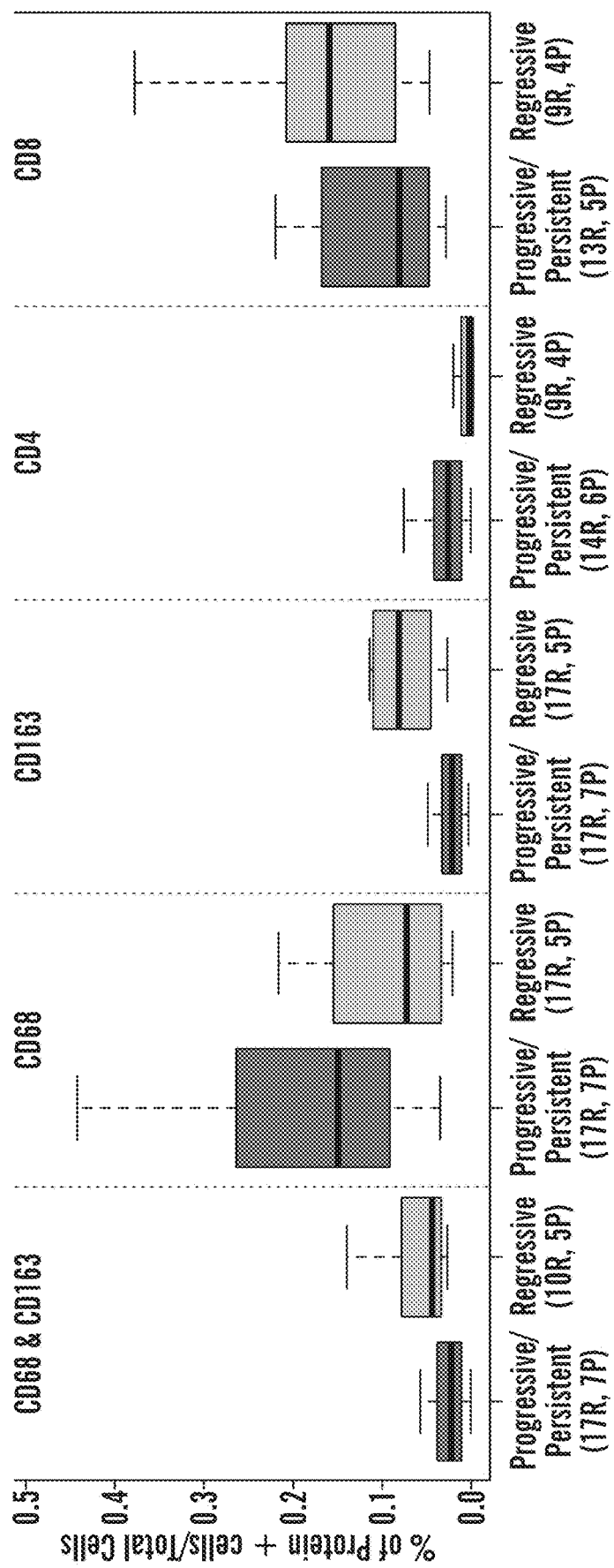
Figures 4F, 4G:
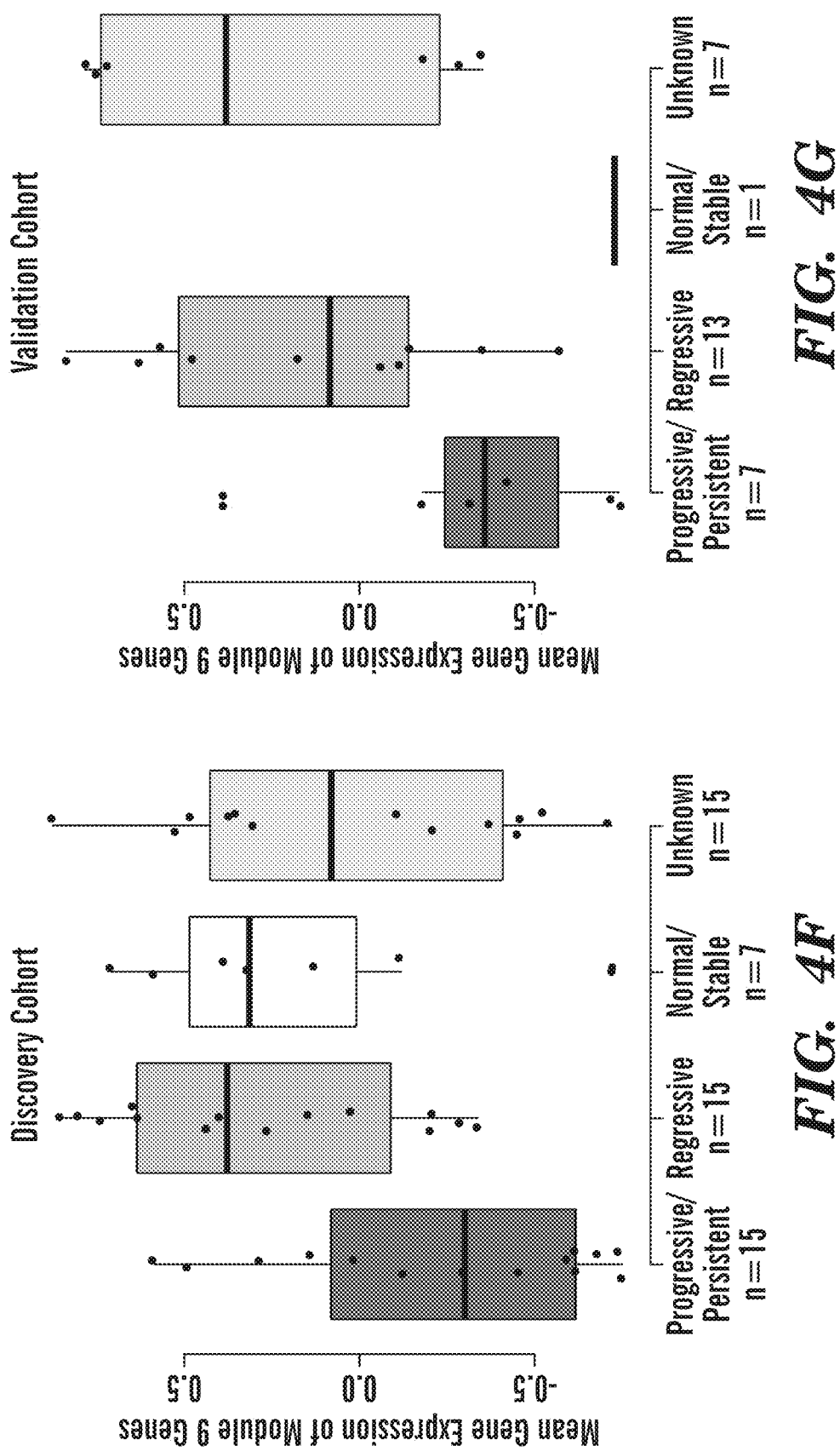
Figure 4H:
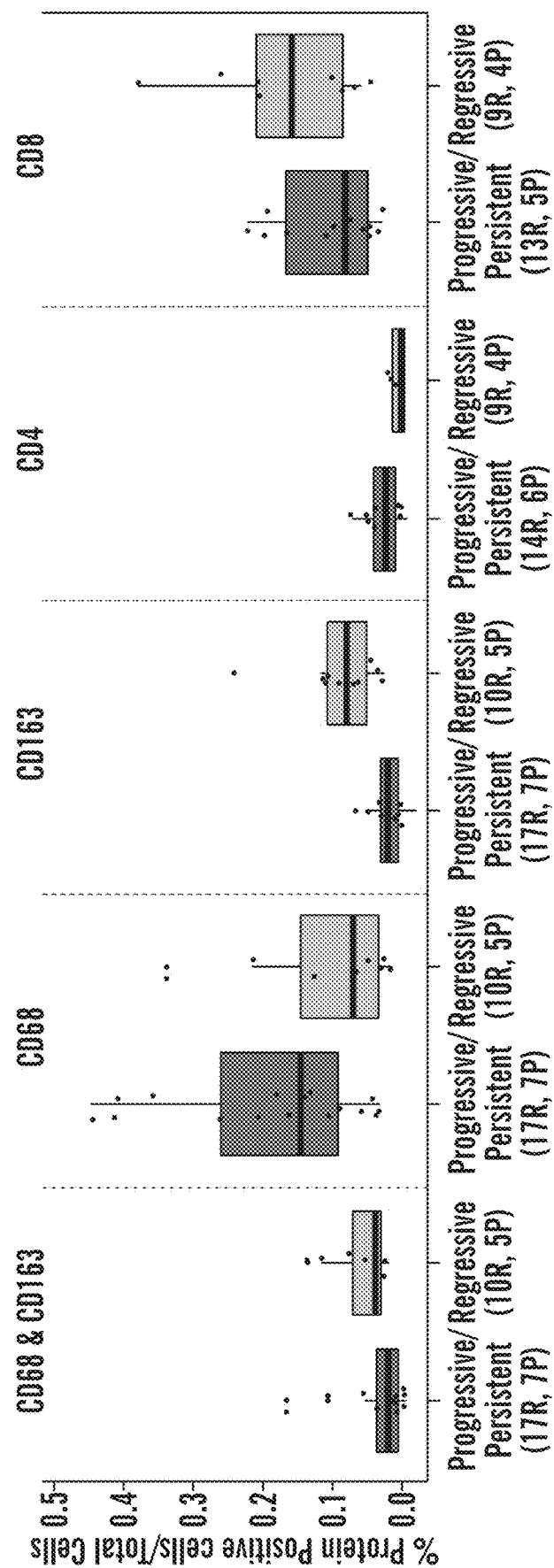

Immunofluorescence Reveals Progression-Associated Modulation of Macrophages and T Cells in Proliferative PMLs In order to confirm the relationship between the immune cell types associated with Module 9 and histologic progression/persistence of PMLs in the Proliferative subtype, immunofluorescent staining of macrophages/monocytes (n=52 regions enumerated from n=16 subjects), CD4 (n=50 regions enumerated from n=17 subjects), and CD8 T cells (n=47 regions enumerated from n=16 subjects) was performed (Table 7). The results were analyzed across all subjects assayed within the Proliferative subtype and across the subset of subjects where the lesion outcome (progression/persistence versus regression) was concordant with the Module 9 GSVA score (denoted as concordant set). Staining of CD68, a pan macrophage (and tumor associated macrophage) marker, suggestive of M1 type macrophages, was increased in progressive/persistent lesions (p<<0.001 in the concordant set). In contrast, staining of CD163 in combination with CD68, thought to be suggestive of M2 type macrophages, were decreased among the progressive/persistent lesions in the Proliferative subtype (p<<0.001 using all subjects and p=0.0007 in the concordant set, respectively, linear model) (FIG. 4D-4E). Additionally, CD4 T cells were increased (p<<0.001 in the concordant set, linear model) and CD8 T cells were decreased (p<<0.001 in the concordant set) in PMLs that progress/persist. Interestingly, among progressive/persistent lesions, the CD8 T cells had a distinct localization pattern (p=0.07 in the concordant set, linear model), where CD8 T cells both lined and were embedded within the epithelium in areas where dysplasia is present (FIG. 4D). The immunofluorescence results did not reach significance, with the exception of CD163, when just the lesion outcome was used without regard to the Module 9 score.

Discussion

Lung squamous cell carcinoma (LUSC) is the second most common form of lung cancer and arises in the epithelial layer of the bronchial airways. It is often preceded by the development of lung squamous premalignant lesions (PMLs). The presence of dysplastic persistent and or progressive PMLs is a marker of increased risk for LUSC (6). Currently, however, effective tools to identify PMLs at highest risk of progression to invasive carcinoma are lacking (7). The development of markers predictive of disease progression will be important in identifying patients at highest risk for LUSC development and in identifying biological pathways exploitable for LUSC chemoprevention. Towards this goal, described herein is profiling via RNA-Seq bronchial brushes and endobronchial biopsies obtained from subjects undergoing longitudinal lung cancer screening by chest computed tomography (CT) and auto-fluorescence bronchoscopy. Four transcriptionally distinct groups of biopsies are identified, one of these labelled Proliferative and found to be associated with high-grade dysplasia. Patients with Proliferative PMLs can also be identified via gene expression measured from cells in the non-involved large airway epithelium. It was further found that persistent/progressive Proliferative PMLs are characterized by decreased expression of genes involved in interferon signaling and antigen processing/presentation pathways. Consistent with these gene expression findings it was found that progressive/persistent Proliferative PMLs are depleted for CD68+/CD163+ macrophages and CD8 T cells by immunofluorescence. Collectively, these data indicate both the potential to identify a subset of patients with progressive/persistent LUSC PMLs, who are at risk for developing invasive lung cancer, on the basis of airway gene expression; as well as the potential to decrease the risk for progression in these patients by augmenting the immune response associated with regression.

Previous studies indicate a range of genomic alterations associated with bronchial dysplasia. Increased expression of EGFR and Ki67 staining of epithelial cells is associated with increasing histologic severity and subsequent histologic progression (6, 17). Altered protein levels of TP53, CCND1, CCNE1, BAX, and BCL2 have been associated with CIS or lung cancer occurrence independent of histological grade (18). Telomere shortening and maintenance (19) and loss of heterozygosity in regions frequently detected in lung cancer (3p, 5q, 9p, 13q, 17p) have been observed in early hyperplasia/metaplasia lesions (20-22) and found to increase in frequency and size in higher-grade dysplasia. Genomic gains in loci containing SOX2, TP63, EGFR, MYC, CEP3, and CEP5 are also associated with progression of high-grade dysplasia (23). Despite the numerous genomic alterations associated with PML histological grade and progression, a comprehensive PML molecular classification system to complement the pathologic classification of PML is lacking. Use of an unsupervised class discovery approach that led to the identification of four distinct molecular PML subtypes (Proliferative, Inflammatory, Secretory, and Normal-like).

The transcriptional patterns differentiating the PML subtypes are robust and a 22-gene panel identified in the Discovery Cohort can be used to distinguish between the different molecular subtypes in an independent Validation Cohort. Interestingly, while prior lung cancer history may influence airway gene expression and about two-thirds of the subjects have a prior history of lung cancer, we do not detect a significant association between lung cancer history and molecular subtype, and there is a similar diversity of molecular subtypes between biopsies collected from subjects with and without a lung cancer history. The Proliferative subtype is enriched with dysplastic PMLs from current smokers and is characterized by up-regulation of metabolic (OXPHOS/ETC/TCA) and cell cycle pathways and down-regulation of cilia-associated pathways. Previous work indicates increases in metabolic pathways in the airways of subjects with dysplastic lesions (13), in PMLs adjacent to LUSC tumor (24), and in smokers at high-risk for lung cancer (25) as well as increases in proliferation (via Ki67 levels, as mentioned above) that have been utilized as an endpoint in lung cancer chemoprevention(26, 27). Identification of patients with Proliferative lesions are useful to enrich lung cancer chemoprevention trials with high-risk subjects or to identify patients who would benefit from more frequent lung cancer screening The Inflammatory subtype is predominated by PMLs from former smokers, but interestingly is not significantly enriched for dysplasia, despite similarly decreased expression of cilia-associated pathways, suggesting an abnormal epithelium. The Inflammatory subtype also shows increased expression of a gene module enriched for genes involved in inflammation and regulation of lymphocytes and leukocytes (Module 8). This gene module is also elevated in Secretory lesions predominated by lesions from current smokers and exhibiting increased expression of goblet cell markers. Interestingly, IL1B is part of this inflammation-related gene module, which is of great interest as the inhibition of IL1B has recently been shown to reduce lung cancer incidence (28).

Our prior work has extensively studied gene expression alterations in normal-appearing airway epithelium by profiling cells obtained via brushing the mainstem bronchus during bronchoscopy (8, 29,35). As part of this work, gene expression alterations were described that reflect the presence of bronchial dysplasia (31). In the current study, for the first time both bronchial brushes and endobronchial biopsies were collected during the same procedure allowing identification of gene expression differences in bronchial brushings from normal appearing airway which indicate the presence of Proliferative subtype PMLs. In both the Discovery and Validation cohorts, applying the predictor used to identify Proliferative subtype PMLs (based on PML biopsy gene expression) to the gene expression data from the normal-appearing airway brushings resulted in predictions of the Proliferative subtype that were very specific (91%) but not sensitive (31-38%). Brushes classified as Proliferative have increased expression of cell cycle pathways and decreased expression of cilia-associated genes, suggesting that they are more similar to squamous metaplasia than normal epithelium. Potentially, a subset of patients may harbor widespread airway damage that serves as a marker for the presence of this type of high-grade PML leading to modest sensitivity, but high specificity. In other cases, the area of damage that gives rise to these Proliferative PMLs may be more localized, and therefore potentially more difficult to detect by brushing contributing to decreased sensitivity. These findings indicate that therapeutics to target changes throughout the entire airway epithelium may be necessary in some subjects, whereas, more site-specific ablation (e.g. photodynamic therapy) may be more effective in certain cases. Another possibility and area of future research, is that a Proliferative subtype brush is a predictor of incident LUSC.

The molecular profiling of PMLs and the identification of gene co-expression modules also provides an opportunity to identify the molecular determinants of subsequent PML progression. One of the nine gene co-expression modules used to define the molecular subtypes was significantly different between biopsies that progress or persist compared to biopsies that regress within the Proliferative subtype in both the DC and VC cohorts. The module contains genes whose expression is decreased in the persistent/progressive biopsies that are involved in interferon signaling and antigen processing and presentation. These gene expression changes were correlated with a decreased abundance of innate and adaptive immune cells via computational prediction. By immunofluorescent staining of FFPE biopsy sections it was confirmed that the progressive/persistent Proliferative lesions with low Module 9 GSVA scores had fewer CD163+ macrophages and CD8+T cells and the CD8+T cells had a distinct localization pattern. These lesions also contained greater numbers of CD4+T cells, and it will be important in future work to assess if these cells are T regulatory cells promoting an immune suppressive environment.

The presence of tumor-associated macrophages with the polarized phenotypes (M1 as pro-inflammatory or M2 as anti-inflammatory) has been associated with lung cancer prognosis. The presence of predominantly M2 macrophages, marked by the expression of CD163, has been associated with worse survival. However, in the context of lung PMLs this relationship is not well studied. The present finding that regressive Proliferative PMLs have more CD163+ cells and increased expression of genes involved in IFNg signaling is consistent with what has been seen in the PMLs that precede oral squamous cell carcinoma where the presence of CD163+ macrophages with active IFNg signaling is associated with better outcomes (36). Additionally, fewer CD8+ T cells and lower expression of HLA class I genes and B2M were observed in progressive/persistent lesions within the Proliferative subtype. Disruptions in proper T cell mediated immunosurveillence have been described in several studies showing that impaired HLA class I antigen processing and presentation including down-regulation or loss of B2M (37, 38) and interferon signaling (39) in lung tumors affects response and acquired resistance to checkpoint inhibitors. Lung tumors lacking an HLA-I complex had lower cytotoxic CD8+ lymphocyte infiltration, and this was also associated with lower levels of PD-L1. Additionally, studies have also suggested negative impacts on efficacy of check point inhibitors as well as survival in patients with LC that have tumors with increased CD4+ T cells expressing T regulatory markers (FOXP3, CD25) resulting in immunosuppressive state suggested to hinder the recruitment and effector functions of CD8+ T cells (40, 41). Future DNA sequencing data on the PMLs profiled here may indicate heterozygous or homozygous loss of B2M or mutations in other genes in the interferon and antigen processing and presentation pathways; however, even in the case of acquired resistance, mutations and copy number changes could not explain the down-regulation of these pathways across all subjects, suggesting that other epigenetic alterations or signaling pathways may play a role. In fact, epigenetic therapy, specifically DNA methyltransferase inhibitors (42), has been shown to enhance response to immune checkpoint therapy and up-regulate many of the genes down-regulated in progressive/ persistent lesions within the Proliferative subtype including HLA class I genes (HLA-B and HLA-C), B2M, CD58, TAP1, immune-proteasome subunits PSMB9 and PSMB8, and the transcription factor IRF9. Unraveling the mechanisms of innate and adaptive immune down-regulation in this subset of PMLs will be important to identifying potential immunoprevention therapies.

The present data indicates that there are subtype-specific transcriptomic alterations predictive of subsequent LUSC premalignant lesion progression that are the result of a lack of infiltrating immune cells in the lesion microenvironment. These data suggest that biomarkers for determining PML subtype and assessing immune infiltration may have utility for the detection of aggressive PMLs that require more intensive clinical management and genes altered in these PMLs may serve as lung chemoprevention candidates. These biomarkers could either be measured directly in PML tissue, or as indicated by the present data, they can be measured in a surrogate tissue such as bronchial airway epithelium. A benefit of biomarkers predicting aggressive PML behavior measured in surrogate tissue is the potential that these biomarkers can also predict the behavior of PMLs not directly observed during bronchoscopy.

Materials and Methods

Subject Population and Sample Collection

Figure 14:
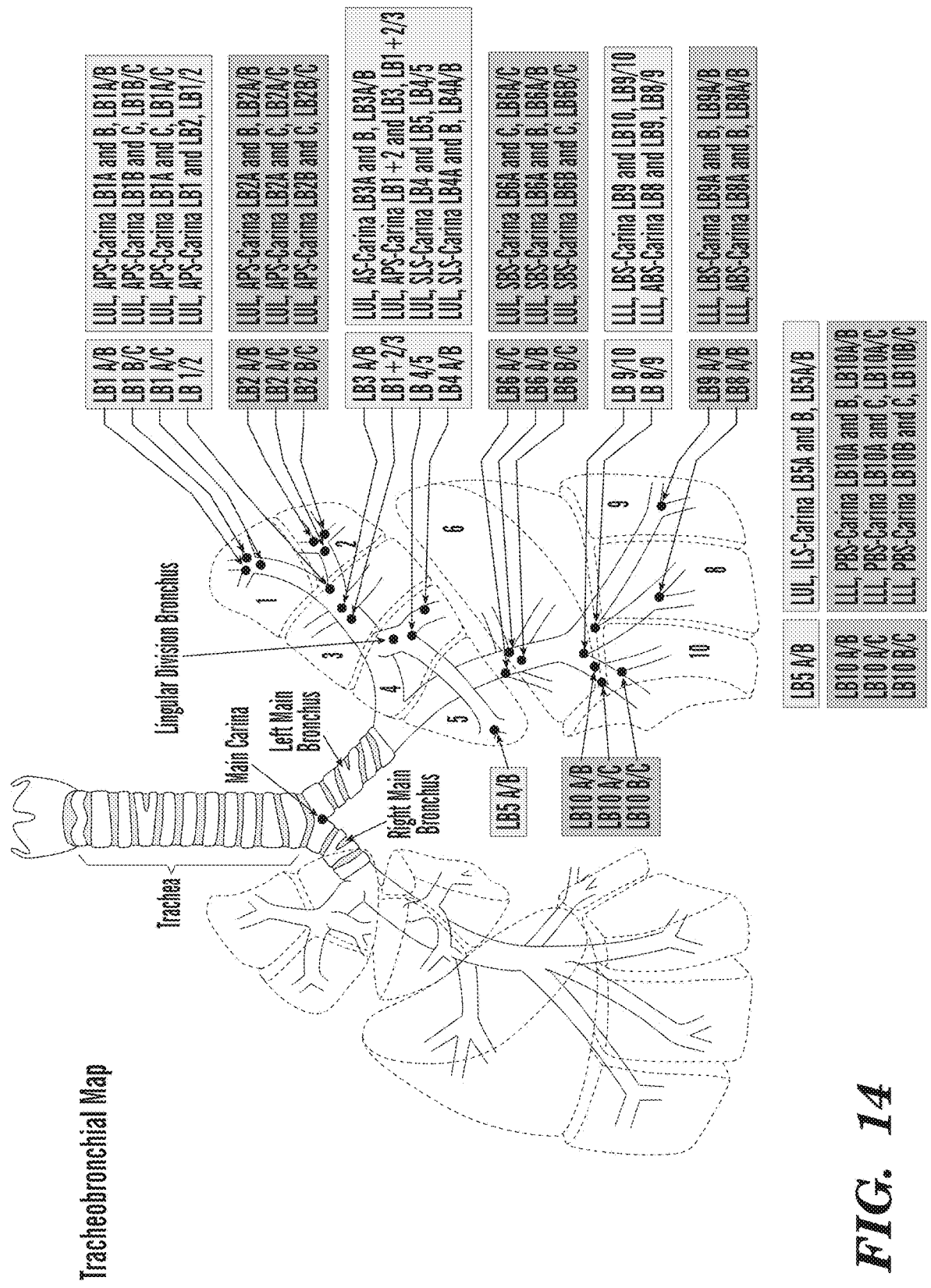
FIG. 14 depicts a tracheobronchial map of the locations of the sites sampled by endobronchial biopsy.
Figure 14:
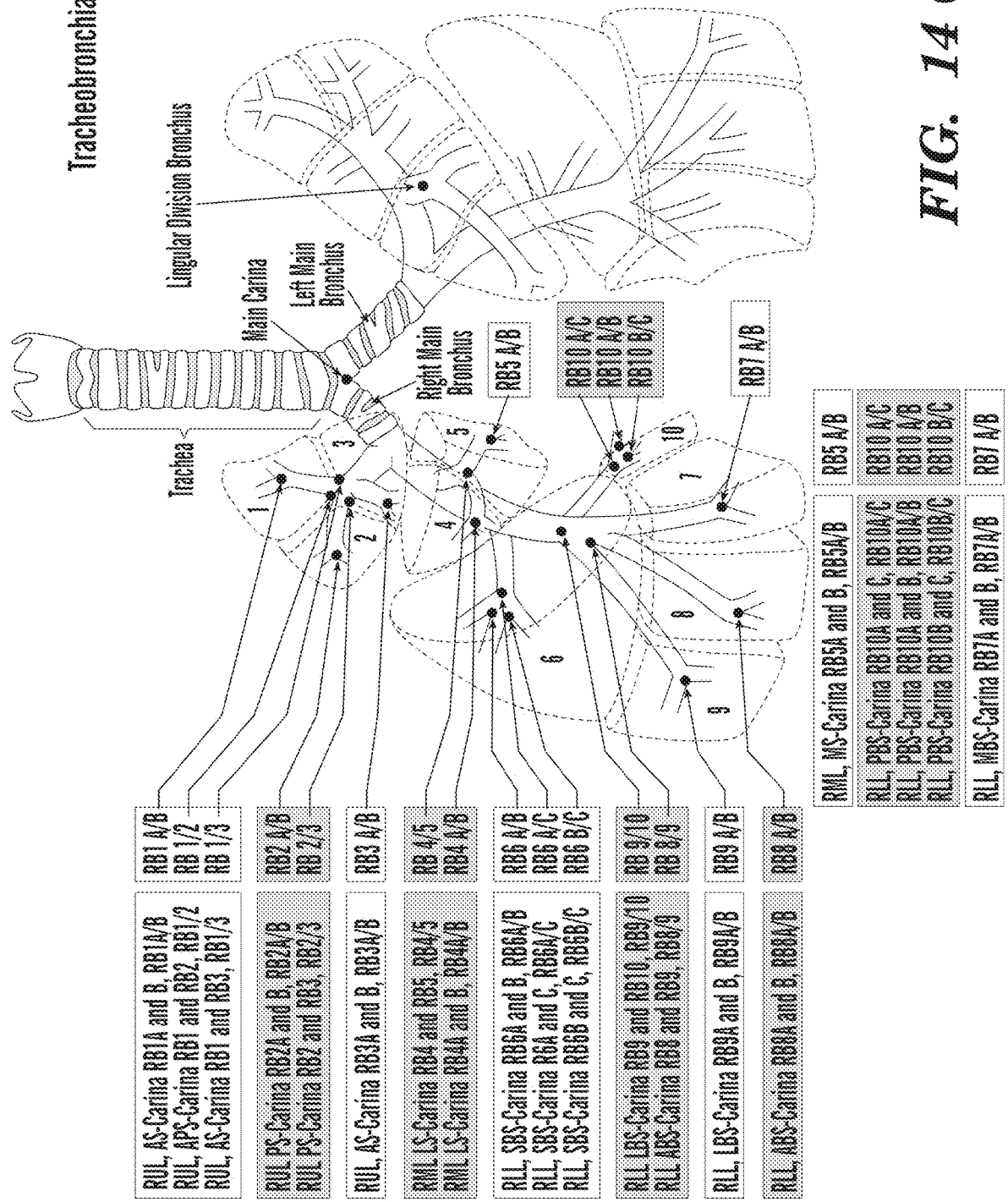
Figure 15:
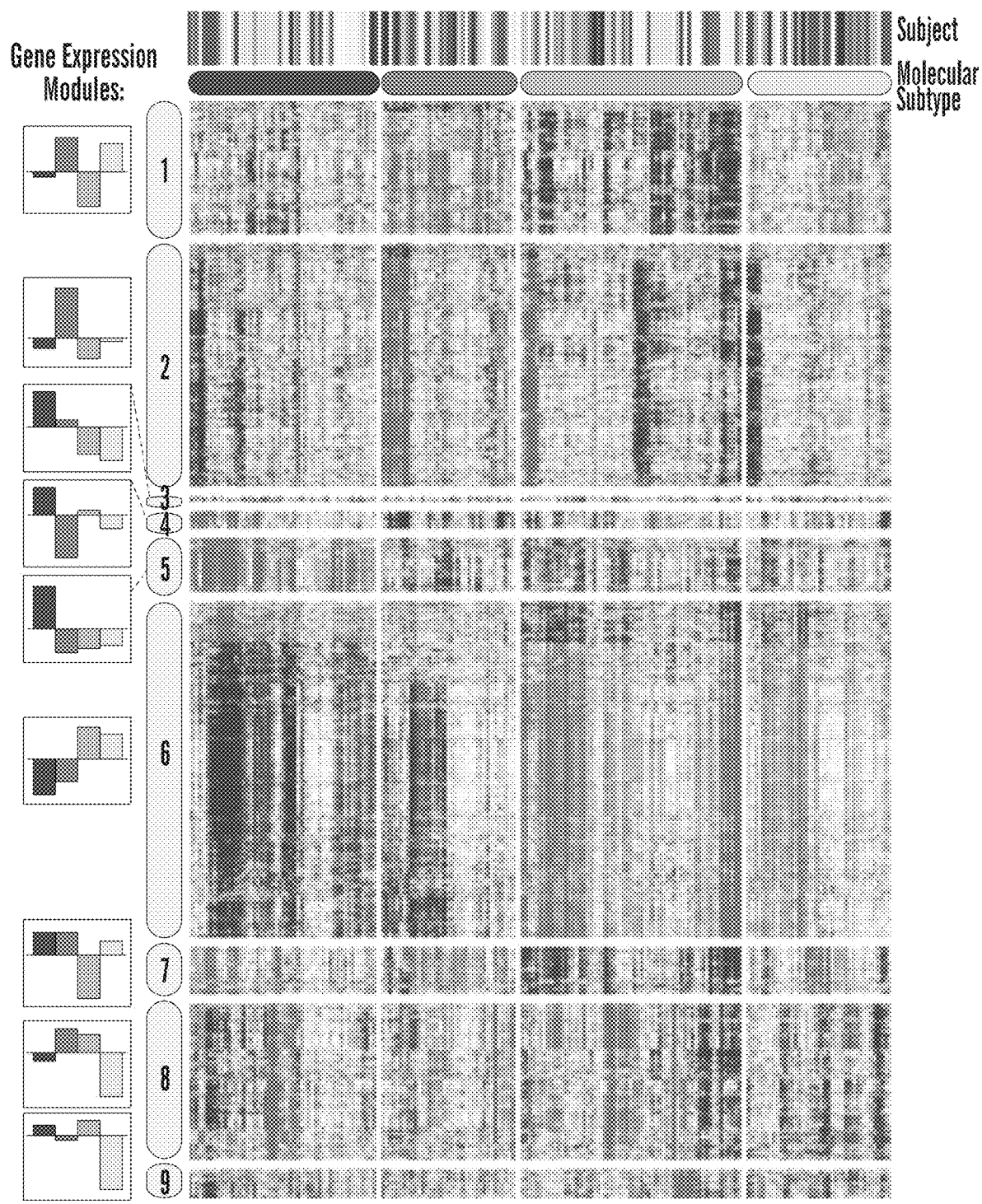
FIG. 15 depicts the distribution of subject among the discovery cohort endobronchial biopsies across the four molecular subtypes. Genes (n=3,936) organized into 9 gene co-expression modules were used to discover four molecular subtypes (Proliferative, Inflammatory, Secretory, and Normal-like) across the 190 discovery cohort (DC) biopsies using consensus clustering. The heatmap shows semi-supervised hierarchal clustering of z-score normalized gene expression across the 3,936 genes and 190 DC biopsies. The top color bars represent the subject the sample was derived and molecular subtype membership: Proliferative (n=52 samples), Inflammatory (n=37 samples), Secretory (n=61 samples), and Normal-like (n=40 samples). On the left side of the heatmap, the mean module GSVA score is plotted for each subtype.
Figure 15:
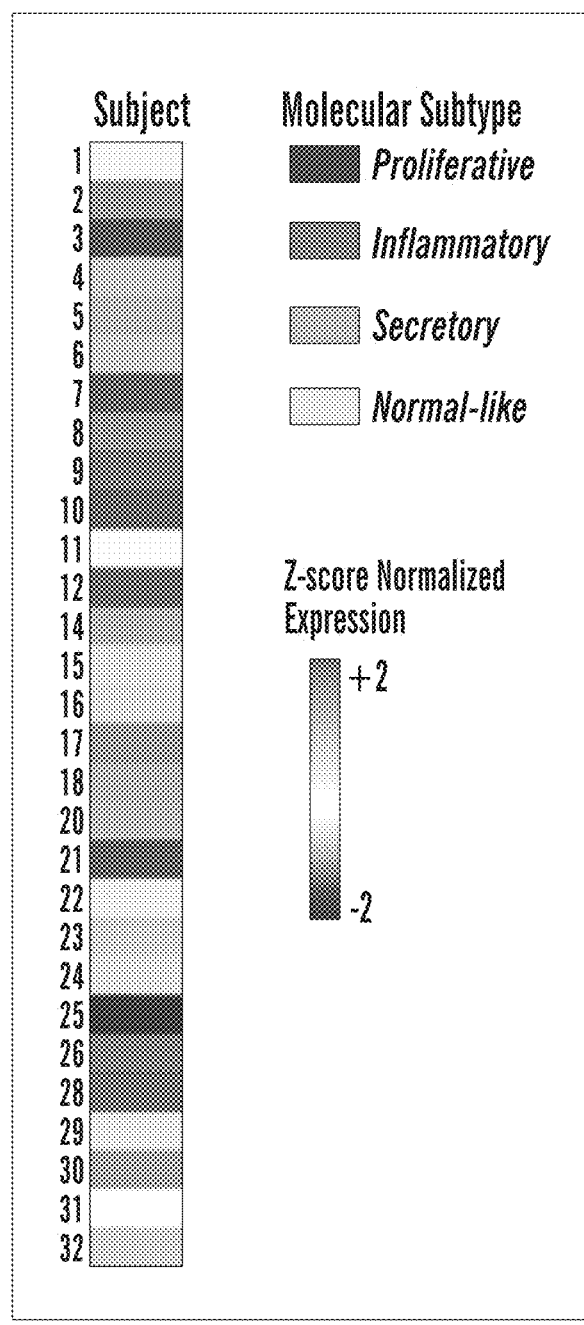
Figure 16:
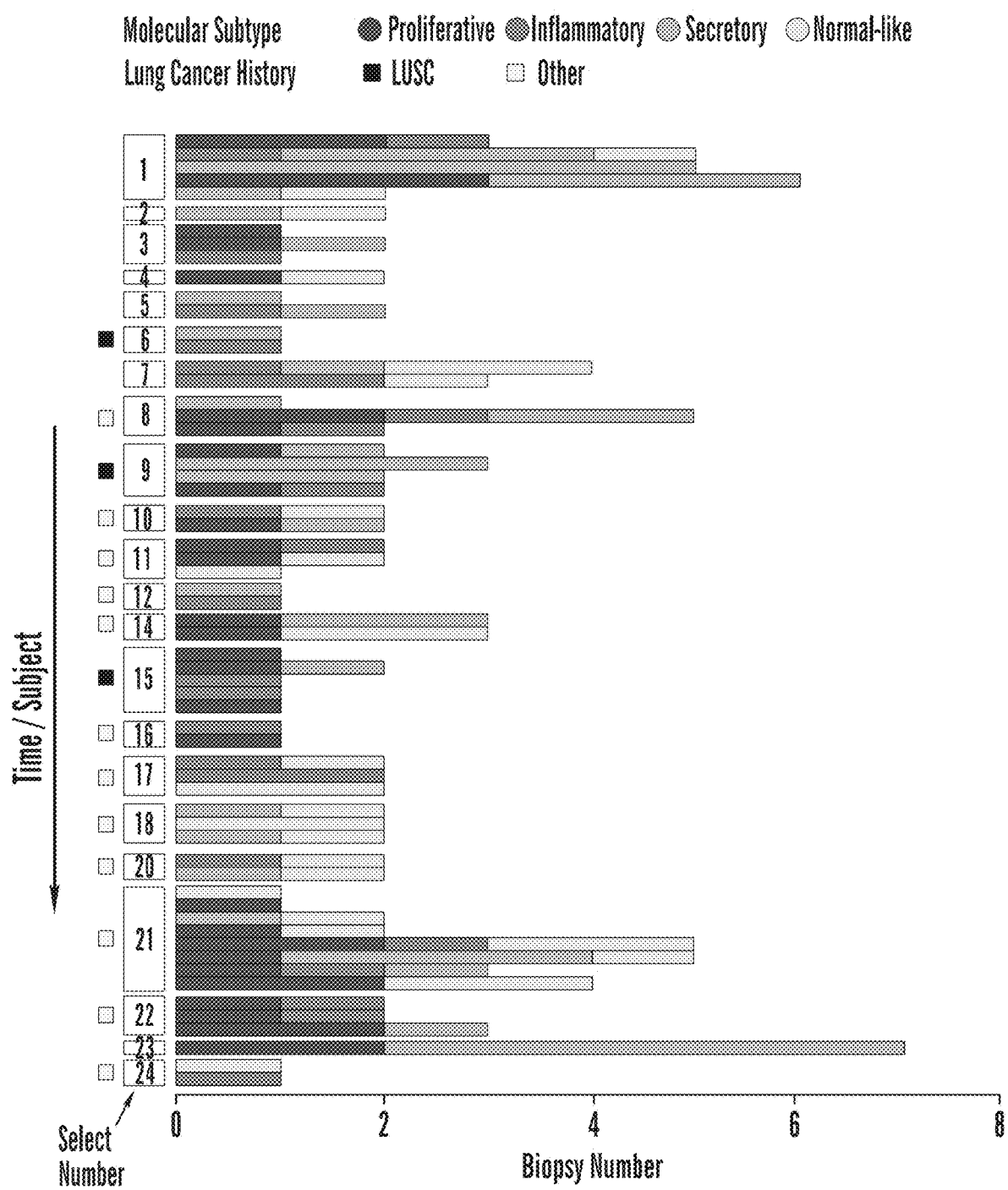
FIG. 16 depicts the molecular subtype distribution for each subject across bronchoscopy procedures. The barplot shows for each subject and each bronchoscopy procedure the number of biopsies sampled and their corresponding molecular subtype. The y-axis indicates the subject number and whether or not that subject had a prior history of either lung squamous cell carcinoma (LUSC) or another type of lung cancer (Other). The discovery cohort includes subjects 1 through 32 and the validation cohort includes subjects 33 through 52. We did not detect a difference in the diversity of subtype classifications within a subject based on prior history of lung cancer (mean Shannon entropy of subtype classifications within patients with a history of lung cancer=1.12, n=32 vs. patients without a history of lung cancer=1.25, n=17; Wilcoxon Rank Sum test p-value=0.43).
Figure 16:
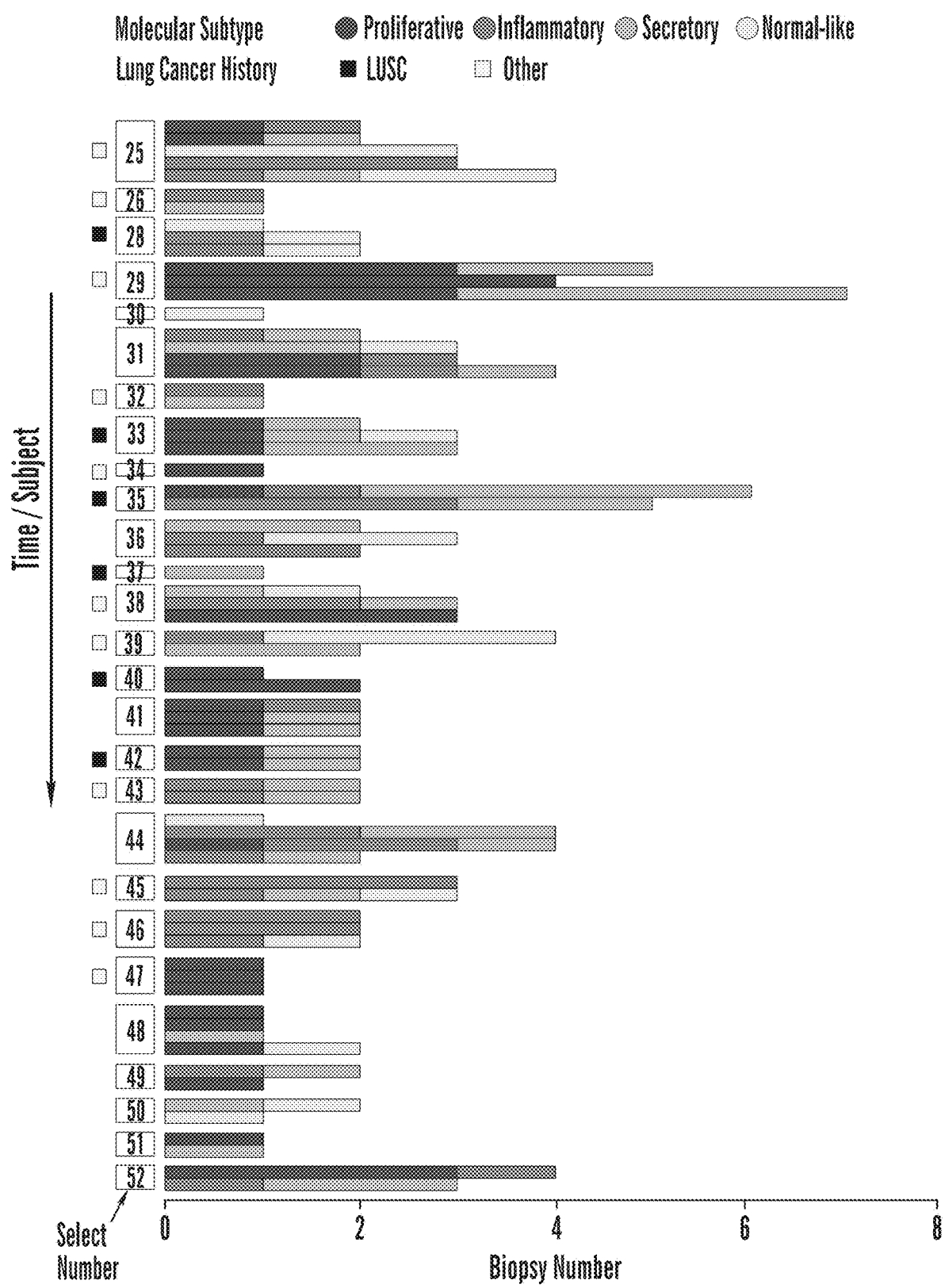

Endobronchial biopsies and brushings were obtained from high-risk subjects undergoing lung cancer screening at approximately 1-year intervals by white light and autofluorescence bronchoscopy and computed tomography at Roswell. The bronchoscopy included visualization of the vocal cords, trachea, main carina, and orifices of the sub-segmental bronchi visible without causing trauma to the bronchial wall. All abnormal and suspicious areas are biopsied twice and the lung anatomic location is recorded (FIG. 14, Table 8). One biopsy was used for routine pathological evaluation and the other for molecular profiling. Additionally, a brushing was obtained from a normal appearing area of the left or right mainstem bronchus for research. Morphological criteria used to evaluate the biopsies are in accordance with World Health Organization (WHO) guidance (43). Eligibility for screening includes either a previous history of aerodigestive cancer and no disease at the time of enrollment or age greater than 50, a current or previous history of smoking for a minimum exposure of 20 pack-years and at least one additional risk factor including moderate chronic obstructive pulmonary disease (COPD) (defined as forced expiratory volume (FEV1)<70%), confirmed asbestos related lung disease or a strong family history of lung cancer (at least 1-2 first degree relatives). All research specimens were stored in RNA Allprotect (Qiagen) and stored at −80 degrees C.

Subjects were selected that had biopsies collected in repeat locations via serial bronchoscopies; however, after RNA isolation, samples from 3 subjects had a single biopsy and 1 subject had a single brushing. mRNA sequencing was performed on a discovery cohort (DC) of samples comprising of endobronchial biopsies and brushes collected between 2010 and 2012 (n=30 subjects, n=197 biopsies, and n=91 brushings). mRNA sequencing was subsequently performed on a validation cohort (VC) of samples comprising of endobronchial biopsies and brushes collected between 2012 and 2015 (n=20 subjects, n=111 biopsies, and n=49 brushings). Brush histology was defined by the worst biopsy histology observed at the same time point. Biopsy progression/regression was defined for each biopsy based on the histology of the biopsy and the worst histology recorded for the same lung anatomic location in the future. Histology changes between normal, hyperplasia, and metaplasia were classified as "normal stable", decreases in histological dysplasia grade or changes from dysplastic histology to normal/hyperplasia/metaplasia were classified as "regressive", lack of future histological data was classified as "unknown", and everything else was classified as "progressive/persistent." The Institutional Review Boards at Boston University Medical Center and Roswell approved the study and all subjects provided written informed consent.

RNA-Seq Library Preparation, Sequencing, and Data Processing

Total RNA was extracted from endobronchial biopsies and bronchial brushings using miRNeasy™ Mini Kit or AllPrep™ DNA/RNA/miRNA Universal Kit (Qiagen). Sequencing libraries were prepared from total RNA samples using Illumina TruSeq™ RNA Kit v2 and multiplexed in groups of four using Illumina TruSeq™ Paired-End Cluster Kit. Each sample was sequenced on the Illumina HiSeg™ 2500 to generate paired-end 100-nucleotide reads. Demultiplexing and creation of FASTQ files were performed using Illumina CASAVA™ 1.8.2 or BaseSpace. Samples were aligned using hg19 and 2-pass STAR (44) alignment. Gene and transcript level counts were calculated using RSEM (45) using Ensembl™ v74 annotation. Quality metrics were calculated by STAR and RSeQC (46). Samples were excluded were sex annotation did not correlate with gene expression across CYorf15A (ENSG00000131002), DDX3Y (ENSG00000067048), KDM5D (ENSG00000012817), RPS4Y1 (ENSG00000129824), USP9Y (ENSG00000114374), and UTY (ENSG00000183878) (n=4 samples). Sample relatedness within a patient was confirmed using Peddy™ software (47).

Samples with a high-rate of heterozygosity (more than 3 standard deviations above the median) or samples with low relatedness to samples from the same patient (more than 3 standard deviations below the median) were removed from further analyses (n=11 samples, 2 brushes and 9 biopsies). Samples were subsequently divided into the discovery and validation cohorts (as outlined above) and by tissue type (biopsy or brush). Subsequent sample and gene filtering was conducted separately on each set as follows: First, EdgeR™ (48) was used to compute normalized data (library sizes normalized using TMM, trimmed mean of M-values, and log 2 counts per million computed) and genes were excluded that either had an interquartile range equal to zero or a sum across samples equal or less than 1. Samples were excluded based on values greater than 2 standard deviations from the mean for more than one of the following criteria: 1) mean Pearson correlation with all other samples calculated across all filtered genes 2) the $1^{st}$ or $2^{nd}$ principal components calculated using the filtered gene expression matrix 3) transcript integrity number (TIN, computed by RSeQC). After sample filtering, gene filtering was recomputed as described above on the final set of high-quality samples. The data are available from NCBI's Gene Expression Omnibus using the accession GSE109743.

Derivation of Molecular Subtypes

The DC biopsies (n=190 samples, n=16653 genes) and brushes (n=89 samples, n=16058 genes) were used to derive the molecular subtypes. Two additional RNA-Seq datasets were used during the derivation of the molecular subtypes: the TCGA squamous cell carcinoma (LUSC) tumors (10) (n=471 samples, n=17887 genes) and a dataset of tracheobronchial samples from mice treated with n-nitrosotris-(2-choroethyl)urea (NTCU) (n=25 samples, n=14897 genes). The mice develop lesions that are histologically and molecularly comparable to human lesions and that progress to LUSC and the samples represent a range of histology (normal, mild dysplasia, moderate dysplasia, severe dysplasia, carcinoma in situ (CIS), and LUSC tumor). The mouse data are available from NCBI's Gene Expression Omnibus using the accession ID GSE111091. Sample and gene filtering from the TCGA LUSC tumors and the mouse tissue were processed as described elsewhere herein.

Weighted correlation network analysis (9) (WGCNA) was used with default parameters to derive Modules of gene co-expression across the 4 datasets described above. Residual gene expression values adjusting for RNA quality (median TIN) and batch (Illumina flow cell) were used as input for WGCNA for the biopsy and brush datasets. For the mouse dataset, residual gene expression values adjusting for RNA quality (median TIN), mouse strain, and sample type (laser capture microdissected versus whole tissue) were used as input for WGCNA. Log 2 counts per million (cpm) values were used as input for WGCNA for the LUSC tumor samples. Gene sets were created for each co-expression Module for each dataset and then combined to create a compendium of gene sets generated from each of the 4 datasets. For each gene set in the compendium, the first principal component (PC1) was calculated across each z-score normalized dataset. For each dataset, a Pearson correlation matrix of PC1 values across all gene sets in the compendium was computed and thresholds were set as follows: r>0.85 was set to 1 and r<=0.85 set to 0. The four matrices were subsequently summed, and gene sets derived from biopsy co-expression Modules that were correlated to another non-biopsy derived gene set across all datasets were retained (n=9 Modules retained). The genes defining the retained biopsy Modules were required to be present in the biopsy Module and at least in one of the correlated gene sets.

The filtering process above yielded a reduced set of genes (n=3,936) that was used to define the molecular subtypes in the biopsy data. The residual gene expression values across the reduced set of genes for the discovery biopsies was used as input for consensus clustering (49). Consensus clustering was performed setting k (number of groups) to 10, the number of iterations to 1000, the subsampling to 80%, the clustering algorithm to partitioning around mediods, and the distance metric to Pearson correlation. The optimal value for k was 4 based on the relative change in area under the cumulative distribution function calculated based on the consensus matrix for each k.

Molecular Subtype Predictor

The DC biopsies across the filtered genes were used to derive a molecular subtype predictor. First, Pearson correlation metrics were determined between each gene and the Module eigengenes (PC1 for each of the 9 Modules). Genes were retained as part of a Module if the correlation value was the highest for the Module in which it was assigned. The average Pearson correlation of the retained genes to the Module eigengene was computed, and the number of genes chosen from each Module for the predictor was inversely proportional to this metric. Second, the genes most highly correlated to the Module eigengene were chosen to represent the Module in the predictor. The 22 genes resulting from this analysis across the DC biopsy data were used to train a nearest centroid predictor using the pamr package with a threshold of zero and predict the molecular subtype across the VC biopsies. Prior to predicting the molecular subtype of these test sets, the training and test sets were combat (50) adjusted and z-score normalized across combined training and test data. Using the methods described above we derived molecular subtypes using consensus clustering across the VC biopsies and compared these to the predicted subtypes.

Identification of Biological Processes Associated with Gene Modules and Molecular Subtypes Biological processes and pathways enriched in each of the nine Modules used to discover the molecular subtypes in the DC were identified using EnrichR (51). Each Module was separated into genes positively or negatively correlated with the Module eigengene, the Ensembl IDs were converted to Gene Symbols using biomaRt, and the following databases were queried: GO Biological Process 2015, KEGG 2016, WikiPathways 2016, TargetScan microRNA, Transcription Factor PPIs, TRANSFAC and JASPAR PWMs, OMIM Disease, Reactome 2016, and Biocarta 2016. Processes/pathways with an FDR<0.05 were considered to be significantly enriched. The contribution of each gene Module to the DC biopsy molecular subtypes was evaluated by testing if GSVA (14) scores for each Module were significantly (FDR<0.05) associated with the molecular subtypes using a linear mixed effect model with patient as a random effect via limma.

Identification of Clinical and Biological Phenotype Associations with Molecular Subtype The molecular subtypes in the DC biopsies were annotated according to the behavior of each gene Module by calculating whether or not GSVA (14) scores for each Module were significantly up- or down-regulated (FDR<0.05) in a particular molecular subtype versus all other samples using a linear mixed effects model with patient as a random effect via limma. Additionally, the biological pathways and transcription factors associated with each subtype were identified using GSEA (52) and mSigDB (53) gene sets using genes ranked by the t-statistic for their association with each subtype. The ranked lists were created using the limma (54) and edgeR (48) packages to identify differentially expressed genes associated with subtype membership.

Each linear model used voom-transformed (55) data and included membership in the subtype of interest, batch, and RNA quality (TIN) as covariates and patient as a random effect. Pathways enriched in the ranked lists (FDR<0.05) were used to annotate the molecular subtypes. FDR values for individual genes were derived from this analysis or analogous models using only samples of normal/hyperplasia histology or dysplasia histology.

For the DC and VC biopsies, residual gene expression values were used to predict smoking status, LUSC tumor subtype, and the relative abundance of epithelial and immune cells for each sample. Smoking status (current versus former/never) was predicted for each sample as described previously (13). Smoking status was determined at each time point for each subject by calculating the mean of the prediction scores (>0 for current prediction and <0 for former/never prediction) across all biopsies and brushes sampled. The LUSC tumor subtype was determined as described previously (11) across the genes predictive of the LUSC molecular subtype (12). The ESTIMATE algorithm (56) was used to infer relative epithelial, stromal, and immune cell content. Immune cell type specific signatures from Bindea et al. (15) and epithelial cell type specific signatures from Dvorak et al. (50) were used to generate GSVA(14) scores across samples for each signature. Additionally, residual gene expression values calculated using log RPKM values were inputted into the xCell (16) to infer relative abundances of 64 different cell types. The above categorical phenotypes along with additional clinical variables such as biopsy histology, subject, previous lung cancer history, sex, and biopsy progression/regression status were associated with molecular subtype using Fisher's Exact Test. Continuous variables were associated with molecular subtype using a linear model via limma.

In order to characterize the molecular alterations associated with lesion outcome, a linear mixed effects model was used to assess module GSVA score differences between progressive/persistent versus regressive lesions within each molecular subtype with patient as a random effect via limma. We estimated differences in the immune cell content (separately for xCell and Bindea et al.) between progressive/persistent versus regressive lesions in the Proliferative subtype via a linear mixed effects model correcting for epithelial cell content ('Epithelial' in xCell and 'Normal mucosa' in Bindea et al.) and patient as a random effect. We focused on cell types that were significantly different (FDR<0.05) between progressive/persistent versus regressive lesions in the Proliferative subtype in both the discovery and validation cohorts.

Relationship Between the Biopsies and Brushes

It was desired to quantify the predictive performance of the brush with regards to the presence of a biopsy of the Proliferative subtype. A subset of the 22-gene molecular subtype predictor was used to predict the presence or absence of the Proliferative subtype across the DC and VC brushes and biopsies. Specifically, 8 genes (out of the 22) were used that corresponded to Modules 4 through 7 (significantly up- or down-regulated in the Proliferative subtype) to classify samples as Proliferative or not using the same methodology described above for the molecular subtype predictor. Sensitivity and specificity performance metrics were calculated based on the ability of a Proliferative subtype prediction in the DC or VC brushes to indicate the presence of at least one biopsy of the Proliferative subtype. In order to further understand the Proliferative subtype predictions in the brushes, the behavior of the modules that define the Proliferative subtype in the DC biopsies (based on methods above) was analyzed across the DC and VC brushes.

Immunofluorescent Staining and Quantitation

Standard formalin fixation and embedding techniques were employed at Roswell where 5-micron sections were cut from the FFPE samples used for the routine pathological evaluation at Roswell (Table 7). Prior to staining, samples were de-waxed with xylene and rehydrate through a graded series of ethanol solutions. AR or citrate buffer was used for antigen retrieval, tissue was incubated with primary antibodies overnight at 4° C. and probed with secondary antibodies with fluorescent conjugates (Invitrogen Alexa Fluor 488, 594, 647) for 1 hour at room temperature. Immunostaining was performed using the primary antibodies listed in Table 9. Imaging was performed using an Aperio Slide Scanner for scoring and a Carl Zeiss Axio (20x and 40 x objectives) and a Carl Zeiss LSM 710 NLO confocal microscope for capturing additional images. Digital slides were analyzed with the Definiens Tissue Studio (Definiens Inc.) for the enumeration of immunofluorescence staining. The enumeration of the immunofluorescence scored each stain including DAPI positive cells. The enumeration was conducted on different regions (independent areas of tissue) present on a slide (1-5 regions/biopsy) for each biopsy. For each region, the percentage of positively staining cells for a given protein was calculated by dividing the number of positively stained cells by the total number of DAPI positive cells. A binomial mixed effects model via the lme4 R package was used to assess differences in the percentages of cells staining positive for a given protein in each region between progressive/persistent versus regressive biopsies using the total cells stained in each region as weights and adjusting for the slide number as a random effect. The models were used across samples from the Proliferative subtype and across samples from the Proliferative subtype where the biopsy outcome (progressive/persistent versus regressive) agreed with the Module 9 GSVA score (scores less than 0 are associated with progression/persistence and scores greater than 0 are associated with regression). Each region was also qualitatively scored as either positive or negative for having a distinct CD8 T cell localization pattern where cells lined and were embedded within the epithelium.

REFERENCES

1. National Lung Screening Trial Research Team, D. R. Aberle, A. M. Adams, C. D. Berg, W. C. Black, J. D. Clapp, R. M. Fagerstrom, I. F. Gareen, C. Gatsonis, P. M. Marcus, J. D. Sicks, Reduced lung-cancer mortality with low-dose computed tomographic screening, *N Engl. J Med.* 365, 395-409 (2011).
2. P. F. Pinsky, C. D. Berg, Applying the National Lung Screening Trial eligibility criteria to the US population: what percent of the population and of incident lung cancers would be covered? *J Med Screen* 19, 154-156 (2012).
3. J. D. Campbell, S. A. Mazzilli, M. E. Reid, S. S. Dhillon, S. Platero, J. Beane, A. E. Spira, The Case for a Pre-Cancer Genome Atlas (PCGA), *Cancer Prev Res (Phila)* 9, 119-124 (2016).
4. J. Beane, J. D. Campbell, J. Lel, J. Vick, A. Spira, Genomic approaches to accelerate cancer interception, *Lancet Oncol.* 18, e494-e502 (2017).
5. O. AUERBACH, A. P. STOUT, E. C. HAMMOND, L. GARFINKEL, Changes in bronchial epithelium in relation to cigarette smoking and in relation to lung cancer, *N Engl. J. Med.* 265, 253-267 (1961).
6. D. T. Merrick, D. Gao, Y. E. Miller, R. L. Keith, A. E. Baron, W. Feser, T. C. Kennedy, P. J. Blatchford, S. Braudrick, F. R. Hirsch, L. Heasley, P. A. Bunn, W. A. Franklin, Persistence of Bronchial Dysplasia Is Associated with Development of Invasive Squamous Cell Carcinoma, *Cancer Prevention Research* 9, 96-104 (2016).
7. T. Ishizumi, A. McWilliams, C. MacAulay, A. Gazdar, S. Lam, Natural history of bronchial preinvasive lesions, *Cancer Metastasis Rev.* 29, 5-14 (2010).
8. J. Beane, P. Sebastiani, G. Liu, J. S. Brody, M. E. Lenburg, A. Spira, Reversible and permanent effects of tobacco smoke exposure on airway epithelial gene expression, *Genome Biol.* 8, R201 (2007).
9. P. Langfelder, S. Horvath, WGCNA: an R package for weighted correlation network analysis, *BMC Bioinformatics* 9, 559 (2008).
0. J. D. Campbell, A. Alexandrov, J. Kim, J. Wala, A. H. Berger, C. S. Pedamallu, S. A. Shukla, G. Guo, A. N. Brooks, B. A. Murray, M. Imielinski, X. Hu, S. Ling, R. Akbani, M. Rosenberg, C. Cibulskis, A. Ramachandran, E. A. Collisson, D. J. Kwiatkowski, M. S. Lawrence, J. N. Weinstein, R. G. W. Verhaak, C. J. Wu, P. S. Hammerman, A. D. Cherniack, G. Getz, Cancer Genome Atlas Research Network, M. N. Artyomov, R. Schreiber, R. Govindan, M. Meyerson, Distinct patterns of somatic genome alterations in lung adenocarcinomas and squamous cell carcinomas, *Nature Publishing Group* 48, 607-616 (2016).
11. Cancer Genome Atlas Research Network, Comprehensive genomic characterization of squamous cell lung cancers, *Nature* 489, 519-525 (2012).
12. M. D. Wilkerson, X. Yin, K. A. Hoadley, Y. Liu, M. C. Hayward, C. R. Cabanski, K. Muldrew, C. R. Miller, S. H. Randell, M. A. Socinski, A. M. Parsons, W. K. Funkhouser, C. B. Lee, P. J. Roberts, L. Thorne, P. S. Bernard, C. M. Perou, D. N. Hayes, Lung squamous cell carcinoma mRNA expression subtypes are reproducible, clinically important, and correspond to normal cell types, *Clin. Cancer Res.* 16, 4864-4875 (2010).
13. J. Beane, S. A. Mazzilli, A. M. Tassinari, G. Liu, X. Zhang, H. Liu, A. Dy Buncio, S. S. Dhillon, S. J. Platero, M. E. Lenburg, M. E. Reid, S. Lam, A. E. Spira, Detecting the Presence and Progression of Premalignant Lung Lesions via Airway Gene Expression, *Clin. Cancer Res.*, clincanres.2540.2016 (2017).
14. S. Hanzelmann, R. Castelo, J. Guinney, GSVA: gene set variation analysis for microarray and RNA-seq data, *BMC Bioinformatics* 14, 7 (2013).
15. G. Bindea, B. Mlecnik, M. Tosolini, A. Kirilovsky, M. Waldner, A. C. Obenauf, H. Angell, T. Fredriksen, L. Lafontaine, A. Berger, P. Bruneval, W. H. Fridman, C. Becker, F. Pages, M. R. Speicher, Z. Trajanoski, J. Galon, Spatiotemporal dynamics of intratumoral immune cells reveal the immune landscape in human cancer, *Immunity* 39, 782-795 (2013).
16. D. Aran, Z. Hu, A. J. Butte, xCell: digitally portraying the tissue cellular heterogeneity landscape, *Genome Biol.* 18, 220 (2017).
17. D. T. Merrick, J. Kittelson, R. Winterhalder, G. Kotantoulas, S. Ingeberg, R. L. Keith, T. C. Kennedy, Y. E. Miller, W. A. Franklin, F. R. Hirsch, Analysis of c-ErbB1/epidermal growth factor receptor and c-ErbB2/HER-2 expression in bronchial dysplasia: evaluation of potential targets for chemoprevention of lung cancer, *Clin. Cancer Res.* 12, 2281-2288 (2006).
18. M. Jeanmart, S. Lantuejoul, F. Fievet, D. Moro, N. Sturm, C. Brambilla, E. Brambilla, Value of immunohistochemical markers in preinvasive bronchial lesions in risk assessment of lung cancer, *Clin. Cancer Res.* 9, 2195-2203 (2003).
19. S. Lantuejoul, C. Raynaud, D. Salameire, S. Gazzeri, D. Moro-Sibilot, J.-C. Soria, C. Brambilla, E. Brambilla, Telomere maintenance and DNA damage responses during lung carcinogenesis, *Clin. Cancer Res.* 16, 2979-2988 (2010).
20. I. I. Wistuba, C. Behrens, S. Milchgrub, D. Bryant, J. Hung, J. D. Minna, A. F. Gazdar, Sequential molecular abnormalities are involved in the multistage development of squamous cell lung carcinoma, *Oncogene* 18, 643-650 (1999).
21. I. I. Wistuba, C. Behrens, A. K. Virmani, G. Mele, S. Milchgrub, L. Girard, J. W. Fondon, H. R. Garner, B. McKay, F. Latif, M. I. Lerman, S. Lam, A. F. Gazdar, J. D Minna, High resolution chromosome 3p allelotyping of human lung cancer and preneoplastic/preinvasive bronchial epithelium reveals multiple, discontinuous sites of 3p allele loss and three regions of frequent breakpoints, *Cancer Res.* 60, 1949-1960 (2000).
22. I. Nakachi, J. L. Rice, C. D. Coldren, M. G. Edwards, R. S. Stearman, S. C. Glidewell, M. Varella-Garcia, W. A. Franklin, R. L. Keith, M. T. Lewis, B. Gao, D. T. Merrick, Y. E. Miller, M. W. Geraci, Application of SNP microarrays to the genome-wide analysis of chromosomal instability in premalignant airway lesions, *Cancer Prev Res (Phila)* 7, 255-265 (2014).
23. P. P. Massion, Y. Zou, H. Uner, P. Kiatsimkul, H. J. Wolf, A. E. Baron, T. Byers, S. Jonsson, S. Lam, F. R. Hirsch, Y. E. Miller, W. A. Franklin, M. Varella-Garcia, Recurrent genomic gains in preinvasive lesions as a biomarker of risk for lung cancer, *PLoS ONE* 4, e5611 (2009).
24. A. C. Gower, A. Spira, M. E. Lenburg, Discovering biological connections between experimental conditions based on common patterns of differential gene expression, *BMC Bioinformatics* 12, 381 (2011).
25. S. M. J. Rahman, X. Ji, L. J. Zimmerman, M. Li, B. K. Harris, M. D. Hoeksema, I. A. Trenary, Y. Zou, J. Qian, R. J. C. Slebos, J. Beane, A. Spira, Y. Shyr, R. Eisenberg, D. C. Liebler, J. D. Young, P. P. Massion, The airway epithelium undergoes metabolic reprogramming in individuals at high risk for lung cancer, *JCI Insight* 1, e88814 (2016).
26. R. L. Keith, P. J. Blatchford, J. Kittelson, J. D. Minna, K. Kelly, P. P. Massion, W. A. Franklin, J. Mao, D. O. Wilson, D. T. Merrick, F. R. Hirsch, T. C. Kennedy, P. A. Bunn, M. W. Geraci, Y. E. Miller, Oral iloprost improves endobronchial dysplasia in former smokers, *Cancer Prev Res (Phila)* 4, 793-802 (2011).
27. S. Lam, S. J. Mandrekar, Y. Gesthalter, K. L. Allen Ziegler, D. K. Seisler, D. E. Midthun, J. T. Mao, M. C. Aubry, A. McWilliams, D. D. Sin, T. Shaipanich, G. Liu, E. Johnson, A. Bild, M. E. Lenburg, D. N. Ionescu, J. Mayo, J. E. Yi, H. Tazelaar, W. S. Harmsen, J. Smith, A. E. Spira, J. Beane, P. J. Limburg, E. Szabo, Cancer Prevention Network, A Randomized Phase IIb Trial of myo-Inositol in Smokers with Bronchial Dysplasia, *Cancer Prev Res (Phila)* 9, 906-914 (2016).
28. P. M. Ridker, J. G. MacFadyen, T. Thuren, B. M. Everett, P. Libby, R. J. Glynn, CANTOS Trial Group, Effect of interleukin-1β inhibition with canakinumab on incident lung cancer in patients with atherosclerosis: exploratory results from a randomised, double-blind, placebo-controlled trial, *Lancet* 390, 1833-1842 (2017).
29. A. Spira, J. Beane, V. Shah, G. Liu, F. Schembri, X. Yang, J. Palma, J. S. Brody, Effects of cigarette smoke on the human airway epithelial cell transcriptome, *Proc. Natl. Acad. Sci. U.S.A.* 101, 10143-10148 (2004).
30. K. Steiling, M. van den Berge, K. Hijazi, R. Florido, J. Campbell, G. Liu, J. Xiao, X. Zhang, G. Duclos, E. Drizik, H. Si, C. Perdomo, C. Dumont, H. O. Coxson, Y. O. Alekseyev, D. Sin, P. Pare, J. C. Hogg, A. McWilliams, P. S. Hiemstra, P. J. Sterk, W. Timens, J. T. Chang, P. Sebastiani, G T O'Connor, A. H. Bild, D. S. Postma, S. Lam, A. Spira, M. E. Lenburg, A dynamic bronchial airway gene expression signature of chronic obstructive pulmonary disease and lung function impairment, *Am. J Respir. Crit. Care Med.* 187, 933-942 (2013).
31. J. Beane, S. A. Mazzilli, A. M. Tassinari, G. Liu, X. Zhang, H. Liu, A. Dy Buncio, S. S. Dhillon, S. Platero, M. Lenburg, M. E. Reid, S. Lam, A. Spira, Detecting the Presence and Progression of Premalignant Lung Lesions via Airway Gene Expression, *Clinical Cancer Research.*
32. A. Spira, J. E. Beane, V. Shah, K. Steiling, G. Liu, F. Schembri, S. Gilman, Y.-M. Dumas, P. Calner, P. Sebastiani, S. Sridhar, J. Beamis, C. Lamb, T. Anderson, N. Gerry, J. Keane, M. E. Lenburg, J. S. Brody, Airway epithelial gene expression in the diagnostic evaluation of smokers with suspect lung cancer, *Nat. Med.* 13, 361-366 (2007).
33. D. H. Whitney, M. R. Elashoff, K. Porta Smith, A. C. Gower, A. Vachani, J. S. Ferguson, G. A. Silvestri, J. S. Brody, M. E. Lenburg, A. Spira, Derivation of a bronchial genomic classifier for lung cancer in a prospective study of patients undergoing diagnostic bronchoscopy, *BMC Med Genomics* 8, 18 (2015).
34. G. A. Silvestri, A. Vachani, D. Whitney, M. Elashoff, K. Porta Smith, J. S. Ferguson, E. Parsons, N. Mitra, J. Brody, M. E. Lenburg, A. Spira, AEGIS Study Team, A Bronchial Genomic Classifier for the Diagnostic Evaluation of Lung Cancer, *N Engl. J. Med.* (2015), doi: 10.1056/NEJMoa1504601.
35. J. Beane, P. Sebastiani, T. H. Whitfield, K. Steiling, Y.-M. Dumas, M. E. Lenburg, A. Spira, A prediction model for lung cancer diagnosis that integrates genomic and clinical features, *Cancer Prev Res (Phila)* 1, 56-64 (2008).
36. S. Wang, M. Sun, C. Gu, X. Wang, D. Chen, E. Zhao, X. Jiao, J. Zheng, Expression of CD163, interleukin-10, and interferon-gamma in oral squamous cell carcinoma: mutual relationships and prognostic implications, *Eur. J. Oral Sci.* 122, 202-209 (2014).
37. S. Gettinger, J. Choi, K. Hastings, A. Truini, I. Datar, R. Sowell, A. Wurtz, W. Dong, G. Cai, M. A. Melnick, V. Y. Du, J. Schlessinger, S. B. Goldberg, A. Chiang, M. F. Sanmamed, I. Melero, J. Agorreta, L. M. Montuenga, R. Lifton, S. Ferrone, P. Kavathas, D. L. Rimm, S. M. Kaech, K. Schalper, R. S. Herbst, K. Politi, Impaired HLA Class I Antigen Processing and Presentation as a Mechanism of Acquired Resistance to Immune Checkpoint Inhibitors in Lung Cancer, *Cancer Discov* 7, 1420-1435 (2017).
38. C. Pereira, P. Gimenez-Xavier, E. Pros, M. J. Pajares, M. Moro, A. Gomez, A. Navarro, E. Condom, S. Moran, G. Gomez-Lopez, O. Graña, M. Rubio-Camarillo, A. Martinez-Marti, J. Yokota, J. Carretero, J. M. Galbis, E. Nadal, D. Pisano, G. Sozzi, E. Felip, L. M. Montuenga, L. Roz, A. Villanueva, M. Sanchez-Cespedes, Genomic Profiling of Patient-Derived Xenografts for Lung Cancer Identifies B2M Inactivation Impairing Immunorecognition, *Clin. Cancer Res.* 23, 3203-3213 (2017).
39. J. Gao, L. Z. Shi, H. Zhao, J. Chen, L. Xiong, Q. He, T. Chen, J. Roszik, C. Bernatchez, S. E. Woodman, P.-L. Chen, P. Hwu, J. P. Allison, A. Futreal, J. A. Wargo, P. Sharma, Loss of IFN-y Pathway Genes in Tumor Cells as a Mechanism of Resistance to Anti-CTLA-4 Therapy, *Cell* 167, 397-404.e9 (2016).
40. A. Kotsakis, F. Koinis, A. Katsarou, M. Gioulbasani, D. Aggouraki, N. Kentepozidis, V. Georgoulias, E.-K. Vetsika, Prognostic value of circulating regulatory T cell subsets in untreated non-small cell lung cancer patients, *Sci Rep* 6, 39247 (2016).
41. S.-P. Wu, R.-Q. Liao, H.-Y. Tu, W.-J. Wang, Z.-Y. Dong, S.-M. Huang, W.-B. Guo, L.-Y. Gou, H.-W. Sun, Q. Zhang, Z. Xie, L.-X. Yan, J. Su, J.-J. Yang, W.-Z. Zhong, X.-C. Zhang, Y.-L. Wu, Stromal PD-L1-Positive Regulatory T cells and PD-1-Positive CD8-Positive T cells Define the Response of Different Subsets of Non-Small Cell Lung Cancer to PD-1/PD-L1 Blockade Immunotherapy, *J Thorac Oncol* 13, 521-532 (2018).
42. H. Li, K. B. Chiappinelli, A. A. Guzzetta, H. Easwaran, R.-W. C. Yen, R. Vatapalli, M. J. Topper, J. Luo, R. M. Connolly, N. S. Azad, V. Stearns, D. M. Pardoll, N. Davidson, P. A. Jones, D. J. Slamon, S. B. Baylin, C. A. Zahnow, N. Ahuja, Immune regulation by low doses of the DNA methyltransferase inhibitor 5-azacitidine in common human epithelial cancers, *Oncotarget* 5, 587-598 (2014).
43. International Agency for Research on Cancer, *Who Classification of Tumours of the Lung, Pleura, Thymus and Heart* (World Health Organization, 2015).
44. A. Dobin, C. A. Davis, F. Schlesinger, J. Drenkow, C. Zaleski, S. Jha, P. Batut, M. Chaisson, T. R. Gingeras, STAR: ultrafast universal RNA-seq aligner, *Bioinformatics* 29, 15-21 (2013).

45. B. Li, C. N. Dewey, RSEM: accurate transcript quantification from RNA-Seq data with or without a reference genome, *BMC Bioinformatics* 12, 323 (2011).
46. L. Wang, S. Wang, W. Li, RSeQC: quality control of RNA-seq experiments, *Bioinformatics* 28, 2184-2185 (2012).
47. B. S. Pedersen, A. R. Quinlan, Who's Who? Detecting and Resolving Sample Anomalies in Human DNA Sequencing Studies with Peddy, *Am. J Hum. Genet.* 100, 406-413 (2017).
48. M. D. Robinson, D. J. McCarthy, G. K. Smyth, edgeR: a Bioconductor package for differential expression analysis of digital gene expression data, *Bioinformatics* 26, 139-140 (2010).
49. M. D. Wilkerson, D. N. Hayes, ConsensusClusterPlus: a class discovery tool with confidence assessments and item tracking, *Bioinformatics* 26, 1572-1573 (2010).
50. J. T. Leek, W. E. Johnson, H. S. Parker, A. E. Jaffe, J. D. Storey, The sva package for removing batch effects and other unwanted variation in high-throughput experiments, *Bioinformatics* 28, 882-883 (2012).
51. E. Y. Chen, C. M. Tan, Y. Kou, Q. Duan, Z. Wang, G. V. Meirelles, N. R. Clark, A. Ma'ayan, Enrichr: interactive and collaborative HTML5 gene list enrichment analysis tool, *BMC Bioinformatics* 14, 128 (2013).
52. A. Subramanian, P. Tamayo, V. K. Mootha, S. Mukherjee, B. L. Ebert, M. A. Gillette, A. Paulovich, S. L. Pomeroy, T. R. Golub, E. S. Lander, J. P. Mesirov, Gene set enrichment analysis: a knowledge-based approach for interpreting genome-wide expression profiles, *Proc. Natl. Acad. Sci.* USA. 102, 15545-15550 (2005).
53. A. Liberzon, C. Birger, H. Thorvaldsdottir, M. Ghandi, J. P. Mesirov, P. Tamayo, The Molecular Signatures Database (MSigDB) hallmark gene set collection, *Cell Syst* 1, 417-425 (2015).
54. M. E. Ritchie, B. Phipson, D. Wu, Y. Hu, C. W. Law, W. Shi, G. K. Smyth, limma power differential expression analyses for RNA-sequencing and microarray studies, *Nucleic Acids Res.* 43, e47 (2015).
55. C. W. Law, Y. Chen, W. Shi, G. K. Smyth, Voom: precision weights unlock linear model analysis tools for RNA-seq read counts, *Genome Biol.* 15, R29 (2014).
56. K. Yoshihara, M. Shahmoradgoli, E. Martinez, R. Vegesna, H. Kim, W. Torres-Garcia, V. Treviño, H. Shen, P. W. Laird, D. A. Levine, S. L. Carter, G. Getz, K. Stemke-Hale, G. B. Mills, R. G. W. Verhaak, Inferring tumour purity and stromal and immune cell admixture from expression data, *Nat Commun* 4, 2612 (2013).

TABLE 1

Demographic and Clinical Annotation on Subjects in both the Discovery and Validation cohorts. Statistical tests between the Discovery and Validation cohorts were performed using Fisher's Exact Test for categorical variables and Student's T-Test for continuous variable. Percentages are reported for categorical variables and mean and standard deviations are reported for continuous variables.

| Variable | Discovery Cohort (n = 30 Subjects) | Validation Cohort (n = 20 Subjects) | p-value |
|---|---|---|---|
| Average # Biopsies/Subject | 6.6 (5.7) | 5.25 (2.9) | 0.3 |
| Average # Bronchoscopies/Subject | 2.8 (1.5) | 2.4 (0.8) | 0.27 |
| Average Time Between Bronchoscopies (Days) | 368.2 (201.4) | 360.1 (212.5) | 0.87 |
| Male | 15/30 (50) | 12/20 (60) | 0.57 |
| White | 27/30 (90) | 17/20 (85) | 0.67 |
| Age (at Baseline Clinical Visit) | 58.8 (7.6) | 58.7 (8.3) | 0.97 |
| Ever smoker (at Baseline Clinical Visit) | 29/30 (96.7) | 19/20 (95) | 1 |
| Prior History of Lung Cancer | 21/30 (70) | 12/20 (60) | 0.55 |
| COPD (FEV1/FVC <= 0.7, at Baseline Clinical Visit) | 17/27 (63.0) | 8/18 (44.4) | 0.24 |
| GOLD 1 (FEV1% > 80) | 2/27 (7.4) | 2/18 (11.1) | 1 |
| GOLD 2 (FEV1% < 80 and > 50) | 12/27 (44.4) | 5/18 (27.8) | 0.35 |
| GOLD 3 (FEV1% < 50 and > 30) | 3/27 (11.1) | 1/18 (5.6) | 0.64 |
| Occupational Asbestos | 13/30 (43.3) | 9/20 (45) | 1 |
| Occupational High-Risk Job | 14/30 (46.7) | 12/20 (60) | 0.4 |

| Variable | Discovery Cohort (n = 30) | Validation Cohort (n = 20) | P-value |
|---|---|---|---|
| Average # Biopsies/Subject | 6.6 (5.7) | 5.25 (2.9) | 0.3 |
| Average # Bronchoscopies/Subject | 3.1 (1.6) | 2.5 (0.7) | 0.08 |
| Average Time Between Bronchoscopies (Days) | 348.6 (197.5) | 366.8 (208.3) | 0.69 |
| Male | 15/30 (50) | 12/20 (60) | 0.81 |
| White | 27/30 (90) | 17/20 (85) | 1 |
| Age (at Baseline Clinical Visit) | 58.8 (7.6) | 58.7 (8.3) | 0.97 |
| Ever smoker (at Baseline Clinical Visit) | 29/30 (96.7) | 19/20 (95) | 1 |
| Pack-years | 49.8 (22.1) | 41.3 (20.7) | 0.17 |
| Prior History of Lung Cancer | 21/30 (70) | 12/20 (60) | 0.82 |
| LUSC | 5/30 (16.7) | 5/20 (25) | 0.73 |
| Other | 16/30 (53.3) | 7/20 (35) | 0.6 |
| COPD (FEV1/FVC <= 0.7, at Baseline Clinical Visit) | 17/27 (63.0) | 8/18 (44.4) | 0.61 |
| GOLD 1 (FEV1% > 80) | 2/27 (7.4) | 2/18 (11.1) | 1 |
| GOLD 2 (FEV1% < 80 and > 50) | 12/27 (44.4) | 5/18 (27.8) | 0.56 |
| GOLD 3 (FEV1% < 50 and > 30) | 3/27 (11.1) | 1/18 (5.6) | 1 |
| Occupational Asbestos | 13/30 (43.3) | 9/20 (45) | 1 |
| Occupational High-Risk Job | 14/30 (46.7) | 12/20 (60) | 0.62 |

TABLE 2

Clinical Annotation on Samples in both the Discovery and Validation cohorts. Statistical tests between the Discovery and Validation cohorts within either the biopsies or brushes were performed using Fisher's Exact Test and percentages are reported.

| Sample Type | Discovery Cohort Biopsies | Discovery Cohort Brushes | Validation Cohort Biopsies | Validation Cohort Brushes | P-value Biopsies | P-value Brushes |
|---|---|---|---|---|---|---|
| Histology | | | | | 0.05 | 0.42 |
| Normal | 38/190 (20) | 6/89 (6.7) | 23/105 (21.9) | 0/48 (0) | | |
| Hyperplasia | 30/190 (15.8) | 11/89 (12.4) | 31/105 (29.5) | 9/48 (18.8) | | |
| Metaplasia | 46/190 (24.2) | 15/89 (16.9) | 14/105 (13.3) | 9/48 (18.8) | | |
| Mild Dysplasia | 21/190 (11.1) | 9/89 (10.1) | 13/105 (12.4) | 6/48 (12.5) | | |
| Moderate Dysplasia | 38/190 (20) | 30/89 (33.7) | 20/105 (19.0) | 18/48 (37.5) | | |
| Severe Dysplasia | 12/190 (6.3) | 17/89 (19.1) | 4/105 (3.8) | 6/48 (12.5) | | |
| CIS | 1/190 (0.5) | 0/89 (0) | 0/105 (0) | 0/48 (0) | | |
| Tumor | 0/190 (0) | 1/89 (1.1) | 0/105 (0) | 0/48 (0) | | |
| Unknown Histology | 4/190 (2.1) | 0/89 (0) | 0/105 (0) | 0/48 (0) | | |
| Current smoker (Genomic prediction) | 119/190 (62.6) | 44/89 (49.4) | 38/105 (36.2) | 20/48 (41.7) | 1.80E−05 | 0.47 |
| Progression Status | | | | | 0.39 | |
| Normal/Stable | 47/190 (24.7) | | 35/105 (33.3) | | | |
| Progressive/Persistant | 44/190 (23.2) | | 20/105 (19.0) | | | |
| Regressive | 30/190 (15.8) | | 18/105 (17.1) | | | |
| Unknown | 69/190 (36.3) | | 32/105 (30.5) | | | |
| Histology | | | | | 0.05 | 0.42 |
| Normal | 38/190 (20) | 6/89 (6.7) | 23/105 (21.9) | 0/48 (0) | | |
| Hyperplasia | 30/190 (15.8) | 11/89 (12.4) | 31/105 (29.5) | 9/48 (18.8) | | |
| Metaplasia | 46/190 (24.2) | 15/89 (16.9) | 14/105 (13.3) | 9/48 (18.8) | | |
| Mild Dysplasia | 21/190 (11.1) | 9/89 (10.1) | 13/105 (12.4) | 6/48 (12.5) | | |
| Moderate Dysplasia | 38/190 (20) | 30/89 (33.7) | 20/105 (19.0) | 18/48 (37.5) | | |
| Severe Dysplasia | 12/190 (6.3) | 17/89 (19.1) | 4/105 (3.8) | 6/48 (12.5) | | |
| CIS | 1/190 (0.5) | 0/89 (0) | 0/105 (0) | 0/48 (0) | | |
| Tumor | 0/190 (0) | 1/89 (1.1) | 0/105 (0) | 0/48 (0) | | |
| Unknown Histology | 4/190 (2.1) | 0/89 (0) | 0/105 (0) | 0/48 (0) | | |
| Current smoker (Genomic prediction) | 122/190 (64.3) | 50/89 (56.2) | 53/105 (50.5) | 27/48 (56.3) | 0.03 | 1 |
| Progression Status | | | | | 0.39 | |
| Normal/Stable | 47/190 (24.7) | | 35/105 (33.3) | | | |
| Progressive/Persistent | 44/190 (23.2) | | 20/105 (19.0) | | | |
| Regressive | 30/190 (15.8) | | 18/105 (17.1) | | | |
| Unknown | 69/190 (36.3) | | 32/105 (30.5) | | | |

Table 3. Summary of Molecular Subtype Characteristics in the Discovery Cohort. For each molecular subtype, significant associations are reported with each of the 9 gene modules, clinical characteristics, canonical cell type epithelial and white blood cell gene markers, and pathways.

TABLE 3

Summary of the Molecular Subtype Characteristics in the Discovery Cohort. For each molecular subtype, significant associations are reported with each of the 9 gene modules, clinical characteristics, canonical cell type epithelial and white blood cell gene markers, pathways, and transcription factors.

PROLIFERATIVE

| | |
|---|---|
| Up-regulated Modules | 4, 5, 7 |
| Down-regulated Modules | 6 |
| Clinical Characteristics | Current smoking (86%), Dysplastic biopsies (63%) |
| Biological Characteristics | SCC subytpes - Classical and Basal; TUB1A1, SCGB1A1 down-regulated; KRT5, KI67 up-regulated |
| Pathways | Cell cycle: BUB1B/1/3, CHEK1/2, CDK1/2/4/6, E2F1/3/2/4, MCM4/3/5/6/7, TP53, RB1 |
| | DNA repair: TP53, PARP1, RAD51, BRCA2, FANCA/D2/G/E/M/C, XRCC5/6, ERCC6 |
| | Oxidative Phosphorylation and Electron Transport Chain: ATP synthases, NADH-ubiquinone oxidoreductases, cytochrome C oxidases |
| TFs | E2F |

INFLAMMATORY

| | |
|---|---|
| Up-regulated Modules | 1, 2, 7, 8 |
| Down-regulated Modules | 4, 5, 6 |
| Clinical Characteristics | Former smoking (59%), non-dysplastic biopsies (68%) |
| Biological Characteristics | SCC subytpes - Secretory; TUB1A1, MUC5AC down-regulated |
| Pathways | Extracellular matrix, focal adhesion, and integrin pathways: collagen, integrin, and laminin genes |
| | Cytokine/chemokine: CCL2/14/19/21/28, CXCL12/14/5, CCR1/2/3/4/5, IL1B, IL11RA, IL17RB, IL1R1, IL3RA, EGF, IL15, CX3CR1, TGFB1/B2/B3, KIT |
| | Down-regulation of oxidative phosphorylation, respiratory elecron transport, cell cycle |
| TFs | SRF |

TABLE 3-continued

Summary of the Molecular Subtype Characteristics in the Discovery Cohort. For each molecular subtype, significant associations are reported with each of the 9 gene modules, clinical characteristics, canonical cell type epithelial and white blood cell gene markers, pathways, and transcription factors.

SECRETORY

| | |
|---|---|
| Up-regulated Modules | 6, 8 |
| Down-regulated Modules | 1, 2, 5, 7 |
| Clinical Characteristics | Current smoking (63%), non-dysplastic biopsies (66%) |
| Biological Characteristics | SCC subytpes - Secretory; CD45, MUC5AC, TUB1A1 up-regulated; KI67, KRT5 down-regulated |
| Pathways | Down-regulation of extracellular matrix, focal adhesion, integrin pathways |
| TFs | Down-regulation of E2F |

NORMAL

| | |
|---|---|
| Up-regulated Modules | 1, 6 |
| Down-regulated Modules | 8, 9 |
| Clinical Characteristics | Former smoking (65%), non-dysplastic biopsies (75%) |
| Biological Characteristics | CD45, MUC5AC, KI67 down-regulated; SCGB1A1, KRT5, TUB1A1 up-regulated |
| Pathways | Core Extracellular matrix genes: collagen and laminin genes, WISP1/2 |
| | Down-regulation of innate and adaptive immunity: HLA genes, IRF1/4/7/8, TLR2/4/6/8/10, IKBKB |
| TFs | Down-regulation of PEA3, IRF, NFKB |

PROLIFERATIVE

| | |
|---|---|
| Up-regulated Modules | 4, 5, 7 |
| Down-regulated Modules | 6 |
| Clinical Characteristics | Current smoking (88%), Dysplastic biopsies (63%) |
| Biological Characteristics | LUSC subytpes - Classical and Basal; TUB1A1, SCGB1A1 down-regulated; KRT5, KI67 up-regulated |
| Pathways | Cell cycle: BUB1B/1/3, CHEK1/2, CDK1/2/4/6, E2F1/3/2/4, MCM4/3/5/6/7, TP53, RB1 |
| | DNA repair: TP53, PARP1, RAD51, BRCA2, FANCA/D2/G/E/M/C, XRCC5/6, ERCC6 |
| | Oxidative Phosphorylation and Electron Transport Chain: ATP synthases, NADH-ubiquinone oxidoreductases, cytochrome C oxidases |
| Transcription Factors | E2F |

INFLAMMATORY

| | |
|---|---|
| Up-regulated Modules | 1, 2, 7, 8 |
| Down-regulated Modules | 4, 5, 6 |
| Clinical Characteristics | Former smoking (59%), non-dysplastic biopsies (68%) |
| Biological Characteristics | LUSC subytpes - Secretory; TUB1A1, MUC5AC down-regulated |
| Pathways | Extracellular matrix, focal adhesion, and integrin pathways: collagen, integrin, and laminin genes |
| | Cytokine/chemokine: CCL2/14/19/21/28, CXCL12/14/5, CCR1/2/3/4/5, IL1B, IL11RA, IL17RB, IL1R1, IL3RA, EGF, IL15, CX3CR1, TGFB1/B2/B3, KIT |
| | Down-regulation of oxidative phosphorylation, respiratory elecron transport, cell cycle |
| Transcription Factors | SRF |

SECRETORY

| | |
|---|---|
| Up-regulated Modules | 6, 8 |
| Down-regulated Modules | 1, 2, 5, 7 |
| Clinical Characteristics | Current smoking (77%), non-dysplastic biopsies (66%) |
| Biological Characteristics | LUSC subytpes - Secretory; CD45, MUC5AC, TUB1A1 up-regulated; KI67, KRT5 down-regulated |
| Pathways | Down-regulation of extracellular matrix, focal adhesion, integrin pathways |
| Transcription Factors | Down-regulation of E2F |

NORMAL-LIKE

| | |
|---|---|
| Up-regulated Modules | 1, 6 |
| Down-regulated Modules | 8, 9 |
| Clinical Characteristics | Former smoking (65%), non-dysplastic biopsies (75%) |
| Biological Characteristics | CD45, MUC5AC, KI67 down-regulated; SCGB1A1, KRT5, TUB1A1 up-regulated |
| Pathways | Core Extracellular matrix genes: collagen and laminin genes, WISP1/2 |
| | Down-regulation of innate and adaptive immunity: HLA genes, IRF1/4/7/8, TLR2/4/6/8/10, IKBKB |
| Transcription Factors | Down-regulation of PEA3, IRF, NFK8 |

Example 2

Supplemental Material for Example 1

Materials and Methods

N-nitrosotris-(2-choroethyl)urea (NTCU) mouse sample collection and library preparation. We have previously collected and banked RNA from 40 fresh frozen whole lung sections (curls) and laser microdissected (LCM) tissue isolated with an Acrutus Pixcell™ II, from SWR/J and A/J mice treated with NTCU. Mice had been treated topically with 15 or 25 umol NTCU (25 ul of 40 mM NTCU for 15 or 25 weeks) as part of a study performed in accordance with IACUC approved protocol at RPCC. Samples include examples of: normal (SWR/J n=3 LCM & 3 curls & A/J n=2 LCM & 1 curl), metaplasia/mild dysplasia (SWR/J n=5 LCM & 2 curls), moderate dysplasia (SWR/J n=7 LCM & 4 curls & A/J n=2 LCM & 1 curls), and severe dysplasia (SWR/J n=3 LCM & 2 curls), and carcinoma in situ/LUSC (A/J n=2 LCM & 2 curls). Samples were extracted using the Qiagen mi-RNAeasy kit according to manufacturer's protocol. Sequencing libraries will be prepared from total RNA samples using Illumina® TruSeq® RNA Sample Preparation Kit v2. Each sample was sequenced five per lane on the Illumina® HiSeq 2500 to generate single-end 50-nucleotide reads.

Histological Classification of the NTCU Mouse Samples RNA Sequenced

| Mouse Stains | Sample Type | Normal | Mild Dysplasia | Moderate/ Severe Dysplasia | Severe Dysplasia | CIS/SCC Tumor | Total |
|---|---|---|---|---|---|---|---|
| A/J | LCM | 2/2 | — | 2/2 | — | 2/1 | 6/5 |
| A/J | Curls | 1/1 | — | 1/1 | — | 2/1 | 4/3 |
| SWR/J | LCM | 4/1 | 5/3 | 7/3 | 3/1 | | 19/8 |
| SWR/J | Curls | 3/3 | 2/2 | 4/3 | 2/1 | | 11/9 |
| | | | | | | Total | 40/25 |
| Mean RIN values (SD) | | 4.0 (1.8) | 3.8 (0.5) | 3.3 (0.6) | 2.55 (0.1) | 3.4 (1.2) | |

(n = collected/n = passed QC after sequencing)

NTCU mouse data processing. Demultiplexing and creation of FASTQ files were performed using Illumina CASAVA 1.8.2. Trimmomatic was used to trim adapter sequences as well as to trim reads of poor quality using the following parameters: ILLUMINACLIP:TruSeq3-SE.fa:2:30:10, LEADING:20, TRAILING:20, SLIDINGWINDOW: 4:20, and MINLEN:20. After trimming, greater than 99% of reads were retained in all samples. Samples were subsequently aligned using mm9 and 2-pass STAR(44) alignment. Gene and transcript level counts were calculated using RSEM(45) using Ensembl annotation. Quality metrics were calculated by STAR and RSeQC(46). Initially, 15 samples were removed based on percent of uniquely aligned reads (compared to total reads) less than 15%. Subsequent sample and gene filtering was conducted separately on each set as follows: First, EdgeR(48) was used to compute normalized data (library sizes normalized using TMM, trimmed mean of M-values, and log 2 counts per million computed) and genes were excluded that either had an interquartile range equal to zero or a sum across samples equal or less than 1. Samples were excluded based on values greater than 2 standard deviations from the mean for 1) mean Pearson correlation with all other samples calculated across all filtered genes 2) the 1st or 2nd principal components calculated using the filtered gene expression matrix 3) transcript integrity number (TIN, computed by RSeQC). After sample filtering, gene filtering was recomputed as described above on the final set of high-quality samples. The data are available from NCBI's Gene Expression Omnibus using the accession GSE111091.

Immunofluorescent quantification of cell type and proliferative markers. Basal and ciliated cell type markers (KRT5 and TUB1A1) and the proliferative marker (KI67) were manually enumerated for all epithelium within a biopsy in reference to DAPI staining, with a minimum of 500 cells counted per biopsy. The enumeration was conducted on different regions (independent areas of tissue) present on a slide (1-4 regions/biopsy) for each biopsy. A percent of positively stained cells was calculated for each marker in each region enumerated. A binomial mixed effects model via the lme4 R package was used to assess differences in the percentages of cells staining positive for a given protein in each region between the molecular subtypes using the total cells stained in each region as weights and adjusting for patient as a random effect.

TCGA SCC tumors data processing. Log 2 transcript per million data across 20,500 genes from 476 LUSC tumors was obtained from Campbell (10) et al. Genes were excluded that either had an interquartile range equal to zero or a sum across samples equal or less than 1. Samples were excluded based on values greater than 2 standard deviations from the mean for more than one of the following criteria: 1) mean Pearson correlation with all other samples calculated across all filtered genes 2) the 1st or 2nd principal components calculated using the filtered gene expression matrix 3) transcript integrity number (TIN, computed by RSeQC). After sample filtering, gene filtering was recomputed as described above (n=17,887 genes) on the final set of high-quality samples (n=471 tumors).

Table 5 depicts pathways enriched in the Gene Modules. Enrichr results (FDR<0.05) for selected pathways associated with each gene modules.

| Module Number | Number of Genes | Biological Pathways Associated with Gene Modules | Key Genes | FDR for Difference between Molecular Subtypes |
|---|---|---|---|---|
| 1 | 514 | Extracellular Matrix/ Cell Adhesion | Collagens, Lamins, TGFb | 2.70E−36 |
| 2 | 939 | mRNA processing and splicing | RBMs & SRSF | 7.20E−05 |
| 3 | 20 | Transcriptional regulation in response to stimuli - (AP-1) Immediate/Early response genes | JUN & FOS | 1.90E−01 |
| 4 | 64 | OXPHOS/ETC/TCA | COXs & NDUFs | 3.30E−07 |
| 5 | 209 | Cell Cycle/DNA replication/DNA repair | PCNA, TOP2A, CDC, AURK, RAD, XRCC | 2.00E−31 |
| 6 | 1295 | Cilium organization and assembly | FOXJ1, DYNC | 6.60E−57 |
| 7 | 180 | Ribosomal Proteins/ Translation | RPLs & RPSs | 1.90E−13 |
| 8 | 603 | Immune Activation and Inflammatory Response (leukocyte/lymphocyte regulation) | CD8A, CD86, GATA, STAT, IL1B, CD163, CD68 | 3.30E−07 |
| 9 | 112 | Interferon signaling and Antigen Processing and Presentation | SP100, HLAs, STAT1 | 1.30E−02 |

TABLE 6

Molecular Subtype associations with Clinical and Biological Characteristics within the Discovery Cohort (DC) and the Validation Cohort (VC). Statistical tests within the Discovery and Validation cohorts were performed using Fisher's Exact Fisher's Exact Test Molecular Subtype V. Variable

| Variable | DC P-value | VC P-value |
|---|---|---|
| Genomic Smoking Status | 1.00E−07 | 9.64E−03 |
| Subject | 9.66E−05 | 5.87E−03 |
| Subject/Time | 6.96E−04 | 1.40E−02 |

TABLE 6-continued

Molecular Subtype associations with Clinical and Biological Characteristics within the Discovery Cohort (DC) and the Validation Cohort (VC). Statistical tests within the Discovery and Validation cohorts were performed using Fisher's Exact Fisher's Exact Test Molecular Subtype V. Variable

| Variable | DC P-value | VC P-value |
|---|---|---|
| Histology | 6.75E−03 | 9.99E−08 |
| Location | 2.57E−02 | 6.69E−01 |
| Subject/Location | 6.01E−02 | 1.95E−01 |
| Asbestos Exposure | 1.23E−01 | 7.47E−02 |
| Lung Cancer History | 1.32E−01 | 9.92E−01 |
| Progression Status | 1.60E−01 | 1.67E−05 |
| High-risk Job | 4.31E−01 | 8.30E−01 |
| Sex | 5.62E−01 | 8.90E−01 |
| LUSC Tumor Subtype | 9.99E−08 | 1.80E−06 |
| COPD | 1.62E−01 | 9.38E−03 |
| Genomic Smoking Status | 2.71E−09 | 2.72E−04 |
| Subject | 9.66E−05 | 5.87E−03 |
| Subject/Time | 6.96E−04 | 1.40E−02 |
| Histology | 6.75E−03 | 9.99E−08 |
| Location | 2.57E−02 | 6.69E−01 |
| Subject/Location | 6.01E−02 | 1.95E−01 |
| Asbestos Exposure | 1.23E−01 | 7.47E−02 |
| Lung Cancer History | 1.32E−01 | 9.92E−01 |
| Progression Status | 1.60E−01 | 1.67E−05 |
| High-risk Job | 4.31E−01 | 8.30E−01 |
| Sex | 5.62E−01 | 8.90E−01 |
| LUSC Tumor Subtype | 9.99E−08 | 1.80E−06 |
| COPD Status | 1.62E−01 | 9.38E−03 |

TABLE 7

Statistical associations between Progression/Persistence versus Regression within each Molecular Subtype and Cohort (DC and VC) for each Gene Module. P-values less than 0.05 are reported.

| Cohort | Molecular Subtype | | | | | | | |
|---|---|---|---|---|---|---|---|---|
|  | N DC | N VC | S DC | S VC | I DC | I VC | P DC | P VC |
| Number of Progressive/Persistent Lesions | 5 | 1 | 17 | 7 | 7 | 5 | 15 | 7 |
| Number of Regressive Lesions | 3 | 3 | 8 | 1 | 4 | 1 | 15 | 13 |
| Module Number |  |  |  |  |  |  |  |  |
| 1 | ns | N/A | ns | N/A | ns | N/A | ns | ns |
| 2 | ns | N/A | ns | N/A | ns | N/A | ns | ns |
| 3 | ns | N/A | ns | N/A | ns | N/A | 0.047 | ns |
| 4 | 0.026 | N/A | ns | N/A | ns | N/A | ns | ns |
| 5 | ns | N/A | ns | N/A | ns | N/A | ns | ns |
| 6 | ns | N/A | ns | N/A | ns | N/A | ns | ns |
| 7 | ns | N/A | ns | N/A | ns | N/A | ns | ns |
| 8 | 0.027 | N/A | ns | N/A | 0.005 | N/A | ns | ns |
| 9 | ns | N/A | ns | N/A | ns | N/A | 0.0017 | 0.03 |
| Number of Progressive/Persistent Lesions | 5 | 1 | 17 | 7 | 7 | 5 | 15 | 7 |
| Number of Regressive Lesions | 3 | 3 | 8 | 1 | 4 | 1 | 15 | 13 |
| Module Number |  |  |  |  |  |  |  |  |
| 1 | ns | N/A | ns | N/A | ns | N/A | ns | ns |
| 2 | ns | N/A | ns | N/A | ns | N/A | ns | ns |
| 3 | ns | N/A | ns | N/A | ns | N/A | 0.047 | ns |
| 4 | 0.026 | N/A | ns | N/A | ns | N/A | ns | ns |
| 5 | ns | N/A | ns | N/A | ns | N/A | ns | ns |
| 6 | ns | N/A | ns | N/A | ns | N/A | ns | ns |
| 7 | ns | N/A | ns | N/A | ns | N/A | ns | ns |
| 8 | 0.027 | N/A | ns | N/A | 0.005 | N/A | ns | ns |
| 9 | ns | N/A | ns | N/A | ns | N/A | 0.0017 | 0.03 | ns = not significant and N/A = not enough samples in each group to conduct the analysis.

For molecular subtype, N = normal, S = secretory, I = inflammatory, and P = profilerative

TABLE 8

Lung sites where Endobronchial Biopsies were obtained. The site code, name, and description are reported for each site.

| ID | Name | Description |
|---|---|---|
| 096 | VC | True Vocal Cords, Neck |
| 051 | Mouth | Floor of Mouth |
| 007 | EPIG | Epiglottis |
| 005 | ART | Arytenoids |
| 008 | FVC | False Vocal Cords |
| 095 | TR | Trachea |
| 050 | MC | Main Carina, Carina NOS |
| 086 | RMB | Right Main Bronchus, incl Secondary Carina right |
| 091 | RUL | Right Upper Lobe |
| 093 | RULO | Right Upper Lobe Orifice or opening |
| 094 | RULS | Right Upper Lobe Stump |
| 092 | RULB | Right Upper Lobe Bronchus |
| 087 | RML | Right Middle Lobe |
| 089 | RMLO | Right Middle Lobe Orifice or opening |
| 090 | RMLS | Right Middle Lobe Stump |
| 088 | RMLB | Right Middle Lobe Bronchus |
| 082 | RLL | Right Lower Lobe |
| 084 | RLLO | Right Lower Lobe Orifice |
| 085 | RLLS | Right Lower Lobe Stump |
| 083 | RLLB | Right Lower Lobe Bronchus |
| 006 | BI | Bronchus Intermedius |
| 052 | RB1 | RUL Apical Segment (AS) |
| 060 | RB2 | RUL Posterior Segment (PS) |
| 063 | RB3 | RUL Anterior Segment (ANTS) |
| 053 | RB1/2 | RUL Carina between RB1 and RB2 |
| 054 | RB1/3 | RUL Carina between RB1 and RB3 |
| 061 | RB2/3 | RUL Carina between RB2 and RB3 |
| 059 | RB1A/B | RUL AS Carina between RB1 A and B |
| 062 | RB2A/B | RUL PS Carina between RB2 A and B |
| 064 | RB3A/B | RUL ANTS Carina between RB3 A and B |
| 065 | RB4 | RML Lateral Segment (LS) |
| 068 | RB5 | RML Medial Segment (MS) |
| 066 | RB4/5 | RML LS Carina between RB4 and RB5 |
| 067 | RB4A/B | RML LS Carina between RB4 A and B |
| 069 | RB5A/B | RML MS Carina between RB5 A and B |
| 070 | RB6 | RLL Superior Basal Segment (SBS) |
| 071 | RB6A/B | RLL SBS Carina between RB6A and B |
| 072 | RB6A/C | RLL SBS Carina between RB6A and C |
| 073 | RB6B/C | RLL SBS Carina between RB6B and C |
| 074 | RB7 | RLL Medial Basal Segment (MBS) |
| 075 | RB7A/B | RLL MBS Carina between RB7A and B |
| 076 | RB8 | RLL Anterior Basal Seg (ABS) |
| 077 | RB8/9 | RLL ABS Carina between RB8 and RB9 |
| 078 | RB8A/B | RLL ABS Carina between RB8A and B |
| 079 | RB9 | RLL Lateral Basal Segment (LBS) |
| 080 | RB9/10 | RLL LBS Carina between RB9 and RB10 |
| 081 | RB9A/B | RLL LBS Carina between RB9A and B |
| 055 | RB10 | RLL Posterior Basal Segment (PBS) |
| 056 | RB10A/B | RLL PBS Carina between RB10A and B |
| 057 | RB10A/C | RLL PBS Carina between RB10A and C |

TABLE 8-continued

Lung sites where Endobronchial Biopsies were obtained. The site code, name, and description are reported for each site.

| ID | Name | Description |
|---|---|---|
| 058 | RB10B/C | RLL PBS Carina between RB10B and C |
| 001 | 666 | Location was surgically altered or removed |
| 002 | 777 | Abstractor needs clinician help to code |
| 003 | 888 | Location code is unknown, illegible |
| 004 | 999 | Location code is blank, not noted |
| 043 | LMB | Left Main Bronchus, incl Secondary Carina left |
| 044 | LMBD | Left Main Bronchus, Distal |
| 046 | LUL | Left Upper Lobe |
| 048 | LULO | Left Upper Lobe Orifice or opening |
| 049 | LULS | Left Upper Lobe Stump |
| 035 | LGL | Lingula |
| 037 | LGLO | Lingula Orifice or opening |
| 038 | LGLS | Lingula Stump |
| 047 | LULB | Left Upper Lobe Bronchus |
| 045 | LUDB | Left Upper Division Bronchus |
| 036 | LGLDB | Lingular Division Bronchus, lingular bronchus |
| 039 | LLL | Left Lower Lobe |
| 041 | LLLO | Left Lower Lobe Orifice or opening |
| 042 | LLLS | Left Lower Lobe Stump |
| 040 | LLLB | Left Lower Lobe Bronchus |
| 009 | LB1 + 2 | LUL Apical-Posterior Segment (APS) |
| 018 | LB3 | LUL Anterior Segment |
| 011 | LB1/2 | LUL APS Carina between LB1 and LB2 |
| 010 | LB1 + 2/3 | LUL APS Carina between LB1 + 2 and LB3 |
| 016 | LB2A/C | LUL APS Carina between LB2 A and C |
| 017 | LB2B/C | LUL APS Carina between LB2B and C |
| 019 | LB3A/B | LUL ANTS Carina between LB3A and B |
| 020 | LB4 | LUL Superior Lingular Segment (SLS) |
| 023 | LB5 | LUL Inferior Lingular Segment (ILS) |
| 021 | LB4/5 | LUL SLS Carina between LB4 and LB5 |
| 022 | LB4A/B | LUL SLS Carina between LB4A and B |
| 024 | LB5A/B | LUL ILS Carina between LB5A and B |
| 025 | LB6 | LLL Superior Segment (SS) |
| 026 | LB6A/B | LLL SS Carina between LB6A and B |
| 027 | LB6A/C | LLL SS Carina between LB6A and C |
| 028 | LB6B/C | LLL SS Carina between LB6B and C |
| 029 | LB8 | LLL Antero Medial Basal Segment (AMBS) |
| 030 | LB8/9 | LLL AMBS Carina between LB8 and LB9 |
| 031 | LB8A/B | LLL AMBS Carina between LB8A and B |
| 032 | LB9 | LLL Lateral Basal Segment (LBS) |
| 033 | LB9/10 | LLL LBS Carina between LB9 and LB10 |
| 034 | LB9A/B | LLL LBS Carina between LB9A and B |
| 012 | LB10 | LLL Posterior Basal Segment (PBS) |
| 013 | LB10A/B | LLL PBS Carina between LB10A and B |
| 014 | LB10A/C | LLL PBS Carina between LB10A and C |
| 015 | LB10B/C | LLL PBS Carina between LB10B and C |

TABLE 9

Antibodies used in the Immunofluorescence Studies.

| Antibody | Company | Catalog | Dilution | Antigen retrival | Species |
|---|---|---|---|---|---|
| Immune cell type markers | | | | | |
| CD68 | Dako | m0876 | 1- | AR6 | mous |
| CD163 | Cell Marque | 163m-16 | 1-100 | AR9 | mous |
| CD4 | Thermo Fisher | ms1528S | 1-100 | AR9 | mous |
| CD8 | Dako | M7103 | 1-100 | AR9 | mous |
| Epithelial cell type and proliferation markers | | | | | |
| Ac-α-Tub | Sigma | T6793 | 1-100 | citrat | mous |
| KRT5 | BioLegend | 905-901 | 1-100 | citrat | chicken |
| KI67 | Abcam | ab16667 | 1-100 | citrat | rabbit |

TABLE 10

Genomic smoking status over time by subject. The smoking status of each subject at each time point was computed based on a previously published smoking-associated gene signature[6] (see methods for details). The rows indicate the smoking status across all time points sampled for each patient. The –> symbol indicates changes in smoking status over time. There is not a statistical difference between the distribution of subjects in the smoking status categories between the discovery and validation cohorts by a two-sided Fisher's exact Test ($p = 0.90$). Source data are provided as a Source Data file.

| Genomic smoking status over time | Discovery Cohort Number of Subjects | Validation Cohort Number of Subjects |
|---|---|---|
| Current | 9 | 9 |
| Former | 10 | 5 |
| Current–>Former | 7 | 4 |
| Former–>Current | 3 | 2 |
| Current–>Former–>Current | 1 | 0 |

TABLE 12

Molecular Subtype associations with previous history of lung cancer. Previous history of lung cancer (LC) was categorized as follows: no history (No LC History), a previous history of LC that include a lung squamous cell carcinoma (LC History - LUSC), and a previous history of LC that does not include a lung squamous cell carcinoma (LC History - Other). Statistical tests within the discovery and validation cohorts were performed using two-sided Fisher's exact tests.

| | Variable | | | | | | | |
|---|---|---|---|---|---|---|---|---|
| | Discovery Cohort Biopsies (n = 190) | | | | Validation Cohort Biopsies (n = 105) | | | |
| Molecular Subtype | No LC History | LC History - LUSC | LC History - Other | P-Value | No LC History | LC History - LUSC | LC History - Other | P-Value |
| Proliferative | 14 | 5 | 33 | | 12 | 9 | 7 | |
| Inflammatory | 10 | 6 | 21 | | 12 | 4 | 14 | |
| Secretory | 26 | 8 | 27 | | 14 | 13 | 7 | |
| Normal-like | 9 | 3 | 28 | $p = 0.19$ | 6 | 1 | 6 | $p = 0.10$ |

What is claimed herein is:

1. A method of treating bronchial premalignant lesions, the method comprising:
  administering:
   i. a bronchoscopy-based procedure to survey the central airway and a chest CT scan; and
   ii. at least one anti-proliferative drug;
  to a subject presently lung cancer-free, but having bronchial premalignant lesions, and determined to have:
   an increased level of expression of at least one module 5 gene in a sample obtained from the subject comprising morphologically-normal cells as compared to a non-proliferative lesion reference level, wherein the at least one module 5 gene is selected from the group consisting of:
    RACGAP1 and TPX2;
   a decreased level of expression of at least one module 6 gene in a sample obtained from the subject comprising morphologically-normal cells as compared to a non-proliferative lesion reference level, wherein the at least one module 6 gene is selected from the group consisting of:
    NEK11 and IFT88
  wherein the sample is a bronchial brushing obtained from the right or left mainstem bronchus, an endobronchial biopsy, endobronchial brushing sample, large airway biopsy, large airway brushing sample, nasal epithelial cells or sputum and wherein the sample is obtained from the subject while the subject is presently lung cancer-free, but having bronchial premalignant lesions.

2. The method of claim 1, wherein the subject is further determined to have an increased level of expression of at least one module 7 or module 4 gene as compared to a non-proliferative lesion reference level;
  wherein the at least one module 7 gene is selected from the group consisting of:
   RPS20; EIF4B; RPL18; RPL31; RPS5; STARD7; RPL6; RPLP0; IGBP1; EIF3L; RPL3;
   EIF3D; CCNB11P1; EIF3E; EEF1D; RPS16; FBL; RPS19; GLTSCR2; RPL18A;
   DDX50; RPL28; RPL19; SMARCD2; RPL34; RPS13; C12orf57; RPS12; RPL24;
   EEF1B2; RPS15; RPL22; DPH5; RPS25; CCNI; RPL21; RPL5; RPS10; RPL23;
   SNRPD2; UROD; SERGEF; ECSIT; RPL36; MRPL34; COX4I1; RPL27; TPT1;
   RPS15A; ATP5G2; RNASEH2B; CCDC115; RPL35; POLR1E; RPS6; RPLP1;
   RPL7P9; RPS24; RPL14P1; GCSH; RPS2; RPS11; RPL13A; RPL11; RPS8; RPS27A;
   RPL32; SLC25A26; RPS3A; RPL37; BTF3; RPL10; RPL7; EBAG9; EIF3H; RPL7A;
   RPS3; FAU; TMEM18; RPL30; EEF1A1; ZNF689; RPL8; RPL26; RPL29; PMVK;
   RPL9; RPS14; RPL27A; MRPL16; RPL13; RPSA; SLC25A6; CNBP; RPS9; RPS21;
   RPS7; RPL38; TOMM20; RPL4; MRPL11; RPL15; FAM211A-AS1; EIF3F; ZFAS1;
   RPLP2; RPS27; RPS17L; RPL35A; RPS7P1; RPS17; RPS23; COMMD6; RPL14;
   RPS2P46; EEF1A1P5; NACA; TOMM7; RPL37A; RPL12; RPS4X; RPL23A; ZNF511;
   RPL10A; RPL39; C6orf48; GNB2L1; RPSAP58; RPL15P3; RPL18AP3; RPLP0P6;
   RPS29; RPL21P75; SMIM7; LYRM4; RPS3AP26; RPL7P1; PHB2; RPL21P28;
   UBA52; RPL41P1; RPL41; RPL4P4; RPS23P8; RPS18; EEF1B2P3; RPL3P4;
   EEF1A1P6; RPS28; GASS, RPS3AP6; RPL24P2; RPL6P27; RPL13AP5; RPS2P5;
   RPL36A; RPL7AP6; SNHG6; EEF1G; RPL17; and SNHG8; and
  wherein the at least one module 4 gene is selected from the group consisting of:
   MRPS24; NDUFB4; NDUFB2; PSMD8; NDUFB7; TOMM22; TCEB2; CHCHD2;
   PSMD9; MRPL51; COX6A1; COX7A2; ATP5F1; NDUFB3; PDZD11; NDUFA1;
   MRPS7; ROMO1; COX6B1; TIMM17B; UQCR11; EMC6; COX7B; BLOC1S1;
   COXSB; PSMB7; NDUFB10; ANAPC11; TXNL4A; SNRPG; NDUFS6; TIMM8B;
   NDUFC2; DBI; C14orf2; THOC7; UQCRQ; COX6C; NDUFB6; STOML2; NDUFB8;
   ATP5I; UQCRFS1; MRPL36; MYEOV2; CHCHD1; MINOS1; USMG5; COX8A;
   POLR2L; TMEM11; COX5A; MRPL54; UQCR10; NDUFA12; DRG1; NDUFA13;
   SUMO2; NDUFA4; GPN1; C11orf83; NDUFS3; ATP5J2, and MRPL12.

3. The method of claim 2, wherein the at least one module 7 or module 4 gene is selected from the group consisting of: COX6A1; COX7A2; RPL26; and RPL23.

4. The method of claim 1, wherein the anti-proliferative drug is administered as an inhaled formulation, topical formulation, during a bronchoscopy-based procedure, or systemically.

5. The method of claim 1, wherein the subject is further determined to have a decreased level of expression of at least one module 9 gene as compared to a non-proliferative lesion reference level and/or an increased level of expression of at least one module 10 gene as compared to a non-proliferative lesion reference level;
  wherein the at least one module 9 gene is selected from the group consisting of:
   LAP3; NUB1; CD74; BTN3A1; EIF2AK2; PARP12; SP100; IFI35; LAG3; PSME1;
   APOL4; APOL1; PSME2; TRIM14; DDX58; OAS3; OAS2; BTN3A3; BTN2A1;
   XRN1; IFIH1; STAT1; GBP1; IFIT3; TNFSF10; OPTN; NMI; ZNFX1; RNF114;
   BTN2A2; IRF1; IFI6; APOL3; APOL2; BST2; KLHDC7B; HELZ2; IDO1; TRIM21;
   TRIM22; EPSTI1; CMPK2; TRAFD1; TOR1B; DDX60; IFI44L; IFI44; PARP9;
   HERC6; CXCL9; WARS; PML; NLRC5; IFIT5; UBE2L6; MX1; USF1; ADAR; LY6E;
   GBP4; DTX3L; IL15; IFI27; C2; B2M; BATF2; TAP1; LGALS9; CXCL10; PARP14;
   RNF213; SAMD9L; HLA-DQB1; CIITA; SOCS1; SP140L; TRIM69; BTN3A2; ISG15;
   RUFY4; PLSCR1; HLA-DRB1; HLA-DQA1; ACSL5; C5orf56; HLA-DOA; HLA-DMA;
   TAPSAR1; PSMB8; HLA-DRA; HLA-C; HLA-E; HLA-F; PSMB10; EXOC3L4;
   HCP5; HLA-A; UBD; IRF9; APOL6; HLA-DPB1; PSME2P2; GBP1P1; HLA-DPA1;
   TAPBP; HLA-DQB2; HLA-B; OR2I1P; PSMB9; and HLA-DMB; and
  wherein the at least one module 10 gene is selected from the group consisting of:
   CACNB3 and MAPK10.

6. The method of claim 5, wherein the subject determined to have a decreased level of expression of at least one module 9 gene and/or an increased level of expression of at least one module 10 gene is administered at least one of:
  i. both a bronchoscopy-based procedure to survey the central airway wherein the lesions are biopsied to remove abnormal tissue and a chest CT scan;
  ii. at least every 6 months, one of a bronchoscopy-based procedure to survey the central airway wherein the lesions are biopsied to remove abnormal tissue and a chest CT scan; and/or
  iii. at least one immune stimulating drug.

7. The method of claim 1, wherein the sample comprises morphologically normal tissues, or consists of morphologically-normal tissues or cells.

8. The method of claim 1, wherein the level of expression is the level of expression in a sample further comprising bronchial premalignant lesion cells.

9. The method of claim 1, wherein the subject is a smoker or former smoker.

10. The method of claim 1, wherein the bronchoscopy-based procedure and the chest CT scan are administered at a frequency of at least every 6 months.

11. The method of claim 10, wherein administering the bronchoscopy-based procedure and the chest CT scan to the subject at a frequency of at least every 6 months comprises instructing the subject to repeat the administration of the bronchoscopy-based procedure and the chest CT scan within 6 months.

12. The method of claim 1, wherein the at least one module 5 gene comprises at least RACGAP1 and TPX2; and the at least one module 6 gene comprises at least NEK11 and IFT88.

13. The method of claim 1, wherein the subject is one who does not presently have and has not previously had lung cancer.

14. The method of claim 1, wherein the subject further has:
an increased level of expression, in a sample obtained from the subject comprising morphologically-normal cells as compared to a non-proliferative lesion reference level, of at least one module 5 gene selected from:
  C1orf112; POLDIP2; DBF4; E2F2; NCAPD2; ANLN; DEPDC1; UHRF1;
  SPDL1; TSPAN17; RFC2; RAD51; NOP58; ASPM; PRR11; HMMR; GTSE1;
  WDR62; UBE2T; NDC80; ORC1; RAD54L; PIGS; AURKA; BIRC5; KIF4A;
  ORC6; CDC45; CDC6; CDC7; MCM5; CDKN3; LGMN; GINS1; MYBL2;
  E2F1; SUV39H1; CENPI; GABPB1; MCM4; RNASEH2A; ASF1B; ILVBL;
  EZH2; UBE2S; NCAPG; FOXM1; RAD51AP1; RFC5; TIMELESS; MCM3;
  BYSL; TTK; KIF20A; LMNB1; SMC4; LRRC42; HDAC1; TTF2; CDC20;
  STMN1; CENPF; KIF14; HELLS; MTHFD1L; MASTL; CCDC77; TMPO;
  NCAPH; KIF18A; CCDC18; HNRNPA2B1; ZWINT; CENPK; TUBA1B;
  HJURP; CKS2; CSE1L; SOX4; C17orf53; HNRNPR; DLGAP5; PKMYT1;
  A4GALT; KNSTRN; FAM64A; PVRL2; GINS2; ABCB7; TOP2A; MRPL35;
  PCNA; CCNB1; CDCA8; TROAP; ESPL1; URB2; STX6; CKAP2; BORA;
  BRIP1; CTSV; CPEB2; NUSAP1; KIF23; CASC5; CENPO; KIF11; CEP55;
  WDR12; CENPE; BRCA2; DENR; DIAPH3; FANCI; PLK4; KIF2C; NUF2;
  DTL; INTS7; ILF2; CHAC2; FANCD2; CCNA2; SKP2; G3BP1; MTFR2;
  CDCA5; NCAPG2; NONO; RBMX; GINS4; MKI67; CHEK1; TEX30; CENPH;
  SKA1; EME1; BUB1B; CCNB2; CHAF1B; SPC24; C16orf59; CCNF;
  KIAA1524; KIF15; RPL39L; SLBP; CDC25A; MAD2L1; PTTG1; MELK;
  SKA3; CENPN; KIAA0101; PLK1; CDT1; TK1; PBK; DTYMK; RFWD3;
  FEN1; USP39; CKAP2L; BUB1; CDK1; SHCBP1; ESCO2; RRM2; CKS1B;
  ZWILCH; UBE2C; CKAP5; CCNE2; TYMS; B3GNT8; AURKB; RCC2;
  FARSA; MAF1; KPNA2; SKA2; TRAIP; LIN9; IQGAP3; CDCA2; PARPBP;
  KIF18B; ERCC6L; PTMA; FANCA; H2AFX; FAM72B; FAM111B; XRCC6;
  FAM72A; XRCC2; HYLS1; ARHGAP11A; PRC1; CENPW; LSM2; TRIM59;
  FAM72D; DHFR; KIFC1; and PGAM5; or
the subject further has a decreased level of expression, in a sample obtained from the subject comprising morphologically-normal cells as compared to a non-proliferative lesion reference level, of at least one module 6 gene selected from:
  STPG1; KLHL13; SLC7A2; ZMYND10; ARX; DHX33; WDR54; ARHGAP44;
  CDKL3; PROM1; DNAH9; GAS7; RHBDF1; TEAD3; JARID2; FUZ;
  LRRC23; MKS1; TTC19; PPP5C; IL2ORA; GLT8D1; PLEKHB1; NRXN3;
  CCDC28A; HSF2; TOMM34; CD44; EFCAB1; USP2; NSUN2; DNAH5;
  SPATA7; TRIT1; CC2D2A; SNX29; R3HDM1; SRD5A2; NEDD4L; PPP1R3F;
  ARHGEF5; POLQ; LY75; SDCCAG8; HHAT; GALC; GYG2; DCBLD2;
  LAMC2; SPA17; SNCAIP; ANKS1A; DGKA; TBC1D22B; FOXJ2; DIP2B;
  ZMYND12; NGEF; EML1; EVI5; TP53BP1; ATP11A; IFT80; PPP2R5B;
  MNT; AP3M2; ST6GALNAC2; C16orf80; TRIP13; RPS6KA6; RHOBTB1;
  XRCC1; CLCN4; SLC24A1; ARHGEF1OL; SRI; GRAMD4; TMEM131;
  KIFAP3; SPAG6; POLD3; FKBP6; TULP3; ZCWPW1; TP73; OSBPL6;
  CDC14A; RFX3; PIH1D3; HSP90AA1; HSPB11; ULK2; MAPRE3; CD59;
  WDR47; NFX1; IPO11; MTMR2; ATXN7L3; SF3B2; TFAP2C; RFX2; GP6;
  REM1; KIF9; NSFL1C; PLK1S1; DYNLL1; SLC8B1; DZANK1; C20orf26;
  TASP1; NUDC; CERS4; NAT14; IL5RA; TEKT2; PSMD5; NUP188; ITPR3;
  IFT74; SEC14L3; ANKRD54; CENPM; CBY1; RTDR1; RAB36; TTLL1;
  MCAT; MYH9; DESI1; CERK; KHNYN; PRMT5; CDKL1; SAMD15;
  AHSA1; SIX4; RPS6KA5; IFT52; SPEF1; EPPIN; MOSPD1; ASB9; PCYT1B;
  KLF8; FGF14; CDADC1; MRPS31; SLC25A15; KATNAL1; GDPD3; MMP15;

CCDC113; SLC38A7; HSDL1; NAGPA; USP10; METRN; CLUAP1;
RPGRIP1L; CCP110; IQCH; CORO2B; ACSBG1; ZNF106; CEP152; RP1;
NIPAL2; ZC2HC1A; CHRAC1; NCALD; SQLE; TUSC3; POLR2I; ZFR2;
CAPS; TTC26; RNF32; IQCE; HIBADH; TAX1BP1; FAM188B; RPA3; NRF1;
CEP41; FSD1L; AK1; RGP1; MPDZ; GLIS3; HPS1; LZTS2; SH3PXD2A;
PBLD; TRIM37; DHX40; GALK1; B9D1; PEX12; HNF1B; PPP1R9B;
PRKAR1A; EFNB3; IFT20; SLAIN2; WFS1; TBC1D19; WHSC1; SNX25;
LRP2BP; C11orf63; SNX15; KIAA1377; PPFIBP1; ELK3; PRMT8; AKAP3;
KCNA1; LTBR; OGFOD2; STX2; MDM1; UHRF1BPL; ENO2; ST8SIA1;
RSPH4A; MAK; MCM9; FAM184A; TPD52L1; SASH1; RBM24; CAP2;
PACRG; C6orf118; MDFI; FAM120B; DNPH1; ENPP5; NME5; IK; MSH3;
RAD1; C5orf15; WWC1; CLDN16; ARL6; IFT57; HHLA2; IQCG; KIAA1257;
PLCH1; NEK4; STEAP3; STAM2; NRBP1; DNAH6; PECR; GGCX; PPP1R7;
TAF1B; ORC4; THADA; C2orf42; GRIN3B; ALMS1; BCL9; TRIM62;
DNAJC6; PHTF1; OSCP1; TBCE; RIMS3; CCDC181; RCAN3; IFT46;
CASC1; FILIP1; HMGN3; UBE3D; ARMC2; WDR35; DNAH7; C2orf40;
FAM206A; WDR34; CNTRL; TRIM32; FBXW2; CCDC176; ACYP1; IFT43;
DNAL1; TTLL5; DLST; PPP4R4; ZC2HC1C; FKBP1B; CCDC147; C10orf95;
LRP11; CCDC170; MYCT1; CYSTM1; ENOX1; PROSER1; HSPH1; AKAP1;
ZSCAN18; TRMT1L; CRY2; FAM35A; BBS9; IFT81; TTC21B; B9D2;
DAW1; ENKD1; C20orf85; TCP11; COL21A1; BBS2; PTGER2; TEKT3;
TTF1; C20orf195; TRIP10; PANK2; MGME1; ID1; ERGIC3; HECTD3;
FRMD8; PRDX5; PCNXL4; KTN1; SIX1; WDR60; LRRC61; TUBA4A;
TNFRSF19; AKAP9; STYXL1; C22orf23; RIBC2; CDHR3; RABL5;
KLHDC10; TTBK2; C15orf57; CALML4; THAP10; BBOX1; LRRC6; EGLN3;
FOXJ1; CDC16; RSPH3; STK33; CACNG6; SSBP4; UBAC1; TUBGCP2;
ARHGEF16; ATPIF1; PRRG1; KIF3A; PSMC3IP; NPHP4; MAP1B; PDHA1;
ZSCAN5A; RHPN2; ABHD12B; ZSWIM4; FBXW9; ZNF20; SPATA6;
GAS2L2; CNGA4; IQCA1; VPS13B; RGS22; BTBD3; POLR3F; DPH2;
PIK3C2B; SLC41A1; SPG20; STOML3; MORC4; EPHB2; PDE6B; SEC14L4;
ACTR3B; LRRIQ1; TMEM254; LRRCC1; UNC79; MEIS2; PTGFRN; ISCA1;
CCDC146; HILPDA; KIAA1009; LCA5; PRPH; KCNH3; CD164; LACE1;
PKIB; REPS1; ARMC9; TSGA10; TGFBRAP1; APPL2; TTC5; NMT1;
MYCBPAP; VEZF1; SAP130; ODF2; WDR38; SLC22A23; BPHL; FAM8A1;
C6orf52; TTC29; ANKRD42; NEK1; C11orf70; BTG4; PAQR5; LRRC49;
GIPC2; IFT172; DYNC2L11; SMEK2; ARL3; MDH1B; CIR1; ABI2; MNS1;
HCN4; FAM13A; RASGEF1B; CDKL2; SHROOM3; MTTP; CCDC65;
CERS5; MORN3; C14orf37; SLC38A6; EFCAB11; PTGR2; AK7; SLC27A2;
DNAJA4; BBS4; CCDC33; WDR93; FURIN; SH3GL3; GLYR1; NUDT7;
GALNS; GASB; GFOD2; LRRC46; BCAS3; WRAP53; TP53; WDR45B;
FBXO15; FHAD1; PEX14; IL22RA1; STRIP1; NME7; UCK2; UFC1; USP21;
DYRK3; SMYD2; ADAM15; AQP10; C1orf131; SCCPDH; CNIH3; CALM2;
WDPCP; NPHP1; AMMECR1L; SPAG16; ANKMY1; CCDC39; TRMT10A;
NAF1; ROPN1L; FAM50B;FARS2; DCDC2; RNF44; TCTE1; CYP39A1;
TPBG; IRAK1BP1; ARHGAP18; GBAS; PSPH; AGBL3; TMEM27; ZNF157;
DIAPH2; PRPS1; CXorf57; MCPH1; CETN2; CHMP7; C9orf72; IDNK;
ASTN2; WDR31; CAMK2G; LRRC27; CNNM2; ZNF214; C11orf49; CCDC81;
TTC12; C11orf52; GLB1L2; MTA2; MPZL2; PLCB3; CTF1; TMEM218;
N6AMT2; SPATA4; FSIP1; DIXDC1; PIH1D2; C2orf50; ENKUR; DCP1B;
AKAP6; MIPOL1; NUBPL; VIPAS39; TEX9; INPP1; CCDC122; NBAS;
CCDC74B; RPP38; TRIM36; SPEF2; CAPSL; WDR78; IFLTD1; CLGN;
CETN3; CCDC148; FAM81B; ADPRHL1; FBXL2; UBP1; LURAP1L; CFDP1;
FAM92B; FBXO36; ZNF599; DDAH1; ANKFN1; FAM105B; FAM134B;
CEP112; ENAH; CCDC173; SORBS2; SLFN13; RAB6B; ACSS1; RSPH10B;
AK9; AZIN1; AGPAT5; LRGUK; KDM8; ALS2CR12; SPAG17; FMN2;
GRIP1; ELMSAN1; GNA14; FAM161B; DRAM2; C8orf37; C15orf26;
WHAMM; TIAM1; RPGR; SH3RF2; GALK2; MMP14; C1orf158; HYDIN;
ZNF19; FAM81A; DSCR3; LCA5L; C9orf43; WDR19; DRC1; RAB28;
WDR66; LRRC43; AAED1; FAIM; SLC13A3; RIBC1; C2orf62; KCNB1;
DNAH3; AGPAT6; B4GALT3; C21orf59; C2orf81; CHCHD6; TPPP3;
ZDHHC1; IQCC; KALRN; TMPRSS3; RSPH1; C9orf116; PCSK7; RUSC1;
UBQLN4; TONSL; ORAI2; LRWD1; FBXL13; DUSP14; LRRC56; FDXR;
ALOX15; HS3ST6; SHANK2; PPP1R32; RPS6KA4; UBXN10; C1orf87;
OMA1; DNAJB4; LRRIQ3; WDR63; KLHDC9; FLVCR1; SPATA17;
DUSP19; CCDC104; CCDC138; CCDC74A; TEKT4; SPATA18; INHBB;
BBS5; RPRD2; PACRGL; DHX57; FZD5; C1orf189; FAM175A; HIPK1;

NEK10; AZI2; GLB1L; EFHB; ICA1L; KIAA1407; CDS1; GMPS; ABHD6;

LZTFL1; MEAF6; DNALI1; EXO5; PRSS12; MAPS; CEP44; ZNF474;

PRIMPOL; GDF9; GJB7; TXLNB; DCBLD1; KIAA0895; KIF6; SYTL3;

IQUB; C7orf57; MED30; HEATR2; TP531NP1; TMEM67; FAM219A;

C9orf24; ABCA1; C8orf34; KDM1B; C9orf64; SVEP1; CXorf22; KIAA1958;

STRBP; GAPVD1; ARMC3; LRRC18; DNAAF2; TTC8; AK8; C9orf9;

ZMYND19; STOX1; PPP1R36; CKB; DPCD; LARP6; C16orf71; FAM227B;

STXBP4; C10orf32; SMPD1; APBB1; C11orf65; C11orf74; TUB; XRRA1;

C16orf46; ZNF3; IQCD; RRAD; WDR16; CCNDBP1; MS4A8; MAP1A;

DUSP18; TTC16; COQ4; CCDC103; ENDOG; COQ7; KATNAL2; SPATA33;

RHEBL1; TUBA1A; DNAAF3; HSD11B1L; CYB5D2; TEKT1; TMEM68;

ZNF598; C2CD3; ULK4; MOBP; DEGS2; BMP1; SLC20A2; DYNLRB2;

VWA3B; LDLRAD4; PKIG; FAM178B; CXXC4; TCTN2; TNIP2; PPIC;

ZBBX; ARMC4; NSMCE1; RAB3B; ARL13B; MUC15; TPST1; TOR1AIP2;

FABP6; FAM161A; C14orf142; SPATA24; SLC23A1; HSD17B13; KIAA0232;

DCDC1; PRKCE; MORN4; RBKS; NAT1; LPAR3; MAP6; ZNF584; DNAI2;

LRRC34; CTPS1; KNDC1; AQP4; LRRC48; SNTB1; COPRS; CCDC11;

RSPH9; KLHL6; ZFAND4; ADH6; CCDC96; ABCD2; IQCB1; APOBEC4;

PIFO; CEP19; FAM174A; GSTA3; CHRNA9; C12orf76; BBS1; ZNF497;

IQCK; SH3PXD2B; WDR49; THAP6; BTC; CATSPERD; APITD1; EIF1AD;

TEX26; GPR156; RUVBL1; UNC119B; TMPRSS7; BNIP3; SMIM19; PRR18;

EID2B; PLA2G16; CNTD1; MAP3K19; CCDC121; SEC24C; DSCAML1;

MRVI1-AS1; UMODL1; C8orf47; IRX3; CASC2; AGTRAP; C2orf73; MLF1;

GRAMD1C; PPP1R42; DALRD3; NT5DC1; MCMDC2; P4HTM; ERBB4;

ZNF713; GPS; RIIAD1; C1orf173; TMEM107; CCDC89; C10orf67; ZNF664;

PLD6; FAM216B; C1orf194; TRNAU1AP; FGD6; TIGD2; GLIPR1L2;

KCNE1; WDFY3-AS2; ZFP3; OXTR; BBS12; NME9; RNF135; GPR135;

WRB; CYB5D1; CEP97; FAM104B; NGRN; SPATA13; CSMD1; FANCF;

RUVBL2; CCDC60; CDC125; C10orf107; TNFAIP8L3; DGCR6; C11orf88;

EFHC2; C9orf66; BTBD9; ANKRD45; DNAH2; HIST2H4A; LRTOMT;

EFNA5; C21orf128; PROS1; NELL2; FAM110C; PIGW; RBM43; ZFP90;

TMEM121; EFCAB10; LRRC37B; PGBD2; WBP5; PPIL6; KIAA0825; CDNF;

ARL15; TNFAIP8L1; RAD51D; SMYD3; MRPL40; MORNS; THNSL1;

RASA3; AGBL4; CYP2R1; C2orf76; SLC51B; KLHL32; PRELID2;

TMEM212; ANKRD37; AKAP14; ZNF396; FAM86B1; KATNA1; KIF24;

LYRM7; TMEM17; TMEM232; FAM183A; EFCAB6; TEAD1; SLIT1;

TSPYL4; DYNC2H1; WDR86; IFT140; C17orf97; C1orf170; DNAJB13;

AMY1C; MORN2; NWD1; TUBB4B; ENO4; FOCAD; TCTEX1D4; CERKL;

C9orf171; C12orf55; FAM154B; SNTN; PTPLAD2; C1orf192; FAM47E;

PTPRT; KIF19; TUBB; XPNPEP3; GRM7; ZNF569; C20orf96; ESRRG;

MY018A; TTC30B; ZNF33B; AMZ2; MVB12B; KIAA1211L; HIST3H2BB;

DTHD1; SRC; NEK5; SLC22A4; BCO2; KCNMB2; C5orf42; DNAH10;

WDR96; C4orf22; MEIG1; LEKR1; CCDC151; NUP62CL; MB; HMGN5;

ZNF607; ZNF627; KCNRG; CCDC69; CALM1; FAM179B; PPP1R14C;

FOXJ3; INPP5F; TSEN15; CIPC; DZIP3; L3MBTL3; DMD; ARMCX6; INF2;

FAM83H-AS1; EFCAB2; TATDN3; ECT2L; FAM229B; DDO; ATP1A1OS;

EFCAB7; LDLRAD1; LRRC73; SYS1; TRAF3IP1; NELFE; HSPA1L;

LY6G5C; GPANK1; C10orf115; TRIM39; CASC10; C9orf135; TTC25;

TCTN1; FAM201A; LRRC10B; TMEM231; C4orf47; TTLL10-AS1; OR7E36P;

DENND6B; ITPRIPL2; CRYZL1; PPAPDC2; C21orf49; HN1L; ANKUB1;

CCDC19; TCTEX1D2; ZNF625-ZNF20; TMEM110; CENPBD1P1; LIPE-AS1;

CLDN9; MYCBP; AMZ2P1; BBIP1; FAM187A; CPEB1; IFRD2; FAM166B;

C5orf49; SIAH3; TSTD1; FAM228B; C6orf226; AP4M1; TIAF1; DCDC2B;

ZNF844; DNAJC27-AS1; SLC25A5-AS1; LAMTOR5-AS1; PPP1R26-AS1;

BAIAP2-AS1; FAM66C; LINC01132; DNMBP-AS1; LINC00948; SRGAP3-AS2; UBAC2-AS1; VIM-AS1; TOB1-AS1; ANKRD66; STMND1; LINC00326;

LINC00271; TSPAN19; LYRM9; NKAPP1; PINLYP; SDCBP2-AS1; TEX21P;

LINC00094; C12orf75; TOPORS-AS1; SMKR1; LINC00886; HOGA1; SOX2-OT; ZNF709; ARHGEF26-AS1; ZNF487; WDR92; LINC00883; WDR65;

WDR86-AS1; TUBA4B; LIFR-AS1; USP2-AS1; BDNF-AS; CRNDE; H2AFJ;

ZBEDS-AS1; USP51; DYNLL1-AS1; SRP14-AS1; CCDC153; FMN1; UGDH-AS1; SPATS1; LINC01018; LRRC37BP1; GPR162; APITD1-CORT; FAM86EP; STAU2-AS1; ATXN7L3B; RHPN1-AS1; ABCC6P2; DYX1C1;

C2lorf119; LINC01171; NHLRC4; OR7E47P; LINC00638; AQP4-AS1;

C15orf65; LINC00908; MAFG-AS1; ILF3-AS1; C19orf82; RNF157-AS1;

NAPA-AS1; HMGN3-AS1; FGF14-AS2; and CASC15.

15. The method of claim 14, wherein the level of expression of each of COX6A1; COX7A2; RACGAP1; TPX2; NEK11; IFT88; RPL26; and RPL23 is determined.

* * * * *